United States Patent
Wang et al.

(10) Patent No.: US 11,512,089 B2
(45) Date of Patent: Nov. 29, 2022

(54) SUBSTITUTED [1,2,4]TRIAZOLO[3,4-A]PHTHALAZINES AS MODULATORS OF GABA$_A$ RECEPTOR ACTIVITY

(71) Applicants: SHANGHAI SIMR BIOTECHNOLOGY CO., LTD, Shanghai (CN); SHANGHAI SIMRD BIOTECHNOLOGY CO., LTD, Shanghai (CN)

(72) Inventors: Fei Wang, Shanghai (CN); Jinhua Wu, Shanghai (CN); Yun Jin, Shanghai (CN); Yong Sun, Shanghai (CN); Shuai Li, Shanghai (CN)

(73) Assignees: SHANGHAI SIMR BIOTECHNOLOGY CO., LTD, Shanghai (CN); SHANGHAI SIMRD BIOTECHNOLOGY CO., LTD, Shanghai (CN)

(*) Notice: Subject to any disclaimer, the term of this patent is extended or adjusted under 35 U.S.C. 154(b) by 0 days.

(21) Appl. No.: 16/979,926

(22) PCT Filed: Mar. 12, 2019

(86) PCT No.: PCT/CN2019/077846
§ 371 (c)(1),
(2) Date: Sep. 11, 2020

(87) PCT Pub. No.: WO2019/174577
PCT Pub. Date: Sep. 19, 2019

(65) Prior Publication Data
US 2021/0009598 A1    Jan. 14, 2021

(30) Foreign Application Priority Data
Mar. 12, 2018   (CN) .................. 201810198971.X

(51) Int. Cl.
*A61K 31/5025* (2006.01)
*C07D 487/04* (2006.01)

(52) U.S. Cl.
CPC .................. *C07D 487/04* (2013.01)

(58) Field of Classification Search
CPC .................. A61K 31/5025; C07D 487/04
USPC ......................................... 514/248; 544/234
See application file for complete search history.

(56) References Cited

U.S. PATENT DOCUMENTS

| 2015/0374705 A1 | 12/2015 | Zhang et al. |
| 2020/0165253 A1 | 5/2020 | Li et al. |

FOREIGN PATENT DOCUMENTS

| CN | 103239720 A | 8/2013 |
| CN | 106854207 A | 6/2017 |
| EP | 3388433 A1 | 10/2018 |
| WO | WO-92/22652 A1 | 12/1992 |
| WO | WO-94/13799 A1 | 6/1994 |
| WO | WO-98/50385 A1 | 11/1998 |
| WO | WO-99/06407 A1 | 2/1999 |
| WO | WO-01/34603 A2 | 5/2001 |
| WO | WO-02/42305 A1 | 5/2002 |
| WO | WO-2013/120438 A1 | 8/2013 |
| WO | WO-2017097217 A1 * | 6/2017 ........... A61K 31/502 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Wolff, Manfred E., Ed. Burger's Medicinal Chemistry and Drug Discovery—Fifth Edition, vol. 1: Principles and Practice, New York: John Wiley & Sons, 1994, 975-977.*
Sep. 21, 2021 EESR issued in European application No. 19766771.0.
Lebsack AD et al: "Identification and synthesis of [1,2,4]triazolo[3,4-a]phthalazine derivatives as high-affinity ligands to the @a"2@d-1 subunit of voltage gated calcium channel", Bioorganic & Medicinal Chemistry Letters, Elsevier, Amsterdam, NL, vol. 14, No. 10, May 17, 2004 (May 17, 2004), pp. 2463-2467, XP004841221, ISSN: 0960-894X.
Jun. 24, 2019 International Search Report issued in International Patent Application No. PCT/CN2019/077846.
Jun. 24, 2019 Written Opinion of the International Searching Authority issued in International Patent Application No. PCT/CN2019/077846.

(Continued)

*Primary Examiner* — Douglas M Willis
(74) *Attorney, Agent, or Firm* — Harness, Dickey & Pierce, P.L.C.

(57) ABSTRACT

The present invention discloses phthalazine isoxazole alkoxy derivatives, a preparation method thereof, a pharmaceutical composition, and a use thereof. The present invention provides a compound represented by Formula I, cis-trans isomers thereof, enantiomers thereof, diastereoisomers thereof, racemates thereof, solvates thereof, hydrates thereof, and pharmaceutically acceptable salts or prodrugs thereof. The compound has an excellent inverse agonist effect with respect to α5-GABA$_A$.

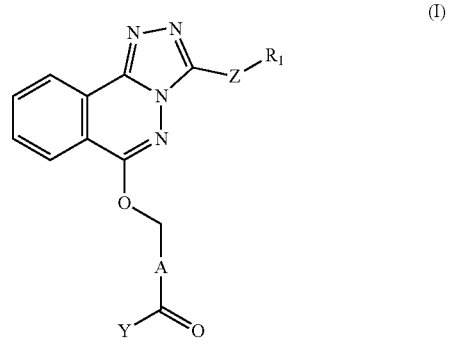

36 Claims, No Drawings

(56) References Cited

OTHER PUBLICATIONS

Zlokovic et al. Nat Rev Neurosci. ; 12(12): 723-738.

Xiao HS et al., "Identification of gene expression profile of dorsal root ganglion in the rat peripheral axotomy model of neuropathic pain."Proc Natl Acad Sci USA. Jun. 11, 2002.

Goeders N E and Kuhar M J (1985) Benzodiazepine binding in vivo with [.sup.3 H]Ro 15-1788. Life Sci 37:345-355.

Wafford K A,Whiting P J and Kemp J A (1993) Differences in affinity and efficacy of benzodiazepine receptor ligands on recombinant GABA.sub.A receptor subtypes. Mol. Pharmacol 43:240-244.

Brickley, S.G. & Mody, I. Extrasynaptic GABAA receptors: their function in the CNS and implications for disease. Neuron 73, 23-34 (2012).

Harris, D. et al. Selective influence on contextual memory: physiochemical properties associated with selectivity of benzodiazepine ligands at GABAA receptors containing the alpha5 subunit. J. Med. Chem. 51, 3788-3803 (2008).

Savic', M.M. et al. PWZ-029, a compound with moderate inverse agonist functional selectivity at GABAA receptors containing 5 subunits, improves passive, but not active, avoidance learning in rats. Brain Res. 1208, 150-159 (2008).

Clément, Y. et al. Gabra5-gene haplotype block associated with behavioral properties of the full agonist benzodiazepine chlordiazepoxide. Behav. Brain Res. 233,474-482 (2012).

Heldt, S.A. & Ressler, K.J. Training-induced changes in the expression of GABAAassociated genes in the amygdala after the acquisition and extinction of Pavlovian fear. Eur. J. Neurosci. 26, 3631-3644 (2007).

Tasan, R.O. et al. Altered GABA transmission in a mouse model of increased trait anxiety. Neuroscience 183, 71-80 (2011).

Andrew G. Leach et al., J. Med. Chem. 2006, 49, 6672-6682.

Bonica et al. The Management of Pain, vol. 1 (the 2nd version), Philadelphia; Lea&Feboger, 1990.

Maehr, J. Che. Ed. 1985,62:114-120.

Farrant M et al. (2005) Variations on an inhibitory theme: phasic and tonic activation of GABA(A) receptors. Nat Rev Neurosci 6:215-229Y.

Yeung JY et al(2003. Tonically activated GABAA receptors in hippocampal neurons are high-affinity, low-conductance sensors for extracellular GABA. Mol Pharmacol; 63: 2-8.

Lee KY et al. Upregulation of high-affinity GABA(A) receptors in cultured rat dorsal root ganglion neurons. Neuroscience 208 (2012) 133-142.

I. Lecker, Y. Yin, D. S. Wang and B. A. Orser, (2013)Potentiation of GABAA receptor activity by volatile anaesthetics is reduced by 5-GABAA receptor-preferring inverse agonists, British Journal of Anaesthesia 110 (S1): i73-i81.

Jones et al.,Pharmacokinetics and metabolism studies on (3-tert-butyl-7-(5-methylisoxazol-3-yl)-2-(1-methyl-1H-1,2,4-triazol-5-ylmethoxy) pyrazolo[1,5-d][1,2,4]triazine, a functionally selective GABAA ?5 inverse agonist for cognitive dysfunction. Bioorg Med Chem Lett. Feb. 15, 2006;16(4):872-5.

Jul. 22, 2022 First Office Action issued in European Patent Application No. 19766771.0.

* cited by examiner

SUBSTITUTED [1,2,4]TRIAZOLO[3,4-A]PHTHALAZINES AS MODULATORS OF GABA$_A$ RECEPTOR ACTIVITY

CROSS-REFERENCE TO RELATED APPLICATIONS

The present application is a U.S. National Phase Application under 35 U.S.C. 371 of International Application No. PCT/CN2019/077846, filed on Mar. 12, 2019, which claims the benefit of Chinese patent application CN201810198971.X filed on Mar. 12, 2018. The entire disclosures of the above applications are incorporated herein by reference in their entireties.

FIELD OF THE INVENTION

The present disclosure relates to a phthalazine isoxazol alkoxy derivative with a regulatory function on α5-GABA$_A$ receptor, a preparation method thereof, a pharmaceutical composition thereof and their application as a medicament.

BACKGROUND

γ-aminobutyric acid (GABA) is an important inhibitory neurotransmitter in mammal central nervous system. There are two classes of GABA receptors in nature. One is GABA$_A$ receptor, which is a member of ligand-gated ion channel superfamily, and the other is GABA$_B$ receptor, which is a member of G protein-coupled receptor superfamily. It is found that there are several subunits in mammal GABA$_A$ receptor, including α1-6, β1-4, γ1-3, δ, ε, θ and ρ1-2, among which α subunit, β subunit and γ subunit are important for forming a complete and functional GABA$_A$ receptor, and α subunit is crucial for the interaction between benzodiazepine and GABA$_A$ receptor.

The percentage of GABA$_A$ receptor that contains α5 subunit (α5-GABA$_A$ receptor) in mammal brain GABA$_A$ receptors is less than 5%. The expression level of α5-GABA$_A$ receptor in cerebral cortex is very low, while the percentage of GABA$_A$ receptor in hippocampal tissue is more than 20%. There is almost no expression in other brain regions. Considering the specific distribution and functional research of α5-GABA$_A$ receptor in hippocampal tissue, a large number of pharmaceutical companies including Roche are working on α5-GABA$_A$ receptor. Many compounds have been synthesized gradually, particularly inverse agonists for α5-GABA$_A$ receptor in hippocampal tissue, and among them α5IA and MRK-016 showed good therapeutic effects on the treatment of cognition related diseases in animal models and clinical trials, especially for Alzheimer's disease. It is widely thought that α5-GABA$_A$ receptor inverse agonists can be used for the treatment of cognition related diseases, especially for Alzheimer's disease. The patent application US 20110224278 A1 discloses α5-GABA$_A$ receptor inverse agonists can be used for the treatment of multi-infarct dementia and stoke related diseases.

In the last decade, studies have shown that the permeability of blood brain barrier (BBB) increases under some disease conditions, especially those neurodegenerative diseases like Alzheimer's and stroke (Zlokovic et al. *Nat Rev Neurosci.;* 12(12): 723-738). As a result, some normally impermeable compounds can get into the brain under these disease conditions and exert pharmacological effects. So the normally impermeable α5-GABA$_A$ receptor inverse agonists potentially can be used for the treatment of Alzheimer's and stroke due to the increased permeability.

In 2002, Dr. Xu Zhang's lab reported that the α5-GABA$_A$ receptor was mainly expressed in the small neurons and its expression level increased in the nerve transection model (Xiao H S et al., "Identification of gene expression profile of dorsal root ganglion in the rat peripheral axotomy model of neuropathic pain." Proc Natl Acad Sci USA. Jun. 11, 2002; 99(12)). The patent application CN103239720A discloses that the α5-GABA$_A$ receptor also expresses in the peripheral nerves system and its expression increases dramatically in the partial sciatic nerve injury model. The α5-GABA$_A$ receptor inverse agonists act to inhibit various pains by selectively binding to the α5-GABA$_A$ receptor of the peripheral nerves system. The animal model data show that the stronger the inverse agonism of the inverse agonist, the better the pain-inhibiting effect is.

There are many researches on the detection whether a compound is an inverse agonist or an antagonist of α5-GABA$_A$ receptors. For example, in the international patent applications WO 92/22652 and WO 94/13799, α subunit combination α5, β3 and γ2 of GABA$_A$ receptor was used to detect the binding of the compounds and the subunit. For screening assay, the method developed by Goeders et al., is widely used (Goeders N E and Kuhar M J (1985) Benzodiazepine binding in vivo with [.sup.3 H]Ro 15-1788. *Life Sci* 37: 345-355). There are also many researches on the detection whether a ligand which can bind with α5-GABA$_A$ receptor is an agonist, an antagonist or an inverse antagonist of α5-GABA$_A$ receptors, for example the method of Wafford K A et al (Wafford K A, Whiting P J and Kemp J A (1993) Differences in affinity and efficacy of benzodiazepine receptor ligands on recombinant GABA.sub.A receptor subtypes. *Mol. Pharmacol* 43: 240-244).

There are several methods to detect the compound permeability to the BBB. It has been reported that an isotope labeled compound ($^3$H)R0-15-1788 (α5-GABA$_A$ receptor selective inverse agonist) can be used to detect the binding of a compound in brain (Jones et al., Pharmacokinetics and metabolism studies on (3-tert-butyl-7-(5-methylisoxazol-3-yl)-2-(1-methyl-1H-1,2,4-triazol-5-ylmethoxy)pyrazolo[1, 5-d][1,2,4]triazine, a functionally selective GABA$_A$ α5 inverse agonist for cognitive dysfunction. *Bioorg Med Chem Lett.* 2006 Feb. 15; 16(4): 872-5). The studies showed that MRK016 could efficiently block the binding of ($^3$H)R0-15-1788 in brain, while MRK016-M3 showed almost no blocking effect. Detecting the tissue distribution of a compound is the other method. For example, the distribution ratio of a compound in blood and brain can be used to determine its permeability to the BBB.

Previous studies have shown that inhibiting or decreasing the α5-GABA$_A$ receptor mediated extrasynaptic inhibition by drugs or genetic method could improve cognitive and learning ability but also cause mild anxiety like behavior (Brickley, S. G. & Mody, I. Extrasynaptic GABA$_A$ receptors: their function in the CNS and implications for disease. *Neuron* 73, 23-34 (2012); Harris, D. et al. Selective influence on contextual memory: physiochemical properties associated with selectivity of benzodiazepine ligands at GABA$_A$ receptors containing the alpha5 subunit. *J. Med. Chem.* 51, 3788-3803 (2008); Savic', M. M. et al. PWZ-029, a compound with moderate inverse agonist functional selectivity at GABA$_A$ receptors containing α5 subunits, improves passive, but not active, avoidance learning in rats. *Brain Res.* 1208, 150-159 (2008); Clement, Y. et al. Gabra5-gene haplotype block associated with behavioral properties of the full agonist benzodiazepine chlordiazepoxide. Behav. *Brain*

*Res.* 233, 474-482 (2012). There are also studies showing that fear and anxiety behaviors are correlated with the decrease of Gabra5 mRNA (Heldt, S. A. & Ressler, K. J. Training-induced changes in the expression of GABA$_A$ associated genes in the amygdala after the acquisition and extinction of Pavlovian fear. *Eur. J. Neurosci.* 26, 3631-3644 (2007); Tasan, R. O. et al. Altered GABA transmission in a mouse model of increased trait anxiety. Neuroscience 183, 71-80 (2011). Paolo Botta et al have reported that the α5-GABA$_A$ receptor plays a key role in the generation of fear and anxiety. Selectively knocking out the expression of α5-GABA$_A$ receptor in some brain regions could induce fear and anxiety behaviors in animals. Taken together, due to their entry into brain and cause of fear and anxiety, it is better to optimize the permeability of α5-GABA$_A$ receptor inverse agonists for drug development.

In 2006, AstraZeneca modified its candidate compound by introducing a methoxyl group into the key position, and found that the solubility of the candidate compound decreased (Andrew G. Leach et al., *J. Med. Chem.* 2006, 49, 6672-6682)

BRIEF SUMMARY OF THE INVENTION

The technical problem to be solved by the present disclosure is that the structures of the existing α5-GABA$_A$ receptor inverse agonists are too monotonous, therefore, the present disclosure provides a phthalazine isoxazol alkoxy derivative, a preparation method thereof, a pharmaceutical composition and a use thereof, the compounds have excellent inverse agonistic effects on α5-GABA$_A$ receptor.

The present disclosure provides a compound represented by formula I, a cis-trans isomer thereof, an enantiomer thereof, a diastereomer thereof, a racemate thereof, a solvate thereof, a hydrate thereof, a pharmaceutically acceptable salt thereof or a prodrug thereof;

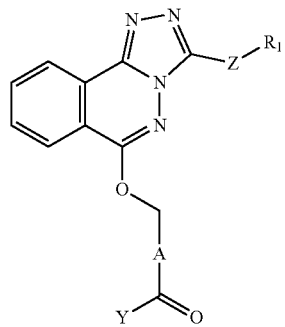

formula I wherein, Z is a 5 or 6 membered heteroaromatic ring containing 1, 2 or 3 heteroatoms independently selected from O, N and S, the heteroaromatic ring is substituted by R$_1$;

R$_1$ is C$_{1-6}$ alkoxyl C$_{1-6}$ alkyl, C$_{1-6}$ alkoxyl substituted by halogen, C$_{3-6}$ cycloalkyl (C$_{1-6}$) alkoxyl, C$_{3-6}$ cycloalkyl (C$_{1-6}$) alkoxyl C$_{1-6}$ alkyl, C$_{3-6}$ heterocycloalkyl, C$_{3-6}$ heterocycloalkyl (C$_{1-6}$) alkyl, C$_{3-6}$ heterocycloalkyloxy (C$_{1-6}$) alkyl, C$_{3-6}$ heterocycloalkyl (C$_{1-6}$) alkoxyl C$_{1-6}$ alkyl, or C$_{1-6}$ alkyl NH(C$_{1-6}$) alkyl, each of which is optionally substituted by 1-4 substituents independently selected from the group consisting of halogen, cyano, hydroxyl, oxo and C$_1$-C$_6$ alkyl;

A is —NR$_2$—, or A is a 5 membered heteroarylene containing 1, 2, 3 or 4 heteroatoms independently selected from O, N and S with at most one of the heteroatoms being O or S, or A is a 6 membered heteroarylene containing 1, 2 or 3 N atoms, or the 5 or 6 membered heteroarylene group is optionally fused to a benzene ring or a pyridine ring, the 5 or 6 membered heteroarylene is optionally substituted by R$_x$ and/or R$_y$, and/or R$_z$, wherein R$_x$ is halogen, —OC(O)R$_1$, —C(O)OR$_1$, —NR$_2$R$_3$, —NR$_2$C(O)R$_3$, —OH or —CN, R$_y$ is halogen, —OC(O)R$_1$, —NR$_2$R$_3$, —NR$_2$C(O)R$_3$, or CN, R$_z$ is —OR$_1$ or —OC(O)R$_1$, provided that when A is a pyridine derivative {i.e., A contains a pyridine ring}, the pyridine ring is optionally in the form of N-oxide, or A is phenylene optionally substituted by 1, 2 or 3 substituents independently selected from the group consisting of halogen, cyano, C$_{1-6}$ alkyl, C$_{2-6}$ linear alkenyl, C$_{2-6}$ alkynyl and C$_{3-6}$ cycloalkyl;

Y is —NY$_1$Y$_2$, —NH—NY$_3$Y$_4$ or hydroxyl;

Y$_1$ is H, C$_{1-6}$ alkyl, or C$_{1-6}$ alkyl substituted by 1-5 substituents, each of the substituents is independently selected from the group consisting of amino, halogen, halogenated-C$_{1-6}$ alkoxyl, hydroxyl, C$_{1-6}$ alkoxyl, (C$_{1-6}$ alkyl, C$_{1-6}$ alkyl)N—, (C$_{1-6}$ alkyl, H)N—, nitro and C$_{1-6}$ alkyl-S(O)$_2$—;

Y$_2$ is H, amino, C$_{1-6}$ alkyl, C$_{1-6}$ alkoxyl, cycloalkyl, C$_{4-6}$ bridged cycloalkyl, heterocycloalkyl, C$_{1-6}$ alkyl-S(O)$_2$—, NH—S(O)$_2$ or heteroaryl, each of which is optionally substituted by 1-5 substituents independently selected from the group consisting of cyano, halogen, halogenated-C$_{1-6}$ alkyl, C$_{1-6}$ alkoxyl, halogenated-C$_{1-6}$ alkoxyl, carboxylic acid-C$_{1-6}$ alkyl, carboxylic C$_{1-4}$ ester-C$_{1-6}$ alkyl, hydroxyl, hydroxyl-C$_{1-6}$ alkyl, C$_{1-6}$ alkoxyl-C$_{1-6}$ alkyl, C$_{1-6}$ alkyl, (C$_{1-6}$ alkyl, C$_{1-6}$ alkyl)N—, (C$_{1-6}$ alkyl, H)N—, nitro, C$_{1-6}$ alkyl-S(O)$_2$—, cyclopropyl, C$_{4-6}$ cycloalkyl, C$_{3-6}$ cycloalkyl substituted by hydroxyl, 4 membered heterocycloalkyl containing 1-3 heteroatoms selected from N, O or S, C$_4$-C$_6$ heterocycloalkyl containing 1-3 heteroatoms selected from N, O or S, 4 membered heterocycloalkyl containing 1-3 heteroatoms selected from N, O or S and substituted by methyl, C$_4$-C$_6$ heterocycloalkyl containing 1-3 heteroatoms selected from N, O or S and substituted by methyl, C$_4$-C$_6$ heterocycloalkyl containing 1-3 heteroatoms selected from N, O or S and substituted by halogen, C$_4$-C$_6$ heterocycloalkyl containing 1-3 heteroatoms selected from N, O or S and substituted by methoxyl, acyl and acylamino;

or, Y$_1$ and Y$_2$ together with the N atom to which they are attached form 4-7 membered heterocycloalkyl, 4-7 membered heterocycloalkenyl, 6-9 membered spirocyclic group or 6-9 membered bridged cyclic group, or the 4-7 membered heterocycloalkyl, 4-7 membered heterocycloalkenyl, 6-9 membered spirocyclic group or 6-9 membered bridged cyclic group contain 0, 1 or more heteroatoms selected from O and N besides the N atom, each of which is optionally substituted by 1-4 substituents independently selected from the group consisting of halogen, cyano, hydroxyl, oxo, C$_1$-C$_6$ alkyl and C$_1$-C$_6$ alkoxyl;

each of Y$_3$ and Y$_4$ is independently selected from the group consisting of H, C$_1$-C$_6$ alkyl, SO$_2$—C$_1$-C$_6$ alkyl, cycloalkyl and heterocyclyl, or each of which is optionally substituted by 1-4 substituents independently selected from the group consisting of halogen, cyano, hydroxyl, C$_1$-C$_6$ alkyl and C$_1$-C$_6$ alkoxyl;

or, $Y_3$ and $Y_4$ together with the N atom to which they are attached form heterocyclyl, or the heterocyclyl is optionally substituted by 1-4 substituents independently selected from the group consisting of halogen, cyano, hydroxyl, oxo, $C_1$-$C_6$ alkyl and $C_1$-$C_6$ alkoxyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

formula I can be represented by formula II,

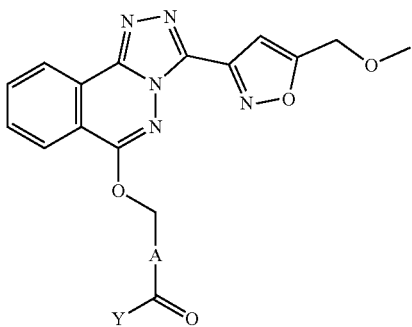

II

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

formula I can be represented by formula III,

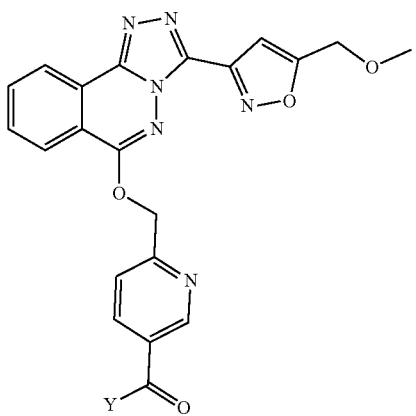

III

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

when Z is a 5 membered heteroaromatic ring containing 1, 2 or 3 heteroatoms independently selected from O, N and S, then the 5 membered heteroaromatic ring containing 1, 2 or 3 heteroatoms independently selected from O, N and S is, for example, a 5 membered heteroaromatic ring containing 2 heteroatoms independently selected from O, N and S, for another example, isoxazole, for another example,

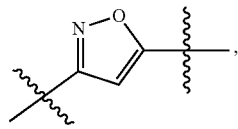 [SMILES: *c1cc(*)on1]

for another example, "

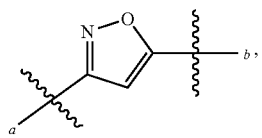

wherein the b end is connected to $R_1$".

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

when $R_1$ is $C_{1-6}$ alkoxyl $C_{1-6}$ alkyl, then the alkyl end can be connected to Z.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

when $R_1$ is $C_{1-6}$ alkoxyl $C_{1-6}$ alkyl, then the $C_{1-6}$ alkoxyl is, for example, $C_{1-3}$ alkoxyl, for another example, methoxyl, ethoxyl, n-propoxyl or isopropoxyl, for another example, methoxyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

when $R_1$ is $C_{1-6}$ alkoxyl $C_{1-6}$ alkyl, then the $C_{1-6}$ alkyl is, for example, $C_{1-3}$ alkyl, for another example, methyl, ethyl, n-propyl or isopropyl, for another example, methyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

when $R_1$ is $C_{1-6}$ alkoxyl $C_{1-6}$ alkyl, then the "$C_{1-6}$ alkoxyl $C_{1-6}$ alkyl" is, for example,

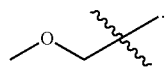

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

when A is a 6 membered heteroarylene containing 1, 2 or 3 N atoms, then the 6 membered heteroarylene containing 1, 2 or 3 N atoms is, for example, pyridyl, for example,

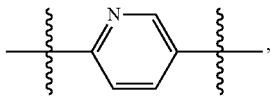 [SMILES: *c1ccc(*)nc1]

for another example, "

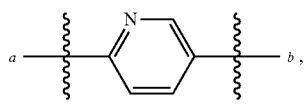

the a end is connected to the methylene".

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

when $Y_1$ is $C_{1-6}$ alkyl, then the $C_{1-6}$ alkyl is, for example, $C_{1-3}$ alkyl, for another example, methyl, ethyl, n-propyl or isopropyl, for another example, methyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

when $Y_1$ is $C_{1-6}$ alkyl substituted by 1-5 substituents, then the number of the substituent is, for example, 1, 2, 3, 4 or 5, for another example, 1 or 2.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

when $Y_1$ is $C_{1-6}$ alkyl substituted by 1-5 substituents, then the $C_{1-6}$ alkyl is, for example, $C_{1-3}$ alkyl, for another example, methyl, ethyl, n-propyl or isopropyl, for another example, methyl or ethyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

when $Y_1$ is $C_{1-6}$ alkyl substituted by 1-5 substituents, and the substituent is $C_{1-6}$ alkoxyl, then the $C_{1-6}$ alkoxyl is, for example, $C_{1-3}$ alkoxyl, for another example, methoxyl, ethoxyl, n-propoxyl or isopropoxyl, for another example, methoxyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

when $Y_1$ is $C_{1-6}$ alkyl substituted by 1-5 substituents, and the substituent is $C_{1-6}$ alkoxyl, then the $C_{1-6}$ alkyl substituted by 1-5 substituents is, for example, 2-methoxyethyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

when $Y_2$ is $C_{1-6}$ alkyl, then the $C_{1-6}$ alkyl is, for example, $C_{1-4}$ alkyl, for another example, methyl, ethyl, n-propyl, isopropyl, n-butyl, isobutyl, sec-butyl or tert-butyl, for another example, methyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

when $Y_2$ is cycloalkyl, then the cycloalkyl is, for example, $C_3$-$C_6$ cycloalkyl, for another example, cyclopropyl, cyclobutyl, cyclopentyl or cyclohexyl, for another example, cyclopropyl or cyclobutyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

when $Y_2$ is $C_{4-6}$ bridged cycloalkyl, then the $C_{4-6}$ bridged cycloalkyl is, for example, bicyclo[1.1.1]pentyl, for another example, bicyclo[1.1.1]pentan-1-yl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

when $Y_2$ is heterocycloalkyl, then the heterocycloalkyl is, for example, 4, 5 or 6 membered heterocycloalkyl containing 1, 2 or 3 heteroatoms selected from O, N and S, for another example, azacyclobutyl, oxacyclobutyl, oxacyclopentyl or oxacyclohexyl, for another example, azetidin-3-yl, oxetan-3-yl, oxolan-3-yl or oxan-4-yl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

when the groups in the definitions of $Y_2$ (i.e., $C_{1-6}$ alkyl, $C_{1-6}$ alkoxyl, cycloalkyl, $C_4$-6 bridged cycloalkyl, heterocycloalkyl, $C_{1-6}$ alkyl-S(O)$_2$—, NH—S(O)$_2$ or heterocycloaryl; unless otherwise specified, this description is applicable to the entire disclosure) are substituted by 1-5 substituents, then the number of the substituent is, for example, 1, 2, 3, 4 or 5, for another example, 1 or 2.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

when the groups in the definitions of $Y_2$ are substituted by halogen, then the halogen is, for example, F, Cl, Br or I, for another example, F.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
when the groups in the definitions of $Y_2$ are substituted by $C_{1-6}$ alkoxyl, then the $C_{1-6}$ alkoxyl is, for example, $C_{1-3}$ alkoxyl, for another example, methoxyl, ethoxyl, n-propoxyl or isopropoxyl, for another example, methoxyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
when the groups in the definitions of $Y_2$ are substituted by halogenated-$C_{1-6}$ alkoxyl, then the halogen is, for example, F, Cl, Br or I.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
when the groups in the definitions of $Y_2$ are substituted by halogenated-$C_{1-6}$ alkoxyl, then the "$C_{1-6}$ alkoxyl" is, for example, $C_{1-3}$ alkoxyl, for another example, methoxyl, ethoxyl, n-propoxyl or isopropoxyl, for another example, methoxyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
when the groups in the definitions of $Y_2$ are substituted by halogenated-$C_{1-6}$ alkoxyl, then the "halogenated-$C_{1-6}$ alkoxyl" is, for example, trifluoromethoxyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
when the groups in the definitions of $Y_2$ are substituted by 4 membered heterocycloalkyl containing 1-3 heteroatoms selected from N, O or S, then the 4 membered heterocycloalkyl containing 1-3 heteroatoms selected from N, O or S is, for example, oxacyclobutyl, for another example, oxetan-3-yl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
when the groups in the definitions of $Y_2$ are substituted by $C_4$-$C_6$ heterocycloalkyl containing 1-3 heteroatoms selected from N, O or S, then the $C_4$-$C_6$ heterocycloalkyl containing 1-3 heteroatoms selected from N, O or S is, for example, oxacyclopentyl, for another example, oxolan-3-yl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
when the groups in the definitions of $Y_2$ are substituted by "4 membered heterocycloalkyl containing 1-3 heteroatoms selected from N, O or S and substituted by methyl", then the "4 membered heterocycloalkyl containing 1-3 heteroatoms selected from N, O or S" is, for example, oxacyclobutyl, for another example, oxetan-3-yl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
when the groups in the definitions of $Y_2$ are substituted by "4 membered heterocycloalkyl containing 1-3 heteroatoms selected from N, O or S and substituted by methyl", then the "4 membered heterocycloalkyl containing 1-3 heteroatoms selected from N, O or S and substituted by methyl" is, for example, 3-methyl-oxetan-3-yl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
when the groups in the definitions of $Y_2$ are substituted by "$C_4$-$C_6$ heterocycloalkyl containing 1-3 heteroatoms selected from N, O or S and substituted by methyl", then the "$C_4$-$C_6$ heterocycloalkyl containing 1-3 heteroatoms selected from N, O or S" is, for example, oxacyclopentyl, for another example, oxolan-3-yl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
when the groups in the definitions of $Y_2$ are substituted by acyl, then the acyl is, for example, $C_{1-3}$ alkyl-C(=O)—, for another example, acetyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
when $Y_1$ and $Y_2$ together with the N atom to which they are attached form 4-7 membered heterocycloalkyl, then the 4-7 membered heterocycloalkyl is, for example, 4 membered, 5 membered, 6 membered or 7 membered heterocycloalkyl, for another example,

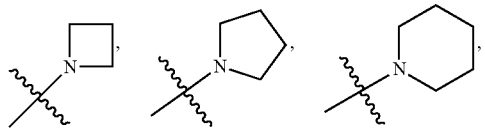

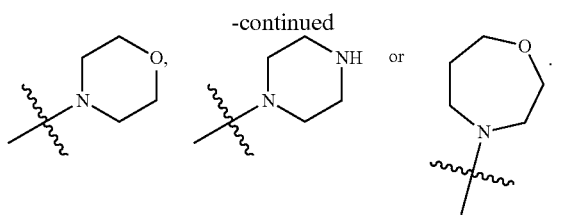

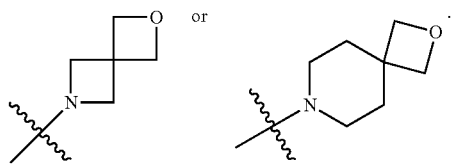 [SMILES: *N1CC2(COC2)C1 ; "or" ; *N1CCC2(CC1)COC2 ; "."]

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

when $Y_1$ and $Y_2$ together with the N atom to which they are attached form a 6-9 membered spirocyclic group, then the 6-9 membered spirocyclic group can be bicyclic or tricyclic.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

when $Y_1$ and $Y_2$ together with the N atom to which they are attached form a 6-9 membered spirocyclic group, then the 6-9 membered spirocyclic group is, for example, 7 membered, 8 membered or 9 membered spirocyclic group, for another example, In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

when $Y_1$ and $Y_2$ together with the N atom to which they are attached form a 6-9 membered bridged cyclic group, then the 6-9 membered bridged cyclic group can be bicyclic or tricyclic.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

when $Y_1$ and $Y_2$ together with the N atom to which they are attached form a 6-9 membered bridged cyclic group, then the 6-9 membered bridged cyclic group is, for example, 7 membered bridged cyclic group, for another example, In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

when $Y_1$ and $Y_2$ together with the N atom to which they are attached form 4-7 membered heterocycloalkyl, 4-7 membered heterocycloalkenyl, 6-9 membered spirocyclic group or 6-9 membered bridged cyclic group, and the groups contain more than one heteroatom selected from O and N, the "more than one" can be 2 or 3.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

when $Y_1$ and $Y_2$ together with the N atom to which they are attached form 4-7 membered heterocycloalkyl, 4-7 membered heterocycloalkenyl, 6-9 membered spirocyclic group or 6-9 membered bridged cyclic group, and the groups are substituted by 1-4 substituents, then the number of the substituent is, for example, 1, 2, 3 or 4, for another example, 1 or 2.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

when $Y_1$ and $Y_2$ together with the N atom to which they are attached form 4-7 membered heterocycloalkyl, 4-7 membered heterocycloalkenyl, 6-9 membered spirocyclic group or 6-9 membered bridged cyclic group, and the groups are substituted by halogen, then the halogen is, for example, F, Cl, Br or I, for another example, F.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

when $Y_1$ and $Y_2$ together with the N atom to which they are attached form 4-7 membered heterocycloalkyl, 4-7 membered heterocycloalkenyl, 6-9 membered spirocyclic group or 6-9 membered bridged cyclic group, and the groups are substituted by $C_1$-$C_6$ alkyl, then the $C_1$-$C_6$ alkyl is, for example, $C_{1-3}$ alkyl, for another example, methyl, ethyl, n-propyl or isopropyl, for another example, methyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

when $Y_1$ and $Y_2$ together with the N atom to which they are attached form 4-7 membered heterocycloalkyl, 4-7 membered heterocycloalkenyl, 6-9 membered spirocyclic group or 6-9 membered bridged cyclic group, and the groups are substituted by $C_1$-$C_6$ alkoxyl, then the $C_1$-$C_6$ alkoxyl is, for example, $C_{1-3}$ alkoxyl, for another example, methoxyl, ethoxyl, n-propoxyl or iso-propoxyl, for another example, methoxyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
Z is a 5 membered heteroaromatic ring containing 1, 2 or 3 heteroatoms independently selected from O, N and S, the heteroaromatic ring is substituted by $R_1$.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
$R_1$ is $C_{1-6}$ alkoxyl $C_{1-6}$ alkyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
A is 6 membered heteroarylene containing 1, 2 or 3 N atoms.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
A is 6 membered heteroarylene containing 1 N atom.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
when $Y_1$ and $Y_2$ are not connected together to form a ring (i.e., not the condition where "$Y_1$ and $Y_2$ together with the N atom to which they are attached form-7 membered heterocycloalkyl, 4-7 membered heterocycloalkenyl, 6-9 membered spirocyclic group or 6-9 membered bridged cyclic group"; unless otherwise specified, this description is applicable to the entire disclosure);
Y is —$NY_1Y_2$ or hydroxyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
when $Y_1$ and $Y_2$ are not connected together to form a ring;
Y is —$NY_1Y_2$.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
when $Y_1$ and $Y_2$ are not connected together to form a ring;
$Y_1$ is H, $C_{1-6}$ alkyl, or, $C_{1-6}$ alkyl substituted by 1-5 $C_{1-6}$ alkoxyl groups.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
when $Y_1$ and $Y_2$ are not connected together to form a ring;
$Y_1$ is H, $C_{1-6}$ alkyl, or, $C_{1-6}$ alkyl substituted by 1-5 $C_{1-6}$ alkoxyl groups, $Y_2$ is identical to $Y_1$.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
when $Y_1$ and $Y_2$ are not connected together to form a ring;
$Y_1$ can be H, methyl or 2-methoxyethyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
when $Y_1$ and $Y_2$ are not connected together to form a ring;
$Y_1$ is H, or, $C_{1-6}$ alkyl substituted by 1-5 $C_{1-6}$ alkoxyl groups.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
when $Y_1$ and $Y_2$ are not connected together to form a ring;
$Y_2$ is H, $C_{1-6}$ alkyl, cycloalkyl, $C_{4-6}$ bridged cycloalkyl, or, heterocycloalkyl, each of which is optionally substituted by 1-5 substituents independently selected from the group consisting of cyano, halogen, $C_{1-6}$ alkoxyl, halogenated-$C_{1-6}$ alkoxyl, hydroxyl, cyclopropyl, 4 membered heterocycloalkyl containing 1-3 heteroatoms selected from N, O or S, $C_4$-$C_6$ heterocycloalkyl containing 1-3 heteroatoms selected from N, O or S, 4 membered heterocycloalkyl containing 1-3 heteroatoms selected from N, O or S and substituted by methyl, $C_4$-$C_6$ heterocycloalkyl containing 1-3 heteroatoms selected from N, O or S and substituted by methyl, and acyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
when $Y_1$ and $Y_2$ are not connected together to form a ring;
$Y_2$ is a group as defined in (1), (2), (3) or (4):
(1) H, $C_{1-6}$ alkyl, cycloalkyl, $C_{4-6}$ bridged cycloalkyl, or, heterocycloalkyl;
(2) $C_{1-6}$ alkyl substituted by 1-5 substituents independently selected from the group consisting of cyano, halogen, hydroxyl, cyclopropyl, $C_{1-6}$ alkoxyl, halogenated-$C_{1-6}$ alkoxyl, 4 membered heterocycloalkyl containing 1-3 heteroatoms selected from N, O or S, $C_4$-$C_6$ heterocycloalkyl containing 1-3 heteroatoms selected from N, O or S, 4 membered heterocycloalkyl containing 1-3 heteroatoms selected from N, O or S and substituted by methyl, and $C_4$-$C_6$ heterocycloalkyl containing 1-3 heteroatoms selected from N, O or S and substituted by methyl;

(3) cycloalkyl substituted by 1-5 substituents independently selected from the group consisting of cyano and halogen;
(4) heterocycloalkyl substituted by 1-5 substituents independently selected from acyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
when $Y_1$ and $Y_2$ are not connected together to form a ring; $Y_2$ is a group as defined in (1), (2), or (4):
(1) $C_{1-6}$ alkyl, cycloalkyl (for example, $C_3$-$C_6$ cycloalkyl), $C_{4-6}$ bridged cycloalkyl, or, heterocycloalkyl
(2) $C_{1-6}$ alkyl substituted by 1-2 substituents independently selected from the group consisting of cyano, hydroxyl, cyclopropyl, $C_{1-6}$ alkoxyl, 4 membered heterocycloalkyl containing 1-3 heteroatoms selected from N, O or S, $C_4$-$C_6$ heterocycloalkyl containing 1-3 heteroatoms selected from N, O or S, 4 membered heterocycloalkyl containing 1-3 heteroatoms selected from N, O or S and substituted by methyl, and, $C_4$-$C_6$ heterocycloalkyl containing 1-3 heteroatoms selected from N, O or S and substituted by methyl;
(4) heterocycloalkyl substituted by 1-2 substituents independently selected from acyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
when $Y_1$ and $Y_2$ are not connected together to form a ring; $Y_2$ is the group as defined in (1), (2), or (4):
(1) heterocycloalkyl;
(2) $C_{1-6}$ alkyl substituted by 1 substituent independently selected from the group consisting of hydroxyl, $C_{1-6}$ alkoxyl, cyclopropyl, 4 membered heterocycloalkyl containing 1-3 heteroatoms selected from N, O or S, $C_4$-$C_6$ heterocycloalkyl containing 1-3 heteroatoms selected from N, O or S, 4 membered heterocycloalkyl containing 1-3 heteroatoms selected from N, O or S and substituted by methyl, and, $C_4$-$C_6$ heterocycloalkyl containing 1-3 heteroatoms selected from N, O or S and substituted by methyl;
(4) heterocycloalkyl substituted by 1 substituent independently selected from acyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
when $Y_1$ and $Y_2$ are not connected together to form a ring; $Y_2$ is $C_{1-6}$ alkyl substituted by 1 substituent independently selected from the group consisting of hydroxyl, cyclopropyl and $C_{1-6}$ alkoxyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
when $Y_1$ and $Y_2$ are not connected together to form a ring; $Y_2$ can be H, methyl, ethyl, isopropyl, bicyclopentyl, cyclopropylmethyl, oxacyclobutylmethyl, methyl(oxacyclobutyl)methyl, tetrahydrofurylmethylene, hydroxyethyl, methoxyethyl, trifluoromethoxyethyl, fluoroethyl, difluoroethyl, trifluoroethyl, methoxypropyl, dimethoxypropyl, cyanopropyl, difluorohydroxypropyl, trifluoropropyl, trifluoroisopropyl, methoxyisopropyl, cyclopropyl, cyclobutyl, cyanocyclopropyl, fluorocyclobutyl, difluorocyclobutyl, acetylazacyclobutyl, difluorocyclohexyl, difluorocyclopentyl, oxacyclobutyl, tetrahydropyranyl or tetrahydrofuranyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
when $Y_1$, $Y_2$ are not connected together to form a ring; $Y_2$ can be ethyl, 3,3-difluorocyclobutyl, tetrahydro-2H-pyran-4-yl, 1-methoxyprop-2-yl, 3-methoxypropyl, 2-methoxyethyl, tetrahydrofuran-2-methylene, isopropyl, cyclopropyl, 2-trifluoromethoxyethyl, 1-methoxy-2-methylisoprop-2-yl, 2,2,2-trifluoroethyl, 2-hydroxyethyl, oxacyclobutyl-3-yl, oxacyclobutyl-3-methyl, 1-cyanocyclopropyl, 3-methyl(oxacyclobutyl)-methyl, 3-fluorocyclobutyl, 2-fluoroethyl, cyclobutyl, 2,2-difluoroethyl, 2,2-difluoro-3-hydroxylpropyl, 3-tetrahydrofuranyl, 1,1,1-trifluoroisopropyl, 3-cyanopropyl, 1,1,1-trifluoropropyl, 1,3-dimethoxyprop-2-yl, bicyclo[1.1.1]pentan-1-yl, 1-acetyl-azetidin-3-yl, 4,4-difluorocyclohexyl, 3,3-difluoro-1-cyclopentylamino, H, methyl or cyclopropylmethyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
when $Y_1$, $Y_2$ are connected together to form a ring (i.e., when "$Y_1$ and $Y_2$ together with the N atom to which they are attached form –7 membered heterocycloalkyl, 4-7 membered heterocycloalkyl, 6-9 membered spirocyclic group or 6-9 membered bridged cyclic group", unless otherwise specified, this description is applicable to the entire disclosure);
$Y_1$ and $Y_2$ together with the N atom to which they are attached form 4-7 membered heterocycloalkyl, 6-9 membered spirocyclic group or 6-9 membered bridged cyclic group, or the 4-7 membered heterocycloalkyl, 6-9 membered spirocyclic group or 6-9 membered bridged cyclic group contains 0 or 1 heteroatom selected from O and N besides the N atom, each of which is optionally substituted by 1-4 substituents independently selected from the group consisting of halogen, cyano, hydroxyl, oxo, $C_1$-$C_6$ alkyl and $C_1$-$C_6$ alkoxyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
when $Y_1$ and $Y_2$ are connected together to form a ring; $Y_1$ and $Y_2$ together with the N atom to which they are attached form a group as defined in (a) or (b):
(a) 4-7 membered heterocycloalkyl, 6-9 membered spirocyclic group or 6-9 membered bridged cyclic group containing 0 or 1 heteroatom selected from O and N besides the N atom;

(b) 4-7 membered heterocycloalkyl containing 0 or 1 heteroatom selected from O and N besides the N atom, which is substituted by 1-4 substituents selected from the group consisting of halogen, cyano, hydroxyl, oxo, $C_1$-$C_6$ alkyl and $C_1$-$C_6$ alkoxyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
  when $Y_1$ and $Y_2$ are connected together to form a ring;
  $Y_1$ and $Y_2$ together with the N atom to which they are attached form a group as defined in (a) or (b):
    (a) 4-7 membered heterocycloalkyl, 6-9 membered spirocyclic group or 6-9 membered bridged cyclic group containing 0 or 1 heteroatom selected from O and N besides the N atom;
    (b) 4-7 membered heterocycloalkyl containing 0 or 1 heteroatom selected from O and N besides the N atom, which is substituted by 1-4 substituents selected from the group consisting of oxo, hydroxyl, $C_1$-$C_6$ alkoxyl, halogen and $C_1$-$C_6$ alkyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
  when $Y_1$ and $Y_2$ are connected together to form a ring;
  $Y_1$ and $Y_2$ together with the N atom to which they are attached form a group as defined in (a) or (b):
    (a) 4-7 membered heterocycloalkyl, 6-9 membered spirocyclic group or 6-9 membered bridged cyclic group containing 0 or 1 heteroatom selected from O and N besides the N atom;
    (b) 4-7 membered heterocycloalkyl containing 0 or 1 heteroatom selected from O and N besides the N atom, which is substituted by 1-4 substituents selected from the group consisting of oxo and $C_1$-$C_6$ alkyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
  when $Y_1$ and $Y_2$ are connected together to form a ring;
  $Y_1$ and $Y_2$ together with the N atom to which they are attached form a group as defined in (a) or (b):
    (a) 6-9 membered bridged cyclic group containing 0 or 1 heteroatom selected from O and N besides the N atom;
    (b) 4-7 membered heterocycloalkyl containing 0 or 1 heteroatom selected from O and N besides the N atom, which is substituted by 1-4 substituents selected from the group consisting of oxo and $C_1$-$C_6$ alkyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
  when $Y_1$ and $Y_2$ are connected together to form a ring;
  $Y_1$ and $Y_2$ together with the N atom to which they are attached form morpholinyl, tetrahydropyrrolyl, piperidinyl, oxazepanyl, oxa-azaspiroheptyl, oxazolyl-azaspirononyl, oxo-oxa-azabicycloheptanyl, difluoropiperidinyl, hydroxypiperidinyl, methoxypiperidinyl, hydroxyazacyclobutyl, methoxyazacyclobutyl, difluoroazacyclobutyl, difluoropyrrolidyl, methylmorpholinyl, dimethylmorpholinyl or methyl-oxo-piperazinyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
  when $Y_1$, $Y_2$ are connected together to form a ring;
  $Y_1$, $Y_2$ together with the N atom to which they are attached form 4,4-difluoropiperidinyl, morpholinyl, 2-oxa-6-azaspiro[3,3]heptyl, 3-hydroxyazacyclobutyl, 3-methoxyazacyclobutyl, (1S,4S)-3-oxo-2-oxa-5-azabicyclo[2.2.1]heptan-5-yl, 2,6-dimethylmorpholinyl, 4-hydroxypiperidinyl, 3,3-difluoroazacyclobutyl, 3-methylmorpholinyl, tetrahydropyrrolyl, piperidinyl, 3,3-difluoropyrrolidyl, 1-methyl-2-oxo-piperazinyl, 2-methylmorpholinyl, 1,4-oxazepanyl, 2-oxazolyl-7-azaspiro[3.5]nonyl or 4-methoxypiperidinyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
  Z is 5 or 6 membered heteroaromatic ring containing 1, 2 or 3 heteroatoms independently selected from O, N and S, the heteroaromatic ring is substituted by $R_1$;
  $R_1$ is $C_{1-6}$ alkoxyl $C_{1-6}$ alkyl;
  A is 6 membered heteroarylene containing 1, 2 or 3 N atoms;
  Y is —$NY_1Y_2$ or hydroxyl;
  $Y_1$ is H, $C_{1-6}$ alkyl, or, $C_{1-6}$ alkyl substituted by 1-5 $C_{1-6}$ alkoxyl groups;
  $Y_2$ is H, $C_{1-6}$ alkyl, cycloalkyl, $C_{4-6}$ bridged cycloalkyl, or, heterocycloalkyl, each of which is optionally substituted by 1-5 substituents independently selected from the group consisting of cyano, halogen, $C_{1-6}$ alkoxyl, halogenated-$C_{1-6}$ alkoxyl, hydroxyl, cyclopropyl, 4 membered heterocycloalkyl containing 1-3 heteroatoms selected from N, O or S, $C_4$-$C_6$ heterocycloalkyl containing 1-3 heteroatoms selected from N, O or S, 4 membered heterocycloalkyl containing 1-3 heteroatoms selected from N, O or S and substituted by methyl, $C_4$-$C_6$ heterocycloalkyl containing 1-3 heteroatoms selected from N, O or S and substituted by methyl, and, acyl;
  or, $Y_1$ and $Y_2$ together with the N atom to which they are attached form 4-7 membered heterocycloalkyl, 6-9 membered spirocyclic group or 6-9 membered bridged cyclic group, or the 4-7 membered heterocycloalkyl, 6-9 membered spirocyclic group or 6-9 membered bridged cyclic group contains 0 or 1 heteroatom selected from O and N besides the N atom, each of which is optionally substituted by 1-4 substituents independently selected from the group consisting of halogen, cyano, hydroxyl, oxo, $C_1$-$C_6$ alkyl and $C_1$-$C_6$ alkoxyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

Z is 5 or 6 membered heteroaromatic ring containing 1, 2 or 3 heteroatoms independently selected from O, N and S, the heteroaromatic ring is substituted by $R_1$;

$R_1$ is $C_{1-6}$ alkoxyl $C_{1-6}$ alkyl;

A is 6 membered heteroarylene containing 1, 2 or 3 N atoms;

Y is —$NY_1Y_2$ or hydroxyl;

$Y_1$ is H, $C_{1-6}$ alkyl, or, $C_{1-6}$ alkyl substituted by 1-5 $C_{1-6}$ alkoxyl groups;

$Y_2$ is a group as defined in (1), (2), (3) or (4):

(1) H, $C_{1-6}$ alkyl, cycloalkyl, $C_{4-6}$ bridged cycloalkyl, or, heterocycloalkyl;

(2) $C_{1-6}$ alkyl substituted by 1-5 substituents independently selected from the group consisting of cyano, halogen, hydroxyl, cyclopropyl, $C_{1-6}$ alkoxyl, halogenated-$C_{1-6}$ alkoxyl, 4 membered heterocycloalkyl containing 1-3 heteroatoms selected from N, O or S, $C_4$-$C_6$ heterocycloalkyl containing 1-3 heteroatoms selected from N, O or S, 4 membered heterocycloalkyl containing 1-3 heteroatoms selected from N, O or S and substituted by methyl, and, $C_4$-$C_6$ heterocycloalkyl containing 1-3 heteroatoms selected from N, O or S substituted by methyl;

(3) cycloalkyl substituted by 1-5 substituents independently selected from the group consisting of cyano and halogen;

(4) heterocycloalkyl substituted by 1-5 substituents independently selected from acyl;

or, $Y_1$, $Y_2$ together with the N atom to which they are attached form a group as defined in (a) or (b):

(a) 4-7 membered heterocycloalkyl, 6-9 membered spirocyclic group or 6-9 membered bridged cyclic group containing 0 or 1 heteroatom selected from O and N besides the N atom;

(b) 4-7 membered heterocycloalkyl containing 0 or 1 heteroatom selected from O and N besides the N atom, which is substituted by 1-4 substituents selected from the group consisting of halogen, cyano, hydroxyl, oxo, $C_1$-$C_6$ alkyl and $C_1$-$C_6$ alkoxyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

Z is a 5 or 6 membered heteroaromatic ring containing 1, 2 or 3 heteroatoms independently selected from O, N and S, the heteroaromatic ring is substituted by $R_1$;

$R_1$ is $C_{1-6}$ alkoxyl $C_{1-6}$ alkyl;

A is 6 membered heteroarylene containing 1, 2 or 3 N atoms;

Y is —$NY_1Y_2$;

$Y_1$ is H, $C_{1-6}$ alkyl, or, $C_{1-6}$ alkyl substituted by 1-5 $C_{1-6}$ alkoxyl groups;

$Y_2$ is a group as defined in (1), (2) or (4):

(1) $C_{1-6}$ alkyl, cycloalkyl (for example, $C_3$-$C_6$ cycloalkyl), $C_{4-6}$ bridged cycloalkyl, or, heterocycloalkyl (2) $C_{1-6}$ alkyl substituted by 1-2 substituents independently selected from the group consisting of cyano, hydroxyl, cyclopropyl, $C_{1-6}$ alkoxyl, 4 membered heterocycloalkyl containing 1-3 heteroatoms selected from N, O or S, $C_4$-$C_6$ heterocycloalkyl containing 1-3 heteroatoms selected from N, O or S, 4 membered heterocycloalkyl containing 1-3 heteroatoms selected from N, O or S and substituted by methyl, and, $C_4$-$C_6$ heterocycloalkyl containing 1-3 heteroatoms selected from N, O or S and substituted by methyl;

(4) heterocycloalkyl substituted by 1-5 (for example, 1-2) substituents independently selected from acyl;

or, $Y_1$ and $Y_2$ together with the N atom to which they are attached form a group as defined in (a) or (b):

(a) 4-7 membered heterocycloalkyl, 6-9 membered spirocyclic group or 6-9 membered bridged cyclic group, which contains 0 or 1 heteroatom selected from O and N besides the N atom;

(b) 4-7 membered heterocycloalkyl containing 0 or 1 heteroatom selected from O and N besides the N atom, which is substituted by 1-4 substituents selected from the group consisting of oxo, hydroxyl, $C_1$-$C_6$ alkoxyl, halogen and $C_1$-$C_6$ alkyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

Z is a 5 or 6 membered heteroaromatic ring containing 1, 2 or 3 heteroatoms independently selected from O, N and S, the heteroaromatic ring is substituted by $R_1$;

$R_1$ is $C_{1-6}$ alkoxyl $C_{1-6}$ alkyl;

A is 6 membered heteroarylene containing 1, 2 or 3 N atoms;

Y is —$NY_1Y_2$;

$Y_1$ is H, or, $C_{1-6}$ alkyl substituted by 1-5 $C_{1-6}$ alkoxyl groups;

$Y_2$ is a group as defined in (1), (2), or (4):

(1) heterocycloalkyl;

(2) $C_{1-6}$ alkyl substituted by 1 substituent independently selected from the group consisting of hydroxyl, $C_{1-6}$ alkoxyl, cyclopropyl, 4 membered heterocycloalkyl containing 1-3 heteroatoms selected from N, O or S, $C_4$-$C_6$ heterocycloalkyl containing 1-3 heteroatoms selected from N, O or S, 4 membered heterocycloalkyl containing 1-3 heteroatoms selected from N, O or S and substituted by methyl, and, $C_4$-$C_6$ heterocycloalkyl containing 1-3 heteroatoms selected from N, O or S and substituted by methyl;

(4) heterocycloalkyl substituted by 1-5 substituents independently selected from acyl;

or, $Y_1$ and $Y_2$ together with the N atom to which they are attached form a group as defined in (a) or (b):

(a) 4-7 membered heterocycloalkyl, 6-9 membered spirocyclic group or 6-9 membered bridged cyclic group containing 0 or 1 heteroatom selected from O and N in addition to N atom;

(b) 4-7 membered heterocycloalkyl containing 0 or 1 heteroatom selected from O and N besides the N atom, which is substituted by 1-4 substituents selected from the group consisting of oxo and $C_1$-$C_6$ alkyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

Z is a 5 or 6 membered heteroaromatic ring containing 1, 2 or 3 heteroatoms independently selected from O, N and S, the heteroaromatic ring is substituted by $R_1$;

$R_1$ is $C_{1-6}$ alkoxyl $C_{1-6}$ alkyl;

A is 6 membered heteroarylene containing 1, 2 or 3 N atoms;

Y is —$NY_1Y_2$;

$Y_1$ is H, or, $C_{1-6}$ alkyl substituted by 1-5 $C_{1-6}$ alkoxyl groups;

Y₂ is C₁₋₆ alkyl substituted by 1 substituent independently selected from the group consisting of hydroxyl, cyclopropyl and C₁₋₆ alkoxyl;

or, Y₁ and Y₂ together with the N atom to which they are attached form a group as defined in (a) or (b):
(a) 6-9 membered bridged cyclic group containing 0 or 1 heteroatom selected from O and N besides the N atom;
(b) 4-7 membered heterocycloalkyl containing 0 or 1 heteroatom selected from O and N besides the N atom, which is substituted by 1-4 substituents selected from the group consisting of oxo and $C_1$-$C_6$ alkyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

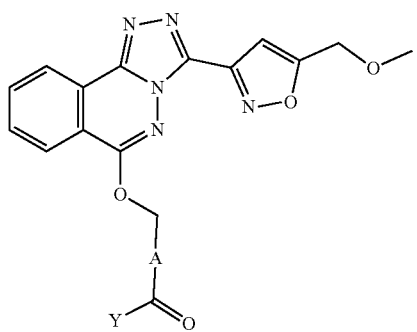

II wherein,
A is pyridyl;
Y is —NY₁Y₂;
Y₁ is H, methyl, or, methoxymethyl;
Y₂ is a group as defined in (1), (2), or (4):
(1) C₁₋₆ alkyl, C₃-C₆ cycloalkyl, C₄₋₆ bridged cycloalkyl, or, heterocycloalkyl;
(2) C₁₋₆ alkyl substituted by 1-2 substituents independently selected from the group consisting of cyano, cyclopropyl, hydroxyl, C₁₋₆ alkoxyl, 4 membered heterocycloalkyl containing 1-3 heteroatoms selected from N, O or S, C₄-C₆ heterocycloalkyl containing 1 heteroatom selected from N or O, 4 membered heterocycloalkyl containing 1-3 heteroatoms selected from N, O or S and substituted by methyl, and, C₄-C₆ heterocycloalkyl containing 1 heteroatom selected from N or O and substituted by methyl;
(4) heterocycloalkyl containing N and substituted by acyl;
or, Y₁ and Y₂ together with the N atom to which they are attached form a group as defined in (a) or (b):
(a) 4-7 membered heterocycloalkyl, 6-9 membered spirocyclic group or 6-9 membered bridged cyclic group, which contains 0 or 1 heteroatom selected from O and N besides the N atom;
(b) 4-7 membered heterocycloalkyl containing 0 or 1 heteroatom selected from O and N besides the N atom, which is substituted by 1-4 substituents selected from the group consisting of oxo, hydroxyl, C alkoxyl and $C_1$-$C_6$ alkyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
Z is a 5 membered heteroaromatic ring containing 1, 2 or 3 heteroatoms independently selected from O, N and S, the heteroaromatic ring is substituted by R₁;
R₁ is C₁₋₆ alkoxyl C₁₋₆ alkyl;
A is 6 membered heteroarylene containing 1, 2 or 3 N atoms;
Y is —NY₁Y₂;
Y₁ is H or C₁₋₆ alkyl;
Y₂ is C₁₋₆ alkyl, cycloalkyl, C₄₋₆ bridged cycloalkyl, or heterocycloalkyl, each of which is optionally substituted by 1-5 (for example, 1 or 2) substituents independently selected from the group consisting of cyano, halogen, C₁₋₆ alkoxyl, cyclopropyl, C₄-C₆ heterocycloalkyl containing 1-3 heteroatoms selected from N, O or S, C₄-C₆ heterocycloalkyl containing 1-3 heteroatoms selected from N, O or S and substituted by methyl, and, acyl;
or, Y₁ and Y₂ together with the N atom to which they are attached form 4-7 membered heterocycloalkyl, or the 4-7 membered heterocycloalkyl contains 0 or 1 heteroatom selected from O and N besides the N atom, each of which is optionally substituted by 1-4 substituents independently selected from the group consisting of halogen, hydroxyl, $C_1$-$C_6$ alkyl and $C_1$-$C_6$ alkoxyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):
Z is a 5 membered heteroaromatic ring containing 1 or 2 heteroatoms independently selected from O and N, the heteroaromatic ring is substituted by R₁;
R₁ is C₁₋₆ alkoxyl C₁₋₆ alkyl;
A is 6 membered heteroarylene containing 1 or 2 N atoms;
Y is —NY₁Y₂;
Y₁ is H or C₁₋₆ alkyl;
Y₂ is C₄₋₆ bridged cycloalkyl, C₁₋₆ alkyl, or, C₁₋₆ alkyl substituted by 1-5 (for example, 1 or 2) substituents independently selected from the group consisting of cyano, C₁₋₆ alkoxyl, cyclopropyl, C₄-C₆ heterocycloalkyl containing 1-3 heteroatoms selected from N, O or S, and C₄-C₆ heterocycloalkyl containing 1-3 heteroatoms selected from N, O or S and substituted by methyl;
cycloalkyl, or, cycloalkyl substituted by 1-5 (for example, 1 or 2) substituents independently selected from halogen;
heterocycloalkyl, or, heterocycloalkyl substituted by 1-5 (for example, 1 or 2) substituents independently selected from acyl;
or, Y₁ and Y₂ together with the N atom to which they are attached form 4-7 membered heterocycloalkyl, or the 4-7 membered heterocycloalkyl contains 0 or 1 heteroatom selected from O and N besides the N atom, each of which is optionally substituted by 1-4 substituents independently selected from the group consisting of halogen, hydroxyl, $C_1$-$C_6$ alkyl and $C_1$-$C_6$ alkoxyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

wherein, Z is a 5 or 6 membered heteroaromatic ring containing 1, 2 or 3 heteroatoms independently selected from O, N and S, the heteroaromatic ring is substituted by $R_1$;

$R_1$ is $C_{1-6}$ alkoxyl $C_{1-6}$ alkyl, $C_{1-6}$ alkoxyl substituted by halogen, $C_{3-6}$ cycloalkyl ($C_{1-6}$) alkoxyl, $C_{3-6}$ cycloalkyl ($C_{1-6}$) alkoxyl $C_{1-6}$ alkyl, $C_{3-6}$ heterocycloalkyl, $C_{3-6}$ heterocycloalkyl ($C_{1-6}$) alkyl, $C_{3-6}$ heterocycloalkyloxy ($C_{1-6}$) alkyl, $C_{3-6}$ heterocycloalkyl ($C_{1-6}$) alkoxyl $C_{1-6}$ alkyl, or, $C_{1-6}$ alkyl NH($C_{1-6}$) alkyl, each of which is optionally substituted by 1-4 substituents independently selected from the group consisting of halogen, cyano, hydroxyl, oxo and $C_1$-$C_6$ alkyl;

A is —$NR_2$—, or A is 5 membered heteroarylene containing 1, 2, 3 or 4 heteroatoms independently selected from O, N and S with at most one of the heteroatoms being O or S, or A is 6 membered heteroarylene containing 1, 2 or 3 N atoms, or the 5 or 6 membered heteroarylene is optionally fused to a benzene ring or a pyridine ring, the 5 or 6 membered heteroarylene is optionally substituted by $R_x$ and/or $R_y$ and/or $R_z$, wherein $R_x$ is halogen, —$R_1$, —$OR_1$, —$OC(O)R_1$, —$C(O)OR_1$, —$NR_2R_3$, —$NR_2C(O)R_3$, —OH, —CN, $R_y$ is halogen, —$R_1$, —$OR_1$, —$OC(O)R_1$, —$NR_2R_3$, —$NR_2C(O)R_3$, or CN, $R_z$ is —$R_1$, —$OR_1$ or —$OC(O)R_1$, provided that when A is a pyridine derivative, the pyridine ring is optionally in the form of N-oxide, or A is phenylene optionally substituted by 1, 2 or 3 substitutes independently selected from the group consisting of halogen, cyano, $C_{1-6}$ alkyl, $C_{2-6}$ linear alkenyl, $C_{2-6}$ alkynyl and $C_{3-6}$ cycloalkyl;

Y is —$NY_1Y_2$, —NH—$NY_3Y_4$ or hydroxyl;

$Y_1$ is H, $C_{1-6}$ alkyl, or, $C_{1-6}$ alkyl substituted by 1-5 substituents, the substituent is independently selected from the group consisting of amino, halogen, halogenated-$C_{1-6}$ alkoxyl, hydroxyl, $C_{1-6}$ alkoxyl, ($C_{1-6}$ alkyl, $C_{1-6}$ alkyl)N—, ($C_{1-6}$ alkyl, H)N—, nitro and $C_{1-6}$ alkyl-$S(O)_2$—;

$Y_2$ is H, amino, $C_{1-6}$ alkyl, $C_{1-6}$ alkoxyl, cycloalkyl, $C_{4-6}$ bridged cycloalkyl, heterocycloalkyl, $C_{1-6}$ alkyl-$S(O)_2$—, NH—$S(O)_2$ or heterocycloaryl, each of which is optionally substituted by 1-5 substituents independently selected from the group consisting of cyano, halogen, halogenated-$C_{1-6}$ alkyl, $C_{1-6}$ alkoxyl, halogenated-$C_{1-6}$ alkoxyl, carboxylic acid-$C_{1-6}$ alkyl, carboxylic $C_{1-4}$ ester-$C_{1-6}$ alkyl, hydroxyl, hydroxyl-$C_{1-6}$ alkyl, $C_{1-6}$ alkoxyl-$C_{1-6}$ alkyl, $C_{1-6}$ alkyl, ($C_{1-6}$ alkyl, $C_{1-6}$ alkyl)N—, ($C_{1-6}$ alkyl, H)N—, nitro, $C_{1-6}$ alkyl-$S(O)_2$—, $C_{4-6}$ cycloalkyl, $C_{3-6}$ cycloalkyl substituted by hydroxyl, $C_4$-$C_6$ heterocycloalkyl containing 1-3 heteroatoms selected from N, O or S, $C_4$-$C_6$ heterocycloalkyl containing 1-3 heteroatoms selected from N, O or S and substituted by methyl, $C_4$-$C_6$ heterocycloalkyl containing 1-3 heteroatoms selected from N, O or S and substituted by halogen, $C_4$-$C_6$ heterocycloalkyl containing 1-3 heteroatoms selected from N, O or S and substituted by methoxyl, acyl and acylamino;

or, $Y_1$ and $Y_2$ together with the N atom to which they are attached form 4-7 membered heterocycloalkyl, 4-7 membered heterocycloalkenyl, 6-9 membered spirocyclic group or 6-9 membered bridged cyclic group, or the 4-7 membered heterocycloalkyl, 4-7 membered heterocycloalkenyl, 6-9 membered spirocyclic group or 6-9 membered bridged cyclic group contains 0, 1 or more heteroatoms besides the N atom, each of which is optionally substituted by 1-4 substituents independently selected from the group consisting of halogen, cyano, hydroxyl, oxo, $C_1$-$C_6$ alkyl and $C_1$-$C_6$ alkoxyl;

each of $Y_3$ and $Y_4$ is independently selected from the group consisting of H, $C_1$-$C_6$ alkyl, $SO_2$—$C_1$-$C_6$ alkyl, cycloalkyl and heterocyclyl, or each of which is optionally substituted by 1-4 substituents independently selected from the group consisting of halogen, cyano, hydroxyl, $C_1$-$C_6$ alkyl and $C_1$-$C_6$ alkoxyl;

or, wherein $Y_3$ and $Y_4$ together with the N atom to which they are attached form heterocyclyl, or the heterocyclyl is optionally substituted by 1-4 substituents independently selected from the group consisting of halogen, cyano, hydroxyl, oxo, $C_1$-$C_6$ alkyl and $C_1$-$C_6$ alkoxyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

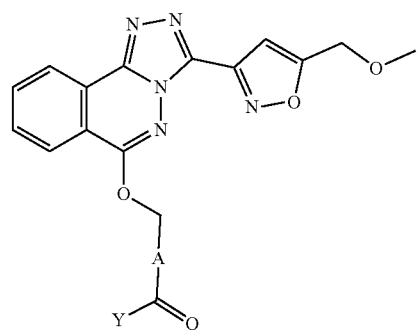

II wherein,
A is 5 membered heteroarylene containing 1, 2 or 3 heteroatoms independently selected from O, N and S with at most one of the heteroatoms being O or S, or 6 membered heteroarylene containing 1, 2 or 3 N atoms or phenylene, the 5 membered heteroarylene, 6 membered heteroarylene and phenylene are optionally substituted by the substituent selected from the group consisting of halogen, cyano and $C_{1-6}$ alkyl;

A is preferably pyridyl;

Y is —$NY_1Y_2$, —NH—$NY_3Y_4$ or hydroxyl;

Y is preferably $NY_1Y_2$ or hydroxyl;

$Y_1$ is H, $C_{1-6}$ alkyl or $C_{1-6}$ alkyl substituted by 1-5 substituents, wherein the substituent is independently selected from the group consisting of amino, halogen, cyano, hydroxyl, $C_{1-6}$ alkoxyl, $C_{1-6}$ halogenated alkoxyl, cycloalkyl, $C_4$-$C_6$ heterocycloalkyl containing 1-3 O atoms, ($C_{1-6}$ alkyl, $C_{1-6}$ alkyl)N—, ($C_{1-6}$ alkyl, H)N— and $C_{1-6}$ alkyl-$S(O)_2$—;

$Y_1$ is preferably H, $C_{1-6}$ alkyl or $C_{1-6}$ alkyl substituted by 1-5 substituents, the substituent is independently selected from the group consisting of hydroxyl, $C_{1-6}$ alkoxyl and $C_{1-6}$ halogenated alkoxyl;

$Y_1$ is more preferably H, $C_{1-6}$ alkyl, or, $C_{1-6}$ alkyl substituted by $C_{1-6}$ alkoxyl;

$Y_1$ is more preferably H, methyl or methoxyethyl;

$Y_1$ is more preferably H, methyl or 2-methoxyethyl;

$Y_2$ is $C_{1-6}$ alkyl, $C_{4-6}$ bridged cycloalkyl or $C_{1-6}$ alkyl substituted by 1-5 substituents, wherein the substituent is independently selected from the group consisting of halogen, cyano, amino, hydroxyl, $C_{1-6}$ alkoxyl, cycloalkyl, $C_4$-$C_6$ heterocycloalkyl containing 1-3 heteroatoms selected from N, O or S, ($C_{1-6}$ alkyl, $C_{1-6}$ alkyl)N—, ($C_{1-6}$ alkyl, H)N— and $C_{1-6}$ alkyl-S(O)$_2$—;

$C_5$-$C_6$ heteroaryl containing 1-3 heteroatoms selected from N, O or S, or $C_5$-$C_6$ heteroaryl containing 1-3 heteroatoms selected from N, O or S and substituted by $C_{1-6}$ alkyl;

$C_{3-6}$ cycloalkyl, or $C_{3-6}$ cycloalkyl substituted by 1-4 substituents, wherein the substituent is independently selected from the group consisting of halogen, cyano, amino, hydroxyl, hydroxyl $C_{1-6}$ alkyl, $C_{1-6}$ alkoxyl, $C_{1-6}$ alkoxyl $C_{1-6}$ alkyl, $C_{1-6}$ alkyl, ($C_{1-6}$ alkyl, $C_1$-6 alkyl)N—, ($C_{1-6}$ alkyl, H)N— and $C_{1-6}$ alkyl-S(O)$_2$—;

$C_4$-$C_6$ heterocycloalkyl containing 1-3 heteroatoms selected from N, O or S, or $C_4$-$C_6$ heterocycloalkyl containing 1-3 heteroatoms selected from N, O or S and substituted by 1-4 substituents, wherein the substituent is independently selected from the group consisting of halogen, amino, hydroxyl, acyl, hydroxyl-$C_{1-6}$ alkyl, $C_{1-6}$ alkoxyl, $C_{1-6}$ alkoxyl-$C_{1-6}$ alkyl, $C_1$-6 alkyl and $C_{1-6}$ alkyl-S(O)$_2$—;

or, $Y_1$ and $Y_2$ together with the N atom to which they are attached form 4-7 membered heterocycloalkyl, 6-9 membered spirocyclic group or 6-9 membered bridged cyclic group, or the 4-7 membered heterocycloalkyl, 6-9 membered spirocyclic group or 6-9 membered bridged cyclic group contains 0, 1 or more heteroatoms besides the N atom, each of which is optionally substituted by 1-4 substituents independently selected from the group consisting of halogen, cyano, hydroxyl, oxo, $C_1$-$C_6$ alkyl and $C_1$-$C_6$ alkoxyl;

each of $Y_3$ and $Y_4$ is independently selected from the group consisting of H, $C_1$-$C_6$ alkyl, SO$_2$—$C_1$-$C_6$ alkyl; or, $Y_3$ and $Y_4$ together with the N atom to which they are attached form heterocyclyl, the heterocyclyl is selected from the group consisting of piperidinyl, morpholinyl, dioxo-thiomorpholinyl and oxo-thiomorpholinyl;

$Y_2$ is preferably H, $C_{1-6}$ alkyl, $C_{4-6}$ bridged cycloalkyl or $C_{1-6}$ alkyl substituted by 1-5 substituents, the substituent is independently selected from the group consisting of halogen, cyano, hydroxyl, $C_{1-6}$ alkoxyl, $C_{1-6}$ halogenated alkoxyl, cycloalkyl, $C_4$-$C_6$ heterocycloalkyl containing 1-3 O atoms, ($C_{1-6}$ alkyl, $C_{1-6}$ alkyl)N— and ($C_{1-6}$ alkyl, H)N—;

$C_{3-6}$ cycloalkyl, or, $C_{3-6}$ cycloalkyl substituted by 1-4 substituents, the substituent is independently selected from the group consisting of halogen, cyano, hydroxyl, hydroxyl $C_{1-6}$ alkyl, $C_{1-6}$ alkoxyl, $C_{1-6}$ alkoxyl $C_{1-6}$ alkyl, $C_{1-6}$ alkyl, ($C_{1-6}$ alkyl, $C_{1-6}$ alkyl)N— and ($C_{1-6}$ alkyl, H)N—;

$C_4$-$C_6$ heterocycloalkyl containing 1-3 heteroatoms selected from N, O or S, or $C_4$-$C_6$ heterocycloalkyl containing 1-3 heteroatoms selected from N, O or S and substituted by 1-4 substituents, wherein the substituent is independently selected from halogen, amino, hydroxyl, acyl, hydroxyl $C_{1-6}$ alkyl, $C_{1-6}$ alkoxyl, $C_{1-6}$ alkoxyl $C_{1-6}$ alkyl and $C_{1-6}$ alkyl;

or, $Y_1$ and $Y_2$ together with the N atom to which they are attached form 4-7 membered heterocycloalkyl, 6-9 membered spirocyclic group or 6-9 membered bridged cyclic group, or the 4-7 membered heterocycloalkyl, 6-9 membered spirocyclic group or 6-9 membered bridged cyclic group contains 0 or 1 heteroatom selected from O and N besides the N atom, each of which is optionally substituted by 1-4 substituents independently selected from the group consisting of halogen, cyano, hydroxyl, oxo, $C_1$-$C_6$ alkyl and $C_1$-$C_6$ alkoxyl;

$Y_2$ is more preferably H, $C_{1-6}$ alkyl, $C_{4-6}$ bridged cycloalkyl or $C_{1-6}$ alkyl substituted by 1-5 substituents, the substituent is independently selected from the group consisting of halogen, cyano, hydroxyl, $C_{1-6}$ alkyl, $C_{1-6}$ alkoxyl, cycloalkyl and $C_4$-$C_6$ heterocycloalkyl containing 1-3 O atoms;

$C_{3-6}$ cycloalkyl or $C_{3-6}$ cycloalkyl substituted by 1-4 substituents, the substituent is independently selected from the group consisting of halogen and cyano;

$C_4$-$C_6$ heterocycloalkyl containing 1-3 heteroatoms selected from N, O or S, or $C_4$-$C_6$ heterocycloalkyl containing 1-3 heteroatoms selected from N, O or S and substituted by acyl;

or, $Y_1$ and $Y_2$ together with the N atom to which they are attached form 4-7 membered heterocycloalkyl, 6-9 membered spirocyclic group or 6-9 membered bridged cyclic group, or the 4-7 membered heterocycloalkyl, 6-9 membered spirocyclic group or 6-9 membered bridged cyclic group contains 0 or 1 heteroatom selected from O and N besides the N atom, each of which is optionally substituted by 1-4 substituents independently selected from the group consisting of halogen, hydroxyl, oxo, $C_1$-$C_6$ alkyl and $C_1$-$C_6$ alkoxyl;

$Y_2$ is more preferably H, methyl, ethyl, isopropyl, bicyclopentyl, cyclopropylmethyl, oxacyclobutylmethyl, methyl(oxacyclobutyl)methyl, tetrahydrofurylmethylene, hydroxyethyl, methoxyethyl, trifluoromethoxyethyl, fluoroethyl, difluoroethyl, trifluoroethyl, methoxypropyl, dimethoxypropyl, cyanopropyl, difluorohydroxypropyl, trifluoropropyl, trifluoroisopropyl, methoxyisopropyl, cyclopropyl, cyclobutyl, cyanocyclopropyl, fluorocyclobutyl, difluorocyclobutyl, acetylazacyclobutyl, difluorocyclohexyl, difluorocyclopentyl, oxacyclobutyl, tetrahydropyranyl or tetrahydrofuranyl;

or, $Y_1$ and $Y_2$ together with the N atom to which they are attached form morpholinyl, tetrahydropyrrolyl, piperidinyl, oxazepanyl, oxa-azaspiroheptyl, oxazolyl-azaspirononyl, oxo-oxa-azabicycloheptanyl, difluoropiperidinyl, hydroxypiperidinyl, methoxypiperidinyl, hydroxyazacyclobutyl, methoxyazacyclobutyl, difluoroazacyclobutyl, difluoropyrrolidyl, methylmorpholinyl, dimethylmorpholinyl or methyl-oxo-piperazinyl;

$Y_2$ is more preferably ethyl, 3,3-difluorocyclobutyl, tetrahydro-2H-pyran-4-yl, 1-methoxyprop-2-yl, 3-methoxypropyl, 2-methoxyethyl, tetrahydrofuran-2-methylene, isopropyl, cyclopropyl, 2-trifluoromethoxyl ethyl, 1-methoxy-2-methylisoprop-2-yl, 2,2,2-trifluoroethyl, 2-hydroxyethyl, oxacyclobutyl-3-yl, oxacyclobutyl-3-methyl, 1-cyanocyclopropyl, 3-methyl(oxacyclobutyl)-methyl, 3-fluorocyclobutyl, 2-fluoroethyl, cyclobutyl, 2,2-difluoroethyl, 2,2-difluoro-3-hydroxypropyl, 3-tetrahydrofuranyl, 1,1,1-trifluoroisopropyl, 3-cyanopropyl, 1,1,1-trifluoropropyl, 1,3-dimethoxyprop-2-yl, bicyclo[1.1.1]pentan-1-yl, 1-acetyl-azetidin-3-yl, 4,4-difluorocyclohexyl, 3,3-difluoro-1-cyclopentylamino, H, methyl or cyclopropylmethyl;

or, $Y_1$, $Y_2$ together with the N atom to which they are attached form 4,4-difluoropiperidinyl, morpholinyl, 2-oxa-6-azaspiro[3,3]heptyl, 3-hydroxyazacyclobutyl, 3-methoxyazacyclobutyl, (1S,4S)-3-oxo-2-oxa-5-azabicyclo[2.2.1]heptan-5-yl, 2,6-dimethylmorpholinyl, 4-hydroxypiperidinyl, 3,3-difluoroazacyclobutyl, 3-methylmorpholinyl, tetrahydropyrrolyl, piperidinyl, 3,3-difluoropyrrolidyl, 1-methyl-2-oxo-piperazinyl, 2-methylmorpholinyl, 1,4-oxazepanyl, 2-oxazolyl-7-azaspiro[3.5]nonyl or 4-methoxypiperidinyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

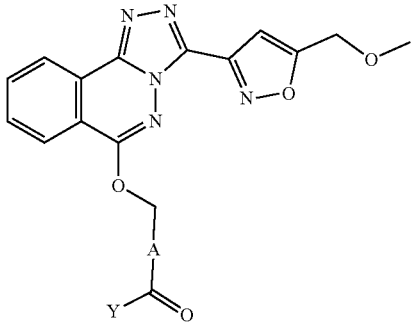

wherein,

A is pyridyl;

Y is —NY$_1$Y$_2$ or hydroxyl;

Y$_1$ is H, C$_{1-6}$ alkyl or C$_{1-6}$ alkyl substituted by 1-5 substituents, the substituent is independently selected from the group consisting of hydroxyl, C$_{1-6}$ alkoxyl and C$_{1-6}$ halogenated alkoxyl;

Y$_2$ is H, C$_{1-6}$ alkyl, C$_{4-6}$ bridged cycloalkyl or C$_{1-6}$ alkyl substituted by 1-5 substituents, the substituent is independently selected from the group consisting of halogen, cyano, hydroxyl, C$_{1-6}$ alkoxyl, C$_{1-6}$ halogenated alkoxyl, cycloalkyl, C$_4$-C$_6$ heterocycloalkyl containing 1-3 O atoms, (C$_{1-6}$ alkyl, C$_{1-6}$ alkyl)N— and (C$_{1-6}$ alkyl, H)N—;

C$_{3-6}$ cycloalkyl, or C$_{3-6}$ cycloalkyl substituted by 1-4 substituents, the substituent is independently selected from the group consisting of halogen, cyano, hydroxyl, hydroxyl C$_{1-6}$ alkyl, C$_{1-6}$ alkoxyl, C$_{1-6}$ alkoxyl C$_{1-6}$ alkyl, C$_{1-6}$ alkyl, (C$_{1-6}$ alkyl, C$_{1-6}$ alkyl)N— and (C$_{1-6}$ alkyl, H)N—;

C$_4$-C$_6$ heterocycloalkyl containing 1-3 heteroatoms selected from N, O or S, or, C$_4$-C$_6$ heterocycloalkyl containing 1-3 heteroatoms selected from N, O or S and substituted by 1-4 substituents, the substituent is independently selected from the group consisting of halogen, amino, hydroxyl, acyl, hydroxyl C$_{1-6}$ alkyl, C$_{1-6}$ alkoxyl, C$_{1-6}$ alkoxyl C$_{1-6}$ alkyl and C$_{1-6}$ alkyl;

or, Y$_1$, Y$_2$ together with the N atom to which they are attached form 4-7 membered heterocycloalkyl, 6-9 membered spirocyclic group or 6-9 membered bridged cyclic group, or the 4-7 membered heterocycloalkyl, 6-9 membered spirocyclic group or 6-9 membered bridged cyclic group contains 0 or 1 heteroatom selected from O and N besides the N atom, each of which is optionally substituted by 1-4 substituents independently selected from the group consisting of halogen, cyano, hydroxyl, oxo, C$_1$-C$_6$ alkyl and C$_1$-C$_6$ alkoxyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

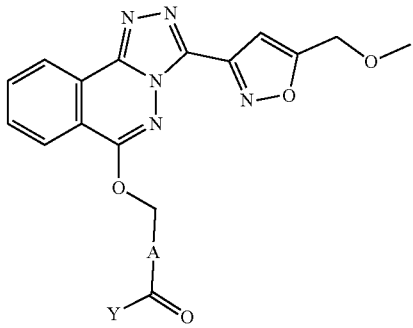

wherein,

A is pyridyl;

Y is —NY$_1$Y$_2$ or hydroxyl;

Y$_1$ is H, C$_{1-6}$ alkyl, or, C$_{1-6}$ alkyl substituted by C$_{1-6}$ alkoxyl;

Y$_2$ is H, C$_{1-6}$ alkyl, C$_{4-6}$ bridged cycloalkyl or C$_{1-6}$ alkyl substituted by 1-5 substituents, the substituent is independently selected from the group consisting of halogen, cyano, hydroxyl, C$_{1-6}$ alkyl, C$_{1-6}$ alkoxyl, cycloalkyl and C$_4$-C$_6$ heterocycloalkyl containing 1-3 O atoms;

C$_{3-6}$ cycloalkyl, or, C$_{3-6}$ cycloalkyl substituted by 1-4 substituents, wherein the substituent is independently selected from the group consisting of halogen and cyano;

C$_4$-C$_6$ heterocycloalkyl containing 1-3 heteroatoms selected from N, O or S, or, C$_4$-C$_6$ heterocycloalkyl containing 1-3 heteroatoms selected from N, O or S and substituted by acyl;

or, Y$_1$ and Y$_2$ together with the N atom to which they are attached form 4-7 membered heterocycloalkyl, 6-9 membered spirocyclic group or 6-9 membered bridged cyclic group, or the 4-7 membered heterocycloalkyl, 6-9 membered spirocyclic group or 6-9 membered bridged cyclic group contains 0 or 1 heteroatom selected from O and N besides the N atom, each of which is optionally substituted by 1-4 substituents independently selected from the group consisting of halogen, hydroxyl, oxo, C$_1$-C$_6$ alkyl and C$_1$-C$_6$ alkoxyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

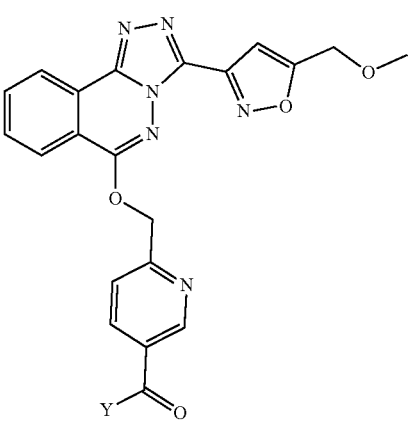

wherein,

Y is —NY$_1$Y$_2$ or hydroxyl;

Y$_1$ is H, methyl or methoxyethyl;

Y$_2$ is H, methyl, ethyl, isopropyl, bicyclopentyl, cyclopropylmethyl, oxacyclobutylmethyl, methyl(oxacyclobutyl)methyl, tetrahydrofurylmethylene, hydroxyethyl, methoxyethyl, trifluoromethoxyethyl, fluoroethyl, difluoroethyl, trifluoroethyl, methoxypropyl, dimethoxypropyl, cyanopropyl, difluorohydroxypropyl, trifluoropropyl, trifluoroisopropyl, methoxyisopropyl, cyclopropyl, cyclobutyl, cyanocyclopropyl, fluorocyclobutyl, difluorocyclobutyl, acetylazacyclobutyl, difluorocyclohexyl, difluorocyclopentyl, oxacyclobutyl, tetrahydropyranyl or tetrahydrofuranyl;

or, Y$_1$, Y$_2$ together with the N atom to which they are attached form morpholinyl, tetrahydropyrrolyl, piperidinyl, oxazepanyl, oxa-azaspiroheptyl, oxazolyl-azaspirononyl, oxo-oxa-azabicycloheptanyl, difluoropiperidinyl, hydroxypiperidinyl, methoxypiperidinyl, hydroxyazacyclobutyl, methoxyazacyclobutyl, difluoroazacyclobutyl, difluoropyrrolidyl, methylmorpholinyl, dimethylmorpholinyl or methyl-oxo-piperazinyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, some groups can be as defined below (unannotated definitions are as described in any one of the above embodiments):

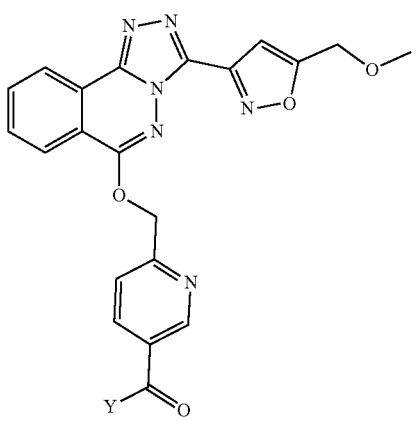

III wherein,

Y is —NY$_1$Y$_2$ or hydroxyl;

Y$_1$ is H, methyl or 2-methoxyethyl;

Y$_2$ is ethyl, 3,3-difluorocyclobutyl, tetrahydro-2H-pyran-4-yl, 1-methoxyprop-2-yl, 3-methoxypropyl, 2-methoxyethyl, tetrahydrofuran-2-methylene, isopropyl, cyclopropyl, 2-trifluoromethoxyethyl, 1-methoxy-2-methylisoprop-2-yl, 2,2,2-trifluoroethyl, 2-hydroxyethyl, oxacyclobutyl-3-yl, oxacyclobutyl-3-methyl, 1-cyanocyclopropyl, 3-methyl(oxacyclobutyl)-methyl, 3-fluorocyclobutyl, 2-fluoroethyl, cyclobutyl, 2,2-difluoroethyl, 2,2-difluoro-3-hydroxypropyl, 3-tetrahydrofuranyl, 1,1,1-trifluoroisopropyl, 3-cyanopropyl, 1,1,1-trifluoropropyl, 1,3-dimethoxyprop-2-yl, bicyclo[1.1.1]pentan-1-yl, 1-acetyl-azetidin-3-yl, 4,4-difluorocyclohexyl, 3,3-difluoro-1-cyclopentylamino, H, methyl or cyclopropylmethyl;

or Y$_1$, Y$_2$ together with the N atom to which they are attached form 4,4-difluoropiperidinyl, morpholinyl, 2-oxa-6-azaspiro[3,3]heptyl, 3-hydroxyazacyclobutyl, 3-methoxyazacyclobutyl, (1S,4S)-3-oxo-2-oxa-5-azabicyclo[2.2.1]heptan-5-yl, 2,6-dimethylmorpholinyl, 4-hydroxypiperidinyl, 3,3-difluoroazacyclobutyl, 3-methylmorpholinyl, tetrahydropyrrolyl, piperidinyl, 3,3-difluoropyrrolidyl, 1-methyl-2-oxo-piperazinyl, 2-methylmorpholinyl, 1,4-oxazepanyl, 2-oxazolyl-7-azaspiro[3.5]nonyl or 4-methoxypiperidinyl.

In an embodiment, in the compound I, cis-trans isomer thereof, enantiomer thereof, diastereomer thereof, racemate thereof, solvate thereof, hydrate thereof, pharmaceutically acceptable salt or prodrug thereof, the compound I is independently selected from:

| Compound No. | Structural formula | Chemical name |
|---|---|---|
| 01 | | 6-{3-[5-(methoxymethyl)isoxazol-3-yl]-[1,2,4]triazolo[3,4-a]phthalazin-6-oxy)methylene}nicotinic acid |

-continued

| Compound No. | Structural formula | Chemical name |
|---|---|---|
| 02 | 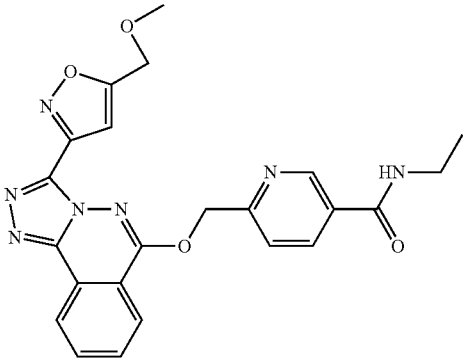 [SMILES: CCNC(=O)c1ccc(COc2nn3c(-c4cc(COC)on4)nnc3c3ccccc23)nc1] | N-ethyl-6-((3-(5-methoxymethylisoxazol-3-yl)-[1,2,4]triazolo[3,4-a]phthalazin-6-oxy)methylene)nicotinamide |
| 03 | 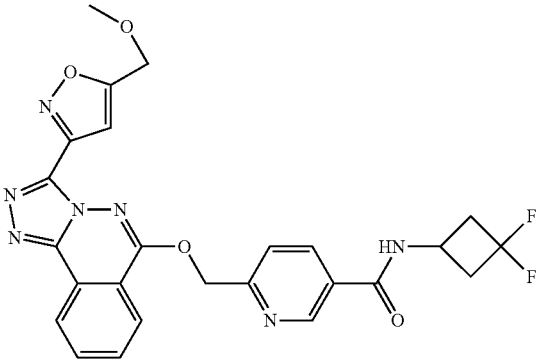 [SMILES: COCc1cc(-c2nnc3c4ccccc4c(OCc4ccc(C(=O)NC5CC(F)(F)C5)cn4)nn23)no1] | N-(3,3-difluorocyclobutyl)-6-((3-(5-methoxymethylisoxazol-3-yl)-[1,2,4]triazolo[3,4-a]phthalazin-6-oxy)methylene)nicotinamide |
| 04 | 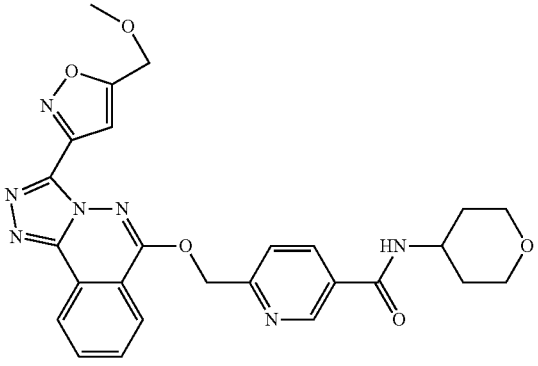 [SMILES: COCc1cc(-c2nnc3c4ccccc4c(OCc4ccc(C(=O)NC5CCOCC5)cn4)nn23)no1] | N-(tetrahydro-2H-pyran-4-yl)-6-((3-(5-methoxymethylisoxazol-3-yl)-[1,2,4]triazolo[3,4-a]phthalazin-6-oxy)methylene)nicotinamide |
| 05 | 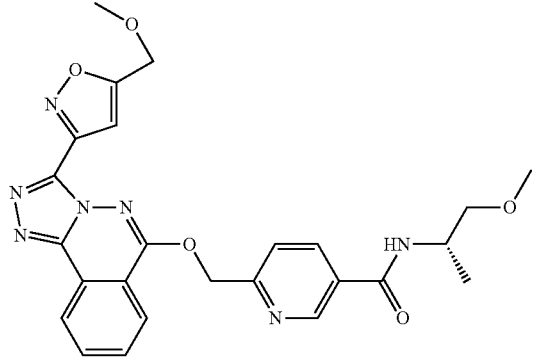 [SMILES: COCc1cc(-c2nnc3c4ccccc4c(OCc4ccc(C(=O)NC(C)COC)cn4)nn23)no1] | (S)-N-(1-methoxypropylamino)-6-((3-(5-methoxymethylisoxazol-3-yl)-[1,2,4]triazolo[3,4-a]phthalazin-6-oxy)methylene)nicotinamide |

-continued

| Compound No. | Structural formula | Chemical name |
|---|---|---|
| 06 | | (S)-N-(tetrahydrofuran-2-methylene)-6-((3-(5-methoxymethylisoxazol-3-yl)-[1,2,4]triazolo[3,4-a]phthalazin-6-oxy)methylene)nicotinamide |
| 07 | | N-(2-methoxyethylamino)-6-((3-(5-methoxymethylisoxazol-3-yl)-[1,2,4]triazolo[3,4-a]phthalazin-6-oxy)methylene)nicotinamide |
| 08 | | N-(3-methoxypropylamino)-6-((3-(5-methoxymethylisoxazol-3-yl)-[1,2,4]triazolo[3,4-a]phthalazin-6-oxy)methylene)nicotinamide |
| 09 | | (R)-N-(1-methoxyprop-2-yl)-6-((3-(5-methoxymethylisoxazol-3-yl)-[1,2,4]triazolo[3,4-a]phthalazin-6-oxy)methylene)nicotinamide |

-continued

| Compound No. | Structural formula | Chemical name |
|---|---|---|
| 10 | | N-((1-methoxyprop-2-yl)-6-((3-(5-methoxymethylisoxazol-3-yl)-[1,2,4]triazolo[3,4-a]phthalazin-6-oxy)methylene)nicotinamide |
| 11 | | N-(isopropylamino)-6-((3-(5-methoxymethylisoxazol-3-yl)-[1,2,4]triazolo[3,4-a]phthalazin-6-oxy)methylene)nicotinamide |
| 12 | | N-(cyclopropylamino)-6-((3-(5-methoxymethylisoxazol-3-yl)-[1,2,4]triazolo[3,4-a]phthalazin-6-oxy)methylene)nicotinamide |
| 13 | | N-(2-trifluoromethoxyethylamino)-6-((3-(5-methoxymethylisoxazol-3-yl)-[1,2,4]triazolo[3,4-a]phthalazin-6-oxy)methylene)nicotinamide |

-continued

| Compound No. | Structural formula | Chemical name |
|---|---|---|
| 14 | | N-(1-methoxy-2-methylisoprop-2-yl)-6-((3-(5-methoxymethylisoxazol-3-yl)-[1,2,4]triazolo[3,4-a]phthalazin-6-oxy)methylene)nicotinamide |
| 15 | | N-(2,2,2-trifluoroethyl)-6-((3-(5-methoxymethylisoxazol-3-yl)-[1,2,4]triazolo[3,4-a]phthalazin-6-oxy)methylene)nicotinamide |
| 16 | | N-(2-hydroxyethyl)-6-((3-(5-methoxymethylisoxazol-3-yl)-[1,2,4]triazolo[3,4-a]phthalazin-6-oxy)methylene)nicotinamide |
| 17 | | N-(oxacyclobutyl-3-yl)-6-{3-[5-(methoxymethyl)isoxazol-3-yl]-[1,2,4]triazolo[3,4-a]phthalazin-6-oxy)methylene}nicotinamide |

-continued

| Compound No. | Structural formula | Chemical name |
|---|---|---|
| 18 | | N-(oxacyclobutyl-3-methyl)-6-{3-[5-(methoxymethyl)isoxazol-3-yl]-[1,2,4]triazolo[3,4-a]phthalazin-6-oxy)methylene}nicotinamide |
| 19 | | N-(1-cyanocyclopropyl)-6-{3-[5-(methoxymethyl)isoxazol-3-yl]-[1,2,4]triazolo[3,4-a]phthalazin-6-oxy)methylene}nicotinamide |
| 20 | | N-((3-methyl(oxacyclobutyl)-methyl)-6-{3-[5-(methoxymethyl)isoxazol-3-yl]-[1,2,4]triazolo[3,4-a]phthalazin-6-oxy)methylene}nicotinamide |
| 21 | | N-(3-fluorocyclobutyl)-6-{3-[5-(methoxymethyl)isoxazol-3-yl]-[1,2,4]triazolo[3,4-a]phthalazin-6-oxy)methylene}nicotinamide |

-continued

| Compound No. | Structural formula | Chemical name |
|---|---|---|
| 22 | | N-(2-fluoroethyl)-6-{3-[5-(methoxymethyl)isoxazol-3-yl]-[1,2,4]triazolo[3,4-a]phthalazin-6-oxy)methylene}nicotinamide |
| 23 | | N-(cyclobutyl)-6-{3-[5-(methoxymethyl)isoxazol-3-yl]-[1,2,4]triazolo[3,4-a]phthalazin-6-oxy)methylene}nicotinamide |
| 24 | | N-(2,2-difluoroethyl)-6-{3-[5-(methoxymethyl)isoxazol-3-yl]-[1,2,4]triazolo[3,4-a]phthalazin-6-oxy)methylene}nicotinamide |
| 25 | | N-(2,2-difluoro-3-hydroxylpropyl)-6-{3-[5-(methoxymethyl)isoxazol-3-yl]-[1,2,4]triazolo[3,4-a]phthalazin-6-oxy)methylene}nicotinamide |

| Compound No. | Structural formula | Chemical name |
| --- | --- | --- |
| 26 | | N-(3-tetrahydrofuranyl)-6-{3-[5-(methoxymethyl)isoxazol-3-yl]-[1,2,4]triazolo[3,4-a]phthalazin-6-oxy)methylene}nicotinamide |
| 27 | | N-(1,1,1-trifluoroisopropyl)-6-{3-[5-(methoxymethyl)isoxazol-3-yl]-[1,2,4]triazolo[3,4-a]phthalazin-6-oxy)methylene}nicotinamide |
| 28 | | N-(2-cyano-ethyl)-6-[3-(5-methoxylmethyl-isoxazol-3-yl)-[1,2,4]triazolo[3,4-a]phthalazin-6-yloxymethyl]-nicotinamide |
| 29 | | N-(3,3,3-trifluoropropyl)-6-{3-[5-(methoxymethyl)isoxazol-3-yl]-[1,2,4]triazolo[3,4-a]phthalazin-6-oxy)methylene}nicotinamide |

| Compound No. | Structural formula | Chemical name |
|---|---|---|
| 30 | | N-(1,3-dimethoxyprop-2-yl)-6-{3-[5-(methoxymethyl)isoxazol-3-yl]-[1,2,4]triazolo[3,4-a]phthalazin-6-oxy)methylene}nicotinamide |
| 31 | | N-(bicyclo[1.1.1]pentan-1-yl)-6-{3-[5-(methoxymethyl)isoxazol-3-yl]-[1,2,4]triazolo[3,4-a]phthalazin-6-oxy)methylene}nicotinamide |
| 32 | | N-(1-acetyl-azetidin-3-yl)-6-{3-[5-(methoxymethyl)isoxazol-3-yl]-[1,2,4]triazolo[3,4-a]phthalazin-6-oxy)methylene}nicotinamide |
| 33 | | N-(4,4-difluorocyclohexyl)-6-{3-[5-(methoxymethyl)isoxazol-3-yl]-[1,2,4]triazolo[3,4-a]phthalazin-6-oxy)methylene}nicotinamide |

| Compound No. | Structural formula | Chemical name |
|---|---|---|
| 34 | | (4,4-difluoropiperidin-1-yl)(6-(((3-(5-methoxymethyl)isoxazol-3-yl)-[1,2,4]triazolo[3,4-a]phthalazin-6-yl)oxy)methylene)pyridin-3-yl)methanone |
| 35 | | N-(3,3-difluoro-1-cyclopentylamino)-6-{3-[5-(methoxymethyl)isoxazol-3-yl]-[1,2,4]triazolo[3,4-a]phthalazin-6-oxy)methylene}nicotinamide |
| 36 | | 6-{3-[5-(methoxymethyl)isoxazol-3-yl]-[1,2,4]triazolo[3,4-a]phthalazin-6-oxy)methylene}nicotinamide |
| 37 | | N,N-(dimethyl)-6-{3-[5(methoxymethyl)isoxazol-3-yl]-[1,2,4]triazolo[3,4-a]phthalazin-6-oxy)methylene}nicotinamide |

-continued

| Compound No. | Structural formula | Chemical name |
|---|---|---|
| 38 | | {6-[3-(5-methoxylmethyl-isoxazol-3-yl)-[1,2,4]triazolo[3,4-a]phthalazin-6-yloxymethyl]-pyridin-3-yl}-morpholin-4-methanone |
| 39 | | (2-oxa-6-azaspiro[3,3]heptyl)(6-(((3-(5-methoxymethyl)isoxazol-3-yl)-[1,2,4]triazolo[3,4-a]phthalazin-6-yl)oxy)methylene)pyridin-3-yl)methanone |
| 40 | | N-methyl-N-(cyclopropylmethyl)-6-{3-[5-(methoxymethyl)isoxazol-3-yl]-[1,2,4]triazolo[3,4-a]phthalazin-6-oxy)methylene}nicotinamide |
| 41 | | (3-hydroxyazacyclobutyl)(6-(((3-(5-methoxymethyl)isoxazol-3-yl)-[1,2,4]triazolo[3,4-a]phthalazin-6-yl)oxy)methylene)pyridin-3-yl)methanone |

-continued

| Compound No. | Structural formula | Chemical name |
|---|---|---|
| 42 | | (3-methoxyazacyclobutyl)(6-(((3-(5-methoxymethyl)isoxazol-3-yl)-[1,2,4]triazolo[3,4-a]phthalazin-6-yl)oxy)methylene)pyridin-3-yl)methanone |
| 43 | | ((1S,4S)-3-oxo-2-oxa-5-azabicyclo[2.2.1]heptan-5-yl)(6-(((3-(5-methoxymethyl)isoxazol-3-yl)-[1,2,4]triazolo[3,4-a]phthalazin-6-yl)oxy)methylene)pyridin-3-yl)methanone |
| 44 | | (2,6-dimethylmorpholinyl)(6-(((3-(5-methoxymethyl)isoxazol-3-yl)-[1,2,4]triazolo[3,4-a]phthalazin-6-yl)oxy)methylene)pyridin-3-yl)methanone |
| 45 | | (4-hydroxypiperidin-1-yl)-6-{3-[5-(methoxymethyl)isoxazol-3-yl]-[1,2,4]triazolo[3,4-a]phthalazin-6-oxymethylene}pyridin-3-ylmethanone |

| Compound No. | Structural formula | Chemical name |
|---|---|---|
| 46 | | (3,3-difluoroazacyclobutyl)(6-(((3-(5-methoxymethyl)isoxazol-3-yl)-[1,2,4]triazolo[3,4-a]phthalazin-6-yl)oxy)methylene)pyridin-3-yl)methanone |
| 47 | | (3-methylmorpholinyl)(6-(((3-(5-methoxymethyl)isoxazol-3-yl)-[1,2,4]triazolo[3,4-a]phthalazin-6-yl)oxy)methylene)pyridin-3-yl)methanone |
| 48 | | (tetrahydropyrrolyl)(6-(((3-(5-methoxymethyl)isoxazol-3-yl)-[1,2,4]triazolo[3,4-a]phthalazin-6-yl)oxy)methylene)pyridin-3-yl)methanone |
| 49 | | (6-(((3-(5-(methoxymethyl)isoxazol-3-yl)-[1,2,4]triazolo[3,4-a]phthalazin-6-yl)oxy)methyl)pyridin-3-yl)(piperidin-1-yl)methanone |

-continued

| Compound No. | Structural formula | Chemical name |
| --- | --- | --- |
| 50 | | N-methyl-N-(cyclopropyl)-6-{3-[5-(methoxymethyl)isoxazol-3-yl]-[1,2,4]triazolo[3,4-a]phthalazin-6-oxy)methylene}nicotinamide |
| 51 | | (3,3-difluoropyrrolidyl)-6-{3-[5-(methoxymethyl)isoxazol-3-yl]-[1,2,4]triazolo[3,4-a]phthalazin-6-oxy)methylenepyridin-3-yl)methanone |
| 52 | | N,N-(di(2-methoxylethyl))-6-{3-[5-(methoxymethyl)isoxazol-3-yl]-[1,2,4]triazolo[3,4-a]phthalazin-6-oxy)methylene}nicotinamide |
| 53 | | (1-methyl-2-oxo-piperanzinyl)(6-(((3-(5-methoxymethyl)isoxazol-3-yl)-[1,2,4]triazolo[3,4-a]phthalazin-6-yl)oxy)methylene)pyridin-3-yl)methanone |

-continued

| Compound No. | Structural formula | Chemical name |
|---|---|---|
| 54 | | (2-methylmorpholinyl)(6-(((3-(5-methoxymethyl)isoxazol-3-yl)-[1,2,4]triazolo[3,4-a]phthalazin-6-yl)oxy)methylene)pyridin-3-yl)methanone |
| 55 | | (1,4-oxazepanyl)(6-(((3-(5-methoxymethyl)isoxazol-3-yl)-[1,2,4]triazolo[3,4-a]phthalazin-6-yl)oxy)methylene)pyridin-3-yl)methanone |
| 56 | | (6-[3-(5-methoxymethyl-isoxazol-3-yl)-[1,2,4]triazolo[3,4-a]phthalazin-6-yl)oxymethyl]-pyridin-3-yl}-(2-oxa-7-aza-spiro[3.5]non-7-yl)-methanone |
| 57 | | (6-(((3-(5-(methoxymethyl)isoxazol-3-yl)-[1,2,4]triazolo[3,4-a]phthalazin-6-yl)oxo)methyl)pyridin-3-yl)(4-methoxypiperidin-1-yl)methanone |

-continued
| Compound No. | Structural formula | Chemical name |
|---|---|---|
| 58 | 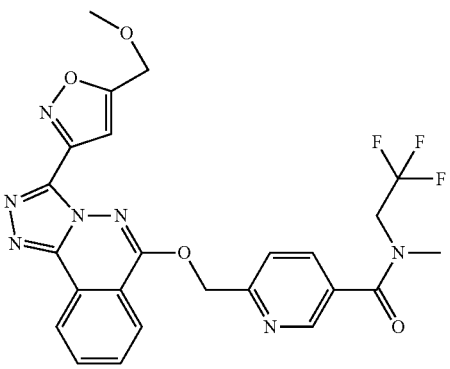 [SMILES: COCc1cc(-c2nnc3c4ccccc4c(OCc4ccc(C(=O)N(C)CC(F)(F)F)cn4)nn23)no1] | N-methyl-N-(2,2,2-trifluoroethyl)-6-{3-[5-(methoxymethyl)isoxazol-3-yl]-[1,2,4]triazolo[3,4-a]phthalazin-6-oxy)methylene}nicotinamide |
| 59 | 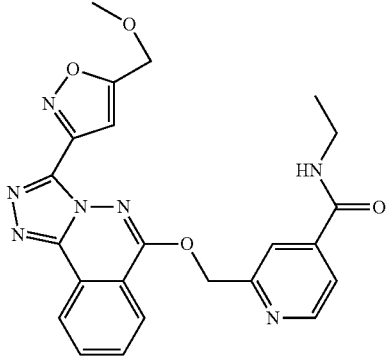 [SMILES: CCNC(=O)c1ccnc(COc2nn3c(-c4cc(COC)on4)nnc3c3ccccc23)c1] | N-ethyl-6-((3-(5-methoxymethylisoxazol-3-yl)-[1,2,4]triazolo[3,4-a]phthalazin-6-oxy)methylene)isonicotinamide |
| 60 | 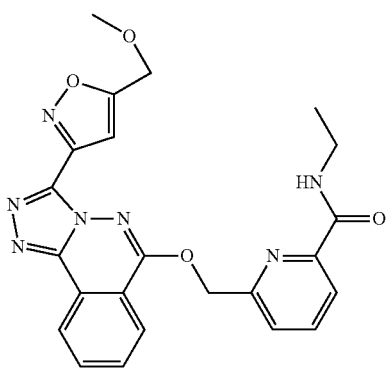 [SMILES: CCNC(=O)c1cccc(COc2nn3c(-c4cc(COC)on4)nnc3c3ccccc23)n1] | N-ethyl-6-((3-(5-methoxymethylisoxazol-3-yl)-[1,2,4]triazolo[3,4-a]phthalazin-6-oxy)methylene)picolinamide |

The present disclosure also provides a method for preparing the compound represented by formula (II) or (III), wherein the method comprises:

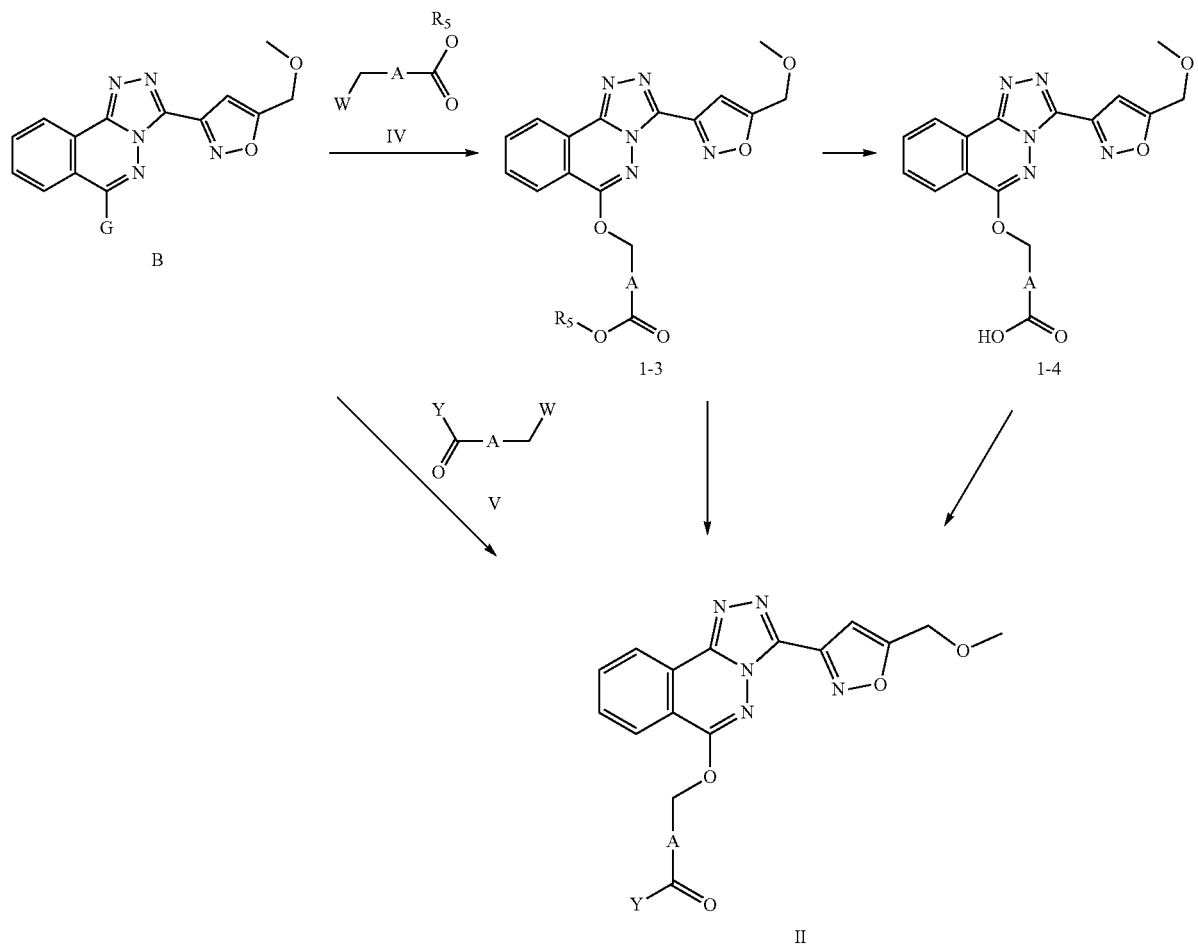

a) reacting a compound represented by formula B

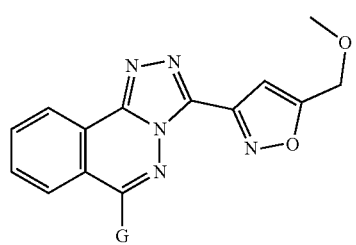

with a compound represented by formula IV

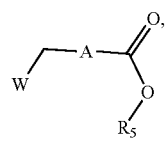

wherein G and W are optionally selected from Cl, Br, I, OH, OTs, OTf, OMs, etc., $R_5$ is alkyl (for example, $C_1$-$C_6$ alkyl, for another example, methyl, ethyl or tert-butyl) or benzyl, followed by reacting the compound represented by formula (1-3)

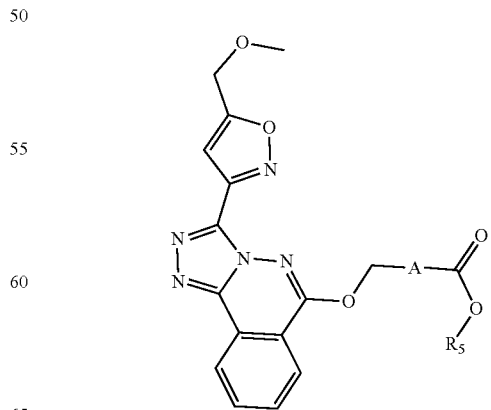

with Y—H;

or, b) reacting a compound represented by formula (1-4)

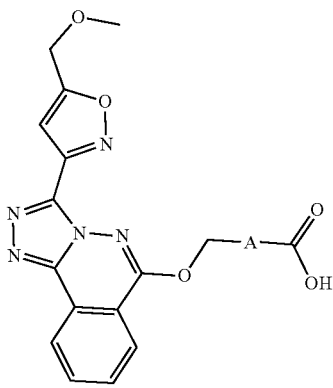

with Y—H;

or, c) subjecting a compound represented by formula (1-3) to saponification to give a compound represented by formula (1-4), followed by reacting with Y—H;

or, d) reacting a compound represented by formula B

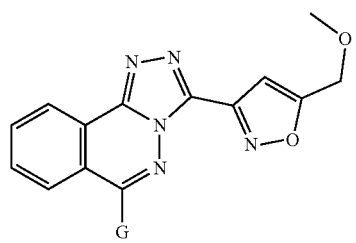

with a compound represented by formula V

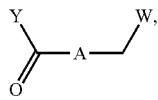

wherein Y and A are as defined above.

The compound represented by B

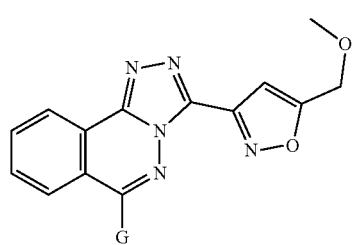

is reacted with a compound represented by formula IV

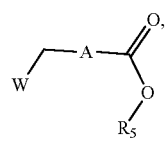

wherein G and W are optionally selected from substituents such as Cl, Br, I, OH, OTs, OTf and OMs etc. The reaction can be carried out under the conditions described in the examples or under conditions known to those skilled in the art. For example, the reaction can be carried out in the presence of LDA, NaH, potassium tert-butoxide or sodium tert-butoxide in a suitable solvent (such as dioxane) at room temperature (such as 20° C.). Alternatively, the reaction can be carried out under Mitsunobu conditions (PPh3, DEAD), phase transfer catalyst (TBAB, crown ether) and other conditions to prepare ether.

The reaction of the compound represented by formula 1-3

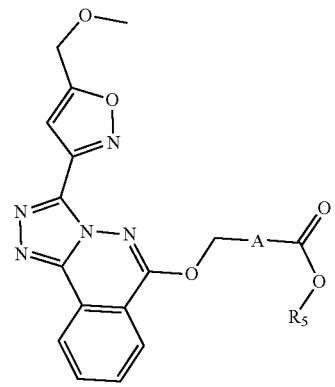

with Y—H to give the compound represented by formula (II) or (III) can be carried out under the conditions described in the examples or under conditions known to those skilled in the art. For example, the reaction can be carried out in the presence of trimethylaluminum in a suitable solvent (such as dioxane) at an elevated temperature (such as 85-95° C.).

The reaction of the compound represented by formula (1-4)

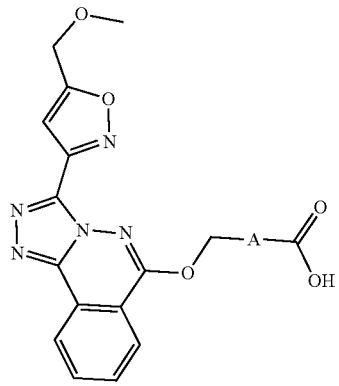

with Y—H to give the compound represented by formula (II) or (III) can be carried out under the conditions described in the examples or under conditions known to those skilled in the art. For example, the reaction can be carried out in the presence of Hûnigs base (N,N-diisopropylethylamine) and O-(benzotriazol-1-yl)-N,N,N',N'-tetramethyluronium tetrafluoroborate in a suitable solvent (such as dimethylformamide) at room temperature. Alternatively, the reaction can be carried out in the presence of 1,1'-carbonyldiimidazole in a suitable solvent (such as dimethylformamide) at an elevated temperature (such as 80° C.). In addition, the reaction can also be carried out in the presence of 1-ethyl-3-(3-dimethylaminopropyl)carbodiimide hydrochloride, N1-hydroxybenzotriazole and Hûnigs base (N,N-diisopropylethylamine) in a suitable solvent (such as dichloromethane) at room temperature.

The saponification of the compound represented by formula (1-3)

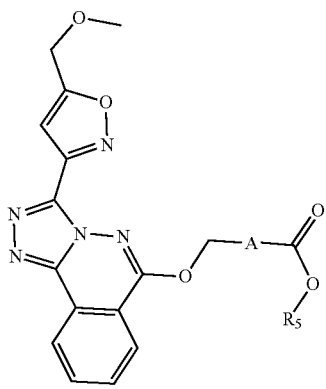

into the compound represented by formula (1-4) can be carried out under the conditions described in the embodiments or under conditions known to those skilled in the art. For example, the reaction can be carried out in the presence of sodium hydroxide in a suitable solvent (such as water) at room temperature. Alternatively, the reaction can be carried out in the presence of sodium hydroxide or lithium hydroxide in a suitable solvent (such as tetrahydrofuran or water) at room temperature. Alternatively, it can be carried out under other conditions or under conditions known to those skilled in the art, such as hydrogenation conditions to remove benzyl group, acidic conditions to hydrolyze tert-butyl group and so on.

The reaction of the compound represented by formula B

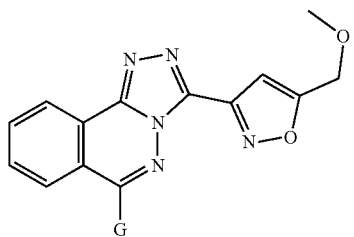

and the compound represented by formula V

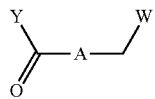

to give the compound represented by formula (II) or (III) can be carried out under the conditions described in the examples or under conditions known to those skilled in the art. For example, the reaction can be carried out in the presence of LDA, NaH, potassium tert-butoxide or sodium tert-butoxide, etc., and in an suitable solvent (such as dioxane, THF and DMF, etc.) at room temperature (such as 20° C.). Alternatively, the reaction can be carried out under Mitsunobu conditions (PPh3, DEAD), phase transfer catalysts (TBAB, crown ether, etc.) and other conditions to prepare ether. The product is produced in a suitable solvent (such as dioxane, THF, DMF, etc.) at an elevated temperature (such as 80° C.) under conditions of corresponding a base or catalyst.

The present disclosure also provides a compound of formula (I) as described above, which is prepared by the methods described above.

The compound represented by formula (I) can be the compound represented by formula (II) or (III) as defined above.

The compound of formula (I), (II) or (III) and the pharmaceutically acceptable salt thereof of the present disclosure can be prepared by the following methods.

If the preparation method is not described in the examples, then the compounds represented by formula (I), (II) or (III) and its intermediate products can be prepared according to a similar method or by the method described above. The known raw materials in this art can be commercially available, or can be prepared in a similar way based on known methods or known methods in the art.

It is understandable that the compounds of the general formula (I), (II) or (III) of the present disclosure can be derivatized on the functional group to give the derivatives which can be converted into the parent compound in vivo.

The present disclosure also provides a pharmaceutical composition comprising a substance A and a pharmaceutically acceptable carrier and/or adjuvant, wherein the substance A is the compound I (for example, the compound II or III), cis-trans isomer thereof, enantiomer thereof, diastereoisomer thereof, racemate thereof, solvate thereof, hydrate thereof, pharmaceutically acceptable salt thereof or prodrug thereof.

The substance A can be the compound I, pharmaceutically acceptable salt thereof or prodrug thereof, can also be the compound I or pharmaceutically acceptable salt thereof, can also be the compound I.

The amount of the substance A can be a therapeutically effective dose.

The pharmaceutical composition can comprise a therapeutically effective dose of one or more of the compound I (for example, compound II or III) or pharmaceutically acceptable salt thereof, and a pharmaceutically acceptable carrier and/or adjuvant.

The pharmaceutical composition can also comprise therapeutic and/or prophylactic ingredients known or used in other fields.

The present disclosure provides a use of pharmaceutical compositions comprising a therapeutically effective amount of the substance A (which can be α5-$GABA_A$ inverse agonist) While the substance A (which can be α5-$GABA_A$ inverse agonist) can be administered in the form of raw chemical compounds, it is preferred to introduce the active ingredient, optionally in the form of a physiologically acceptable salt, in a pharmaceutical composition together with one or more additives, excipients, carriers, buffers, diluents, and/or other customary pharmaceutical auxiliaries.

In a preferred embodiment, the present disclosure provides a pharmaceutical composition comprising the substance A (which can be α5-$GABA_A$ inverse agonist), wherein the substance A (which can be α5-$GABA_A$ inverse agonist) is mixed with one or more pharmaceutically acceptable carriers, and optionally other therapeutic and/or prophylactic ingredients known or used in the art. The carrier(s) must be "acceptable" in the sense of being compatible with the other ingredients of the formulation and not harmful to the recipient thereof.

Pharmaceutical compositions for use according to the disclosure can be those suitable for oral, rectal, bronchial, nasal, pulmonal, topical (including buccal and sublingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the present disclosure, in which matrices may be in the form of shaped articles, e.g., films or microcapsules.

The compound for use according to the present disclosure, together with a conventional additives, or diluent, can thus be prepared into the form of pharmaceutical compositions and unit dosages thereof. Such forms include solids, and in particular tablets, filled capsules, powder and pellet forms, and liquids, in particular aqueous or nonaqueous solutions, suspensions, emulsions, elixirs, and capsules filled with the same, all forms for oral administration, suppositories for rectal administration, and sterile injectable solutions for parenteral use. Such pharmaceutical compositions and unit dosage forms thereof can comprise conventional ingredients in conventional proportions, with or without additional active compounds or ingredients, and such unit dosage forms can contain any suitable effective amount of the active ingredient commensurate with the intended daily dosage range to be employed.

The compound for use according to the present invention can be administered in a wide variety of oral and parenteral dosage forms. It will be obvious to those skilled in the art that the following dosage forms can comprise, as the active component, either a compound of the present disclosure or a pharmaceutically acceptable salt of a compound of the present disclosure.

For preparing pharmaceutical compositions from a compound for use according to the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets preferably contain from 5% or 10% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in water-polyethylene glycol.

The compound for use according to the present disclosure can thus be formulated for parenteral administration (e.g., by injection, for example bolus injection or continuous infusion) and can be presented in unit dose form in ampoules, pre-filled syringes, small volume infusion or in multi-dose containers with an added preservative. The compositions can take such forms as suspensions, solutions, or emulsions in oily or aqueous vehicles, and can contain formulation agents such as suspending, stabilizing and/or dispersing agents. Alternatively, the active ingredient can be in powder form, obtained by aseptic isolation of sterile solid or by lyophilization from solution, for constitution with a suitable vehicle, e.g., sterile, pyrogen-free water, before use.

Aqueous solutions suitable for oral use can be prepared by dissolving the active component in water and adding suitable colorants, flavouring agents, stabilisers and thickeners, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations, intended for conversion shortly before use to liquid form preparations for oral administration. Such liquid forms include solutions, suspensions, and emulsions. In addition to the active component such preparations may comprise colorants, flavouring agents, stabilisers, buffers, artificial and natural sweeteners, dispersants, thickeners, solubilizing agents, and the like.

For topical administration to the epidermis, the compound of the present disclosure can be formulated as ointments, creams or lotions, or as a transdermal patch. Ointments and creams can, for example, be formulated with an aqueous or oily base with the addition of suitable thickeners and/or gelling agents. Lotions can be formulated with an aqueous or oily base and will in general also contain one or more emulsifying agents, stabilisers, dispersants, suspending agents, thickeners, or colorants.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions can be provided in single or multi-dose form.

Administration to the respiratory tract can also be achieved by means of an aerosol formulation in which the active ingredient is provided in a pressurised pack with a suitable propellant such as a chlorofluorocarbon (CFC), for example dichlorodifluoromethane, trichlorofluoromethane, or dichlorotetrafluoroethane, carbon dioxide, or other suitable gas. The aerosol can conveniently also contain a surfactant such as lecithin. The dose of drug can be controlled by provision of a metered valve.

Alternatively the active ingredients can be provided in the form of a dry powder, for example, a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition can be presented in unit dose form for example in capsules or cartridges of, e.g., gelatin, or blister packs from which the powder can be administered by means of an inhaler.

In compositions intended for administration to the respiratory tract, including intranasal compositions, the compound will generally have a small particle size for example of the order of 5 microns or less. Such a particle size can be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration can be found in the latest edition of Remington's Pharmaceutical Sciences (Maack Publishing Co., Easton, Pa.).

The amount of active components in unit dosage form varies based on particular application and the efficacy of active components, which can be adjusted from 0.01 mg to about 0.1 g. For example, in medical application, 0.01 to about 100 mg of such medicine can be administrated in capsule three times a day. If necessary, the composition can also contain other compatible therapeutic agents.

The present disclosure also provides a use of a substance A as $\alpha 5$-GABA$_A$ receptor modulator, wherein the substance A is the compound I (for example, compound II or III), cis-trans isomer thereof, enantiomer thereof, diastereoisomer thereof, racemate thereof, solvate thereof, hydrate thereof, pharmaceutically acceptable salt or prodrug thereof.

The $\alpha 5$-GABA$_A$ receptor modulator can be $\alpha 5$-GABA$_A$ receptor inverse agonist.

The substance A can be the compound I, pharmaceutically acceptable salt thereof or prodrug thereof, can also be the compound I.

The substance A can be used alone or in combination with other drugs.

The present disclosure also provides a use of a substance A or the pharmaceutical composition as described above in the manufacture of a medicament, wherein the substance A is the compound I (for example, compound II or III), cis-trans isomer thereof, enantiomer thereof, diastereoisomer thereof, racemate thereof, solvate thereof, hydrate thereof, pharmaceutically acceptable salt or prodrug thereof.

The substance A can be the compound I, pharmaceutically acceptable salt thereof or prodrug thereof, can also be the compound I.

The substance A can be used alone or in combination with other drugs.

The amount of the substance A can be a therapeutically effective dose.

The medicament can be used for treating, preventing or ameliorating a disease mediated by $\alpha 5$-GABA$_A$ receptor ligand. The disease mediated by $\alpha 5$-GABA$_A$ receptor ligand is one or more selected from, for example, cognitive diseases, Alzheimer's disease, dysmnesia, Down's syndrome, amyotrophic lateral sclerosis (ALS), drug addiction, restless leg syndrome, cognitive deficiency, multi-infarct dementia, pain, stroke, and attention deficit, for another example, pain.

The medicament can be used for treating, preventing or ameliorating one or more of the following diseases (for example, pain): cognitive diseases, Alzheimer's disease, dysmnesia, Down's syndrome, amyotrophic lateral sclerosis (ALS), drug addiction, restless leg syndrome, cognitive deficiency, multi-infarct dementia, pain, stroke, and attention deficit.

In a preferred embodiment, the pain is one or more of neuropathic pain, inflammatory pain and cancer pain.

In a preferred embodiment, the pain is selected from: headache, facial pain, neck pain, shoulder pain, back pain, thoracic pain, abdominal pain, dorsopathy, waist pain, lower limb pain, muscle and bone pain, vascular pain, gout, arthritis pain, visceral pain, the pain caused by infectious diseases (for example, AIDS pain and postherpetic neuralgia), boniness pain, sickle cell anemia associated pain, autoimmune disease associated pain, multiple sclerosis associated pain or inflammation associated pain, injury or surgery caused chronic pain, nociceptive pain, painful diabetes, trigeminal neuralgia, waist or cervix radiculopathy, glossopharyngeal neuralgia, autonomic nerve reflex pain, reflex sympathetic dystrophy pain, nerve root avulsion pain, cancer pain, chemical injury pain, toxin pain, nutrition deficiency pain, virus or bacteria infection pain, and degenerative osteoarthropathy pain.

The present disclosure also provides a method for treating, preventing or ameliorating a disease, comprising administering to a patient an effective dose of a substance A or the pharmaceutical composition as described above, wherein the substance A is the compound I (for example, compound II or III), cis-trans isomer thereof, enantiomer thereof, diastereoisomer thereof, racemate thereof, solvate thereof, hydrate thereof, pharmaceutically acceptable salt or prodrug thereof.

The substance A can be the compound I, pharmaceutically acceptable salt thereof or prodrug thereof, can also be the compound I.

The substance A can be used alone or in combination with other drugs.

The amount of the substance A can be a therapeutically effective dose.

The disease can be a disease mediated by $\alpha 5$-GABA$_A$ receptor ligand. The disease mediated by $\alpha 5$-GABA$_A$ receptor ligand is, for example, one or more selected from: cognitive diseases, Alzheimer's disease, dysmnesia, Down's syndrome, amyotrophic lateral sclerosis (ALS), drug addiction, restless leg syndrome, cognitive deficiency, multi-infarct dementia, pain, stroke, and attention deficit, for another example, pain.

The disease is, for example, one or more of the following diseases (for example, pain): cognitive diseases, Alzheimer's disease, dysmnesia, Down's syndrome, amyotrophic lateral sclerosis (ALS), drug addiction, restless leg syndrome, cognitive deficiency, multi-infarct dementia, pain, stroke, and attention deficit.

In a preferred embodiment, the pain is one or more of neuropathic pain, inflammatory pain and cancer pain.

In a preferred embodiment, the pain is selected from the group consisting of headache, facial pain, neck pain, shoulder pain, back pain, thoracic pain, abdominal pain, dorsopathy, waist pain, lower limb pain, muscle and bone pain, vascular pain, gout, arthritis pain, visceral pain, the pain caused by infectious diseases, boniness pain, sickle cell anemia associated pain, autoimmune disease associated pain, multiple sclerosis or inflammation associated pain, injury or surgery caused chronic pain, nociceptive pain, painful diabetes, trigeminal neuralgia, waist or cervix radiculopathy, glossopharyngeal neuralgia, autonomic nerve reflex pain, reflex sympathetic dystrophy pain, nerve root avulsion pain, cancer pain, chemical injury pain, toxin pain, nutrition deficiency pain, virus or bacteria infection pain, and degenerative osteoarthropathy pain.

For therapeutic application, the original dose of the compound used in this disclosure is 0.001 mg to 10 mg/kg body weight per day. Nevertheless, the dose can vary based on patient's requirement, the severity of the disease to be treated and the compound to be used. Generally speaking, the dose that is below the optimal dose of the compound is used at the beginning, then gradually increasing the dose to achieve the optimal effect. For convenience, total daily dose can be further divided when desired.

The pharmaceutical composition of the present disclosure can also be used in combination with other drugs for the treatment of pain, Alzheimer's disease, multi-infarct dementia and stroke, including but not limited to morphine, gabapentin and the like. Therefore, the present disclosure provides a medicament for treating pain, Alzheimer's disease, multi-infarct dementia and stroke. The medicament is not only effective but also has no obvious side effects, another object of the present disclosure is to provide a medicament with high safety for special patient groups, such as the elderly, patients with liver or kidney function decline, or cardiovascular diseases.

Unless otherwise specified, the following definitions are used to illustrate and define the meaning and scope of various terms used in the description of the present disclosure herein.

"Z is 5 or 6 membered heteroaromatic ring containing 1, 2 or 3 heteroatoms independently selected from O, N and S, the heteroaromatic ring is substituted by $R_1$" is an explanation for

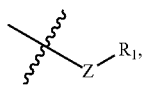

and both of them have the same meaning.

The N atom referred to in the description "6-9 membered bridged cyclic group contains . . . besides the N atom" represents the N atom to which $Y_1$ and $Y_2$ are attached.

As used herein, "neuropathic pain" represents the pain caused by the primary damage and dysfunction of the nervous system.

As used herein, "inflammatory pain" represents the pain caused by local acute inflammation or chronic inflammation.

As used herein, "cancer pain" represents the pain occurs during the development process of malignant tumor. Currently, it is thought that there are three mechanisms of cancer pain, i.e., the pain caused directly by cancer development, the pain caused after cancer treatment and the concurrent painful diseases of cancer patients.

As used herein, "treatment" also includes preventive administration, preventing or eliminating the diseases after the establishment of the diseases.

As used herein, "patient" is defined as any warm-blooded animal, including but not limited to mice, cavies, dogs, horses or humans. Preferably, the patient is human.

As used herein, "acute pain" is defined as the pain caused by the injury of skin, body structure or internal organs and/or noxious stimulation of the diseases, or the pain caused by the abnormal function of muscle or internal organs that does not produce a real tissue injury.

As used herein, "chronic pain" is defined as the pain that lasts a period of time that exceeds the common course or healing time of acute diseases, or that is associated with the chronic pathological processes that cause persistent pain, or that relapses for several months or years with certain interval. If pain still exists after treatment that should cure the disease or exceeding the common course, such pain can be regarded as chronic pain. The time duration that the pain lasts depends on the nature of pain and the treatment process associated with pain. If the pain exceeds common treatment process, then this pain is chronic. Chronic pain includes but not limits to headache, facial pain, neck pain, shoulder pain, thoracic pain, abdominal pain, back pain, waist pain, lower limb pain, muscle and bone pain, somatoform disorder associated pain, visceral pain, painful diabetic neuropathy, vascular pain, gout, arthritis pain, cancer pain, autonomic nerve reflex pain, the pain caused by infectious diseases (such as AIDS and herpes zoster), the pain caused by autoimmune disease (such as rheumatism), the pain caused by acute or chronic inflammation, postoperative pain and post-burning pain.

The medicaments disclosed by this disclosure can efficiently treat the chronic pain defined as above, and the medicaments disclosed by this disclosure can be used to treat hyperalgia accompanied with other diseases, including hyperalgesia, allodynia, algesia enhancement and pain memory enhancement. This disclosure will improve the treatment of pain.

As used herein, "headache" can be divided into primary headache and secondary headache. Primary headache includes tension headache, migraine headache and cluster headache, and secondary headache is caused by other diseases. Headache is caused when pain sensitive tissue on head and face undergoes lesion or get stimulated. These pain sensitive tissues are distributed on scalp, face, oral cavity and throat. Since they are mainly muscles and vessels in head with abundant nerve fibers and sensitive to pain, headache is caused when these tissues are injured.

As used herein, "facial pain" includes but is not limited to trigeminal neuralgia, atypical facial pain, facial palsy and facial spasm.

As used herein, "trigeminal neuralgia" is a unique chronic painful disease, also referred as tic douloureux, representing transient, paroxysmal and repeated electric shock-like severe pain in trigeminal nerve area, or accompanied with ipsilateral facial spasm. Trigeminal neuralgia can be divided into two classes: primary and secondary. Primary trigeminal neuralgia means no neurological sign is found clinically and no organic disease is detected. Secondary trigeminal neuralgia means neurological signs are found clinically and organic diseases such as tumor and inflammation are detected.

As used herein, "atypical facial pain" represents pain caused by various diseases, appearing as persistent burning pain, non-intermittent and independent of particular action or stimulation. The pain is often bilateral and exceeds the area of trigeminal nerve to even cervical skin. The etiology can be the stimulation of nasosinusitis, malignant tumor, jaw and skull base infection or injured trigeminal nerve.

As used herein, "neck pain, back pain, shoulder pain" represent the pain caused by acute or chronic muscle strain and bone joint degeneration and injury. The common diseases that cause neck, shoulder and upper limb pain include cervicoshoulder myofascitis, neck desmitis, cervical spondylopathy, scapulohumeral periarthritis, thoracic outlet syndrome, external humeral epicondylitis, etc. Alternatively, these terms represent the pain caused by autoimmune diseases rheumatoid arthritis, ankylosing spondylitis and rheumatic arthritis. Other diseases that can cause neck pain, back pain and shoulder pain are tumors on neck and shoulder, neuritis, arteriovenous disease and various infections as well as referred pain induced by lesions of thoracic and abdominal organs.

As used herein, "thoracic, abdominal, and back pain" represent the pain caused by diseases in thoracic and abdominal organs and thoracic and abdominal wall tissues, including but not limited to intercostal neuralgia, intercostal chondritis, angina pectoris, abdominal pain (acute abdominal organ pain) and waist and back myofascial pain syndrome.

As used herein, "waist pain, lower limb pain" represent low back, lumbosacral, sacroiliac, hip, buttocks and lower limb pain. Generally, waist pain and lower limb pain are not independent diseases, but a common feature of various diseases, with diverse clinical manifestation and complex etiology. Such pain is mainly induced by degeneration and injury, including but not limited to the pain involving lumbar disc herniation, acute lumbar sprain, ischialgia, osteoporosis, third lumbar trans-verse process syndrome, *piriformis* syndrome, knee osteoarthritis, coccygodynia and calcanodynia.

As used herein, "muscle and bone pain" includes but is not limited to myofascial pain, trauma-caused pain and chronic regional pain syndrome.

As used herein, "painful diabetes" represents the pain caused by nerve injury concurrent with diabetes. The nerve injury in diabetes is caused at least partly by blood flow reduction and hyperglycemia. Some diabetes patients do not suffer neuropathy, while others suffer this disease at early stage. Diabetic neuropathy can be divided into mononeuropathy that involves one or several lesion sites and systemic polyneuropathy. The polyneuropathy can be dispersive and symmetrical, generally and mainly involving mode of sensation (Merrit's Textbook of Neurology, the 9th version, edited by LPRownland LP). The manifestation of diabetic neuropathy includes plant nerve dysfunction, and cause dysregulation involving heart, smooth muscle and gland, resulting in hypotension, diarrhea, constipation and impotence. Diabetic neuropathy often develops in stages. The early stage takes place in nerve ending area. Plant neuropathy or sensory neuropathy occurs in feet and brain neuropathy occurs in face and periocular area with intermittent pain and the sense of tingling. In the following stages, the pain become more severe and occurs more frequently. Finally, when analgesia happens in one area, the disease develops into painless neuropathy. Due to lack of pain as the sign of injury, the risk of severe tissue damage is greatly increased.

As used herein, "visceral pain" includes but is not limited to the pain of inflammatory bowel syndrome (MS), with or without chronic fatigue syndrome (CFS), inflammatory bowel disease (IBD) and interstitial cystitis.

As used herein, "vascular pain" represents the pain generated by the following one or more factors. Firstly, improper perfusion of tissue, resulting in temporary or persistent ischemia, e.g., the ischemia in limb muscles during physical exercise. Secondly, delayed change, e.g., ulcer or gangrene in skin or abdominal organs. Thirdly, the sudden and accelerated change of diameter of great vessels, e.g., the change of arterial aneurysm. Fourthly, aortic rupture, resulting in blood spillover and the stimulation of nociceptive fibers in peritoneum or pleura parietal layers. Fifthly, strong cramp caused by the severe stimulation of artery endothelium by intra-arterial injection. Sixthly, the damage of venous return, leading to a large number of edema of rapidly expanded fascia compartment (Bonica et al. The Management of Pain, Volume 1 (the 2nd version), Philadelphia; Leas & Feboger, 1990). The examples include but are not limited to arteriosclerosis obliterans, thromboangiitis angiitis, acute arterial closure, embolism, congenital arteriovenous aneurysm, vasospasm diseases, Rayaud's disease, acrocyanosis, acute venous closure, thrombophlebitis, varicosity and lymphedema.

As used herein, "autonomic nerve reflex pain" represents the pain caused by "reflex sympathetic dystrophy". For reflex sympathetic dystrophy, after the body suffers an acute or chronic injury, severe ambulatory pain occurs and the body is sensitive to the sense of touch and pain, probably accompanied with edema and blood disorder, following symptoms like skin and musculoskeletal nutrition dystrophia and atrophy.

As used herein, "postoperative pain" represents a complex physiological response of body to the disease itself and the tissue injury caused by operation, showing an unpleasant psychological and behavior experience.

As used herein, "arthritis pain" includes but is not limited to the pain caused by osteoarthritis, rheumatoid arthritis, joint ankylosing spondylitis, psoriatic arthropathy, gout, pseudo gout, infectious arthritis, tendinitis, bursitis, bone damage and joint soft tissue inflammation.

As used herein, "postherpetic neuralgia" represents the subcutaneously long-standing severe pain in rash site after the healing of the rash of herpes zoster.

As used herein, "nociceptive pain" represents the pain caused by the tissue injury delivered by nociceptors, or the pain caused by the extended excitement of nociceptors. The pain caused by the extended excitement of nociceptors can be induced by both the persisting noxious stimulation of nociceptors, or the sensitization thereof, or both, or they can be induced by these factors and extended by their persistence, various reflex mechanisms and other factors.

The graphical representations of racemates, ambiscalemic and scalemic or the compound in the form of pure enantiomer used herein are from Maehr, *J. Che. Ed.* 1985, 62: 114-120. Unless otherwise specified, wedge-shaped bonds and dashed bonds are used to indicate the absolute configuration of a stereocenter. When the compounds described herein contain olefinic double bonds or other geometric asymmetric centers, unless otherwise specified, they include E and Z geometric isomers. Likewise, all tautomeric forms are included within the scope of the present disclosure.

Compounds of formula (I), (II), (III) can form pharmaceutically acceptable acid addition salts. Examples of such pharmaceutically acceptable salts are salts of compounds of formula (I), (II), (III) with physiologically compatible mineral acids, such as hydrochloric acid, sulphuric acid, *sulphurous* acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salt" refers to such salts. Compounds of formula (I), (II), (III) which comprise an acidic group, e.g., a COOH group, can further form salts with bases. Examples of such salts are alkaline, earth-alkaline and ammonium salts e.g., Na—, K—, Ca— and trimethylammonium salt. The term "pharmaceutically acceptable salt" also refers to such salts.

The term "prodrug" is a functional derivative of the compound represented by formula (I), (II) or (III), which is easily converted into the compound represented by formula (I), (II) or (III) in vivo. Suitable such derivatives can be selected and prepared by conventional techniques well known to those skilled in the art, for example, see Design of Prodrugs, ed. H. Bundgaard, Elsevier, 1985.

The compound of the present disclosure can contain an unnatural proportion of atomic isotopes on one or more of the atoms constituting the compound, the isotopes have the same atomic number, but their atomic mass or mass number is different from those that predominantly exist in nature. For example, the compounds can be labeled with radioisotopes, such as deuterium ($^2$H), tritium ($^3$H), iodine-125 ($^{15}$I), or C-14 ($^{14}$C). All changes in the isotopic composition of the compounds of the present disclosure, whether radioactive or not, are included within the scope of the present disclosure. Isotope variants may improve certain therapeutic advantages, such as deuterium enrichment can increase in vivo half-life or reduce dosage requirements, or provide compounds as standard for the characterization of biological samples. Isotopically enriched compounds within the general formula (I), (II) or (III) can be prepared by conventional techniques well known to those skilled in the art, or by methods similar to those described in the routes and embodiments herein, using appropriate isotope-enriched reagents and/or intermediates without redundant experimentation.

The following definitions of the general terms apply irrespective of whether the terms in question appear alone or in combination.

The nomenclature used in this application is based on AutoNom™ 2000, a Beilstein Institute computerized system for the generation of IUPAC systematic nomenclature. Chemical structures shown herein were obtained using ChemDraw version 12. Any open valency appearing on a carbon, oxygen, sulfur or nitrogen atom in the structures herein indicates the presence of a hydrogen atom.

The term "substituted", unless specifically defined otherwise, means that the specified group or moiety can bear 1, 2, 3, 4, 5 or 6 substituents. Where any group carries multiple substituents and a variety of possible substituents is provided, the substituents are independently selected and need not be the same.

The term "unsubstituted" means that the specified group bears no substituents.

The term "optionally substituted" means that the specified group is unsubstituted or substituted by one or more substituents, independently selected from the group consisting of the group of possible substituents.

When indicating the number of substituents, the term "one or more" means from one substituent to the highest possible number of substitution, i.e., replacement of one hydrogen up to replacement of all hydrogens by substituents. 1, 2, 3, 4 or 5 substituents are preferred, unless specifically defined otherwise.

The term "halogen" refers to fluorine, chlorine, bromine and iodine, in particular fluorine.

The term "lower-alkyl" denotes a saturated straight- or branched-chain group containing from 1 to 6 carbon atoms, which is interchangeable with $C_{1-6}$ alkyl described herein. The examples of $C_{1-6}$ alkyl include methyl, ethyl, propyl, isopropyl, n-butyl, isobutyl, sec-butyl or tert-butyl, as well as those groups specifically illustrated by the examples herein below. In particular lower-alkyl groups are methyl and n-butyl.

The term "lower-alkoxy" denotes a group —O—R wherein R is lower-alkyl as defined above.

The term "lower-alkyl substituted by halogen" refers to lower-alkyl groups which are mono- or multiply substituted with halogen. Examples of lower-alkyl substituted by halogen groups are e.g., $CFH_2$, $CF_2H$, $CF_3$, $CF_3CH_2$, $CF_3(CH_2)_2$, $(CF_3)_2CH$ or $CF_2H$—$CF_2$, as well as those groups specifically illustrated by the examples herein below.

The term "lower-alkyl substituted by hydroxyl" denotes a lower-alkyl group as defined above wherein at least one of the hydrogen atoms of the alkyl group is replaced by a hydroxy group. Examples of lower-alkyl substituted by hydroxy include but are not limited to methyl, ethyl, propyl, isopropyl, isobutyl, sec-butyl, tert-butyl, pentyl or n-hexyl substituted by one or more hydroxy group(s), in particular with one, two or three hydroxyl groups, preferably with one or two hydroxyl group.

The term "cycloalkyl" refers to a monovalent saturated cyclic hydrocarbon group of 3 to 7 ring carbon atoms, in particular 3 to 6 carbon atoms, such as cyclopropyl, cyclobutyl, cyclopentyl or cyclohexyl, as well as those groups specifically illustrated by the examples herein below.

The term "heterocyclyl" refers to a saturated or partly unsaturated monocyclic or polycyclic ring containing a heteroatom, preferably 3 to 7 membered saturated or partly unsaturated monocyclic ring containing one, two or three ring heteroatoms selected from N, O and S. One or two ring heteroatoms are preferred. In particular, heterocyclyl are 4 to 6 membered heterocyclyl comprising one or two ring heteroatoms selected from N, O and S. S is optionally substituted by two oxo groups. Examples for heterocyclyl moieties are pyrrolidinyl, tetrahydrofuranyl, tetrahydropyranyl, tetrahydrothienyl, tetrahydropyridinyl, tetrahydropyrrolyl, azetidinyl, thiazolidinyl, oxazolidinyl, piperidinyl, morpholinyl, thiomorpholinyl, 1,1-dioxo-thiomorpholin-4-yl, piperazinyl, azepanyl, diazepanyl, oxazacycloheptanyl or dihydrooxazolyl, as well as those groups specifically illustrated by the examples herein below. Specific heterocyclyl groups include morpholin-4-yl, piperidin-1-yl, pyrrolidin-1-yl, thiomorpholin-4-yl, and 1,1-dioxo-thiomorpholin-4-yl, preferably, the heterocyclyl is morpholin-4-yl, pyrrolidin-1-yl, and 1,1-dioxo-thiomorpholin-4-yl.

The term "bridged cyclic compound (or bridged cyclic group)" refers to the cyclic hydrocarbons in which any two rings in the compound share two carbon atoms that are not directly connected, and can be divided into bicyclic hydrocarbons, tricyclic hydrocarbons, and tetracyclic hydrocarbons, etc., according to the number of the rings.

The term "spirocyclic compound (or spirocyclic group)" refers to polycyclic compounds in which two monocyclic rings share one carbon atom. The shared carbon atom is called a spiro atom.

The term "aryl" refers to a monovalent aromatic carbocyclic ring system, comprising 6 to 14, in particular 6 to 10, carbon atoms and having at least one aromatic ring or multiple condensed rings in which at least one ring is aromatic. Examples for aryl are phenyl, naphthyl, biphenyl or indanyl, as well as those groups specifically illustrated by the examples herein below. Preferred aryl is phenyl. Aryl can also be substituted e.g., as defined below and in the claims.

The term "heteroaryl" refers to an aromatic group containing heteroatoms, preferably an aromatic 5 to 6 membered monocyclic ring or 9 to 10 membered bicyclic ring containing 1, 2 or 3 atoms selected from nitrogen, oxygen and/or sulphur, such as furyl, pyridinyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, thiadiazolyl, benzoimidazolyl, indolyl, indazolyl, benzothiazolyl, benzoisothiazolyl, benzoxazolyl, benzoisoxazolyl, quinolinyl or isoquinolinyl, as well as those groups specifically illustrated by the examples herein below. Heteroaryl can also be substituted, e.g., as defined below and in the claims. More particularly heteroaryl groups are 5-fluoro-pyridin-2-yl.

DETAILED DESCRIPTION

Preparation Example 1

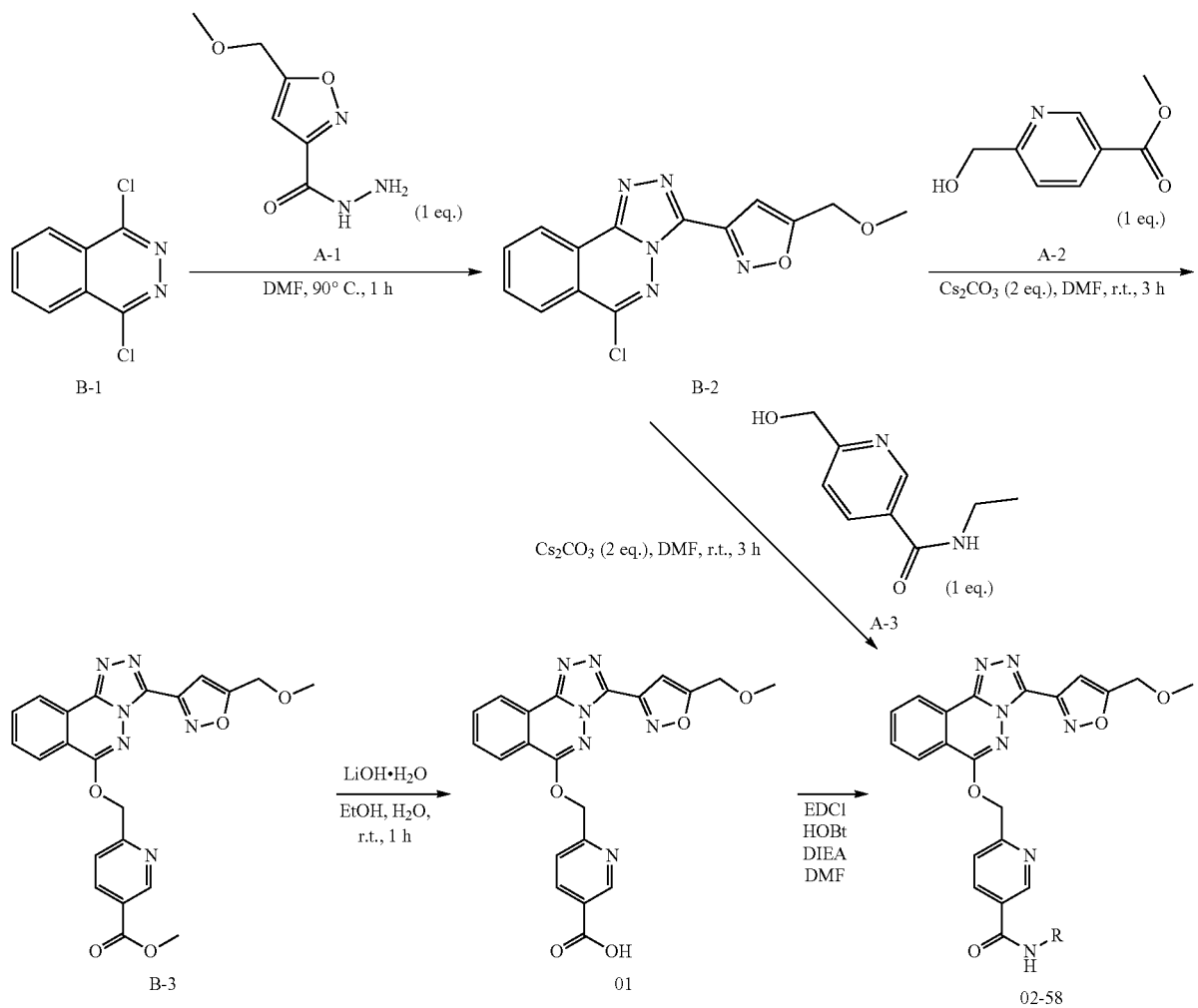

3-(6-chloro-[1,2,4]triazolo[3,4-a]phthalazin-3-yl)-5-(methoxymethyl)isoxazole (B-2)

B-1 (0.8 g, 4 mmol) (CAS: 4752-10-7) and A-1 (0.75 g, CAS: 625120-12-9) were mixed in DMF (10 mL) and stirred at 90° C. for 1 hour. TLC showed the complete consumption of the starting materials, and the mixture was cooled to room temperature and poured into ice water (100 mL). The resulting precipitate was collected by filtration, washed with water for 3 times, and dried to give product B-2 (1 g crude) as a light yellow solid.

Preparation Example 2 methyl 6-[3-(5-methoxymethyl-isoxazol-3-yl)-[1,2,4]triazolo[3,4-a]phthalazin-6-yloxymethyl]-nicotinate (B-3)

B-2 (1 g crude), A-2 (CAS: 56026-36-9) (0.53 g, 3.2 mmol) and cesium carbonate (2.1 g, 6.4 mmol) were mixed in DMF (20 mL) and stirred at room temperature for 16 hours. TLC showed that the complete consumption of the starting materials, and the mixture was poured into ice water (200 mL). The resulting precipitate was collected by filtration, washed with water for 3 times, and dried to give product B-3 (0.93 g crude) as a light brown solid.

Example 1

6-[3-(5-methoxymethyl-isoxazol-3-yl)-[1,2,4]triazolo[3,4-a]phthalazin-6-yloxymethyl]-nicotinic acid (01)

Lithium hydroxide (4.96 g, 95.29 mmol) was dissolved in 60 mL of water, and then added into a suspension of B-3 (8.5 g, 19.06 mmol) in methanol (150 mL) and stirred for 3 hours. The reaction solution was poured into water, and the pH value was adjusted to 4. The mixture was filtered by suction to give a yellow solid. The obtained yellow solid was slurried with ethanol, then slurried with methyl tert-butyl ether, and dried under suction with an oil pump to give a pale yellow powder (5.3 g, 64%). $^1$H NMR (400 MHz, DMSO-$d_6$): δ 13.42 (s, 1H), 9.10 (s, 1H), 8.58 (d, J=8.0 Hz, 1H), 8.38 (d, J=8.4 Hz, 1H), 8.34-8.32 (m, 1H), 8.15-8.11 (m, 1H), 8.00-7.98 (m, 1H), 7.87 (d, J=8.0 Hz, 1H), 7.15 (s, 1H), 5.80 (s, 2H), 4.71 (s, 2H), 3.39 (s, 3H). LCMS: Rt=3.059 min, [M+H]$^+$=432.

Example 2

N-ethyl-6-[3-(5-methoxymethyl-isoxazol-3-yl)-[1,2,4]triazolo[3,4-a]phthalazin-6-yloxymethyl]-nicotinamide (02)

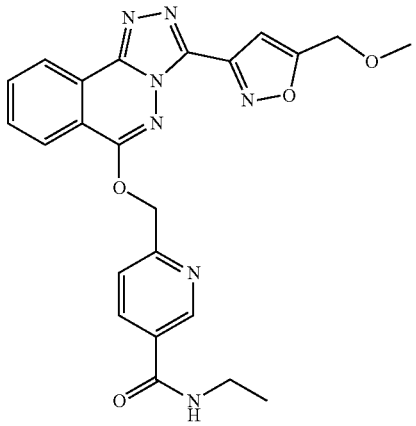 [SMILES: CCNC(=O)c1ccc(COc2nn3c(-c4cc(COC)on4)nnc3c3ccccc23)nc1]

The experimental operation was as described in Preparation Example 2: compound B-2 and A-3 (refer to patent application WO2013/120438A) were reacted to give 81 mg of the target compound as an off-white solid with a yield of 46%.

$^1$H NMR (400 MHz, DMSO-d$_6$) δ ppm 9.03 (d, J=1.71 Hz, 1H), 8.69 (t, J=5.35 Hz, 1H), 8.60 (d, J=7.86 Hz, 1H), 8.38 (d, J=7.99 Hz, 1H), 8.25 (dd, J=8.15, 2.17 Hz, 1H), 8.14 (m, 1H), 8.01 (m, 1H), 7.84 (d, J=8.15 Hz, 1H), 7.19 (s, 1H), 5.78 (s, 2H), 4.71 (s, 2H), 3.31-3.29 (m, 5H), 1.13 (t, J=7.20 Hz, 3H); LC-MS: m/z (ES+) for $C_{23}H_{21}N_7O_4$ 460 [M+1]$^+$.

Example 3

N-(3,3-difluoro-cyclobutyl)-6-[3-(5-methoxymethyl-isoxazol-3-yl)-[1,2,4]triazolo[3,4-a]phthalazin-6-yloxymethyl]-nicotinamide (03)

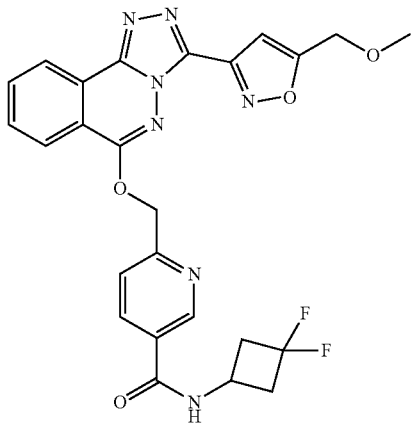 [SMILES: COCc1cc(-c2nnc3c4ccccc4c(OCc4ccc(C(=O)NC5CC(F)(F)C5)cn4)nn23)no1]

Compound 01 (50 mg crude), HOBt (24 mg, 0.18 mmol) and EDCI (34 mg, 0.18 mmol) were sequentially added into 2 mL of DMF, and 3,3-difluorocyclobutylamine hydrochloride (CAS: 637031-93-7) and then N,N-diisopropylethylamine (0.063 mL, 0.36 mmol) were sequentially added to the mixture. The resulting mixture was stirred at room temperature overnight. TLC (dichloromethane:methanol=20:1) showed the complete consumption of the raw materials. The mixture was poured into ice water (10 mL) and extracted 3 times with ethyl acetate/methanol (20:1, 15 mL). The combined organic layer was washed 3 times with water (20 mL), and 1 time with brine (20 mL), dried (anhydrous sodium sulfate) and evaporated. The residue was purified by preparative TLC (dichloromethane/methanol=20/1) to give the target compound as a pale yellow solid, 33.7 mg, yield 54%, the appearance was pale yellow solid.

$^1$H NMR (400 MHz, CDCl$_3$) δ ppm 9.02 (s, 1H), 8.54 (d, J=6.70 Hz, 1H), 8.23 (dd, J=24.11, 6.77 Hz, 2H), 7.91 (s, 1H), 7.84-7.65 (m, 2H), 7.48 (s, 1H), 6.93 (s, 1H), 5.72 (s, 2H), 4.60 (s, 2H), 4.47 (s, 1H), 3.47 (s, 3H), 3.06 (s, 2H), 2.69 (d, J=5.72 Hz, 2H); LC-MS: m/z (ES+) for $C_{25}H_{21}F_2N_7O_4$ 522 [M+1]$^+$.

Example 4

6-[3-(5-methoxymethyl-isoxazol-3-yl)-[1,2,4]triazolo[3,4-a]phthalazin-6-yloxymethyl]-N-(tetrahydro-pyran-4-yl)-nicotinamide (04)

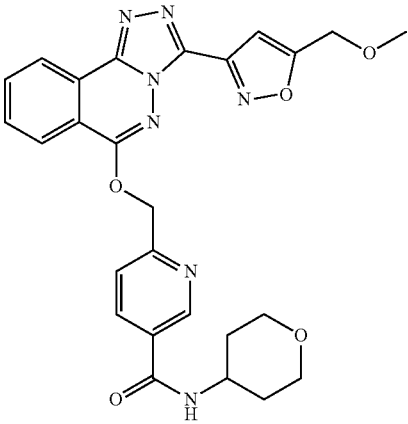 [SMILES: COCc1cc(-c2nnc3c4ccccc4c(OCc4ccc(C(=O)NC5CCOCC5)cn4)nn23)no1]

The experimental operation was as described in Example 3: the condensation reaction of compound 01 and 4-aminotetrahydropyran hydrochloride (CAS: 33024-60-1) gave 24 mg of the target compound as a yellow solid with a yield of 39%.

$^1$H NMR (400 MHz, CDCl$_3$) δ ppm 8.95 (s, 1H), 8.63 (d, J=7.89 Hz, 1H), 8.30 (d, J=8.04 Hz, 1H), 8.24-8.13 (m, 1H), 7.97 (t, J=7.55 Hz, 1H), 7.83 (dd, J=18.12, 7.97 Hz, 2H), 7.18 (d, J=7.47 Hz, 1H), 7.04 (s, 1H), 5.77 (s, 2H), 4.67 (s, 2H), 4.24-4.09 (m, 1H), 3.97 (d, J=9.68 Hz, 2H), 3.59-3.40 (m, 5H), 1.94 (d, J=11.39 Hz, 2H), 1.59 (dq, J=12.16, 4.16 Hz, 2H); LC-MS: m/z (ES+) for $C_{26}H_{25}N_7O_5$ 516 [M+1]$^+$.

Example 5

(S)—N-(2-methoxy-1-methyl-ethyl)-6-[3-(5-methoxymethyl-isoxazol-3-yl)-[1,2,4]triazolo[3,4-a]phthalazin-6-yloxymethyl]-nicotinamide (05)

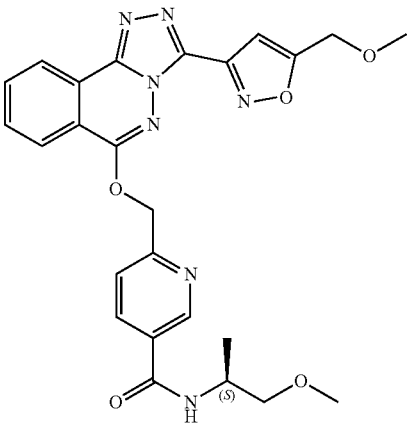

The experimental operation was as described in Example 3: the condensation reaction of compound 01 and (S)-(+)-1-methoxy-2-propylamine (CAS: 99636-32-5) gave 18.3 mg of the target compound as a light yellow solid with a yield of 30%.

$^1$H NMR (400 MHz, CDCl$_3$) δ ppm 9.00 (s, 1H), 8.69 (d, J=7.41 Hz, 1H), 8.32 (d, J=7.45 Hz, 1H), 8.15 (d, J=7.22 Hz, 1H), 7.97 (t, J=7.12 Hz, 1H), 7.89-7.73 (m, 2H), 7.05 (s, 1H), 6.49 (d, J=6.21 Hz, 1H), 5.80 (s, 2H), 4.70 (s, 2H), 4.51-4.25 (m, 1H), 3.68-3.50 (m, 3H), 3.50-3.42 (m, 2H), 3.38 (s, 3H), 1.36-1.28 (m, 3H); LC-MS: m/z (ES+) for C$_{25}$H$_{25}$N$_7$O$_5$ 504 [M+1]$^+$.

Example 6

(S)-6-[3-(5-methoxymethyl-isoxazol-3-yl)-[1,2,4]triazolo[3,4-a]phthalazin-6-yloxymethyl]-N-(tetrahydro-furan-2-ylmethyl)-nicotinamide (06)

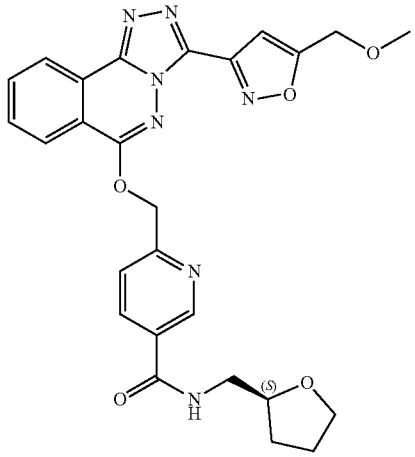

The experimental operation was as described in Example 3: the condensation reaction of compound 01 and (S)-(+)-tetrahydrofurfurylamino (CAS: 7175-81-7) gave 17.7 mg of the target compound as a light yellow solid with a yield of 29%.

$^1$H NMR (400 MHz, CDCl$_3$) δ ppm 9.02 (s, 1H), 8.69 (d, J=6.06 Hz, 1H), 8.33 (d, J=5.78 Hz, 1H), 8.25-8.07 (m, 1H), 8.06-7.92 (m, 1H), 7.90-7.70 (m, 2H), 7.06 (s, 1H), 6.65 (s, 1H), 5.80 (s, 2H), 4.70 (s, 2H), 4.22-3.96 (m, 1H), 3.94-3.70 (m, 3H), 3.52 (s, 3H), 3.40-3.20 (m, 1H), 2.13-1.83 (m, 3H), 1.64-1.51 (m, 1H);

LC-MS: m/z (ES+) for C$_{26}$H$_{25}$N$_7$O$_5$ 516 [M+1]$^+$.

Example 7

N-(2-methoxy-ethyl)-6-[3-(5-methoxymethyl-isoxazol-3-yl)-[1,2,4]triazolo[3,4-a]phthalazin-6-yloxymethyl]-nicotinamide (07)

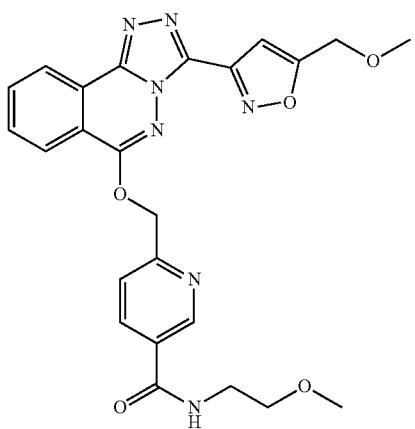 [SMILES: COCCNC(=O)c1ccc(COc2nn3c(-c4cc(COC)on4)nnc3c3ccccc23)nc1]

The experimental operation was as described in Example 3: the condensation reaction of compound 01 and 2-methoxyethylamine (CAS: 109-85-3) gave 17.2 mg of the target compound as a light yellow solid with a yield of 29%.

$^1$H NMR (400 MHz, CDCl$_3$) δ ppm 9.02 (s, 1H), 8.70 (d, J=7.79 Hz, 1H), 8.34 (d, J=7.68 Hz, 1H), 8.17 (d, J=7.14 Hz, 1H), 7.99 (t, J=7.48 Hz, 1H), 7.85 (t, J=7.65 Hz, 2H), 7.06 (s, 1H), 6.61 (s, 1H), 5.81 (s, 2H), 4.71 (s, 2H), 3.77-3.62 (m, 2H), 3.62-3.54 (m, 2H), 3.52 (s, 3H), 3.39 (s, 3H); LC-MS: m/z (ES+) for C$_{24}$H$_{23}$N$_7$O$_5$ 490 [M+1]$^+$.

Example 8

6-[3-(5-methoxymethyl-isoxazol-3-yl)-[1,2,4]triazolo[3,4-a]phthalazin-6-yloxymethyl]-N-(3-methoxy-propyl)-nicotinamide (08)

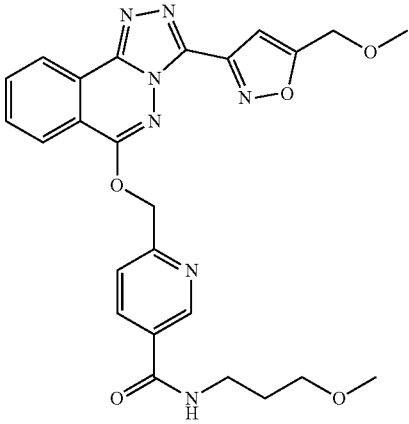 [SMILES: COCCCNC(=O)c1ccc(COc2nn3c(-c4cc(COC)on4)nnc3c3ccccc23)nc1]

The experimental operation was as described in Example 3: the condensation reaction of compound 01 and 3-methoxypropylamine (CAS: 5332-73-0) gave 9.2 mg of the target compound as an off-white solid with a yield of 13%.

$^1$H NMR (400 MHz, CDCl$_3$) δ ppm 8.97 (d, J=1.66 Hz, 1H), 8.70 (d, J=7.93 Hz, 1H), 8.34 (d, J=8.03 Hz, 1H), 8.18 (dd, J=8.08, 2.07 Hz, 1H), 7.99 (t, J=7.52 Hz, 1H), 7.86 (m, 2H), 7.21-7.12 (m, 1H), 7.07 (s, 1H), 5.81 (s, 2H), 4.70 (s, 2H), 3.60 (td, J=8.60, 5.54 Hz, 4H), 3.39 (s, 3H), 3.52 (s, 3H), 1.96-1.82 (m, 2H); LC-MS: m/z (ES+) for C$_{25}$H$_{25}$N$_7$O$_5$ 504 [M+1]$^+$.

Example 9

(R)—N-(2-methoxy-1-methyl-ethyl)-6-[3-(5-methoxymethyl-isoxazol-3-yl)-[1,2,4]triazolo[3,4-a]phthalazin-6-yloxymethyl]-nicotinamide (09)

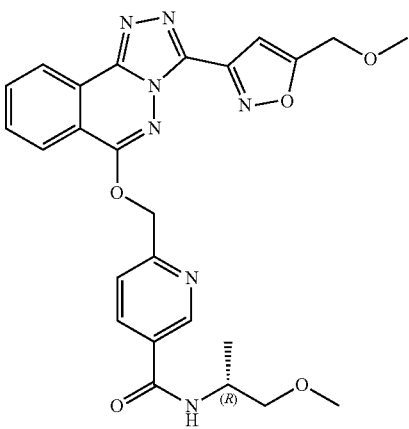

The experimental operation was as described in Example 3: the condensation reaction of compound 01 and (R)-(−)-1-methoxy-2-propylamine (CAS: 99636-38-1) gave 29.6 mg of the target compound as an off-white solid with a yield of 42%.

$^1$H NMR (400 MHz, CDCl$_3$) δ ppm 9.00 (d, J=1.04 Hz, 1H), 8.67 (d, J=7.90 Hz, 1H), 8.31 (d, J=8.03 Hz, 1H), 8.16 (dd, J=8.05, 1.91 Hz, 1H), 7.96 (t, J=7.48 Hz, 1H), 7.83 (t, J=8.13 Hz, 2H), 7.04 (s, 1H), 6.54 (d, J=7.68 Hz, 1H), 5.79 (s, 2H), 4.69 (s, 2H), 4.49-4.27 (m, 1H), 3.51 (s, 3H), 3.49 (d, J=3.91 Hz, 1H), 3.43 (dd, J=9.47, 4.03 Hz, 1H), 3.39 (s, 3H), 1.32-1.27 (m, 3H); LC-MS: m/z (ES+) for C$_{25}$H$_{25}$N$_7$O$_5$ 504 [M+1]$^+$.

Example 10
N-(2-methoxy-1-methyl-ethyl)-6-[3-(5-methoxymethyl-isoxazol-3-yl)-[1,2,4]triazolo[3,4-a]phthalazin-6-yloxymethyl]-nicotinamide (10)

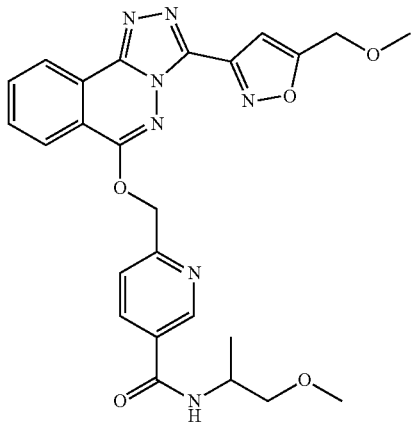 [SMILES: COCc1cc(-c2nnc3c4ccccc4c(OCc4ccc(C(=O)NC(C)COC)cn4)nn23)no1]

The experimental operation was as described in Example 3: the condensation reaction of compound 01 and 1-methoxy-2-propylamine (CAS: 37143-54-7) gave 27.4 mg of the target compound as an off-white solid with a yield of 39%.

$^1$H NMR (400 MHz, CDCl$_3$) δ ppm 9.00 (s, 1H), 8.68 (d, J=7.86 Hz, 1H), 8.32 (d, J=7.99 Hz, 1H), 8.21-8.10 (m, 1H), 7.97 (t, J=7.48 Hz, 1H), 7.84 (t, J=8.11 Hz, 2H), 7.05 (s, 1H), 6.52 (d, J=7.39 Hz, 1H), 5.79 (s, 2H), 4.69 (s, 2H), 4.38 (m, 1H), 3.52 (s, 3H), 3.38 (s, 3H), 3.43 (dd, J=9.46, 3.96 Hz, 1H), 3.51-3.48 (m, 1H), 1.30 (d, J=6.72 Hz, 3H); LC-MS: m/z (ES+) for C$_{25}$H$_{25}$N$_7$O$_5$ 504 [M+1]$^+$.

Example 11
N-isopropyl-6-[3-(5-methoxymethyl-isoxazol-3-yl)-[1,2,4]triazolo[3,4-a]phthalazin-6-yloxymethyl]-nicotinamide (11)

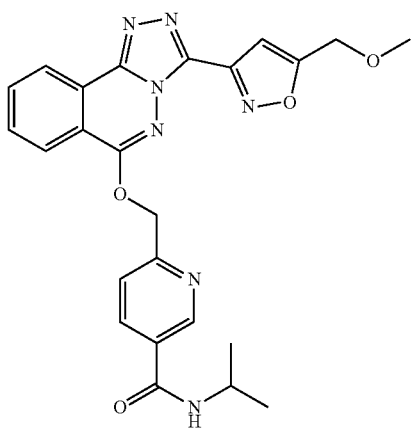 [SMILES: COCc1cc(-c2nnc3c4ccccc4c(OCc4ccc(C(=O)NC(C)C)cn4)nn23)no1]

The experimental operation was as described in Example 3: the condensation reaction of compound 01 and isopropylamine (CAS: 75-31-0) gave 13.3 mg of the target compound as a light yellow solid with a yield of 15%.

$^1$H NMR (400 MHz, CDCl$_3$) δ ppm 8.97 (d, J=1.5 Hz, 1H), 8.68 (d, J=8.3 Hz, 1H), 8.32 (d, J=7.8 Hz, 1H), 8.16 (dd, J=2.2, 8.1 Hz, 1H), 7.98 (t, J=7.8 Hz, 1H), 7.90-7.76 (m, 2H), 7.04 (s, 1H), 6.16 (d, J=6.8 Hz, 1H), 5.79 (s, 2H), 4.70 (s, 2H), 4.30 (qd, J=6.7, 13.8 Hz, 1H), 3.57-3.45 (m, 3H), 1.28 (d, J=6.4 Hz, 6H); LC-MS: m/z (ES+) for C$_{24}$H$_{23}$N$_7$O$_4$ 474 [M+1]$^+$.

Example 12
N-cyclopropyl-6-[3-(5-methoxymethyl-isoxazol-3-yl)-[1,2,4]triazolo[3,4-a]phthalazin-6-yloxymethyl]-nicotinamide (12)

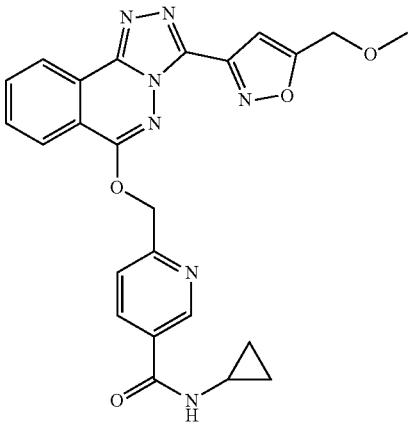 [SMILES: COCc1cc(-c2nnc3c4ccccc4c(OCc4ccc(C(=O)NC5CC5)cn4)nn23)no1]

The experimental operation was as described in Example 3: the condensation reaction of compound 01 and cyclopropylamine (CAS: 765-30-0) gave 29.0 mg of the target compound as a light yellow solid with a yield of 33%.

$^1$H NMR (400 MHz, CDCl$_3$) δ ppm 8.94 (d, J=2.0 Hz, 1H), 8.70 (d, J=7.8 Hz, 1H), 8.34 (d, J=8.3 Hz, 1H), 8.18-8.11 (m, 1H), 7.99 (t, J=7.8 Hz, 1H), 7.91-7.77 (m, 2H), 7.03 (s, 1H), 6.46 (br. s., 1H), 5.80 (s, 2H), 4.71 (s, 2H), 3.53 (s, 3H), 2.97-2.87 (m, 1H), 0.95-0.85 (m, 2H), 0.70-0.62 (m, 2H); LC-MS: m/z (ES+) for C$_{24}$H$_{21}$N$_7$O$_4$ 472 [M+1]$^+$.

Example 13
6-[3-(5-methoxymethyl-isoxazol-3-yl)-[1,2,4]triazolo[3,4-a]phthalazin-6-yloxymethyl]-N-(2-trifluoromethoxy-ethyl)-nicotinamide (13)

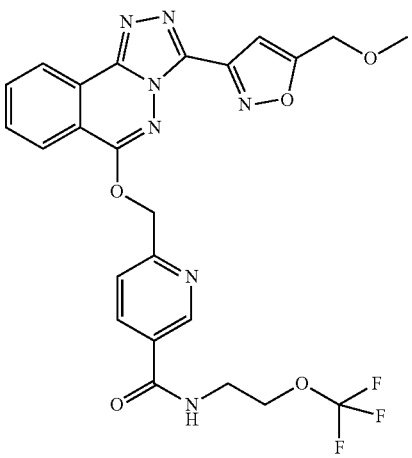 [SMILES: COCc1cc(-c2nnc3c4ccccc4c(OCc4ccc(C(=O)NCCOC(F)(F)F)cn4)nn23)no1]

The experimental operation was as described in Example 3: the condensation reaction of compound 01 and 2-(trifluoromethoxy)ethylamine hydrochloride (CAS: 886050-51-7) gave 34.7 mg of the target compound as a light yellow solid with a yield of 34.5%.

$^1$H NMR (400 MHz, CDCl$_3$) δ ppm 9.01 (s, 1H), 8.68 (d, J=7.8 Hz, 1H), 8.34 (d, J=8.3 Hz, 1H), 8.20 (dd, J=2.0, 8.3 Hz, 1H), 7.99 (t, J=7.3 Hz, 1H), 7.92-7.78 (m, 2H), 7.04 (s, 1H), 5.80 (s, 2H), 4.69 (s, 2H), 4.17 (t, J=5.1 Hz, 2H), 3.76 (q, J=4.9 Hz, 2H), 3.52 (s, 3H); LC-MS: m/z (ES+) for C$_{24}$H$_{20}$F$_3$N$_7$O$_5$ 544 [M+1]$^+$.

Example 14

N-(2-methoxy-1,1-dimethyl-ethyl)-6-[3-(5-methoxymethyl-isoxazol-3-yl)-[1,2,4]triazolo[3,4-a]phthalazin 6-yloxymethyl]-nicotinamide (14)

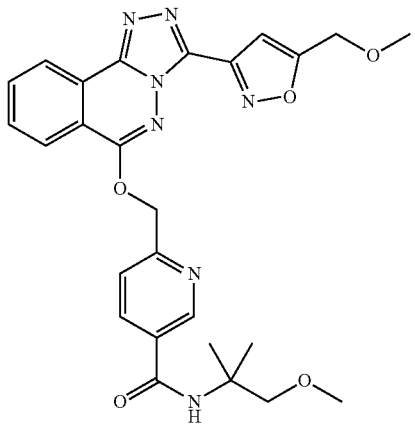 [SMILES: COCc1cc(-c2nnc3c4ccccc4c(OCc4ccc(C(=O)NC(C)(C)COC)cn4)nn23)no1]

The experimental operation was as described in Example 3: the condensation reaction of compound 01 and 1-methoxy-2-methyl-2-propylamine (CAS: 20719-68-0) gave 28.3 mg of the target compound as a light yellow solid with a yield of 30%.

$^1$H NMR (400 MHz, CDCl$_3$) δ ppm 8.96 (s, 1H), 8.67 (d, J=7.8 Hz, 1H), 8.31 (d, J=8.3 Hz, 1H), 8.18-8.08 (m, 1H), 7.97 (t, J=7.6 Hz, 1H), 7.89-7.74 (m, 2H), 7.06 (s, 1H), 6.46 (br. s., 1H), 5.79 (s, 2H), 4.69 (s, 2H), 3.51 (s, 3H), 3.47-3.42 (m, 2H), 3.40 (s, 3H), 1.47 (s, 6H); LC-MS: m/z (ES+) for C$_{27}$H$_{27}$N$_7$O$_5$ 530 [M+1]$^+$.

Example 15

6-[3-(5-methoxymethyl-isoxazol-3-yl)-[1,2,4]triazolo[3,4-a]phthalazin-6-ylhydroxymethyl]-N-(2,2,2-trifluoroethyl)-nicotinamide (15)

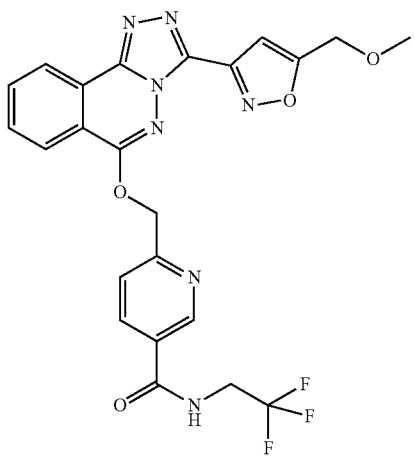 [SMILES: COCc1cc(-c2nnc3c4ccccc4c(OCc4ccc(C(=O)NCC(F)(F)F)cn4)nn23)no1]

The experimental operation was as described in Example 3: the condensation reaction of compound 01 and trifluoro-ethylamine hydrochloride (CAS: 373-88-6) gave 16 mg of the target compound as a light yellow solid.

$^1$H NMR (400 MHz, DMSO-d$_6$) δ ppm 9.35 (s, 1H), 9.08 (s, 1H), 8.58 (d, J=7.3 Hz, 1H), 8.37 (s, 1H), 8.30 (d, J=5.4 Hz, 1H), 8.13 (s, 1H), 8.00 (s, 1H), 7.88 (d, J=7.3 Hz, 1H), 7.17 (s, 1H), 5.79 (s, 2H), 4.70 (s, 2H), 4.12 (s, 2H), 3.52 (s, 3H); LC-MS: m/z (ES+) for C$_{23}$H$_{18}$F$_3$N$_7$O$_4$ 514 [M+1]$^+$.

Example 16

N-(2-hydroxy-ethyl)-6-[3-(5-methoxymethyl-isoxazol-3-yl)-[1,2,4]triazolo[3,4-a]phthalazin-6-yloxymethyl]-nicotinamide (16)

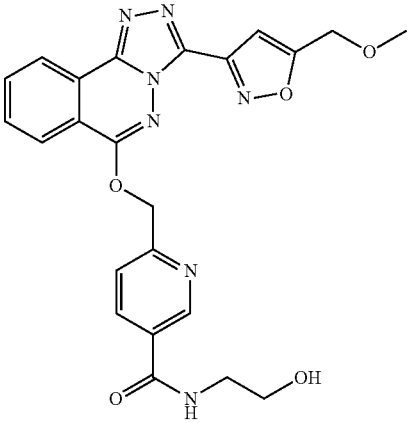 [SMILES: COCc1cc(-c2nnc3c4ccccc4c(OCc4ccc(C(=O)NCCO)cn4)nn23)no1]

The experimental operation was as described in Example 3: the condensation reaction of compound 01 and ethanolamine (CAS: 141-43-5) gave 11.4 mg of the target compound as a light yellow solid with a yield of 10%.

$^1$H NMR (400 MHz, CDCl$_3$) δ ppm 9.03 (s, 1H), 8.67 (d, J=7.3 Hz, 1H), 8.33 (d, J=7.8 Hz, 1H), 8.23 (d, J=8.3 Hz, 1H), 7.99 (t, J=7.8 Hz, 1H), 7.90-7.78 (m, 2H), 7.06 (s, 1H), 5.79 (s, 2H), 4.69 (s, 2H), 3.80 (t, J=4.9 Hz, 2H), 3.61 (m, 2H), 3.51 (s, 3H); LC-MS: m/z (ES+) for C$_{23}$H$_{21}$N$_7$O$_5$ 476 [M+1]$^+$.

Example 17

6-[3-(5-methoxymethyl-isoxazol-3-yl)-[1,2,4]triazolo[3,4-a]phthalazin-6-yloxymethyl]-N-oxetan-3-yl-nicotinamide (17)

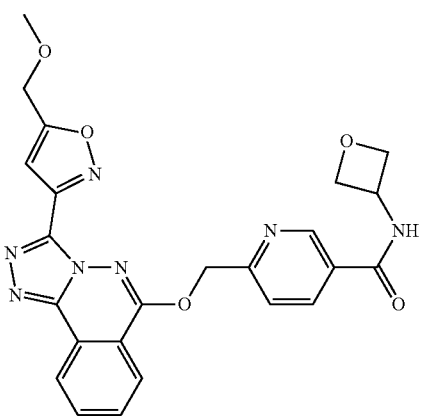 [SMILES: COCc1cc(-c2nnc3c4ccccc4c(OCc4ccc(C(=O)NC5COC5)cn4)nn23)no1]

The experimental operation was as described in Example 3: the condensation reaction of compound 01 and oxetane-3-amine hydrochloride (CAS: 491588-41-1) gave 22.3 mg of the target compound as a light yellow solid with a yield of 25%.

¹H NMR (400 MHz, CDCl₃) δ ppm 8.99 (s, 1H), 8.60 (d, J=7.8 Hz, 1H), 8.30 (d, J=7.8 Hz, 1H), 8.23 (d, J=7.8 Hz, 1H), 8.03-7.91 (m, 1H), 7.89-7.75 (m, 2H), 7.04 (s, 1H), 5.75 (s, 2H), 5.20-5.06 (m, 1H), 4.93 (t, J=6.6 Hz, 2H), 4.65 (s, 2H), 4.64-4.52 (m, 2H), 3.46 (s, 3H); LC-MS: m/z (ES+) for C₂₄H₂₁N₇O₅ 488 [M+1]⁺.

Example 18

N-(oxetan-3-methyl)-6-{3-[5-(methoxymethyl)isoxazol-3-yl]-[1,2,4]triazolo[3,4-a]phthalazin-6-oxy)methylene}nicotinamide (18)

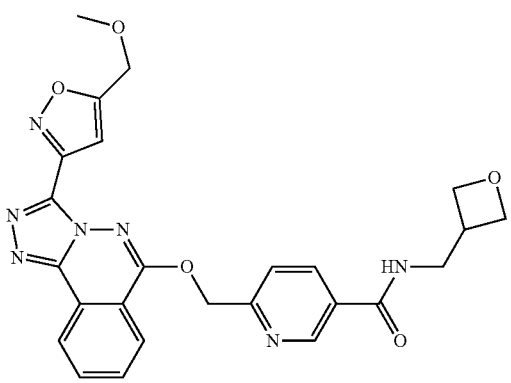 [SMILES: COCc1cc(-c2nnc3c4ccccc4c(OCc4ccc(C(=O)NCC5COC5)cn4)nn23)no1]

The experimental operation was as described in Example 3: the condensation reaction of compound 01 and 3-aminomethyloxetane (CAS: 6246-05-5) gave 22.3 mg of the target compound as a light yellow solid with a yield of 25%.

¹H NMR (400 MHz, DMSO-d₆) δ ppm 9.03 (s, 1H), 8.83 (s, 1H), 8.568 (d, J=8 Hz, 1H), 8.35 (d, J=8 Hz, 1H), 8.254 (d, J=6 Hz, 1H), 8.12-8.10 (m, 1H), 8.00-7.98 (m, 1H), 7.855 (d, J=8 Hz, 1H), 7.185 (s, 1H), 5.76 (s, 2H), 4.71 (s, 2H), 4.638 (t, J=6.3 Hz, 2H), 4.347 (t, J=6.2 Hz, 2H), 3.569 (t, J=6.4 Hz, 2H), 3.39 (s, 3H), 3.18-3.15 (m, 1H); LC-MS: Rt=3.263 min, [M+H]⁺=502.

Example 19

N-(1-cyanocyclopropyl)-6-{3-[5-(methoxymethyl)isoxazol-3-yl]-[1,2,4]triazole[3,4-a]phthalazin-6-oxy)methylene}nicotinamide (19)

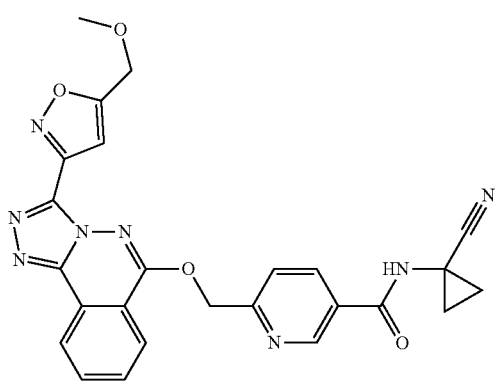 [SMILES: COCc1cc(-c2nnc3c4ccccc4c(OCc4ccc(C(=O)NC5(C#N)CC5)cn4)nn23)no1]

The experimental operation was as described in Example 3: the condensation reaction of compound 01 and 1-amino-1-cyclopropylnitrile hydrochloride (CAS: 127946-77-4) gave the product (54 mg, 36.2%) as a white solid.

¹H NMR (400 MHz, CDCl₃) (400 MHz, DMSO-d₆): 9.57 (s, 1H), 9.036 (s, 1H), 8.58 (d, J=7.6 Hz, 1H), 8.37 (d, J=8.4 Hz, 1H), 8.37 (dd, J=8.4 Hz, 2.0 Hz, 1H), 8.15-8.12 (m, 1H), 8.02-7.99 (m, 1H), 7.89-7.87 (m, 1H), 7.18 (s, 1H), 5.79 (s, 2H), 4.71 (s, 2H), 3.39-3.34 (m, 3H), 1.61-1.58 (m, 2H), 1.33-1.29 (m, 2H). LC-MS: Rt=2.911 min, [M+H]⁺=497.

Example 20

N-((3-methyl(oxetanyl)-methyl)-6-{3-[5(methoxymethyl)isoxazol-3-yl]-[1,2,4]triazole[3,4-a]phthalazin-6-oxy)methylene}nicotinamide (20)

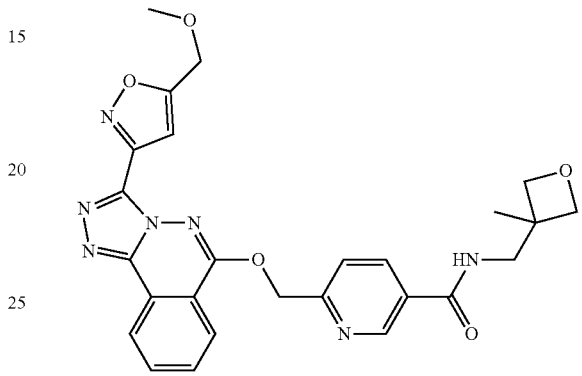

The experimental operation was as described in Example 3: the condensation reaction of compound 01 and 3-methyl-3-aminomethyl-1-oxetane (CAS: 153209-97-3) gave the product (30.7 mg, 26%) as a white solid.

¹H NMR (400 MHz, CDCl₃) (400 MHz, DMSO-d₆): δ 9.06 (s, 1H), 8.88-8.84 (m, 1H), 8.60 (d, J=7.2 Hz, 1H), 8.38 (d, J=8.0 Hz, 1H), 8.27 (d, J=6.4 Hz, 1H), 8.16-8.13 (m, 1H), 8.03-7.99 (m, 1H), 7.88-7.86 (d, J=8.0 Hz, 1H), 7.21 (s, 1H), 5.79 (s, 2H), 4.72 (s, 2H), 4.46 (d, J=6.0 Hz, 2H), 4.21 (d, J=5.6 Hz, 2H), 3.50-3.49 (m, 2H), 3.39 (s, 3H), 1.26 (s, 3H). LC-MS: Rt=2.840 min, [M+H]⁺=516.0.

Example 21

N-(3-fluorocyclobutyl)-6-{3-[5-(methoxymethyl)isoxazol-3-yl]-[1,2,4]triazole[3,4-a]phthalazin-6-oxy)methylene}nicotinamide (21)

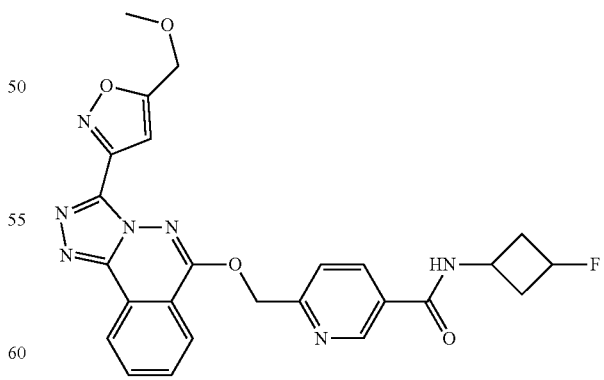

The experimental operation was as described in Example 3: the condensation reaction was carried out with compound 01 and 3-fluorocyclobutylamine (CAS: 234616-60-4), the reaction mixture obtained was separated and purified by prep-HPLC to give the product (48.2 mg, 41%) as a white solid.

$^1$H NMR (400 MHz, DMSO-d$_6$): δ 9.05 (d, J=2.0 Hz, 1H), 8.92 (d, J=7.2 Hz, 1H), 8.59 (d, J=7.6 Hz, 1H), 8.37 (d, J=8.0 Hz, 1H), 8.28-8.26 (m, 1H), 8.16-8.12 (m, 1H), 8.03-7.99 (m, 1H), 7.86 (d, J=8.0 Hz, 1H), 7.19 (s, 1H), 5.78 (s, 2H), 5.37-4.81 (m, 1H), 4.72 (s, 2H), 4.54-3.97 (m, 2H), 3.39 (s, 3H), 2.78-2.70 (m, 2H), 2.33-2.23 (m, 2H). LC-MS: Rt=3.830 min, [M+H]$^+$=504.0.

Example 22

N-2-difluoroethyl-6-(((3-(5-(methoxymethyl)isoxazol-3-yl)-[1,2,4]triazolo[3,4-a]peptidazin-6-yl)oxy)methyl)nicotinamide (22)

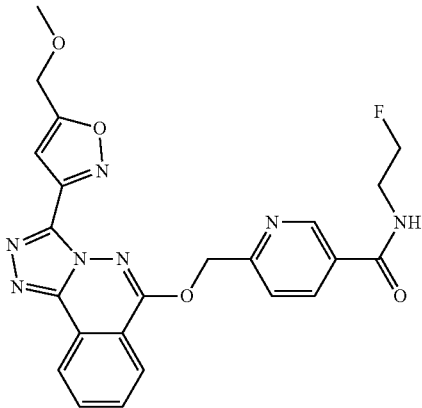 [SMILES: COCc1cc(-c2nnc3c4ccccc4c(OCc4ccc(C(=O)NCCF)cn4)nn23)no1]

The experimental operation was as described in Example 3: the condensation reaction of compound 01 and 2-fluoroethylamine hydrochloride (CAS: 460-08-2) gave 29.8 mg of the target compound as an off-white solid with a yield of 39.0%.

1H NMR (400 MHz, DMSO-d$_6$) δ ppm 9.10-8.94 (m, 2H), 8.59 (d, J=7.8 Hz, 1H), 8.39 (d, J=7.8 Hz, 1H), 8.32-8.26 (m, 1H), 8.14 (t, J=7.6 Hz, 1H), 8.06-7.97 (m, 1H), 7.85 (d, J=7.8 Hz, 1H), 7.19 (s, 1H), 5.78 (s, 2H), 4.71 (s, 2H), 4.61 (t, J=5.1 Hz, 1H), 4.49 (t, J=4.9 Hz, 1H), 3.70-3.52 (m, 3H), 2.06-1.90 (m, 2H); LC-MS: m/z (ES+) for C23H20FN7O4 478 [M+1]$^+$.

Example 23

N-cyclobutyl-6-(((3-(5-(methoxymethyl)isoxazol-3-yl)-[1,2,4]triazolo[3,4-a]peptidazin-6-yl)oxy)methyl)nicotinamide (23)

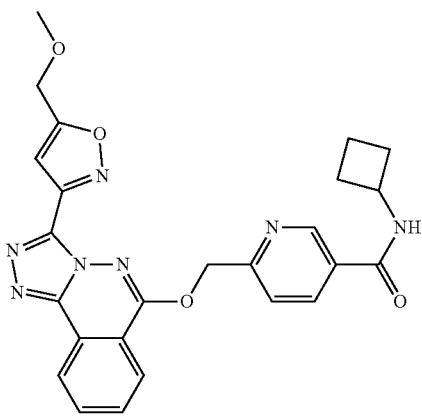 [SMILES: COCc1cc(-c2nnc3c4ccccc4c(OCc4ccc(C(=O)NC5CCC5)cn4)nn23)no1]

The experimental operation was as described in Example 3: the condensation reaction of compound 01 and cyclobutylamine (CAS: 2516-34-9) gave 42.3 mg of the target compound as an off-white solid with a yield of 54.5%.

1H NMR (400 MHz, DMSO-d$_6$) δ ppm 9.03 (s, 1H), 8.87 (d, J=7.3 Hz, 1H), 8.60 (d, J=7.8 Hz, 1H), 8.38 (d, J=7.8 Hz, 1H), 8.26 (d, J=6.4 Hz, 1H), 8.20-8.09 (m, 1H), 8.07-7.94 (m, 1H), 7.84 (d, J=8.3 Hz, 1H), 7.27-7.11 (m, 2H), 5.86-5.69 (m, 2H), 5.32 (s, 1H), 4.71 (s, 2H), 4.42 (dd, J=8.3, 16.1 Hz, 2H), 2.21 (s, 1H), 2.12-1.90 (m, 3H), 1.75-1.60 (m, 2H); LC-MS: m/z (ES+) for C25H23N7O4 486 [M+1]$^+$.

Example 24

N-2,2-difluoroethyl-6-(((3-(5-(methoxymethyl)isoxazol-3-yl)-[1,2,4]triazolo[3,4-a]peptidazin-6-yl)oxy)methyl)nicotinamide (24)

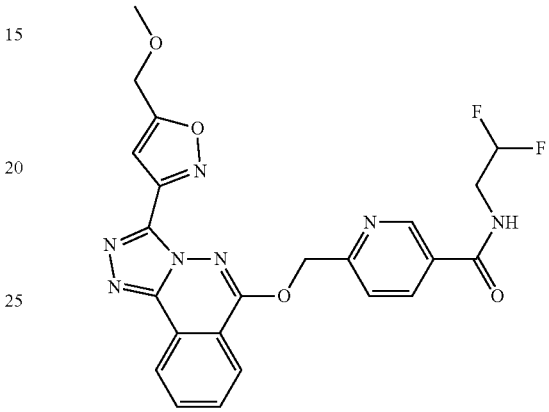

The experimental operation was as described in Example 3: the condensation reaction of compound 01 and 2,2-difluoroethylamine (CAS: 430-67-1) gave 13.7 mg of the target compound as an off-white solid with a yield of 14.5%.

_H NMR (400 MHz, DMSO-d$_6$) δ ppm 9.14-9.02 (m, 2H), 8.58 (d, J=7.8 Hz, 1H), 8.37 (d, J=7.8 Hz, 1H), 8.27 (dd, J=2.0, 8.3 Hz, 1H), 8.16-8.06 (m, 1H), 8.02-7.93 (m, 1H), 7.85 (d, J=8.3 Hz, 1H), 7.17 (s, 1H), 6.26 (d, J=3.9 Hz, 1H), 6.14-6.08 (m, 1H), 5.97 (d, J=3.9 Hz, 1H), 5.77 (s, 2H), 4.69 (s, 2H), 3.76-3.60 (m, 3H); LC-MS: m/z (ES+) for C23H19F2N7O4 496 [M+1]$^+$.

Example 25

N-(2,2-difluoro-1-propyl-3-yl)-6-(((3-(5-(methoxymethyl)isoxazol-3-yl)-[1,2,4]triazolo[3,4-a]peptidazin-6-yl)oxy)methyl)nicotinamide (25)

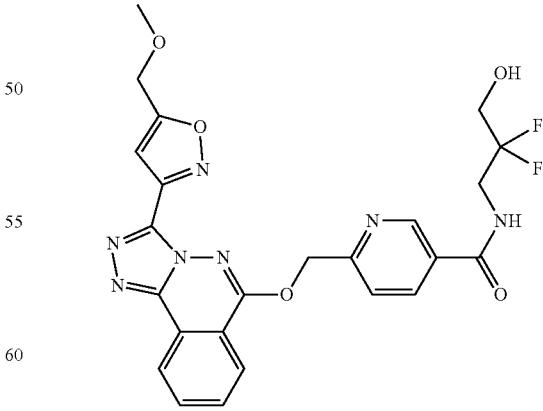

The experimental operation was as described in Example 3: the condensation reaction of compound 01 and 3-amino-2,2-difluoropropan-1-ol (CAS: 155310-11-5) gave 70.1 mg of the target compound as an off-white solid with a yield of 83.4%.

¹H NMR (400 MHz, DMSO-d₆) δ ppm 9.11-8.95 (m, 1H), 8.58 (d, J=7.8 Hz, 1H), 8.37 (d, J=7.8 Hz, 1H), 8.28 (dd, J=2.0, 8.3 Hz, 1H), 8.12 (t, J=7.6 Hz, 1H), 7.99 (t, J=7.6 Hz, 1H), 7.85 (d, J=8.3 Hz, 1H), 7.17 (s, 1H), 5.77 (s, 2H), 5.55 (t, J=6.1 Hz, 1H), 4.69 (s, 2H), 3.87-3.74 (m, 1H), 3.70-3.58 (m, 2H); LC-MS: m/z (ES+) for C24H21F2N7O5 526 [M+1]⁺.

Example 26

6-[3-(5-methoxymethyl-isoxazol-3-yl)-[1,2,4]triazolo[3,4-a]phthalazin-6-yloxymethyl]-N-(tetrahydrofuran-3-yl)-nicotinamide (26)

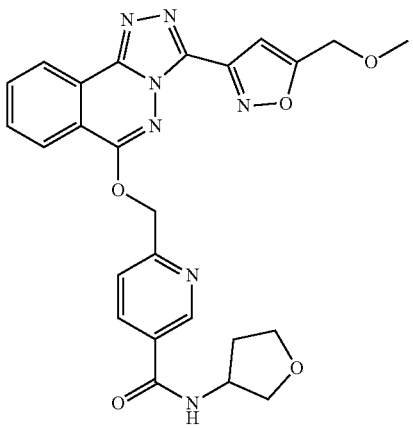 [SMILES: COCc1cc(-c2nnc3c4ccccc4c(OCc4ccc(C(=O)NC5CCOC5)cn4)nn23)no1]

The experimental operation was as described in Example 3: the condensation reaction of compound 01 and 3-amino-tetrahydrofuran hydrochloride (CAS: 204512-94-7) gave 17.7 mg of the target compound as an off-white solid with a yield of 19%.

¹H NMR (400 MHz, CDCl₃) δ ppm 9.00 (s, 1H), 8.63 (d, J=7.8 Hz, 1H), 8.30 (d, J=7.8 Hz, 1H), 8.17 (dd, J=1.7, 8.1 Hz, 1H), 7.95 (t, J=7.6 Hz, 1H), 7.88-7.76 (m, 2H), 7.01 (s, 1H), 6.85 (d, J=7.3 Hz, 1H), 5.76 (s, 2H), 4.80-4.70 (m, 1H), 4.68 (s, 2H), 3.99 (q, J=7.8 Hz, 1H), 3.94-3.87 (m, 1H), 3.87-3.77 (m, 2H), 3.51 (s, 3H), 2.45-2.31 (m, 1H), 2.03-1.96 (m, 1H); LC-MS: m/z (ES+) for C25H23N7O5 502 [M+1]⁺.

Example 27

6-[3-(5-methoxymethyl-isoxazol-3-yl)-[1,2,4]triazolo[3,4-a]phthalazin-6-ylhydroxymethyl]-N-(2,2,2-trifluoro-1-methyl-ethyl)-nicotinamide (27)

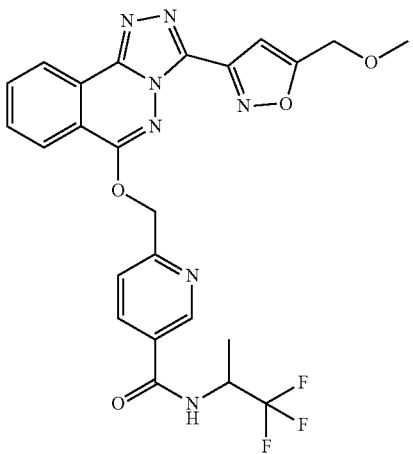 [SMILES: COCc1cc(-c2nnc3c4ccccc4c(OCc4ccc(C(=O)NC(C)C(F)(F)F)cn4)nn23)no1]

The experimental operation was as described in Example 3: the condensation reaction of compound 01 and 1,1,1-trifluoroisopropylamine hydrochloride (CAS: 2968-32-3) gave 77.6 mg of the target compound as an off-white solid with a yield of 80%.

¹H NMR (400 MHz, DMSO-d₆) δ ppm 9.11 (d, J=8.8 Hz, 1H), 9.07 (d, J=2.0 Hz, 1H), 8.60 (d, J=7.8 Hz, 1H), 8.38 (d, J=8.3 Hz, 1H), 8.30 (dd, J=2.0, 8.3 Hz, 1H), 8.14 (t, J=7.6 Hz, 1H), 8.06-7.97 (m, 1H), 7.89 (d, J=8.3 Hz, 1H), 7.19 (s, 1H), 5.80 (s, 2H), 4.95-4.80 (m, 1H), 4.71 (s, 2H), 1.37 (d, J=7.3 Hz, 3H); LC-MS: m/z (ES+) for C24H20F3N7O4 528 [M+1]⁺.

Example 28

N-(2-cyano-ethyl)-6-[3-(5-methoxymethyl-isoxazol-3-yl)-[1,2,4]triazolo[3,4-a]phthalazin-6-yloxymethyl]-nicotinamide (28)

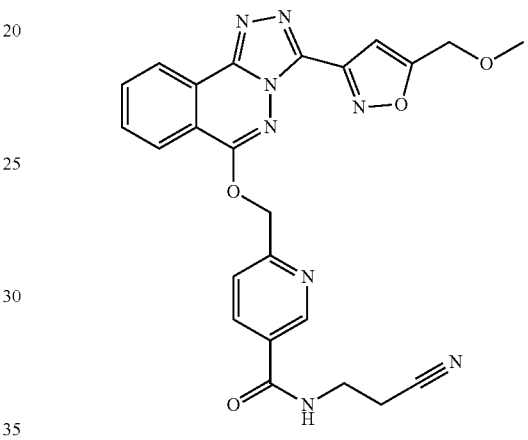

The experimental operation was as described in Example 3: the condensation reaction of compound 01 and 3-aminopropionitrile (CAS: 151-18-8) gave 38.5 mg of the target compound as an off-white solid with a yield of 43%.

¹H NMR (400 MHz, DMSO-d₆) δ ppm 9.19-8.95 (m, 2H), 8.57 (s, 1H), 8.43-8.19 (m, 2H), 8.17-7.77 (m, 3H), 7.17 (s, 1H), 5.76 (s, 2H), 4.69 (s, 2H), 3.64-3.50 (m, 5H), 2.88-2.69 (m, 2H). LC-MS: m/z (ES+) for C24H20N8O4 485 [M+1]⁺.

Example 29

N-(3,3,3-trifluoropropyl)-6-{3-[5-(methoxymethyl)isoxazol-3-yl]-[1,2,4]triazole[3,4-a]phthalazin-6-oxy)methylene}nicotinamide (29)

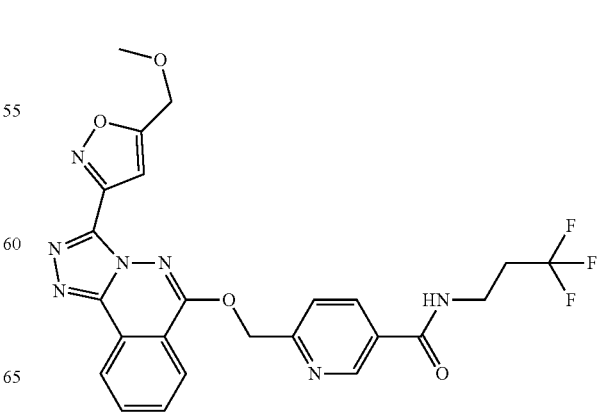

The experimental operation was as described in Example 3: the condensation reaction was carried out with compound 01 and 3,3,3-trifluoropropylamine (CAS: 460-39-9), the reaction mixture obtained was separated and purified by prep-HPLC to give a white solid (30 mg, 20%).
$^1$H NMR (400 MHz DMSO-d$_6$): δ 9.036 (s, 1H) 8.953-8.925 (m, 1H) 8.614-8.593 (d, J=8.4 Hz, 1H) 8.405-8.384 (d, J=8.4 Hz, 1H) 8.241-8.236 (m, 1H) 8.166-8.125 (t, J=5.4 Hz, 1H) 8.035-7.993 (t, J=5.6 Hz, 1H) 7.886-7.866 (d, J=8 Hz, 1H) 7.202 (s, 1H) 5.790 (s, 2H) 4.715 (s, 2H) 3.529-3.515 (m, 2H) 3.389 (s, 3H) 2.553-2.524 (m, 2H); LC-MS: Rt=3.697 min, [M+H]$^+$=528.

Example 30

N-(1,3-dimethoxyprop-2-yl)-6-{3-[5-(methoxymethyl)isoxazol-3-yl]-[1,2,4]triazolo[3,4-a]phthalazin-6-oxy)methylene}nicotinamide (30)

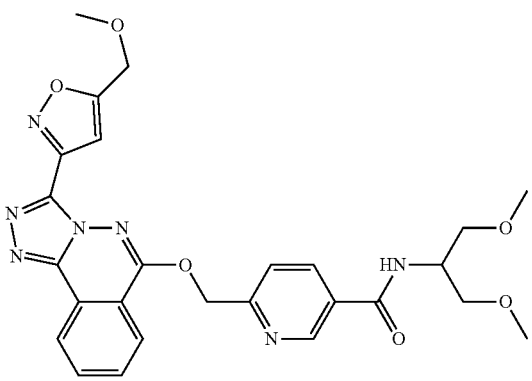 [SMILES: COCc1cc(-c2nnc3c4ccccc4c(OCc4ccc(C(=O)NC(COC)COC)cn4)nn23)no1]

The experimental operation was as described in Example 3: the condensation reaction of compound 01 and 2-amino-1,3-dimethoxypropane (CAS: 78531-29-0) gave a white solid (46 mg, 31%).
$^1$H NMR (400 MHz, DMSO-d$_6$): δ 9.048 (s, 1H) 8.601-8.591 (m, 2H) 8.386-8.367 (d, J=7.6 Hz, 1H) 8.289-8.263 (m, 1H) 8.157-8.119 (t, J=7.6 Hz, 1H) 8.026-7.988 (t, J=7.6 Hz, 1H) 7.864-7.843 (d, J=8.4 Hz, 1H) 7.191 (s, 1H) 5.782 (s, 2H) 4.715 (s, 2H) 4.326-4.307 (m, 1H) 3.491-3.428 (m, 4H) 3.391 (s, 3H) 3.262 (s, 6H); LC-MS: Rt=3.311 min, [M+H]$^+$=534.

Example 31

N-(bicyclo[1.1.1]pentan-1-yl)-6-{3-[5-(methoxymethyl)isoxazol-3-yl]-[1,2,4]triazolo[3,4-a]phthalazin-6-oxy)methylene}nicotinamide (31)

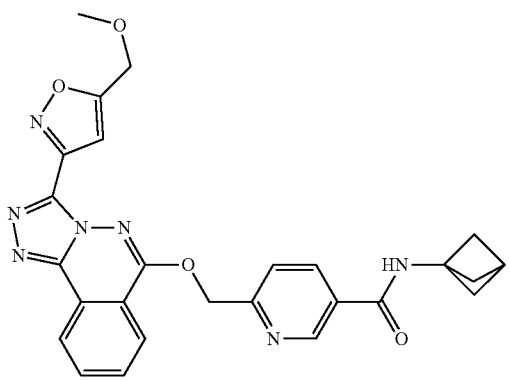 [SMILES: COCc1cc(-c2nnc3c4ccccc4c(OCc4ccc(C(=O)NC56CC(C5)C6)cn4)nn23)no1]

The experimental operation was as described in Example 3: the condensation reaction of compound 01 and bicyclo[1.1.1]-1-pentylamine (CAS: 22287-35-0) gave a white solid (38 mg, 28%).
$^1$H NMR (400 Mhz, DMSO-d$_6$): δ 9.216 (s, 1H), 9.024 (s, 1H), 8.603-8.583 (d, J=8 Hz, 1H), 8.393-8.373 (d, J=8 Hz, 1H), 8.254-8.234 (d, J=8 Hz, 1H), 8.157-8.120 (t, J=7.4 Hz, 1H), 8.026-7.988 (t, J=7.6 Hz, 1H), 7.851-7.831 (d, J=8 Hz, 1H), 7.179 (s, 1H), 5.773 (s, 2H), 4.712 (s, 2H), 3.389 (s, 3H), 2.479 (s, 1H), 2.100 (s, 6H); LC-MS: Rt=3.693 min, [M+H]$^+$=498.

Example 32

N-(1-acetyl-azetidin-3-yl)-6-{3-[5-(methoxymethyl)isoxazol-3-yl]-[1,2,4]triazolo[3,4-a]phthalazin-6-oxy)methylene}nicotinamide (32)

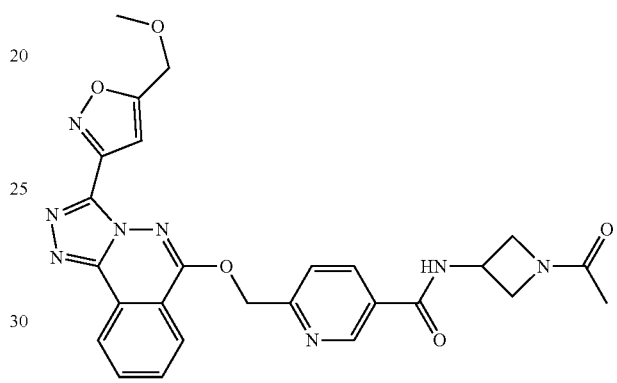

The experimental operation was as described in Example 3: the condensation reaction of compound 01 and 1-acetyl-azetidinylamine hydrochloride (CAS: 1462921-50-1) gave a white solid (23 mg, 15%).
$^1$H NMR (400 MHz, DMSO-d$_6$): δ 9.258-9.241 (d, J=6.8 Hz, 1H), 9.075 (s, 1H), 8.605-8.587 (d, J=7.2 Hz, 1H), 8.395-8.375 (d, J=8 Hz, 1H), 8.304-8.277 (m, 1H), 8.160-8.121 (t, J=5.2 Hz, 1H), 8.031-7.993 (t, J=5.1 Hz, 1H), 7.893-7.873 (d, J=8 Hz, 1H) 7.199 (s, 1H) 5.790 (s, 2H) 4.716 (s, 2H) 4.690-4.673 (m, 1H) 4.451-4.409 (t, J=5.6 Hz, 1H), 4.158-4.052 (m, 2H), 3.879-3.841 (m, 1H), 3.391 (s, 3H), 1.774 (s 3H); LC-MS: Rt=2.514 min, [M+H]$^+$=529.

Example 33

N-(4,4-difluorocyclohexyl)-6-{3-[5-(methoxymethyl)isoxazol-3-yl]-[1,2,4]triazolo[3,4-a]phthalazin-6-oxy)methylene}nicotinamide (33)

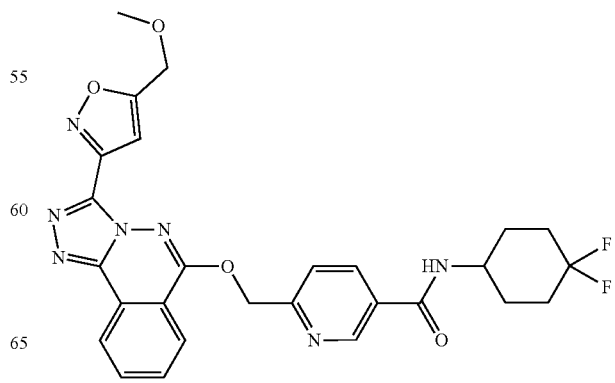

The experimental operation was as described in Example 3: the condensation reaction of compound 01 and 4,4-difluorocyclohexylamine hydrochloride (CAS: 675112-70-6) gave a white solid (36 mg, 23%).

¹H NMR (400 MHz, DMSO-d$_6$) δ 9.03 (s, 1H), 8.551 (t, J=8.2 Hz, 2H), 8.339 (d, J=8 Hz, 1H), 8.27-8.24 (m, 1H), 8.116 (t, J=7.2 Hz, 1H), 7.985 (t, J=7.4 Hz, 1H), 7.867 (d, J=8 Hz, 1H), 7.18 (s, 1H), 5.76 (s, 2H), 4.72-4.71 (m, 2H), 4.02-4.00 (m, 1H), 3.395 (s, 3H), 2.08-1.88 (m, 6H), 1.69-1.62 (m, 2H). LCMS: Rt=3.715 min, [M+H]$^+$=550.

Example 34

(4,4-difluoropiperidin-1-yl)(6-(((3-(5-methoxymethyl)isoxazol-3-yl)-[1,2,4]triazolo[3,4-a]phthalazin-6-yl)oxy)methylene)pyridin-3-yl)methanone (34)

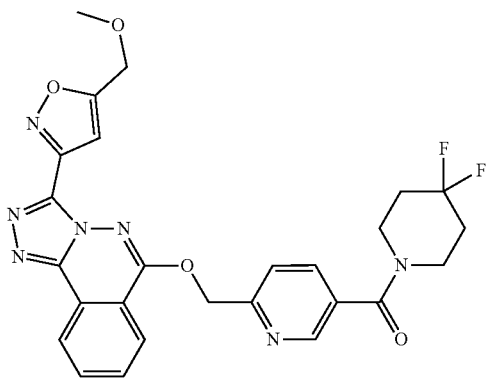 [SMILES: COCc1cc(-c2nnc3c4ccccc4c(OCc4ccc(C(=O)N5CCC(F)(F)CC5)cn4)nn23)no1]

The experimental operation was as described in Example 3: the condensation reaction of compound 01 and 4,4-difluoropiperidine hydrochloride (CAS: 144230-52-4) gave 48 mg of the target compound as a white solid with a yield of 55.3%.

¹H NMR (400 MHz, DMSO-d$_6$) δ ppm 8.71 (d, J=1.5 Hz, 1H), 8.59 (d, J=7.8 Hz, 1H), 8.37 (d, J=7.8 Hz, 1H), 8.16-8.10 (m, 1H), 8.02-7.94 (m, 2H), 7.83 (d, J=8.3 Hz, 1H), 7.22 (s, 1H), 5.76 (s, 2H), 4.72 (s, 2H), 3.74 (m, 2H), 3.51 (m, 2H), 3.43 (s, 3H), 2.12-1.99 (m, 4H); LC-MS: m/z (ES+) for C$_{26}$H$_{23}$F$_2$N$_7$O$_4$ 536 [M+1]$^+$.

Example 35

N-(3,3-difluoro-1-cyclopentylamino)-6-{3-[5-(methoxymethyl)isoxazol-3-yl]-[1,2,4]triazolo[3,4-a]phthalazin-6-oxy)methylene}nicotinamide (35)

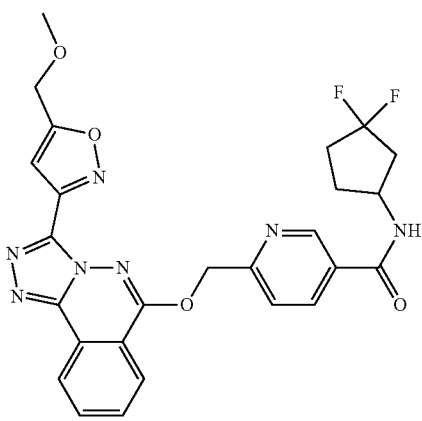 [SMILES: COCc1cc(-c2nnc3c4ccccc4c(OCc4ccc(C(=O)NC5CCC(F)(F)C5)cn4)nn23)no1]

The experimental operation was as described in Example 3: the condensation reaction of compound 01 and 3,3-difluoro-1-cyclopentylamine (CAS: 1462921-50-1) gave a white solid (19 mg, 13%).

¹H NMR (400 MHz, DMSO-d$_6$): δ 9.044 (s, 1H), 8.809-8.791 (d, J=7.2 Hz, 1H), 8.615-8.594 (d, J=8.4 Hz, 1H), 8.393-8.373 (d, J=8 Hz, 1H), 8.276-8.250 (m, 1H), 8.164-8.127 (t, J=4.9 Hz, 1H), 8.035-7.995 (t, J=5.3 Hz, 1H), 7.876-7.855 (d, J=8.4 Hz, 1H), 7.200 (s, 1H), 5.790 (s, 2H), 4.716 (s, 2H), 4.466-4.407 (m, 1H), 3.442-3.356 (br, 3H), 2.161-2.117 (m, 6H); LC-MS: Rt=3.650 min, [M+H]$^+$=536.

Example 36

6-(((3-(5-(methoxymethyl)isoxazol-3-yl)-[1,2,4]triazolo[3,4-a]peptidazine-6-yl)oxo)methyl)nicotinamide (36)

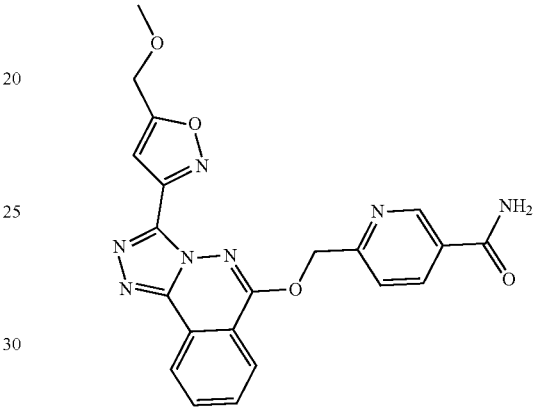

The experimental operation was as described in Example 3: the condensation reaction of compound 01 and ammonium chloride (CAS: 12125-02-9) gave 8.8 mg of the target compound as an off-white solid with a yield of 12.7%.

¹H NMR (400 MHz, DMSO-d$_6$) δ ppm 9.07 (s, 1H), 8.57 (d, J=7.8 Hz, 1H), 8.45-8.22 (m, 2H), 8.17-7.91 (m, 2H), 7.81 (d, J=8.3 Hz, 1H), 7.63 (s, 1H), 7.23-7.06 (m, 1H), 5.76 (br. s., 2H), 5.29 (s, 1H), 4.69 (s, 2H), 1.64 (s, 3H); LC-MS: m/z (ES+) for C21H17N7O4 432 [M+1]$^+$.

Example 37

6-[3-(5-Methoxymethyl-isoxazol-3-yl)-[1,2,4]triazolo[3,4-a]phthalazin-6-ylhydroxymethyl]-N,N-dimethyl-nicotinamide (37)

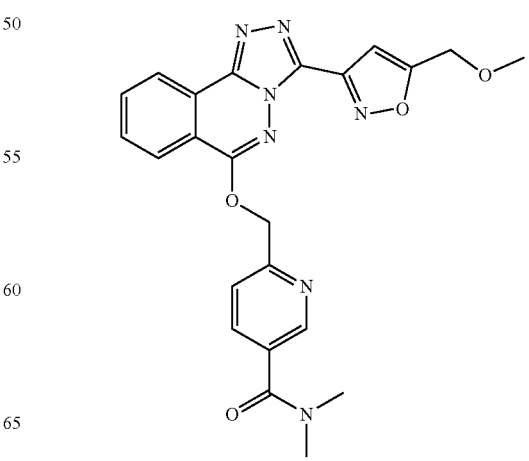

The experimental operation was as described in Example 3: the condensation reaction of compound 01 and dimethylamine (CAS: 124-40-3) gave 9.4 mg of the target compound as a white solid with a yield of 18%.

¹H NMR (400 MHz, CDCl₃) δ ppm 8.71 (d, J=8.71 Hz, 2H), 8.33 (d, J=7.70 Hz, 1H), 7.99 (t, J=7.13 Hz, 1H), 7.89-7.78 (m, 3H), 7.10 (s, 1H), 5.80 (s, 2H), 4.70 (s, 2H), 3.52 (s, 3H), 3.13 (s, 3H), 3.01 (s, 3H); LC-MS: m/z (ES+) for C₂₃H₂₁N₇O₄ 460 [M+1]⁺.

Example 38

{6-[3-(5-methoxymethyl-isoxazol-3-yl)-[1,2,4]triazolo[3,4-a]phthalazin-6-yloxymethyl]-pyridin-3-yl}-morpholin-4-methanone (38)

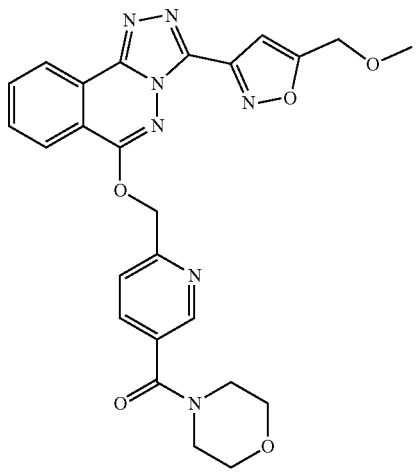 [SMILES: COCc1cc(-c2nnc3c4ccccc4c(OCc4ccc(C(=O)N5CCOCC5)cn4)nn23)no1]

The experimental operation was as described in Example 3: the condensation reaction of compound 01 and morpholine (CAS: 110-91-8) gave the target compound (14.9 mg) as a pale yellow solid with a yield of 12%, and the appearance was white solid.

¹H NMR (400 MHz, CDCl₃) δ ppm 8.71 (s, 2H), 8.33 (d, J=7.78 Hz, 1H), 7.98 (t, J=6.74 Hz, 1H), 7.81-7.84 (m, 3H), 7.10 (s, 1H), 5.79 (s, 2H), 4.69 (s, 2H), 3.97-3.55 (m, 6H), 3.54-3.35 (m, 5H); LC-MS: m/z (ES+) for C₂₅H₂₃N₇O₅ 502 [M+1]⁺.

Example 39

(2-oxa-6-azaspiro[3,3]heptanyl)(6-(((3-(5-methoxymethyl)isoxazol-3-yl)-[1,2,4]triazolo[3,4-a]phthalazin-6-yl)oxy)methylene)pyridin-3-yl)methanone (39)

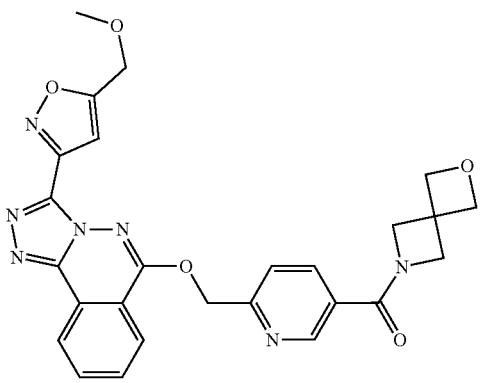 [SMILES: COCc1cc(-c2nnc3c4ccccc4c(OCc4ccc(C(=O)N5CC6(COC6)C5)cn4)nn23)no1]

The experimental operation was as described in Example 3: the condensation reaction of compound 01 and 2-oxa-6-azaspiro[3,3]heptane (CAS: 174-78-7) gave a white solid (50 mg, 9.6%) after preparative liquid phase chromatography.

¹H NMR (400 MHz, DMSO-d₆) δ 8.827 (d, J=2 Hz, 1H), 8.585 (d, J=8 Hz, 1H), 8.364 (d, J=8 Hz, 1H), 8.14-8.11 (m, 1H), 8.08-8.05 (m, 1H), 8.02-7.98 (m, 1H), 7.828 (d, J=8 Hz, 1H), 5.76 (s, 2H), 4.72 (s, 2H), 4.70-4.65 (m, 2H), 4.49 (s, 2H), 4.24 (s, 2H), 3.40 (s, 3H). LCMS: Rt=2.883 min, [M+H]⁺=514.

Example 40

N-methyl-N-(cyclopropylmethyl)-6-{3-[5-(methoxymethyl)isoxazol-3-yl]-[1,2,4]triazolo[3,4-a]phthalazin-6-oxy)methylene}nicotinamide (40)

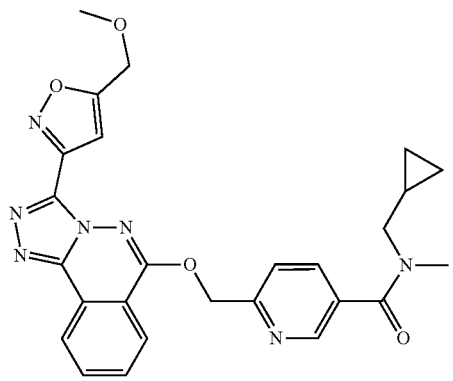 [SMILES: COCc1cc(-c2nnc3c4ccccc4c(OCc4ccc(C(=O)N(C)CC5CC5)cn4)nn23)no1]

The experimental operation was as described in Example 3: the condensation reaction was carried out with compound 01 and 1-cyclopropyl-N-methylmethylamine (CAS: 18977-45-2), the reaction mixture obtained was purified by RP-HPLC to give a white solid (40 mg, 29%).

¹H NMR (400 MHz, DMSO-d₆): 8.671-8.641 (m, 1H), 8.607-8.587 (d, J=8 Hz, 1H), 8.394-8.374 (d, J=8 Hz, 1H), 8.159-8.122 (t, J=7.4 Hz, 1H), 8.027-7.988 (t, J=7.8 Hz, 1H), 7.919 (s, 1H), 7.817-7.798 (d, J=7.6 Hz, 1H), 7.233-7.218 (m, 1H), 5.773 (s, 2H), 4.725 (s, 2H), 3.401 (s, 3H), 3.385 (m, 1H), 3.064-2.996 (m, 4H), 1.075-0.910 (m, 1H), 0.520-0.298 (m, 3H), 0.001 (m, 1H);

LC-MS: Rt=3.256 min, [M+H]⁺=500.

Example 41

(3-hydroxyazetidinyl)(6-(((3-(5-methoxymethyl)isoxazol-3-yl)-[1,2,4]triazole[3,4-a]phthalazin-6-yl)oxy)methylene)pyridin-3-yl)methanone (41)

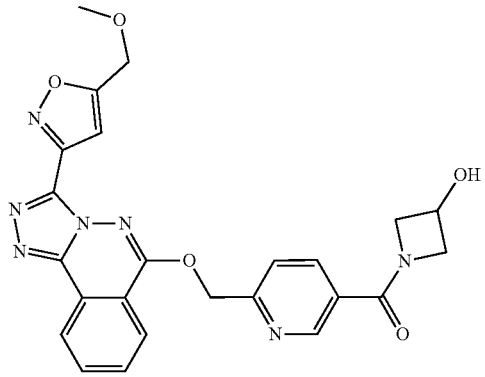 [SMILES: COCc1cc(-c2nnc3c4ccccc4c(OCc4ccc(C(=O)N5CC(O)C5)cn4)nn23)no1]

The experimental operation was as described in Example 3: the condensation reaction was carried out with compound 01 and azetidine-3-ol (CAS: 45347-82-8), the reaction mixture obtained was purified by RP-HPLC to give a white solid (40 mg, 16%).

¹H NMR (400 MHz, DMSO-d₆) δ 8.844 (d, J=1.6 Hz, 1H), 8.594 (d, J=8 Hz, 1H), 8.377 (d, J=7.6 Hz, 1H), 8.15-8.07 (m, 2H), 8.006 (t, J=7.8 Hz, 1H), 7.818 (d, J=8.4 Hz, 1H), 7.20 (s, 1H), 5.76 (s, 2H), 5.80-5.77 (m, 3H), 4.72 (s, 2H), 4.51-4.45 (m, 2H), 4.29-4.25 (m, 1H), 4.08-4.07 (m, 1H), 3.82-3.78 (m, 1H), 3.40 (s, 3H). LCMS: Rt=2.749 min, [M+H]⁺=488.

Example 42

(3-methoxyazetidinyl)(6-(((3-(5-methoxymethyl)isoxazol-3-yl)-[1,2,4]triazolo[3,4-a]phthalazin-6-yl)oxy)methylene)pyridin-3-yl)methanone (42)

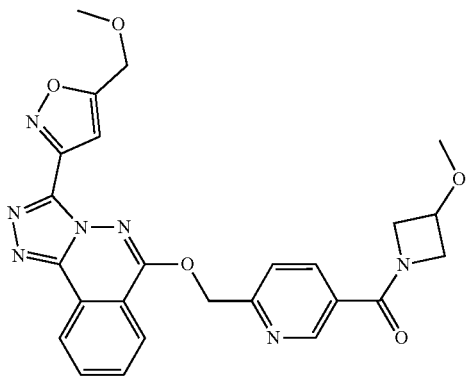 [SMILES: COCc1cc(-c2nnc3c4ccccc4c(OCc4ccc(C(=O)N5CC(OC)C5)cn4)nn23)no1]

The experimental operation was as described in Example 3: the condensation reaction was carried out with compound 01 and 3-methoxyazetidine (CAS: 110925-17-2), the reaction mixture obtained was purified by RP-HPLC to give a white solid. (40 mg, 16%).

¹H NMR (400 MHz, DMSO-d₆) δ 8.844 (d, J=1.6 Hz, 1H), 8.594 (d, J=8 Hz, 1H), 8.377 (d, J=7.6 Hz, 1H), 8.15-8.07 (m, 2H), 8.006 (t, J=7.8 Hz, 1H), 7.818 (d, J=8.4 Hz, 1H), 7.20 (s, 1H), 5.76 (s, 2H), 5.80-5.77 (m, 3H), 4.72 (s, 2H), 4.51-4.45 (m, 2H), 4.29-4.25 (m, 1H), 4.08-4.07 (m, 1H), 3.82-3.78 (m, 1H), 3.40 (s, 3H). LCMS: Rt=2.749 min, [M+H]⁺=488.

Example 43

((1S,4S)-3-oxo-2-oxa-5-azabicyclo[2.2.1]heptan-5-yl)(6-(((3-(5-methoxymethyl)isoxazol-3-yl)-[1,2,4]triazolo[3,4-a]phthalazin-6-yl)oxy)methylene)pyridin-3-yl)methanone (43)

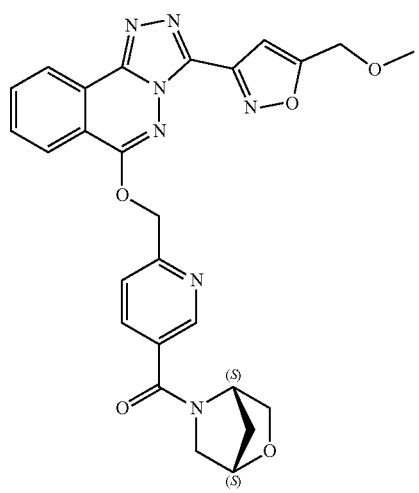

The experimental operation was as described in Example 3: the condensation reaction of compound 01 and bridged cyclic morpholine hydrochloride (CAS: 31560-06-2) gave 31.2 mg of the target compound as a light yellow solid with a yield of 33%.

¹H NMR (400 MHz, CDCl₃) δ ppm 8.80 (d, J=13.2 Hz, 1H), 8.70 (d, J=7.8 Hz, 1H), 8.34 (d, J=8.3 Hz, 1H), 8.03-7.80 (m, 4H), 7.10 (s, 1H), 5.80 (d, J=3.9 Hz, 2H), 5.06 (s, 0.5H), 4.74 (s, 0.5H), 4.70 (s, 2H), 4.61 (s, 0.5H), 4.40 (s, 0.5H), 4.09-3.94 (m, 1H), 3.92-3.78 (m, 1H), 3.72-3.57 (m, 1H), 3.52 (s, 3H), 3.47 (s, 1H), 2.05-1.89 (m, 2H); LC-MS: m/z (ES+) for C₂₆H₂₃N₇O₅ 514 [M+1]⁺.

Example 44

(2,6-dimethylmorpholinyl)(6-(((3-(5-methoxymethyl)isoxazol-3-yl)-[1,2,4]triazolo[3,4-a]phthalazin-6-yl)oxy)methylene)pyridin-3-yl)methanone (44)

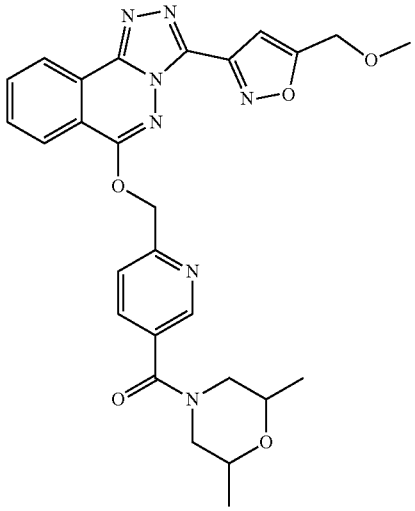 [SMILES: COCc1cc(-c2nnc3c4ccccc4c(OCc4ccc(C(=O)N5CC(C)OC(C)C5)cn4)nn23)no1]

The experimental operation was as described in Example 3: the condensation reaction of compound 01 and 2,6-dimethylmorpholine (CAS: 141-91-3) gave 19.7 mg of the target compound as a light yellow solid with a yield of 20%.

¹H NMR (400 MHz, CDCl₃) δ ppm 8.70 (s, 2H), 8.33 (d, J=7.8 Hz, 1H), 7.98 (t, J=7.3 Hz, 1H), 7.92-7.75 (m, 3H), 7.10 (s, 1H), 5.80 (s, 2H), 4.70 (s, 2H), 4.56 (m, 1H), 3.65 (m, 2H), 3.52 (s, 3H), 2.88 (m, 1H), 2.60 (m, 1H), 1.26 (s, 3H), 1.08 (s, 3H); LC-MS: m/z (ES+) for C₂₇H₂₇N₇O₅ 530 [M+1]⁺.

Example 45

(4-hydroxypiperidin-1-yl)-6-{3-[5-(methoxymethyl)isoxazol-3-yl]-[1,2,4]triazolo[3,4-a]phthalazin-6-oxy)methylene}pyridin-3-ylmethanone (45)

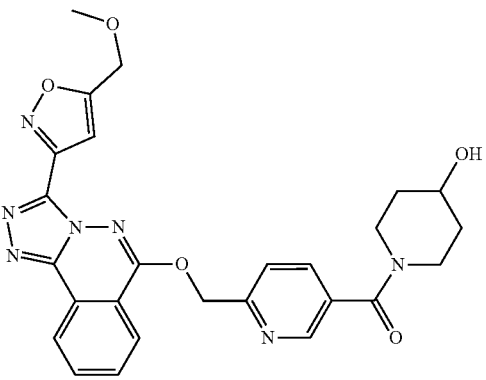 [SMILES: COCc1cc(-c2nnc3c4ccccc4c(OCc4ccc(C(=O)N5CCC(O)CC5)cn4)nn23)no1]

The experimental operation was as described in Example 3: the condensation reaction of compound 01 and 4-piperidinol (CAS: 5382-16-1) gave the target compound as a white solid (40 mg, 37%).

$^1$H NMR (400 MHz, DMSO-d$_6$) 8.644 (d, J=1.6 Hz, 1H), 8.589 (d, J=7.6 Hz, 1H), 8.373 (d, J=8 Hz, 1H), 8.15-8.11 (m, 1H), 8.01-7.98 (m, 1H), 7.91-7.89 (m, 1H), 7.807 (d, J=8.4 Hz, 1H), 7.22 (s, 1H), 5.76 (s, 2H), 4.82 (s, 1H), 4.72 (s, 2H), 4.01-3.98 (m, 1H), 3.74 (s, 1H), 3.53-3.46 (m, 1H), 3.40 (s, 3H), 3.26-3.25 (m, 1H), 3.15-3.12 (m, 1H), 1.83-1.66 (m, 2H), 1.43-1.32 (m, 2H). LCMS: Rt=2.788 min, [M+H]$^+$=516.

Example 46

(3,3-difluoroazetidin-1-yl)(6-(((3-(5-(methoxymethyl)isoxazol-3-yl)[1,2,4]triazolo[3,4-a]phthalazin-6-yl)oxy)methyl)pyridin-3-yl)methanone (46)

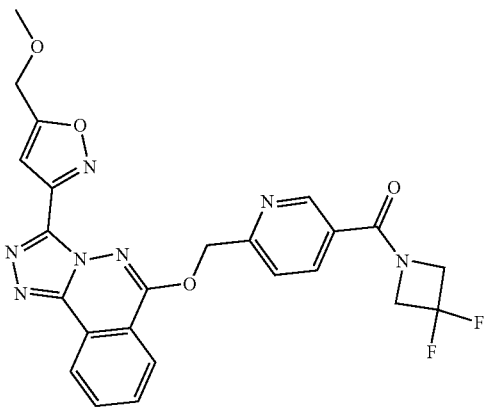 [SMILES: COCc1cc(-c2nnc3c4ccccc4c(OCc4ccc(C(=O)N5CC(F)(F)C5)cn4)nn23)no1]

The experimental operation was as described in Example 3: the condensation reaction of compound 01 and 3,3-difluoroazetidine hydrochloride (CAS: 288315-03-7) gave 35 mg of the target compound as a white solid with a yield of 42.7%.

1H NMR (400 MHz, DMSO-d$_6$) δ ppm 8.90 (d, J=2.0 Hz, 1H), 8.60 (d, J=7.8 Hz, 1H), 8.38 (d, J=7.8 Hz, 1H), 8.18-8.11 (m, 2H), 8.04-7.98 (m, 1H), 7.84 (d, J=8.3 Hz, 1H), 7.19 (s, 1H), 5.79 (s, 2H), 4.83 (s, 2H), 4.72 (m, 2H), 4.51 (m, 2H), 3.42 (s, 3H); LC-MS: m/z (ES+) for C24H19F2N7O4 508 [M+1]$^+$.

Example 47

(6-(((3-(5-(methoxymethyl)isoxazol-3-yl)-[1,2,4]triazolo[3,4-a]phthalazin-6-yl)oxy)methyl)pyridin-3-yl)(3-methylmorpholino)methanone (47)

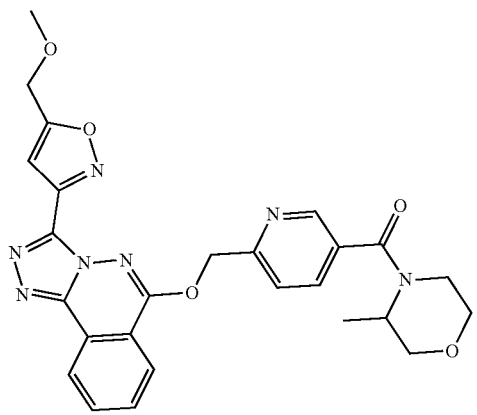 [SMILES: COCc1cc(-c2nnc3c4ccccc4c(OCc4ccc(C(=O)N5CCOCC5C)cn4)nn23)no1]

The experimental operation was as described in Example 3: the condensation reaction of compound 01 and 3-methylmorpholine (CAS: 42185-06-8) gave 36 mg of the target compound as a white solid with a yield of 43.1%.

$^1$H NMR (400 MHz, DMSO-d$_6$) δ ppm 8.67-8.63 (m, 1H), 8.57 (d, J=7.8 Hz, 1H), 8.35 (d, J=8.3 Hz, 1H), 8.15-8.09 (m, 1H), 8.02-7.96 (m, 1H), 7.92 (dd, J=2.0, 7.8 Hz, 1H), 7.81 (d, J=8.3 Hz, 1H), 7.21 (s, 1H), 5.75 (s, 2H), 4.71 (s, 2H), 3.78 (m, 1H), 3.61-3.53 (m, 2H), 3.49-3.41 (m, 3H), 3.33 (m, 4H), 1.25 (d, J=5.9 Hz, 3H); LC-MS: m/z (ES+) for C26H25N7O5 516 [M+1]$^+$.

Example 48

(tetrahydropyrrolyl)(6-(((3-(5-methoxymethyl)isoxazol-3-yl)-[1,2,4]triazolo[3,4-a]phthalazin-6-yl)oxy)methylene)pyridin-3-yl)methanone (48)

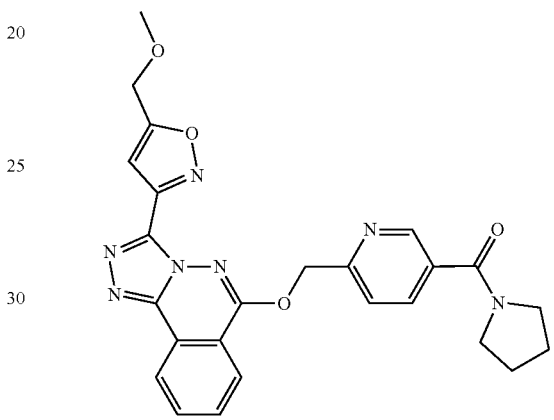

The experimental operation was as described in Example 3: the condensation reaction of compound 01 and pyrrolidine (CAS: 123-75-1) gave 14 mg of the target compound as a white solid with a yield of 17.8%.

$^1$H NMR (400 MHz, DMSO-d$_6$) δ ppm 8.76 (d, J=1.5 Hz, 1H), 8.59 (d, J=7.8 Hz, 1H), 8.37 (d, J=7.8 Hz, 1H), 8.17-8.10 (m, 1H), 8.04-7.97 (m, 2H), 7.80 (d, J=7.8 Hz, 1H), 7.20 (s, 1H), 5.76 (s, 2H), 4.72 (s, 2H), 3.51-3.45 (m, 4H), 3.43 (s, 3H), 1.90-1.80 (m, 4H); LC-MS: m/z (ES+) for C$_{25}$H$_{23}$N$_7$O$_4$ 486 [M+1]$^+$.

Example 49

(6-(((3-(5-(methoxymethyl)isoxazol-3-yl)-[1,2,4]triazolo[3,4-a]phthalazin-6-yl)oxy)methyl)pyridin-3-yl)(piperidin-1-yl)methanone (49)

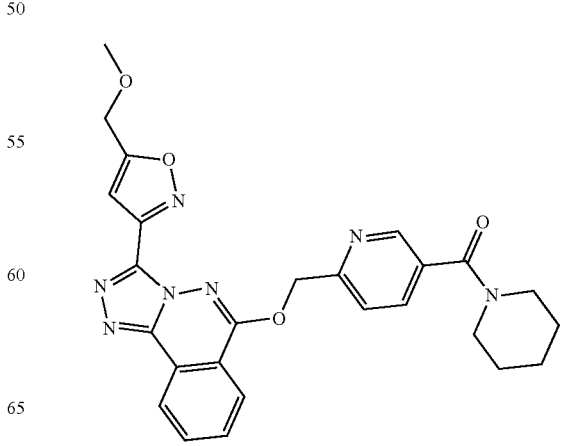

The experimental operation was as described in Example 3: the condensation reaction of compound 01 and piperidine (CAS: 110-89-4) gave 38 mg of the target compound as a white solid with a yield of 47.0%.

$^1$H NMR (400 MHz, DMSO-d$_6$) δ ppm 8.66-8.53 (m, 2H), 8.36 (d, J=8.3 Hz, 1H), 8.12 (t, J=7.6 Hz, 1H), 8.02-7.96 (m, 1H), 7.89 (dd, J=2.2, 8.1 Hz, 1H), 7.80 (d, J=8.3 Hz, 1H), 7.21 (s, 1H), 5.75 (s, 2H), 4.71 (s, 2H), 3.59 (m, 2H), 3.43 (s, 3H), 3.26 (d, J=4.9 Hz, 2H), 1.65-1.51 (m, 4H), 1.46 (m, 2H); LC-MS: m/z (ES+) for C$_{26}$H$_{25}$N$_7$O$_4$ 500 [M+1]$^+$.

Example 50

N-methyl-N-(cyclopropyl)-6-{3-[5-(methoxymethyl)isoxazol-3-yl]-[1,2,4]triazolo[3,4-a]phthalazin-6-oxy)methylene}nicotinamide (50)

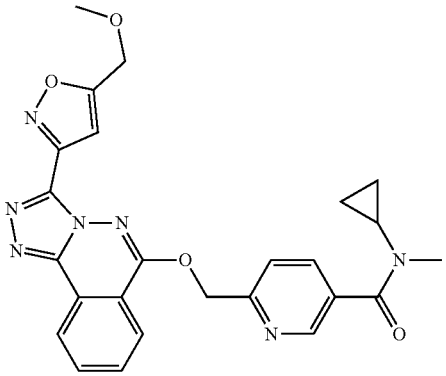 [SMILES: COCc1cc(-c2nnc3c4ccccc4c(OCc4ccc(C(=O)N(C)C5CC5)cn4)nn23)no1]

The experimental operation was as described in Example 3: the condensation reaction of compound 01 and N-methylcyclopropylamine (CAS: 5163-20-2) gave a white solid (32 mg, 29%).

$^1$H NMR (400 MHz DMSO-d$_6$): δ 8.752 (s, 1H), 8.611-8.592 (d, J=7.6 Hz, 1H), 8.399-8.380 (d, J=7.6 Hz, 1H), 8.163-8.122 (m, 1H), 8.031-7.990 (m, 2H), 7.791-7.771 (d, J=8.0 Hz, 1H), 7.231 (s, 1H), 5.779 (s 2H), 4.723 (s, 2H), 3.397 (s, 3H), 2.992-2.945 (m, 4H), 0.464-0.379 (m, 4H), 0.001 (m, 1H); LC-MS: Rt=3.141 min, [M+H]$^+$=486.

Example 51

(3,3-difluoropyrrolidinyl)(6-(((3-(5-methoxymethyl)isoxazol-3-yl)-[1,2,4]triazolo[3,4-a]phthalazin-6-yl)oxy)methylene)pyridin-3-yl)methanone (51)

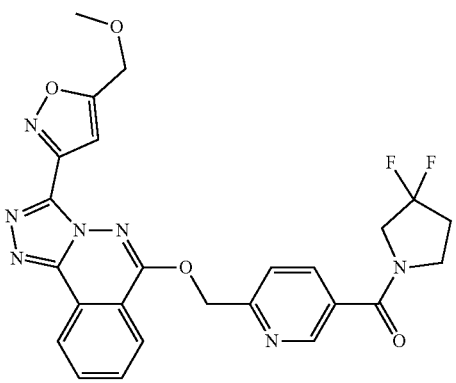 [SMILES: COCc1cc(-c2nnc3c4ccccc4c(OCc4ccc(C(=O)N5CCC(F)(F)C5)cn4)nn23)no1]

The experimental operation was as described in Example 3: the condensation reaction of compound 01 and 3,3-difluoropyrrolidine (CAS: 316131-01-8) gave the product (112 mg, 46.7%) as a white solid.

$^1$H NMR (400 MHz, DMSO-d$_6$): 8.81 (s, 1H), 8.58 (d, J=8.0 Hz, 1H), 8.36 (d, J=8.0 Hz, 1H), 8.15-8.11 (m, 1H), 8.08-8.05 (m, 1H), 8.02-7.98 (m, 1H), 7.83 (d, J=8.4 Hz, 1H), 7.20 (s, 1H), 5.77 (s, 2H), 4.72 (s, 2H), 3.98-3.89 (m, 2H), 3.76-3.68 (m, 2H), 3.40 (s, 3H), 2.47-2.41 (m, 2H). LC-MS: Rt=3.125 min, [M+H]$^+$=521.9.

Example 52

N,N-(Bis(2-methoxyethyl))-6-{3-[5-(methoxymethyl)isoxazol-3-yl]-[1,2,4]triazolo[3,4-a]phthalazin-6-oxy)methylene}nicotinamide (52)

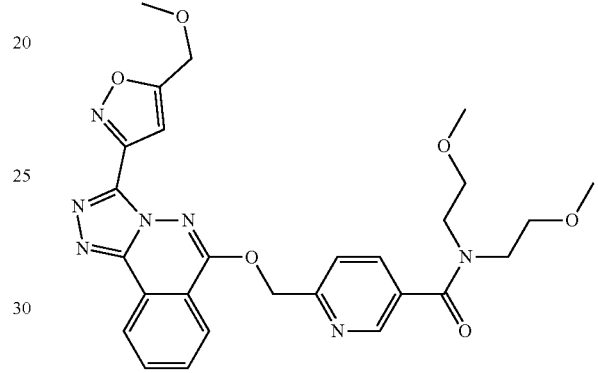

The experimental operation was as described in Example 3: the condensation reaction was carried out with compound 01 and bis(2-methoxyethyl)amine (CAS: 111-95-5), the reaction mixture obtained was separated and purified by prep-HPLC to give the product (33.9 mg, 29%) as a light yellow solid.

$^1$H NMR (400 MHz, DMSO-d$_6$): δ 8.71 (d, J=1.6 Hz, 1H), 8.58 (d, J=7.6 Hz, 1H), 8.36 (d, J=8.0 Hz, 1H), 8.15-8.11 (m, 1H), 8.01-8.00 (m, 1H), 7.89 (dd, J=8.0 Hz, J=2.0 Hz, 1H), 7.79 (d, J=7.6 Hz, 1H), 7.23 (s, 1H), 5.76 (s, 2H), 4.73 (s, 2H), 3.64-3.63 (m, 2H), 3.56-3.55 (m, 2H), 3.40-3.39 (m, 7H), 3.30 (s, 3H), 3.13 (s, 3H). LC-MS: Rt=3.432 min, [M+H]$^+$=548.1.

Example 53

(1-methyl-2-oxo-piperazinyl)(6-(3-(5-methoxymethyl)isoxazol-3-yl)-[1,2,4]triazolo[3,4-a]phthalazin-6-yl)oxy)methylene)pyridin-3-yl)methanone (53)

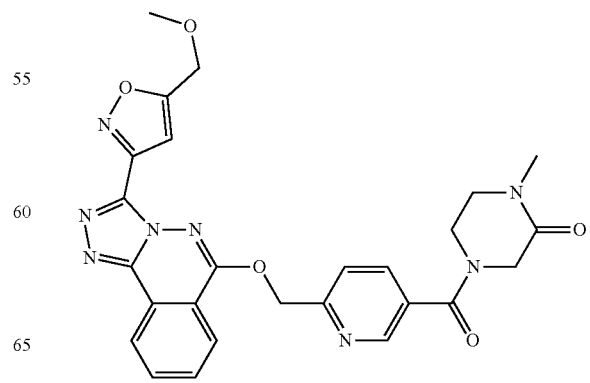

The experimental operation was as described in Example 3: the condensation reaction was carried out with compound 01 and 1-methylpiperazine-2-one (CAS: 59702-07-7), the reaction mixture was purified by preparative liquid phase chromatography to give a white solid. The reaction mixture was diluted with water, filtered, and the filter cake was purified with reversed phase column to give a white solid (50 mg, 41%). $^1$H NMR (400 MHz, DMSO-d$_6$) 8.719 (d, J=1.2 Hz, 1H), 8.577 (d, J=8 Hz, 1H), 8.36 (d, J=7.6 Hz, 1H), 8.14-8.10 (m, 1H), 8.01-7.97 (m, 2H), 7.839 (d, J=8.4 Hz, 1H), 7.20 (s, 1H), 5.76 (s, 2H), 4.72 (s, 2H), 4.16-4.00 (m, 2H), 3.87-3.59 (m, 2H), 3.44-3.40 (m, 5H), 2.87 (s, 3H). LCMS: Rt=2.782 min, [M+H]$^+$=529.

Example 54
(2-methylmorpholinyl)(6-(((3-(5-methoxymethyl)isoxazol-3-yl)-[1,2,4]triazolo[3,4-a]phthalazin-6-yl)oxy)methylene)pyridin-3-yl)methanone (54)

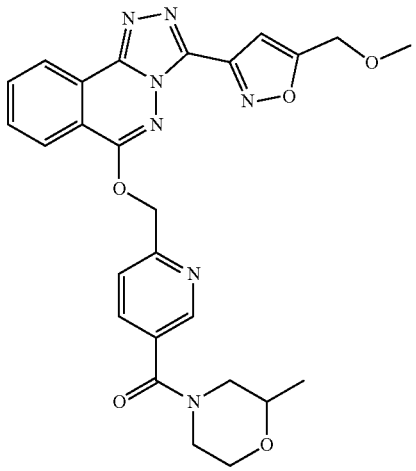 [SMILES: COCc1cc(-c2nnc3c4ccccc4c(OCc4ccc(C(=O)N5CCOC(C)C5)cn4)nn23)no1]

The experimental operation was as described in Example 3: the condensation reaction of compound 01 and 2-methylmorpholine (CAS: 27550-90-9) gave 30.0 mg of the target compound as an off-white solid with a yield of 31%.
$^1$H NMR (400 MHz, CDCl$_3$) δ ppm 8.75-8.68 (m, 2H), 8.34 (d, J=8.3 Hz, 1H), 8.00 (t, J=7.8 Hz, 1H), 7.92-7.79 (m, 3H), 7.11 (s, 1H), 5.81 (s, 2H), 4.71 (s, 2H), 4.66-4.40 (m, 1H), 4.11-3.76 (m, 1H), 3.73-3.41 (m, 7H), 3.36-2.62 (m, 1H), 1.26 (m, 3H); LC-MS: m/z (ES+) for C$_{26}$H$_{25}$N$_7$O$_5$ 516 [M+1]$^+$.

Example 55
(1,4-oxazepanyl)(6-(((3-(5-methoxymethyl)isoxazol-3-yl)-[1,2,4]triazolo[3,4-a]phthalazin-6-yl)oxy)methylene)pyridin-3-yl)methanone (55)

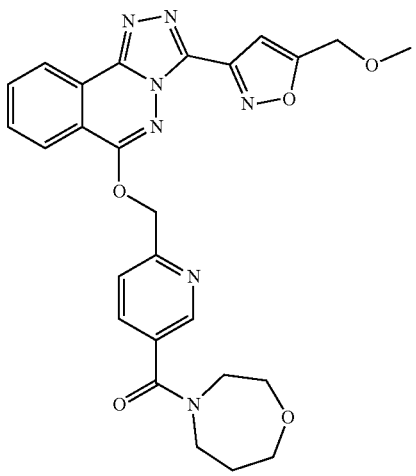 [SMILES: COCc1cc(-c2nnc3c4ccccc4c(OCc4ccc(C(=O)N5CCCOCC5)cn4)nn23)no1]

The experimental operation was as described in Example 3: the condensation reaction of compound 01 and homomorpholine (CAS: 5638-60-8) gave 14.0 mg of the target compound as an off-white solid with a yield of 15%.
$^1$H NMR (400 MHz, CDCl$_3$) δ ppm 8.72-8.57 (m, 2H), 8.31 (d, J=7.8 Hz, 1H), 8.02-7.92 (m, 1H), 7.90-7.74 (m, 3H), 7.09 (s, 1H), 5.77 (s, 2H), 4.67 (s, 2H), 3.92-3.70 (m, 5H), 3.70-3.61 (m, 1H), 3.57-3.50 (m, 2H), 3.49 (s, 3H), 2.03 (q, J=5.6 Hz, 1H), 1.81 (q, J=5.5 Hz, 1H); LC-MS: m/z (ES+) for C$_{26}$H$_{25}$N$_7$O$_5$ 516 [M+1]$^+$.

Example 56
{6-[3-(5-methoxymethyl-isoxazol-3-yl)-[1,2,4]triazolo[3,4-a]phthalazin-6-yloxymethyl]-pyridin-3-yl}-(2-oxa-7-aza-spiro[3.5]non-7-yl)-methanone (56)

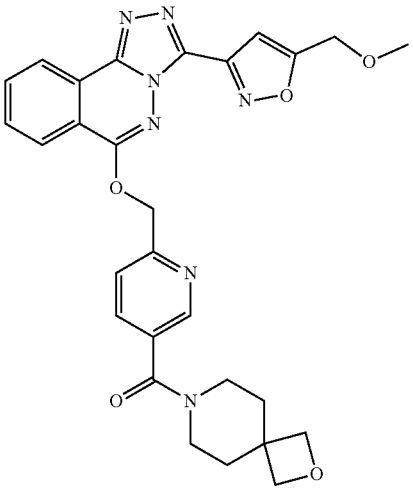 [SMILES: COCc1cc(-c2nnc3c4ccccc4c(OCc4ccc(C(=O)N5CCC6(CC5)COC6)cn4)nn23)no1]

The experimental operation was as described in Example 3: the condensation reaction of compound 01 and 2-oxa-7-azaspiro[3.5]nonane (CAS: 241820-91-7) gave 43.1 mg of the target compound as an off-white solid with a yield of 43%.
$^1$H NMR (400 MHz, DMSO-d$_6$) δ ppm 8.63 (s, 1H), 8.58 (d, J=7.3 Hz, 1H), 8.36 (d, J=8.3 Hz, 1H), 8.12 (t, J=6.8 Hz, 1H), 8.06-7.95 (m, 1H), 7.89 (d, J=7.3 Hz, 1H), 7.81 (d, J=7.8 Hz, 1H), 7.21 (s, 1H), 5.75 (s, 2H), 4.72 (s, 2H), 4.34 (m, 4H), 3.54 (s, 3H), 3.21 (m, 4H), 1.84 (m, 2H), 1.76 (m, 2H); LC-MS: m/z (ES+) for C$_{28}$H$_{27}$N$_7$O$_5$ 542 [M+1]$^+$.

Example 57
(6-(((3-(5-(methoxymethyl)isoxazol-3-yl)-[1,2,4]triazolo[3,4-a]phthalazin-6-yl)oxy)methyl)pyridin-3-yl)(4-methoxypiperidin-1-yl)methanone (57)

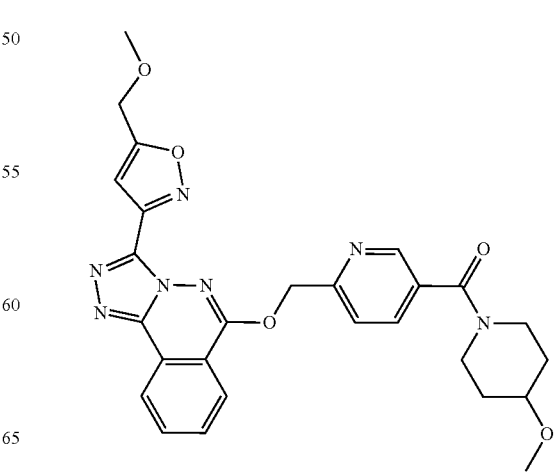

The experimental operation was as described in Example 3: the condensation reaction of compound 01 and 4-methoxypiperidine (CAS: 4045-24-3) gave 31 mg of the target compound as a white solid with a yield of 36.1%.

$^1$H NMR (400 MHz, DMSO-$d_6$) δ ppm 8.67-8.62 (m, 1H), 8.56 (d, J=7.8 Hz, 1H), 8.35 (d, J=8.3 Hz, 1H), 8.11 (t, J=7.3 Hz, 1H), 7.98 (t, J=7.6 Hz, 1H), 7.91 (dd, J=2.0, 7.8 Hz, 1H), 7.80 (d, J=7.8 Hz, 1H), 7.20 (s, 1H), 5.74 (s, 2H), 4.71 (s, 2H), 3.98-3.84 (m, 1H), 3.46 (s, 3H), 3.37-3.28 (m, 3H), 3.25 (s, 3H), 3.15 (m, 1H), 1.94-1.82 (m, 1H), 1.77 (m, 1H), 1.48 (m, 1H), 1.42 (m, 1H); LC-MS: m/z (ES+) for $C_{27}H_{27}N_7O_5$ 530 [M+1]$^+$.

Example 58

N-methyl-N-(2,2,2-trifluoroethyl)-6-{3-[5-(methoxymethyl)isoxazol-3-yl]-[1,2,4]triazolo[3,4-a]phthalazin-6-oxy)methylene}nicotinamide (58)

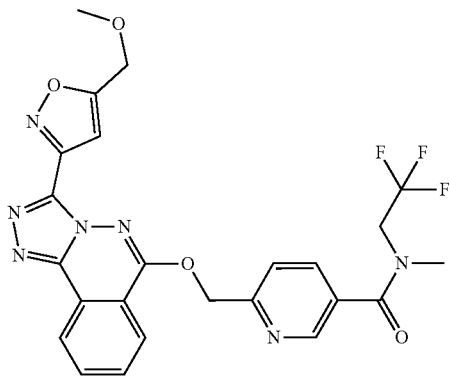 [SMILES: COCc1cc(-c2nnc3c4ccccc4c(OCc4ccc(C(=O)N(C)CC(F)(F)F)cn4)nn23)no1]

The experimental operation was as described in Example 3: the condensation reaction was carried out with compound 01 and N-methyl-2,2,2-trifluoroethylamine (CAS: 2730-67-8), the reaction mixture obtained was separated and purified by prep-HPLC to give the product (50 mg, 40%) as a white solid. $^1$H NMR (400 MHz, DMSO-$d_6$): δ 8.71 (s, 1H), 8.58 (d, J=8.0 Hz, 1H), 8.37 (d, J=8.0 Hz, 1H), 8.15-8.11 (m, 1H), 8.02-8.00 (m, 2H), 7.83 (d, J=8.0 Hz, 1H), 7.20 (s, 1H), 5.78 (s, 2H), 4.72 (s, 2H), 4.40-4.18 (m, 2H), 3.40 (s, 3H), 3.05 (s, 3H). LC-MS: Rt=3.412 min, [M+H]$^+$=528.1.

Example 59

N-ethyl-6-((3-(5-methoxymethylisoxazol-3-yl)-[1,2,4]triazolo[3,4-a]phthalazin-6-oxy)methylene)isonicotinamide (59)

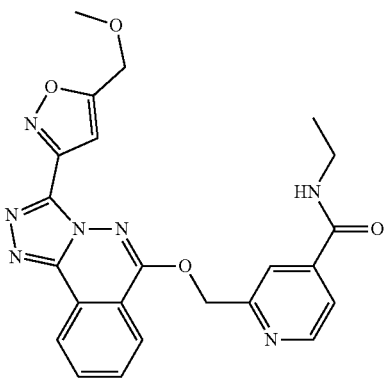

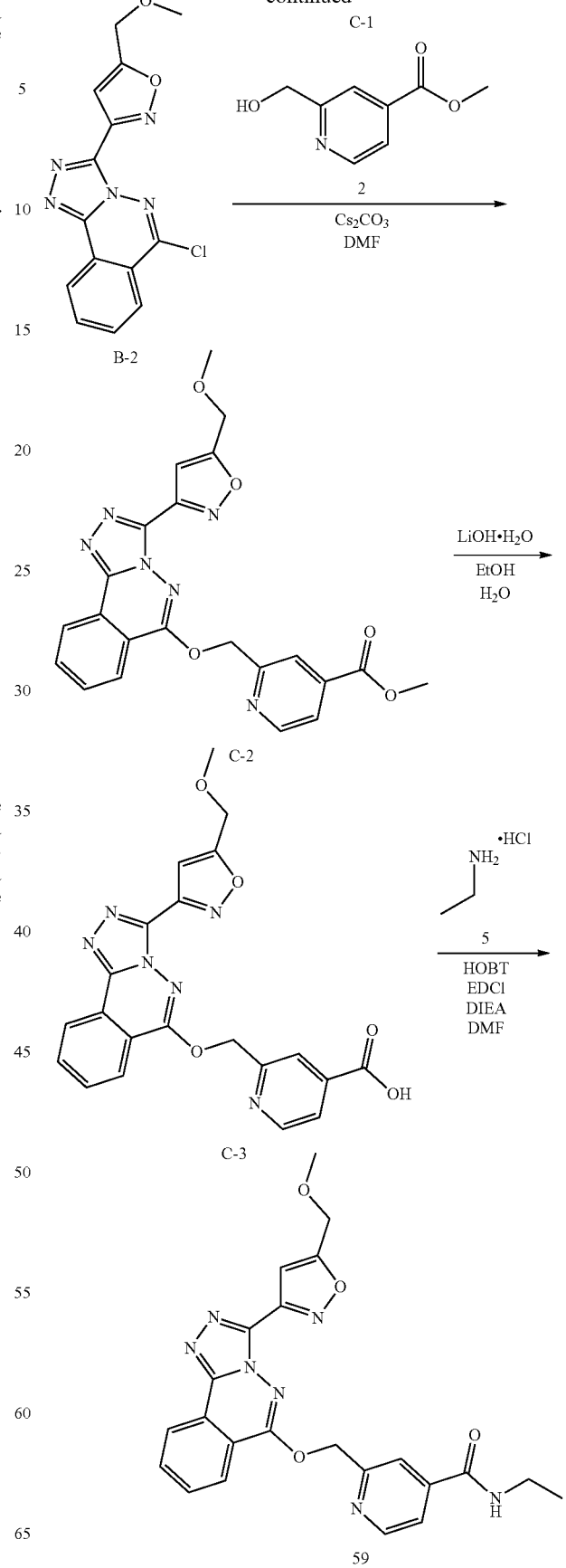

Experimental Process:

Step 1:

Raw materials B-2 (630 mg, 2.0 mmol), C-1 (CAS: 58481-17-7) (334 mg, 2.0 mmol) and Cs₂CO₃ (1.30 g, 4.0 mmol) were sequentially added into DMF (10 mL). The reaction was allowed to run at room temperature overnight. After the completion of the reaction, the reaction mixture was poured into ice water (100 mL), and the resulting precipitate was collected by filtration, washed with water three times to give the product A1 (760 mg, 85.2%) as a yellow solid C-2.

$^1$H NMR (400 MHz, CDCl₃): δ 8.83-8.82 (m, 1H), 8.71 (d, J=8.0 Hz, 1H), 8.35 (d, J=8.0 Hz, 1H), 8.30 (s, 1H), 8.01-7.97 (m, 1H), 7.88-7.84 (m, 2H), 7.11 (s, 1H), 5.84 (s, 2H), 4.71 (s, 2H), 3.96 (s, 3H), 3.51 (s, 3H). LC-MS: Rt=1.43 min, [M+H]⁺=447.

Step 2:

An aqueous solution of lithium hydroxide monohydrate (150 mg, 3.6 mmol, in 4 mL of water) was added into a suspension of C-2 (400 mg, 0.9 mmol) in ethanol (10 mL). Then, the mixture was stirred at room temperature for 1 hour. After the reaction was complete, the reaction mixture was poured into ice water (20 mL) and the pH value was adjusted to 3-4 with 1 N HCl. The precipitated solid was filtered, collected, and washed with water for three times, then dried to give product C-3 as a white solid (360 mg, 92.6%).

1H NMR (400 MHz, DMSO-d₆): δ 8.83-8.82 (m, 1H), 8.59 (d, J=7.6 Hz, 1H), 8.31 (d, J=7.6 Hz, 1H), 8.16-8.12 (m, 2H), 8.03-8.01 (m, 1H), 7.83-7.81 (m, 1H), 7.26 (s, 1H), 5.82 (s, 2H), 4.72 (s, 2H), 3.40-3.36 (m, 3H). LC-MS: Rt=1.12 min, [M+H]⁺=433.

Step 3:

N-ethyl-6-((3-(5-methoxymethylisoxazol-3-yl)-[1,2,4]triazolo[3,4-a]phthalazin-6-oxy)methylene)isonicotinamide (59)

The experimental operation was as described in Example 3: the condensation reaction was carried out with intermediate C-3 and ethylamine hydrochloride (CAS: 557-66-4), and the reaction mixture obtained was separated and purified by prep-HPLC to give the product (82 mg, 50.9%) as a white solid.

$^1$H NMR (400 MHz, DMSO-d₆): δ 8.83-8.80 (m, 1H), 8.77 (d, J=4.0 Hz, 1H), 8.58 (d, J=8.0 Hz, 1H), 8.34 (d, J=8.4 Hz, 1H), 8.15-8.11 (m, 1H), 8.05 (s, 1H), 8.02-7.98 (m, 1H), 7.76-7.75 (m, 1H), 7.25 (s, 1H), 5.78 (s, 2H), 4.72 (s, 2H), 3.40 (s, 3H), 3.30-3.27 (m, 2H), 1.14-1.11 (m, 3H). LC-MS: Rt=3.000 min, [M+H]⁺=460.

Example 60

N-ethyl-6-((3-(5-methoxymethylisoxazol-3-yl)-[1,2,4]triazolo[3,4-a]phthalazin-6-oxy)methylene)picolinamide (60)

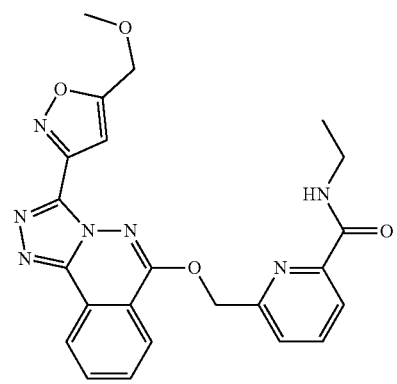

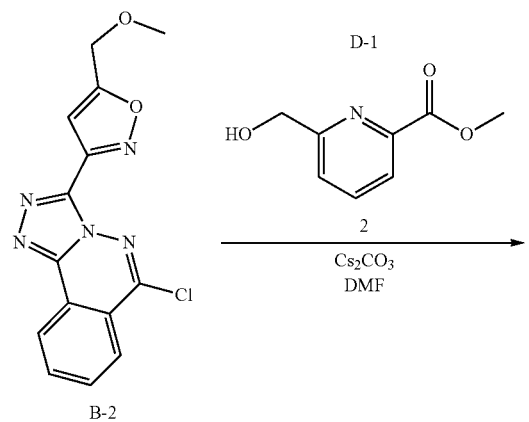

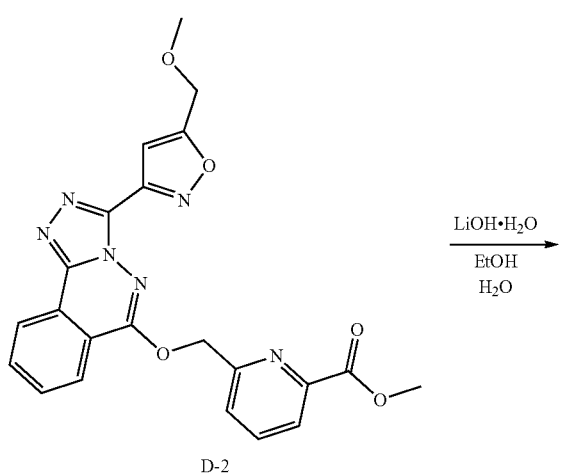

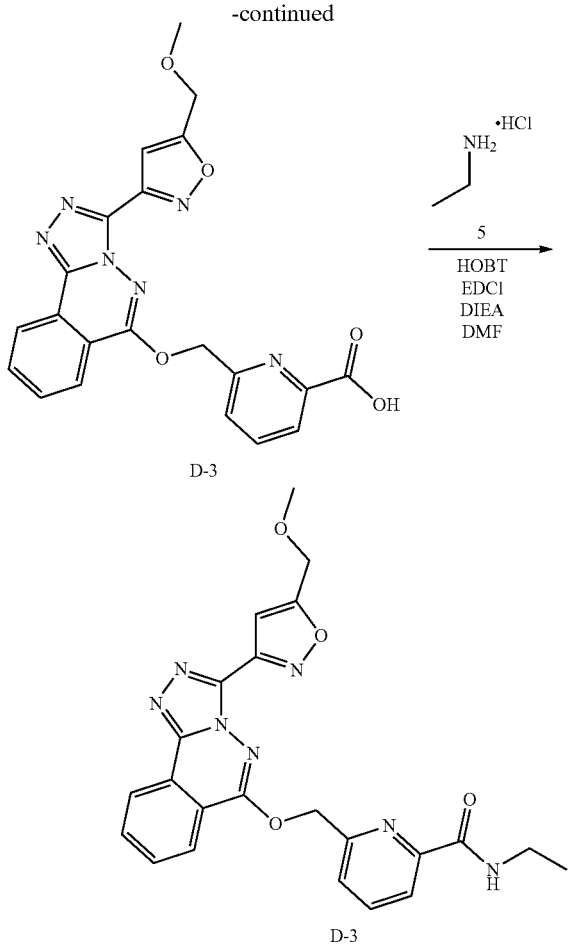

Experimental Process:
Step 1:
The experimental operation was as described in Example 59: Intermediate B-2 and D-1 (CAS: 39977-44-1) were reacted to give the product D-2 (900 mg, crude) as a yellow solid.

$^1$H NMR (400 MHz, CDCl$_3$): δ 8.70 (d, J=8.0 Hz, 1H), 8.32 (d, J=8.0 Hz, 1H), 8.14 (d, J=8.0 Hz, 1H), 8.04-7.93 (m, 3H), 7.87-7.83 (m, 1H), 7.09 (s, 1H), 5.87 (s, 2H), 4.71 (s, 2H), 4.04 (s, 3H), 3.51 (s, 3H). LC-MS: Rt=1.41 min, [M+H]$^+$=447.

Step 2:
The experimental operation was as described in Example 59: Intermediate D-2 was hydrolyzed with LiOH to give the product D-3 (212 mg, 54.5%) as a white solid.

$^1$H NMR (400 MHz, DMSO-d$_6$): δ 8.56 (d, J=8.4 Hz, 1H), 8.31 (d, J=8.4 Hz, 1H), 8.13-8.06 (m, 1H), 8.04-7.98 (m, 2H), 7.98-7.93 (m, 2H), 7.22 (s, 1H), 5.79-5.76 (m, 2H), 3.44-3.35 (m, 3H). LC-MS: Rt=1.07 min, [M+H]$^+$=433.

Step 3:

N-ethyl-6-((3-(5-methoxymethylisoxazol-3-yl)-[1,2,4]triazolo[3,4-a]phthalazin-6-oxy)methylene)picolinamide (60)

The experimental operation was as described in Example 3: the condensation reaction was carried out with intermediate D-3 and ethylamine hydrochloride (CAS: 557-66-4), the reaction mixture obtained was separated and purified by prep-HPLC to give the product 60 (44 mg, 20.8%) as a white solid.

$^1$H NMR (400 MHz, DMSO-d$_6$): δ 8.78-8.75 (m, 1H), 8.59 (d, J=8.0 Hz, 1H), 8.36 (d, J=8.0 Hz, 1H), 8.15-7.97 (m, 5H), 7.16 (s, 1H), 5.78 (s, 2H), 4.69 (s, 2H), 3.37-3.36 (m, 3H), 3.33-3.31 (m, 2H), 1.15-1.11 (m, 3H). LC-MS: Rt=3.083 min, [M+H]$^+$=460.

Effect Embodiment 1

Biological Experiment Method:
Previous studies have revealed that the GABA$_A$ receptors mediate at least two modes of inhibition, the phasic inhibition and the tonic inhibition. When the GABA increases to the millimole level, the GABA$_A$ receptors will be desensitized rapidly, show low affinity for GABA and mediate phasic inhibition. When the GABA activates GABA$_A$ receptors at tens of micromole or hundreds of nano mole level, the high affinity extrasynaptic GABA$_A$ receptors will mediate tonic inhibition and regulate neuronal excitability and signal transmission (Farrant M et al. (2005) Variations on an inhibitory theme: phasic and tonic activation of GABA(A) receptors. Nat Rev Neurosci 6: 215-229Y). Yeung J Y et al reported that the α5-GABA$_A$ receptor can be activated preferably by low level of GABA (Yeung J Y et al (2003). Tonically activated GABA$_A$ receptors in hippocampal neurons are high-affinity, low-conductance sensors for extracellular GABA. Mol Pharmacol; 63: 2-8). K. Y LEE et al reported that the sustainable high-affinity GABA$_A$ current induced by low level GABA is detected in dissociated cultured DRG neurons cultured for 24 hours and 20 μM of GABA can induce about 100 pA/pF high-affinity GABA$_A$ current (Lee K Y et al. Upregulation of high-affinity GABA (A) receptors in cultured rat dorsal root ganglion neurons. Neuroscience 208 (2012) 133-142). In 2013, I. Lecker et al reported that L-655,708, an α5-GABA$_A$ specific inverse agonist, inhibited the current included by low level GABA (5, 50 and 500 nM) in the concentration dependent manner. When the GABA concentration is increased to 1 μM, the inhibition efficacy of the highest dose of L-655,708 is only 15%. When the GABA concentration is higher, there is even no inhibition of L-655,708 on the current induced by GABA (I. Lecker et al (2013). Potentiation of GABA$_A$ receptor activity by volatile anaesthetics is reduced by α5-GABA$_A$ receptor-preferring inverse agonists. British Journal of Anaesthesia 110 (S1): i73-i81).

Cell-Level Screening
The inventors used electrophysiological methods to determine the inverse agonist efficacy of the substances to be tested. The detailed procedures are as follows:
(1) Different subunits of GABA$_A$ receptors were expressed in human embryonic kidney cells 293 (HEK293). The cells were cultured in a culture medium and used as a cell model for screening potential analgesics. The α, β and γ subunits are necessary to form complete functional GABA$_A$ receptors. In this example, the inventors have established the following cell model: (a) α5 subunit (protein sequence is GenBank accession number: NM_000810.3), (β3 subunit (protein sequence is GenBank accession number: NM_000814.5) and γ2 subunit (protein sequence is GenBank accession number: NM_000816.3) were expressed in HEK-293 cell line at the same time, followed by screening the monoclonal cell line. This cell line contained α5-GABA$_A$ receptor and had complete GABA$_A$ receptor function.
(2) The monoclonal stably transfected HEK-293 cells expressing α5-GABA$_A$ receptor were cultured in 10 cm culture dishes. The cells were passaged after reaching 80-90% confluence. During passaging, the culture medium was removed and discarded, 3 mL of DPBS (phosphate buffered saline, Gibco™) was added to the dishes, the dishes were shaken slightly, and DPBS was removed and discarded. 1 mL of trypsin (TrypLE Express, Gibco™) was added and the cells were digested at 37° C. for 1-2 minutes. Then 3 mL of complete medium (DMEM+10% FBS (Gibco™)) was added and the cells at the bottom of the culture dishes were dispersed. The cell suspension were transferred to a 15 mL centrifugal tube (Corning™) and then centrifuged at 200 g for 3 minutes. The supernatant was discarded, 4 mL of complete medium was added, and the cells were resuspended by gently blowing. The cell suspension was diluted by 1:5 or 1:10 for subculturing. The cell suspension was diluted by 1:12 for electrophysiology experiment, and added to a 24 well plate (Corning™) with a glass slide pre-treated with poly-D-lysine placed thereon; the experiment was initiated after the cells were adhered to the slide. The cells for electrophysiology experiment were maintained in culture for no more than 48 hours before use.

(3) Compound concentration: for screening, all compounds were diluted to a final concentration of 100 nM and the concentration of GABA was 0.05 µM. The compounds were at the concentration of 0.3 nM, 3 nM, 10 nM, 30 nM, 100 nM and 300 nM in dose-inverse agonism efficacy (%) experiment. The whole cell patch clamp technique was used in electrophysiology experiments, which can refer to the literature (I. Lecker, Y. Yin, D. S. Wang and B. A. Orser, (2013) Potentiation of $GABA_A$ receptor activity by volatile anaesthetics is reduced by α5-$GABA_A$ receptor-preferring inverse agonists, *British Journal of Anaesthesia* 110 (S1): i73-i81). The extracellular solution (ECS) contained: 150 mM NaCl, 5 mM KCl, 2.5 mM $CaCl_2$, 1 mM $MgCl_2$, 10 mM HEPES and 10 mM glucose (pH 7.4); Patch electrodes were filled with an intracellular solution containing: 140 mM CsCl, 11 mM EGTA, 10 mM HEPES, 2 mM $CaCl_2$, 1 mM $MgCl_2$, 4 mM MgATP, 2 mM TEA (pH 7.3). The currents were recorded by an EPC-10 amplifier and the PatchMaster software (HEKA). Patch electrodes with a resistance of 4-6 MΩ were pulled from borosilicate glass. The ALA-VC3-8PP™ system was used for extracellular administration. Separate cells that grew independently was selected for recording. During recording, the membrane voltage was clamped at −60 mV. During experiment, the cells were firstly perfused with ECS for 20 seconds. When the baseline reached to a stable state, the cells were then perfused with GABA solution. Then the current induced by GABA could be detected. After about 20 to 40 seconds, the current was stable. ECS was switched to compounds solution and the effects of the compounds were detected. At last, the perfusion solution was switched to ECS. The experiment was finished when the post-baseline returned to the pre-baseline before compounds perfusion. Only data whose baseline are less than −120 pA and can be recovered after drug administration will be used for analysis. GABA was diluted at a final concentration of 0.05 µM in ECS. Then, compounds were diluted at the desired concentration in GABA ECS.

(4) Currents were analyzed with the PatchMaster software. The leakage currents ($I_{leak}$), the GABA currents before ($I_{pre}$) and after ($I_{post}$) compounds perfusion were recorded respectively. The effects of compounds were calculated by the following equation: inverse agonism efficacy (%)=100−100*($I_{post}$−$I_{leak}$)/($I_{pre}$−$I_{leak}$). N indicates the number of the experiments.

Example 7 in CN106854207A was used as the reference compound during compound screening, and the activity results were expressed as the ratio of the inverse agonism efficacy of the compound to the inverse agonism efficacy of the reference compound in the same batch of experiments. The inverse agonism efficacy of the reference compound was between 40% and 60%, with N>20.

(6) The screening results of the compounds are shown in Table 1.

TABLE 1

| Compound No. | Inverse agonism efficacy of the compound/inverse agonism efficacy of the reference compound (%) | N |
| --- | --- | --- |
| 02 | 78.0 | 2 |
| 03 | 92.1 | 4 |
| 05 | 90.0 | 3 |
| 06 | 74.9 | 5 |
| 07 | 107.7 | 3 |
| 08 | 110.3 | 3 |
| 10 | 102.9 | 3 |
| 11 | 106.0 | 4 |
| 12 | 94.03 | 3 |
| 17 | 105.1 | 3 |
| 18 | 114.84 | 3 |
| 20 | 118.1 | 3 |
| 23 | 73.73 | 3 |
| 28 | 133.41 | 2 |
| 30 | 85.25 | 3 |
| 31 | 95.1 | 3 |
| 32 | 89.12 | 3 |
| 37 | 72.1 | 4 |
| 38 | 93.4 | 2 |
| 39 | 90.21 | 3 |
| 40 | 78.26 | 3 |
| 42 | 73.3 | 3 |
| 43 | 86.9 | 3 |
| 45 | 88.4 | 4 |
| 46 | 94.6 | 3 |
| 47 | 72.46 | 3 |
| 48 | 78.68 | 3 |
| 49 | 75.24 | 3 |
| 54 | 77.55 | 3 |
| 56 | 110.86 | 3 |

Effect Example 2: Solubility of the Compounds

Experimental Materials and Instrument:

50 mM phosphate buffer pH=7.4: 0.39 g of $NaH_2PO_4 \cdot 2H_2O$, and 1.4025 g of $Na_2HPO_4$ were weighted and placed in an erlenmeyer flask, 240 mL of water was added. The solid was dissolved and mixed thoroughly, the pH value was adjusted to 7.4 with 10M NaOH solution, and the resulting solution was transferred to a 250 mL volumetric flask, followed by adding water to the mark.

Waters e2695 HPLC high performance liquid chromatography, Mettler XSE105 analytical balance.

Experimental Method:

Firstly, a 10 mM stock solution with DMSO as the solvent was prepared, and was diluted with a diluent (ACN: PB buffer 50:50) into 1 µM-200 µM as standard solution.

Kinetic solubility. 30 µL of the stock solution was placed in a 2 mL centrifuge tube, 1470 µL of 50 mM phosphate buffer (pH 7.4) (containing DMSO at a final concentration of 2%) was added. The mixture was shaken at room temperature (1000 rpm/min) for 24 hours, and then filtered. The filtrate was tested by high performance liquid chromatography (UV). The results are shown in Table 2.

Thermodynamic solubility. About 1 mg of the sample was weighted, 1.5 mL of 50 mM phosphate buffer (pH 7.4) was added thereto, and the mixture was shaken at room temperature for 24 hours to ensure that the solution reached a state of saturation. The solution was then filtered, and the filtrate was tested with high-performance liquid chromatography (UV). The results are shown in Table 2.
TABLE 2
| Compound No. | Kinetic solubility μg/mL | Thermodynamic solubility μg/mL |
|---|---|---|
| 02 | 8.02 | 3.39 |
| 04 | 13.13 | |
| 05 | 25.55 | |
| 06 | 13.63 | |
| 07 | 23.22 | |
| 09 | 27.69 | |
| 10 | 18.94 | |
| 11 | 9.23 | 4.40 |
| 12 | 10.89 | 9.05 |
| 13 | 0.57 | |
| 14 | 35.66 | |
| 15 | 0.77 | 0.84 |
| 16 | 49.35 | |
| 18 | 10.75 | |
| 19 | 1.06 | |
| 20 | 10.14 | |
| 21 | 1.18 | |
| 22 | 8.92 | |
| 23 | 9.11 | |
| 24 | 1.39 | 0.74 |
| 25 | 2.71 | |
| 26 | 20.34 | |
| 27 | 5.58 | |
| 28 | 3.68 | |
| 30 | 6.85 | |
TABLE 2-continued
| Compound No. | Kinetic solubility μg/mL | Thermodynamic solubility μg/mL |
|---|---|---|
| 31 | 4.19 | |
| 32 | 29.73 | |
| 33 | 2.99 | |
| 34 | 4.60 | 4.40 |
| 35 | 5.62 | |
| 36 | 0.80 | |
| 37 | 91.90 | 84.73 |
| 38 | 17.75 | 8.7 |
| 39 | 48.45 | |
| 40 | 31.94 | |
| 41 | 6.57 | |
| 42 | 5.89 | 6.02 |
| 43 | 100.27 | |
| 44 | 74.57 | |
| 45 | 6.93 | |
| 47 | 97.8 | |
| 48 | 31.71 | |
| 50 | 3.75 | |
| 51 | 5.62 | |
| 52 | 51.86 | |
| 53 | 28.03 | |
| 54 | 97.92 | |
| 55 | 101.72 | |
| 56 | 12.5 | |
| 57 | 26.49 | |
| 58 | 1.46 | |
TABLE 3
| Compound No. | Kinetic solubility μg/mL | Thermodynamic solubility μg/mL |
|---|---|---|
| 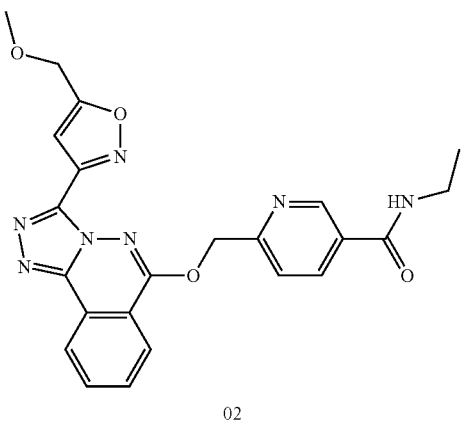 [SMILES: CCNC(=O)c1ccc(COc2nn3c(-c4cc(COC)on4)nnc3c3ccccc23)nc1] 02 | 8.02 | 3.39 |
| 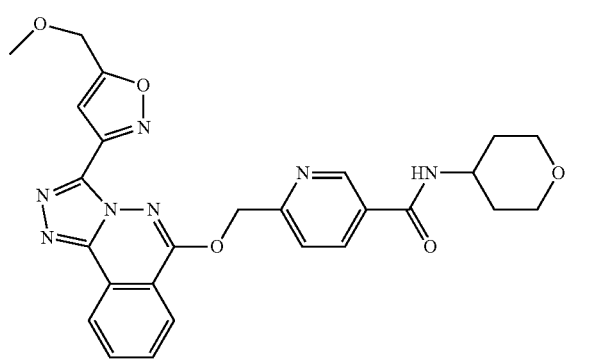 04 | 13.13 | |

TABLE 3-continued
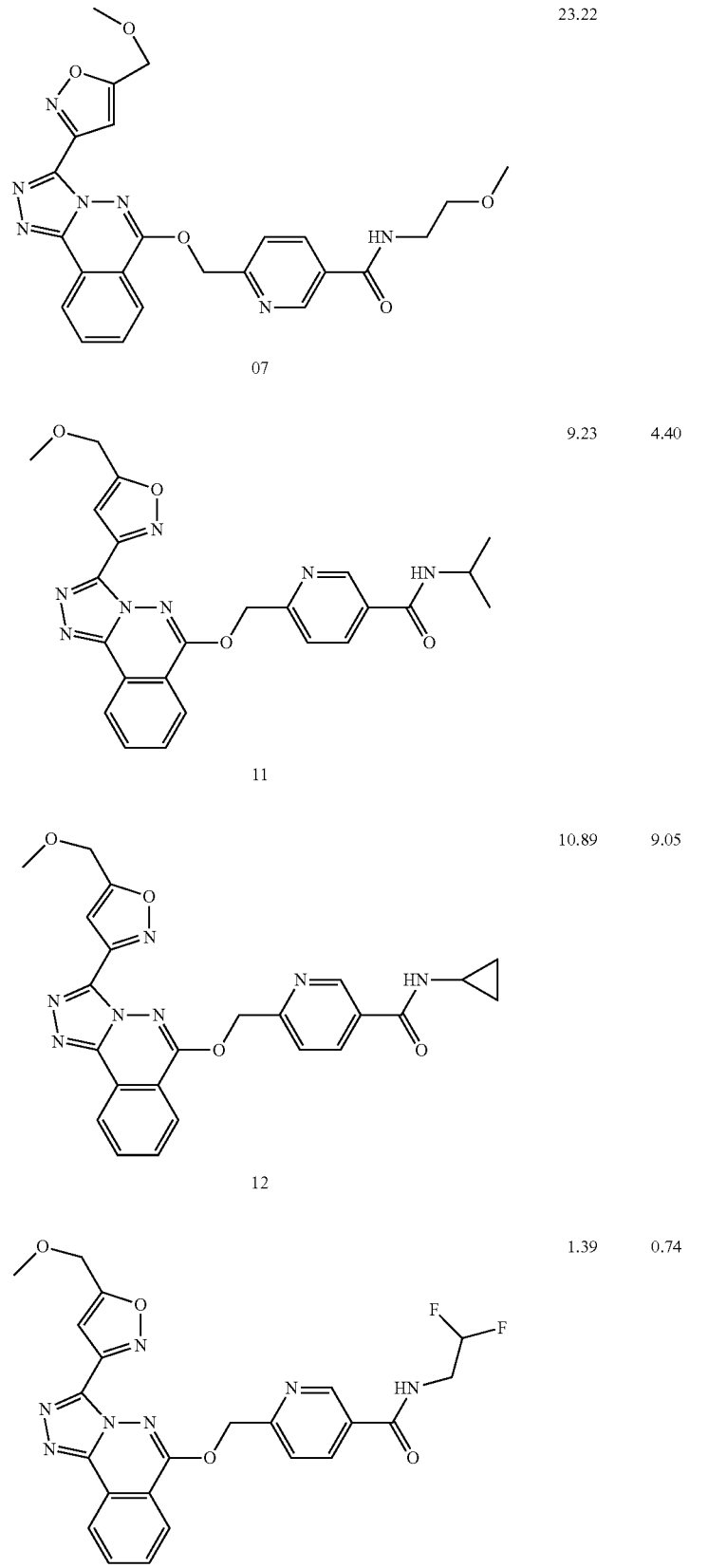
| | | |
|---|---|---|
| 07 | 23.22 | |
| 11 | 9.23 | 4.40 |
| 12 | 10.89 | 9.05 |
| 24 | 1.39 | 0.74 |

TABLE 3-continued

| Compound | Kinetic solubility μg/mL | Thermodynamic solubility μg/mL |
|---|---|---|
| 34 | 4.60 | 4.40 |
| 38 | 17.75 | 8.7 |

| Comparative compound | Kinetic solubility μg/mL | Thermodynamic solubility μg/mL |
|---|---|---|
| compound 07 in CN106854207A | 0.62 | <0.50 |
| | 3.88 | |

TABLE 3-continued
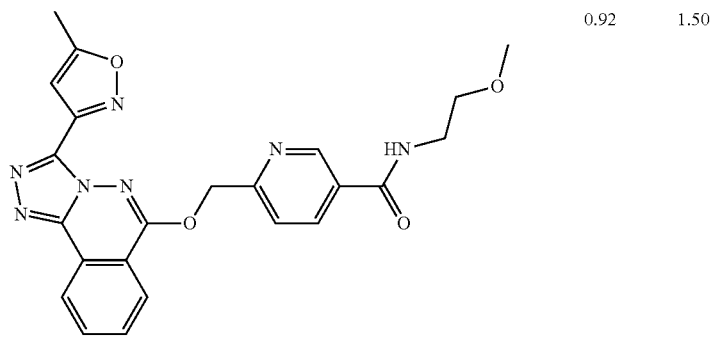
0.92    1.50
Compound 07 in
CN106854207A
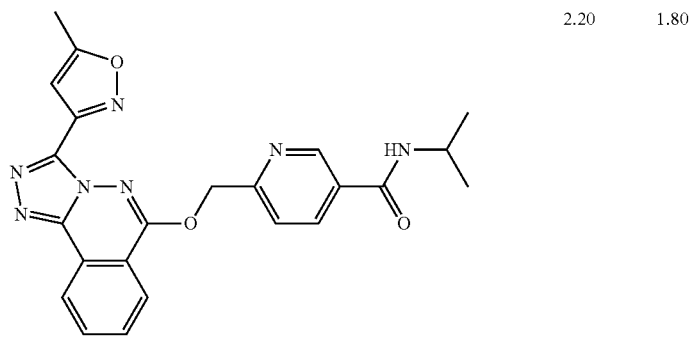
2.20    1.80
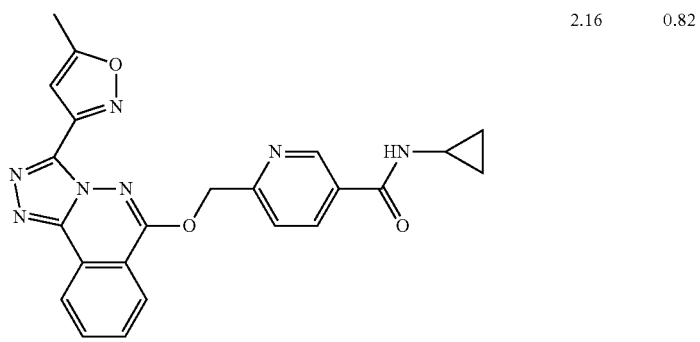
2.16    0.82
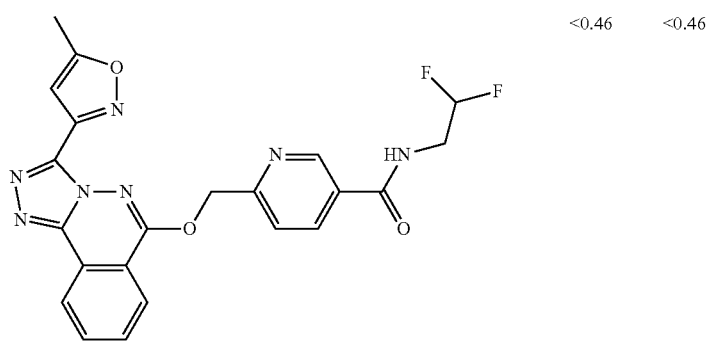
<0.46   <0.46

TABLE 3-continued

| Structure | | |
|---|---|---|
| (compound with 5-methylisoxazole-triazolo-phthalazine-O-CH2-pyridine-C(O)-4,4-difluoropiperidine) | 0.97 | 0.98 |
| (compound with 5-methylisoxazole-triazolo-phthalazine-O-CH2-pyridine-C(O)-morpholine) | 1.95 | 1.70 |

It can be seen from Table 3 that the kinetic and thermodynamic solubility of the methoxymethyl-containing compounds of the present disclosure is twice as much as the methyl-containing reference compound. Therefore the compounds of the present disclosure can significantly reduce the difficulty of formulation development in preclinical and clinical research and improve oral bioavailability.

Effect Example 3: Pharmacokinetic Experiment on Rats

In the pharmacokinetic experiment on rats, the maximum drug concentration ($C_{max}$) in the blood was determined to evaluate the absorption of the compounds in rats. All rats fasted overnight before administration; the test compounds were dissolved and administered orally (po, intragastric administration) to male SD rats, with 3 rats in each group. After administration of the test compounds, blood was collected by jugular vein puncture at 0.25, 0.5, 1.2, and 4.8 hours with 0.25 mL per sample. The plasma drug concentration was determined by LC-MS/MS method, and the pharmacokinetic parameters were calculated by Phoenix WinNonlin7.0. The dose was 1 mg/kg, and the menstruum was 50% PEG400/50% water.

TABLE 4

| Compound No. | PO $C_{max}$ ng/mL |
|---|---|
| 02 | 24.7 |
| Compound 07 in CN106854207A | 19.0 |

TABLE 4-continued

| Compound No. | PO $C_{max}$ ng/mL |
|---|---|
| 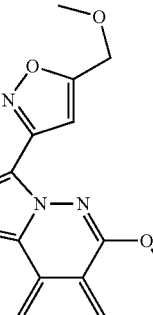 38 | 48.0 |
| 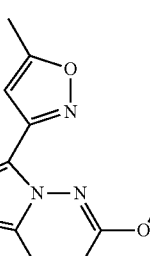 | 22.4 |

It can be seen from Table 4 that, compared with the reference compound containing methyl group, the compounds containing methoxymethyl group of the present disclosure show a higher maximum drug concentration in blood and have pharmacokinetic advantages.

Although the specific examples of the present disclosure have been described above, those skilled in the art should understand that these are only for illustration, and a variety of changes and modifications can be made to these examples without departing from the principle and essence of the present disclosure. Therefore, the protection scope of the present disclosure is defined by the appended claims.

What is claimed is:
1. A compound represented by formula I:

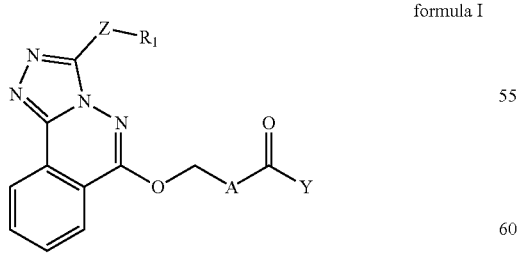

formula I or a pharmaceutically acceptable salt, stereoisomer, or tautomer thereof,
wherein:
Z is a 5- or 6-membered heteroarylene, wherein the 5- or 6-membered heteroarylene contains 1, 2, or 3 heteroatoms independently selected from the group consisting of N, O, and S;
A is phenylene, a 5-membered heteroarylene, or a 6-membered heteroarylene;
  wherein the 5-membered heteroarylene contains 1, 2, 3, or 4 heteroatoms independently selected from the group consisting of N, O, and S;
  wherein at most 1 of the heteroatoms of the 5-membered heteroarylene is O or S;
  wherein the 6-membered heteroarylene contains 1, 2, or 3 N heteroatoms;
  wherein the phenylene is optionally substituted by 1, 2, or 3 substituents independently selected from the group consisting of halogen, CN, $C_{1-6}$alkyl, linear $C_{2-6}$ alkenyl, $C_{2-6}$ alkynyl, and $C_{3-6}$ cycloalkyl; and
  wherein the 5-membered heteroarylene or 6-membered heteroarylene is optionally substituted by 1 or more independently selected $R_x$ substituents;
each $R_x$ is independently halogen, CN, C(O)OR$_1$, OH, OC(O)R$_1$, OR$_1$, or R$_1$;
R$_1$ is $C_{1-6}$ alkylene-NHC$_{1-6}$ alkyl, $C_{1-6}$ alkylene-OC$_{1-6}$ alkyl, $C_{1-6}$ alkylene-OC$_{1-6}$ alkylene-C$_{3-6}$ cycloalkyl, $C_{1-6}$ alkylene-OC$_{1-6}$ alkylene-C$_{3-6}$ heterocycloalkyl, $C_{1-6}$ alkylene-C$_{3-6}$ heterocycloalkyl, OC$_{1-6}$ haloalkyl, OC$_{1-6}$ alkylene-C$_{3-6}$ cycloalkyl, or C$_{3-6}$ heterocycloalkyl, wherein the $C_{1-6}$ alkylene-NHC$_{1-6}$ alkyl, $C_{1-6}$ alkylene-OC$_{1-6}$ alkyl, $C_{1-6}$ alkylene-OC$_{1-6}$ alkylene-C$_{3-6}$ cycloalkyl, $C_{1-6}$ alkylene-OC$_{1-6}$ alkylene-C$_{3-6}$ heterocycloalkyl, $C_{1-6}$ alkylene-C$_{3-6}$ heterocycloalkyl, OC$_{1-6}$ haloalkyl, OC$_{1-6}$ alkylene-C$_{3-6}$ cycloalkyl, or C$_{3-6}$ heterocycloalkyl is optionally substituted by 1, 2, 3, or 4 substituents independently selected from the group consisting of halogen, CN, $C_{1-6}$ alkyl, OH, and =O;
Y is NY$_1$Y$_2$, NHNY$_3$Y$_4$, or OH;
Y$_1$ is H or $C_{1-6}$ alkyl, wherein the $C_{1-6}$ alkyl is optionally substituted by 1, 2, 3, 4, or 5 substituents independently selected from the group consisting of halogen, NH$_2$, NHC$_{1-6}$ alkyl, N(C$_{1-6}$ alkyl)$_2$, NO$_2$, OH, OC$_{1-6}$ alkyl, OC$_{1-6}$ haloalkyl, and S(O)$_2$C$_{1-6}$ alkyl;
Y$_2$ is H, $C_{1-6}$ alkyl, NH$_2$, OC$_{1-6}$ alkyl, S(O)$_2$C$_{1-6}$ alkyl, S(O)$_2$NH$_2$, cycloalkyl, heterocycloalkyl, or heteroaryl;
  wherein the $C_{1-6}$ alkyl, OC$_{1-6}$alkyl, S(O)$_2$C$_{1-6}$ alkyl, cycloalkyl, heterocycloalkyl, or heteroaryl is optionally substituted by 1, 2, 3, 4, or 5 substituents independently selected from the group consisting of halogen, CN, $C_{1-6}$ alkyl, $C_{1-6}$ haloalkyl, $C_{1-6}$ alkylene-C(O)OH, $C_{1-6}$ alkylene-C(O)OC$_{1-4}$ alkyl, $C_{1-6}$ alkylene-OH, $C_{1-6}$ alkylene-OC$_{1-6}$ alkyl, acyl, NHC$_{1-6}$ alkyl, NHacyl, N(C$_{1-6}$ alkyl)$_2$, NO$_2$, OH, OC$_{1-6}$ alkyl, OC$_{1-6}$ haloalkyl, S(O)$_2$C$_{1-6}$ alkyl, C$_{3-6}$ cycloalkyl, 4-membered heterocycloalkyl, and C$_{4-6}$ heterocycloalkyl;
  wherein each 4-membered heterocycloalkyl and C$_{4-6}$ heterocycloalkyl substituent independently contains 1, 2, or 3 heteroatoms independently selected from the group consisting of N, O, and S;
  wherein each C$_{3-6}$ cycloalkyl substituent is optionally and independently substituted by 1 or more OH substituents;
  wherein each 4-membered heterocycloalkyl substituent is optionally and independently substituted by 1 or more CH$_3$ substituents; and wherein each C$_{4-6}$ heterocycloalkyl substituent is optionally and independently substituted by 1 or more substituents independently selected from the group consisting of halogen, CH$_3$, and OCH$_3$;

Y$^1$ and Y$^2$, taken together with the N atom to which they are attached, form a 4- to 7-membered heterocycloalkyl, a 4- to 7-membered heterocycloalkenyl, a spirocyclic 6- to 9-membered heterocyclyl, or a bridged 6- to 9-membered heterocyclyl;

wherein the 4- to 7-membered heterocycloalkyl, 4- to 7-membered heterocycloalkenyl, spirocyclic 6- to 9-membered heterocyclyl, or bridged 6- to 9-membered heterocyclyl optionally contains 1 or more additional heteroatoms independently selected from the group consisting of N and O; and wherein the 4- to 7-membered heterocycloalkyl, 4- to 7-membered heterocycloalkenyl, spirocyclic 6- to 9-membered heterocyclyl, or bridged 6- to 9-membered heterocyclyl is optionally substituted by 1, 2, 3, or 4 substituents independently selected from the group consisting of halogen, CN, C$_{1-6}$ alkyl, OH, OC$_{1-6}$ alkyl, and =O;

Y$_3$ is H, C$_{1-6}$ alkyl, S(O)$_2$C$_{1-6}$ alkyl, cycloalkyl, or heterocyclyl, wherein the C$_{1-6}$ alkyl, S(O)$_2$C$_{1-6}$ alkyl, cycloalkyl, or heterocyclyl is optionally substituted by 1, 2, 3, or 4 substituents independently selected from the group consisting of halogen, CN, C$_{1-6}$ alkyl, OH, and OC$_{1-6}$ alkyl; and Y$_4$ is H, C$_{1-6}$ alkyl, S(O)$_2$C$_{1-6}$ alkyl, cycloalkyl, or heterocyclyl, wherein the C$_{1-6}$ alkyl, S(O)$_2$C$_{1-6}$ alkyl, cycloalkyl, or heterocyclyl is optionally substituted by 1, 2, 3, or 4 substituents independently selected from the group consisting of halogen, CN, C$_{1-6}$ alkyl, OH, and OC$_{1-6}$ alkyl; or Y$^3$ and Y$^4$, taken together with the N atom to which they are attached, form a heterocyclyl, wherein the heterocyclyl is optionally substituted by 1, 2, 3, or 4 substituents independently selected from the group consisting of halogen, CN, C$_{1-6}$ alkyl, OH, OC$_{1-6}$ alkyl, and =O;

with the proviso that if A is pyridinylene, then the pyridinylene is optionally an N-oxide thereof.

2. The compound as defined in claim 1, or a pharmaceutically acceptable salt, stereoisomer, or tautomer thereof, wherein:

Y$_2$ is H, C$_{1-6}$ alkyl, NH$_2$, OC$_{1-6}$ alkyl, S(O)$_2$C$_{1-6}$ alkyl, S(O)$_2$NH$_2$, cycloalkyl, heterocycloalkyl, or heteroaryl;

wherein the C$_{1-6}$ alkyl, OC$_{1-6}$ alkyl, S(O)$_2$C$_{1-6}$ alkyl, cycloalkyl, heterocycloalkyl, or heteroaryl is optionally substituted by 1, 2, 3, 4, or 5 substituents independently selected from the group consisting of halogen, CN, C$_{1-6}$ alkyl, C$_{1-6}$ haloalkyl, C$_{1-6}$ alkylene-C(O)OH, C$_{1-6}$ alkylene-C(O)OC$_{1-4}$ alkyl, C$_{1-6}$ alkylene-OH, C$_{1-6}$ alkylene-OC$_{1-6}$ alkyl, acyl, NHC$_{1-6}$ alkyl, NHacyl, N(C$_{1-6}$ alkyl)$_2$, NO$_2$, OH, OC$_{1-6}$ alkyl, OC$_{1-6}$ haloalkyl, S(O)$_2$C$_{1-6}$ alkyl, C$_{3-6}$ cycloalkyl, and C$_{4-6}$ heterocycloalkyl;

wherein each C$_{4-6}$ heterocycloalkyl substituent independently contains 1, 2, or 3 heteroatoms independently selected from the group consisting of N, O, and S;

wherein each C$_{3-6}$ cycloalkyl substituent is optionally and independently substituted by 1 or more OH substituents; and wherein each C$_{4-6}$ heterocycloalkyl substituent is optionally and independently substituted by 1 or more substituents independently selected from the group consisting of halogen, CH$_3$, and OCH$_3$.

3. The compound as defined in claim 2, wherein the compound is represented by formula II:

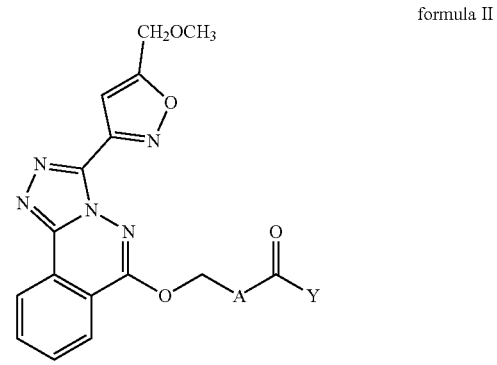

formula II or a pharmaceutically acceptable salt, stereoisomer, or tautomer thereof, wherein:

A is phenylene, a 5-membered heteroarylene, or a 6-membered heteroarylene;

wherein the 5-membered heteroarylene contains 1, 2, 3, or 4 heteroatoms independently selected from the group consisting of N, O, and S;

wherein at most 1 of the heteroatoms of the 5-membered heteroarylene is O or S;

wherein the 6-membered heteroarylene contains 1, 2, or 3 N heteroatoms;

wherein the phenylene is optionally substituted by 1, 2, or 3 substituents independently selected from the group consisting of halogen, CN, and C$_{1-6}$ alkyl; and wherein the 5-membered heteroarylene or 6-membered heteroarylene is optionally substituted by 1 or more independently selected R$_x$ substituents;

each R$_x$ is independently halogen or CN;

Y is NY$_1$Y$_2$, NHNY$_3$Y$_4$, or OH;

Y$_1$ is H or C$_{1-5}$ alkyl, wherein the C$_{1-6}$ alkyl is optionally substituted by 1, 2, 3, 4, or 5 substituents independently selected from the group consisting of halogen, NH$_2$, NHC$_{1-6}$ alkyl, N(C$_{1-6}$ alkyl)$_2$, OH, OC$_{1-6}$ alkyl, OC$_{1-6}$ haloalkyl, and S(O)$_2$C$_{1-6}$ alkyl;

Y$_2$ is C$_{1-6}$ alkyl, cyclopropyl, cyclobutyl, cyclopentyl, cyclohexyl, bridged C$_{4-6}$ cycloalkyl, C$_{4-6}$ heterocycloalkyl, or C$_{5-6}$ heteroaryl;

wherein the C$_{4-6}$ heterocycloalkyl or C$_{5-6}$ heteroaryl contains 1, 2, or 3 heteroatoms independently selected from the group consisting of N, O, and S;

wherein the C$_{1-6}$ alkyl is optionally substituted by 1, 2, 3, 4, or 5 substituents independently selected from the group consisting of halogen, CN, NHC$_{1-6}$ alkyl, N(C$_{1-6}$ alkyl)$_2$, OH, OC$_{1-6}$ alkyl, S(O)$_2$C$_{1-6}$ alkyl, C$_{4-6}$ cycloalkyl, and C$_{4-6}$ heterocycloalkyl;

wherein the cyclopropyl, cyclobutyl, cyclopentyl, or cyclohexyl is optionally substituted by 1, 2, 3, or 4 substituents independently selected from the group consisting of halogen, CN, C$_{1-6}$ alkyl, C$_{1-6}$ alkylene-OH, C$_{1-6}$ alkylene-OC$_{1-6}$ alkyl, NHC$_{1-6}$ alkyl, N(C$_{1-6}$ alkyl)$_2$, OH, OC$_{1-6}$ alkyl, and S(O)$_2$C$_{1-6}$ alkyl;

wherein the $C_{4-6}$ heterocycloalkyl is optionally substituted by 1, 2, 3, or 4 substituents independently selected from the group consisting of halogen, $C_{1-6}$ alkyl, $C_{1-6}$ alkylene-OH, $C_{1-6}$ alkylene-$OC_{1-6}$ alkyl, acyl, OH, $OC_{1-6}$ alkyl, and $S(O)_2C_{1-6}$ alkyl; and wherein the $C_5$ heteroaryl is optionally substituted by 1, 2, or 3 independently selected $C_{1-6}$ alkyl substituents; or $Y^1$ and $Y^2$, taken together with the N atom to which they are attached, form a 4- to 7-membered heterocycloalkyl, a spirocyclic 6- to 9-membered heterocyclyl, or a bridged 6- to 9-membered heterocyclyl;

wherein the 4- to 7-membered heterocycloalkyl, spirocyclic 6- to 9-membered heterocyclyl, or bridged 6- to 9-membered heterocyclyl optionally contains 1 or more additional heteroatoms independently selected from the group consisting of N and O; and wherein the 4- to 7-membered heterocycloalkyl, spirocyclic 6- to 9-membered heterocyclyl, or bridged 6- to 9-membered heterocyclyl is optionally substituted by 1, 2, 3, or 4 substituents independently selected from the group consisting of halogen, CN, $C_{1-6}$ alkyl, OH, $OC_{1-6}$ alkyl, and =O;

$Y_3$ is H, $C_{1-6}$ alkyl, or $S(O)_2C_{1-6}$ alkyl; and
$Y_4$ is H, $C_{1-6}$ alkyl or $S(O)_2C_{1-6}$ alkyl; or $Y^3$ and $Y^4$, taken together with the N atom to which they are attached, form a piperidin-1-yl, morpholin-4-yl, or thiomorpholin-4-yl, wherein the thiomorpholin-4-yl is substituted by 1 or 2 =O substituents.

4. The compound as defined in claim 2, wherein the compound is represented by formula II:

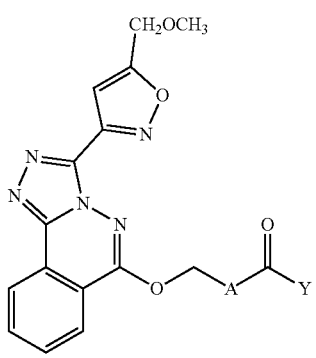

formula II or a pharmaceutically acceptable salt, stereoisomer, or tautomer thereof,
wherein:
A is pyridinylene;
Y is $NY_1Y_2$ or OH;
$Y_1$ is H or $C_{1-6}$ alkyl, wherein the $C_{1-6}$ alkyl is optionally substituted by 1, 2, 3, 4, or 5 substituents independently selected from the group consisting of OH, $OC_{1-6}$ alkyl, and $OC_{1-6}$ haloalkyl; and
$Y_2$ is H, $C_{1-6}$ alkyl, cyclopropyl, cyclobutyl, cyclopentyl, cyclohexyl, bridged $C_{4-6}$ cycloalkyl, or $C_{4-6}$ heterocycloalkyl;
wherein the $C_{4-6}$ heterocycloalkyl contains 1, 2, or 3 heteroatoms independently selected from the group consisting of N, O, and S;

wherein the $C_{1-6}$ alkyl is optionally substituted by 1, 2, 3, 4, or 5 substituents independently selected from the group consisting of halogen, CN, $NHC_{1-6}$ alkyl, $N(C_{1-6}$ alkyl$)_2$, OH, $OC_{1-6}$ alkyl, $OC_{1-6}$ haloalkyl, $C_{4-6}$ cycloalkyl, and $C_{4-6}$ heterocycloalkyl;

wherein the cyclopropyl, cyclobutyl, cyclopentyl, or cyclohexyl is optionally substituted by 1, 2, 3, or 4 substituents independently selected from the group consisting of halogen, CN, $C_{1-6}$ alkyl, $C_{1-6}$ alkylene-OH, $C_{1-6}$ alkylene-$OC_{1-6}$ alkyl, $NHC_{1-6}$ alkyl, $N(C_{1-6}$ alkyl$)_2$, OH, and $OC_{1-6}$ alkyl;

wherein the $C_{4-6}$ heterocycloalkyl is optionally substituted by 1, 2, 3, or 4 substituents independently selected from the group consisting of halogen, $C_{1-6}$ alkyl, $C_{1-6}$ alkylene-OH, $C_{1-6}$ alkylene-$OC_{1-6}$ alkyl, acyl, OH, and $OC_{1-6}$ alkyl; and wherein each $C_{4-6}$ heterocycloalkyl substituent independently contains 1, 2, or 3 O heteroatoms; or $Y^1$ and $Y^2$, taken together with the N atom to which they are attached, form a 4- to 7-membered heterocycloalkyl, a spirocyclic 6- to 9-membered heterocyclyl, or a bridged 6- to 9-membered heterocyclyl;

wherein the 4- to 7-membered heterocycloalkyl, spirocyclic 6- to 9-membered heterocyclyl, or bridged 6- to 9-membered heterocyclyl optionally contains 1 additional heteroatom selected from the group consisting of N and O; and wherein the 4- to 7-membered heterocycloalkyl, spirocyclic 6- to 9-membered heterocyclyl, or bridged 6- to 9-membered heterocyclyl is optionally substituted by 1, 2, 3, or 4 substituents independently selected from the group consisting of halogen, CN, $C_{1-6}$ alkyl, OH, $OC_{1-6}$ alkyl, and =O.

5. The compound as defined in claim 2, wherein the compound is represented by formula II:

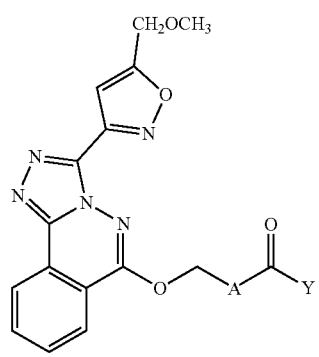

formula II or a pharmaceutically acceptable salt, stereoisomer, or tautomer thereof,
wherein:
A is pyridinylene;
Y is $NY_1Y_2$ or OH;
$Y_1$ is H or $C_{1-6}$ alkyl, wherein the $C_{1-6}$ alkyl is optionally substituted by 1, 2, 3, 4, or 5 independently selected $OC_{1-6}$ alkyl substituents; and
$Y_2$ is H, $C_{1-6}$ alkyl, cyclopropyl, cyclobutyl, cyclopentyl, cyclohexyl, bridged $C_{4-6}$ cycloalkyl, or $C_{4-6}$ heterocycloalkyl;

wherein the C$_{4-6}$ heterocycloalkyl contains 1, 2, or 3 heteroatoms independently selected from the group consisting of N, O, and S;
wherein the C$_{1-6}$ alkyl is optionally substituted by 1, 2, 3, 4, or 5 substituents independently selected from the group consisting of halogen, CN, OH, OC$_{1-6}$ alkyl, C$_{4-6}$ cycloalkyl, and C$_{4-6}$ heterocycloalkyl;
wherein the cyclopropyl, cyclobutyl, cyclopentyl, or cyclohexyl is optionally substituted by 1, 2, 3, or 4 substituents independently selected from the group consisting of halogen and CN;
wherein the C$_{4-6}$ heterocycloalkyl is optionally substituted by 1, 2, 3, or 4 independently selected acyl substituents; and
wherein each C$_{4-6}$ heterocycloalkyl substituent independently contains 1, 2, or 3 O heteroatoms; or
Y$^1$ and Y$^2$, taken together with the N atom to which they are attached, form a 4- to 7-membered heterocycloalkyl, a spirocyclic 6- to 9-membered heterocyclyl, or a bridged 6- to 9-membered heterocyclyl;
wherein the 4- to 7-membered heterocycloalkyl, spirocyclic 6- to 9-membered heterocyclyl, or bridged 6- to 9-membered heterocyclyl optionally contains 1 additional heteroatom selected from the group consisting of N and O; and
wherein the 4- to 7-membered heterocycloalkyl, spirocyclic 6- to 9-membered heterocyclyl, or bridged 6- to 9-membered heterocyclyl is optionally substituted by 1, 2, 3, or 4 substituents independently selected from the group consisting of halogen, C$_{1-6}$ alkyl, OH, OC$_{1-6}$ alkyl, and =O.

6. The compound as defined in claim 1, or a pharmaceutically acceptable salt, stereoisomer, or tautomer thereof, wherein:
Y$_1$ is H or C$_{1-6}$ alkyl, wherein the C$_{1-6}$ alkyl is optionally substituted by 1, 2, 3, 4, or 5 substituents independently selected from the group consisting of halogen, NH$_2$, NHC$_{1-6}$ alkyl, N(C$_{1-6}$ alkyl)$_2$, NO$_2$, OH, OC$_{1-6}$ alkyl, OC$_{1-6}$ haloalkyl, and S(O)$_2$C$_{1-6}$ alkyl; and
Y$_2$ . . . is H, methyl, cyclopropylmethyl, oxetanylmethyl, (methyloxetanyl)methyl, tetrahydrofuranylmethyl, ethyl, fluoroethyl, difluoroethyl, trifluoroethyl, hydroxyethyl, methoxyethyl, trifluoromethoxyethyl, cyanopropyl, trifluoropropyl, difluorohydroxypropyl, methoxypropyl, dimethoxypropyl, isopropyl, trifluoroisopropyl, methoxyisopropyl, cyclopropyl, cyanocyclopropyl, cyclobutyl, fluorocyclobutyl, difluorocyclobutyl, difluorocyclopentyl, difluorocyclohexyl, acetylazetidinyl, oxetanyl, tetrahydrofuranyl, or tetrahydropyranyl; or
Y$^1$ and Y$^2$, taken together with the N atom to which they are attached, form difluoroazetidin-1-yl, hydroxyazetidin-1-yl, methoxyazetidin-1-yl, pyrrolidin-1-yl, difluoropyrrolidin-1-yl, piperidin-1-yl, difluoropiperidin-1-yl, hydroxypiperidin-1-yl, methoxypiperidin-1-yl, methylpiperazinon-1-yl, morpholin-4-yl, methylmorpholin-4-yl, dimethylmorpholin-4-yl, 1,2-oxazepan-2-yl, 1,3-oxazepan-3-yl, or 1,4-oxazepan-4-yl, 2-oxa-6-azaspiro[3.3]heptan-6-yl, 3-oxo-2-oxa-5-azabicyclo[2.2.1]heptan-5-yl, or 2-oxazolyl-7-azaspiro[3.5]nonan-7-yl.

7. The compound as defined in claim 1, or a pharmaceutically acceptable salt, stereoisomer, or tautomer thereof, wherein:
Y$_1$ is H or C$_{1-6}$ alkyl, wherein the C$_{1-6}$ alkyl is optionally substituted by 1, 2, 3, 4, or 5 substituents independently selected from the group consisting of halogen, NH$_2$, NHC$_{1-6}$ alkyl, N(C$_{1-6}$ alkyl)$_2$, NO$_2$, OH, OC$_{1-6}$ alkyl, OC$_{1-6}$ haloalkyl, and S(O)$_2$C$_{1-6}$ alkyl; and
Y$_2$ is H, methyl, cyclopropylmethyl, (tetrahydrofuran-2-yl)methyl, (3-methyloxetanyl)methyl, ethyl, 2-fluoroethyl, 2,2-difluoroethyl, 2,2,2-trifluoroethyl, 2-hydroxyethyl, 2-methoxyethyl, 2-trifluoromethoxyethyl, 1,1,1-trifluoropropyl, 2,2-difluoro-3-hydroxypropyl, 3-cyanopropyl, 3-methoxypropyl, 1-methoxy-2-methylprop-2-yl, isopropyl, 1,1,1-trifluoroisopropyl, 1-methoxyisopropyl, 1,3-dimethoxyisopropyl, cyclopropyl, 1-cyanocyclopropyl, cyclobutyl, 3-fluorocyclobutyl, 3,3-difluorocyclobutyl, 3,3-difluorocyclopentyl, bicyclo[1.1.1]pentan-1-yl, 4,4-difluorocyclohexyl, 1-acetylazetidin-3-yl, oxetan-3-yl, 3-methyloxetanyl, tetrahydrofuran-3-yl, or tetrahydro-2H-pyran-4-yl; or
Y$^1$ and Y$^2$, taken together with the N atom to which they are attached, form 3,3-difluoroazetidin-1-yl, 3-hydroxyazetidin-1-yl, 3-methoxyazetidin-1-yl, pyrrolidin-1-yl, 3,3-difluoropyrrolidin-1-yl, piperidin-1-yl, 4,4-difluoropiperidin-1-yl, 4-hydroxypiperidin-1-yl, 4-methoxypiperidin-1-yl, 4-methyl-3-oxopiperazin-1-yl, morpholin-4-yl, 2-methylmorpholin-4-yl, 3-methylmorpholin-4-yl, 2,6-dimethylmorpholin-4-yl, 1,4-oxazepan-4-yl, (1S,4S)-3-oxo-2-oxa-5-azabicyclo[2.2.1]heptan-5-yl, 2-oxa-6-azaspiro[30.3]heptan-6-yl, or 2-oxazolyl-7-azaspiro[3.5]nonan-1-yl.

8. The compound as defined in claim 1, or a pharmaceutically acceptable salt, stereoisomer, or tautomer thereof, wherein:
A is a 6-membered heteroarylene;
wherein the 6-membered heteroarylene contains 1, 2, or 3 N heteroatoms; and
wherein the 6-membered heteroarylene is optionally substituted by 1 or more independently selected R$_x$ substituents;
R$_1$ is C$_{1-6}$ alkylene-OC$_{1-6}$ alkyl, wherein the C$_{1-6}$ alkylene-OC$_{1-6}$ alkyl is optionally substituted by 1, 2, 3, or 4 substituents independently selected from the group consisting of halogen, CN, C$_{1-6}$ alkyl, OH, and =O;
Y is NY$_1$Y$_2$ or OH;
Y$_1$ is H or C$_{1-6}$ alkyl, wherein the C$_{1-6}$ alkyl is optionally substituted by 1, 2, 3, or 5 independently selected OC$_{1-6}$ alkyl substituents; and
Y$_2$ is H, C$_{1-6}$ alkyl, cycloalkyl, or heterocycloalkyl;
wherein the C$_{1-6}$ alkyl, cycloalkyl, or heterocycloalkyl is optionally substituted by 1, 2, 3, 4, or 5 substituents independently selected from the group consisting of halogen, CN, acyl, OH, OC$_{1-6}$ alkyl, OC$_{1-6}$ haloalkyl, cyclopropyl, 4-membered heterocycloalkyl, and C$_{4-6}$ heterocycloalkyl;
wherein each 4-membered heterocycloalkyl and C$_{4-6}$ heterocycloalkyl substituent independently contains 1, 2, or 3 heteroatoms independently selected from the group consisting of N, O, and S; and
wherein each 4-membered heterocycloalkyl and C$_{4-6}$ heterocycloalkyl substituent is optionally and independently substituted by 1 or more CH$_3$ substituents; or
Y$^1$ and Y$^2$; taken together with the N atom to which they are attached, form a 4- to 7-membered heterocycloalkyl, a spirocyclic 6- to 9-membered heterocyclyl, or a bridged 6- to 9-membered heterocyclyl;
wherein the 4- to 7-membered heterocycloalkyl, spirocyclic 6- to 9-membered heterocyclyl, or bridged 6- to 9-membered heterocyclyl optionally contains 1 additional heteroatom selected from the group consisting of N and O; and wherein the 4- to 7-membered heterocycloalkyl, spirocyclic 6- to 9-membered heterocyclyl, or bridged 6- to 9-membered heterocyclyl is optionally substituted by 1, 2, 3, or 4 substituents independently selected from the group consisting of halogen, CN, $C_{1-6}$ alkyl, OH, $OC_{1-6}$ alkyl, and =O.

9. The compound as defined in claim 1, or a pharmaceutically acceptable, salt, stereoisomer, or tautomer thereof, wherein:

A is a 6-membered heteroarylene;
wherein the 6-membered heteroarylene contains 1, 2, or 3 N heteroatoms; and
wherein the 6-membered heteroarylene is optionally substituted by 1 or more independently selected $R_x$ substituents;

$R_1$ is $C_{1-6}$ alkylene-$OC_{1-6}$ alkyl, wherein the $C_{1-6}$ alkylene-$OC_{1-6}$ alkyl is optionally substituted by 1, 2, 3, or 4 substituents independently selected from the group consisting of halogen, CN, $C_{1-6}$ alkyl, OH, and =O;

Y is $NY_1Y_2$ or OH;
$Y_1$ is H or $C_{1-6}$ alkyl, wherein the $C_{1-6}$ alkyl is optionally substituted by 1, 2, 3, 4, or 5 independently selected $OC_{1-6}$ alkyl substituents; and
$Y_2$ is H, $C_{1-6}$ alkyl, cycloalkyl, or heterocycloalkyl;
wherein the $C_{1-6}$ alkyl is optionally substituted by 1, 2, 3, 4, or 5 substituents independently selected from the group consisting of halogen, CN, OH, $OC_{1-6}$ alkyl, $OC_{1-6}$ haloalkyl, cyclopropyl, 4-membered heterocycloalkyl, and $C_{4-6}$ heterocycloalkyl;
wherein the cycloalkyl is optionally substituted by 1, 2, 3, 4, or 5 substituents independently selected from the group consisting of halogen and CN;
wherein the heterocycloalkyl is optionally substituted by 1, 2, 3, 4, or 5 independently selected acyl substituents;
wherein each 4-membered heterocycloalkyl and $C_{4-6}$ heterocycloalkyl substituent independently contains 1, 2, or 3 heteroatoms independently selected from the group consisting of N, O, and S; and
wherein each 4-membered heterocycloalkyl and $C_{4-6}$ heterocycloalkyl substituent is optionally and independently substituted by 1 or more $CH_3$ substituents; or $Y^1$ and taken together with the N atom to which they are attached, form a 4- to 7-membered heterocycloalkyl, a spirocyclic 6- to 9-membered heterocyclyl, or a bridged 6- to 9-membered heterocyclyl;
wherein the 4- to 7-membered heterocycloalkyl, spirocyclic 6- to 9-membered heterocyclyl, or bridged 6- to 9-membered heterocyclyl optionally contains 1 additional heteroatom selected from the group consisting of N and O; and
wherein the 4- to 7-membered heterocycloalkyl, spirocyclic 6- to 9-membered heterocyclyl, or bridged 6- to 9-membered heterocyclyl is optionally substituted by 1, 2, 3, or 4 substituents independently selected from the group consisting of halogen, CN, $C_{1-6}$ alkyl, OH, $OC_{1-6}$ alkyl, and =O.

10. The compound as defined in claim 1, or a pharmaceutically acceptable salt, stereoisomer, or tautomer thereof, wherein:

A is a 6-membered heteroarylene;
wherein the 6-membered heteroarylene contains 1, 2, or 3 N heteroatoms; and
wherein the 6-membered heteroarylene is optionally substituted by 1 or more independently selected $R_x$ substituents;

$R_1$ is $C_{1-6}$ alkylene-$OC_{1-6}$ alkyl, wherein the $C_{1-6}$ alkylene-$OC_{1-6}$ alkyl is optionally substituted by 1, 2, 3, or 4 substituents independently selected from the group consisting of halogen, CN, $C_{1-6}$ alkyl, OH, and =O;

Y is $NY_1Y_2$;
$Y_1$ is H or $C_{1-6}$ alkyl, wherein the $C_{1-6}$ alkyl is optionally substituted by 1, 2, 3, 4, or 5 independently selected $OC_{1-6}$ alkyl substituents; and
$Y_2$ is $C_{1-6}$ alkyl, cycloalkyl, or heterocycloalkyl;
wherein the $C_{1-6}$ alkyl is optionally substituted by 1 or 2 substituents independently selected from the group consisting of CN, OH, $OC_{1-6}$ alkyl, cyclopropyl, 4-membered heterocycloalkyl, and $C_{4-6}$ heterocycloalkyl;
wherein the cycloalkyl is optionally substituted by 1, 2, 3, 4, or 5 substituents independently selected from the group consisting of halogen and CN;
wherein the heterocycloalkyl is optionally substituted by 1 or 2 independently selected acyl substituents;
wherein each 4-membered heterocycloalkyl and $C_{4-6}$ heterocycloalkyl substituent independently contains 1, 2, or 3 heteroatoms independently selected from the group consisting of N, O, and S; and
wherein each 4-membered heterocycloalkyl and $C_{4-6}$ heterocycloalkyl substituent is optionally and independently substituted by 1 or more $CH_3$ substituents; or $Y^1$ and $Y^2$, taken together with the N atom to which they are attached, form a 4- to 7-membered heterocycloalkyl, a spirocyclic 6- to 9-membered heterocyclyl, or a bridged 6- to 9-membered heterocyclyl;
wherein the 4- to 7-membered heterocycloalkyl, spirocyclic 6- to 9-membered heterocyclyl, or bridged 6- to 9-membered heterocyclyl optionally contains 1 additional heteroatom selected from the group consisting of N and O; and
wherein the 4- to 7-membered heterocycloalkyl, spirocyclic 6- to 9-membered heterocyclyl, or bridged 6- to 9-membered heterocyclyl is optionally substituted by 1, 2, 3, or 4 substituents independently selected from the group consisting of halogen, $C_{1-6}$ alkyl, OH, $OC_{1-6}$ alkyl, and =O.

11. The compound as defined in claim 1, or a pharmaceutically acceptable salt, stereoisomer, or tautomer thereof, wherein:

A is a 6-membered heteroarylene;
wherein the 6-membered heteroarylene contains 1, 2, or 3 N heteroatoms; and
wherein the 6-membered heteroarylene is optionally substituted by 1 or more independently selected $R_x$ substituents;

$R_1$ is $C_{1-6}$ alkylene-$OC_{1-6}$ alkyl, wherein the $C_{1-6}$ alkylene-$OC_{1-6}$ alkyl is optionally substituted by 1, 2, 3, or 4 substituents independently selected from the group consisting of halogen, CN, $C_{1-6}$ alkyl, OH, and =O;

Y is $NY_1Y_2$;
$Y_1$ is H or $C_{1-6}$ alkyl, wherein the $C_{1-6}$ alkyl is optionally substituted by 1, 2, 3, 4, or 5 independently selected $OC_{1-6}$ alkyl substituents; and
$Y_2$ is $C_{1-6}$ alkyl or heterocycloalkyl;
wherein the $C_{1-6}$ alkyl is optionally substituted by 1 substituent selected from the group consisting of OH, $OC_{1-6}$ alkyl, cyclopropyl, 4-membered heterocycloalkyl, and $C_{4-6}$ heterocycloalkyl;

wherein the heterocycloalkyl is optionally substituted by 1 acyl substituents;

wherein each 4-membered heterocycloalkyl and $C_{4-6}$ heterocycloalkyl substituent independently contains 1, 2, or 3 heteroatoms independently selected from the group consisting of N, O, and S; and wherein each 4-membered heterocycloalkyl and $C_{4-6}$ heterocycloalkyl substituent is optionally and independently substituted by 1 or more $CH_3$ substituents; or $Y^1$ and $Y^2$, taken together with the N atom to which they are attached, form a 4- to 7-membered heterocycloalkyl, a spirocyclic 6- to 9-membered heterocyclyl; or a bridged 6- to 9-membered heterocyclyl;

wherein the 4- to 7-membered heterocycloalkyl, spirocyclic 6- to 9-membered heterocyclyl, or bridged 6- to 9-membered heterocyclyl optionally contains 1 additional heteroatom selected from the group consisting of N and O; and wherein the 4- to 7-membered heterocycloalkyl is optionally substituted by 1, 2, 3, or 4 substituents independently selected from the group consisting of $C_{1-6}$ alkyl and =O.

12. The compound as defined in claim 1, or a pharmaceutically acceptable salt, stereoisomer, or tautomer thereof, wherein:

A is a 6-membered heteroarylene;
  wherein the 6-membered heteroarylene contains 1, 2, or 3 N heteroatoms; and
  wherein the 6-membered heteroarylene is optionally substituted by 1 or more independently selected $R_x$ substituents;

$R_1$ is $C_{1-6}$ alkylene-$OC_{1-6}$ alkyl, wherein the $C_{1-6}$ alkylene-$OC_{1-6}$ alkyl is optionally substituted by 1, 2, 3, or 4 substituents independently selected from the group consisting of halogen, CN, $C_{1-6}$ alkyl, OH, and =O;

Y is $NY_1Y_2$;

$Y_1$ is H or $C_{1-6}$ alkyl, wherein the $C_{1-6}$ alkyl is optionally substituted by 1, 2, 3, 4, or 5 independently selected $OC_{1-6}$ alkyl substituents; and $Y_2$ is $C_{1-6}$ alkyl;
  wherein the $C_{1-6}$ alkyl is optionally substituted by 1 substituent selected from the group consisting of OH, $OC_{1-6}$ alkyl, and cyclopropyl; or $Y^1$ and $Y^2$, taken together with the N atom to which they are attached, form a 4- to 7-membered heterocycloalkyl or a bridged 6- to 9-membered heterocyclyl;
  wherein the 4- to 7-membered heterocycloalkyl or bridged 6- to 9-membered heterocyclyl optionally contains 1 additional heteroatom selected from the group consisting of N and O; and
  wherein the 4- to 7-membered heterocycloalkyl is optionally substituted by 1, 2, 3, or 4 substituents independently selected from the group consisting of $C_{1-6}$ alkyl and =O.

13. The compound as defined in claim 1, or a pharmaceutically acceptable salt, stereoisomer, or tautomer thereof, wherein:

Z is a 5-membered heteroarylene, wherein the 5-membered heteroarylene contains 1, 2, or 3 heteroatoms independently selected from the group consisting of N, O, and S;

A is a 6-membered heteroarylene;
  wherein the 6-membered heteroarylene contains 1, 2, or 3 N heteroatoms; and
  wherein the 6-membered heteroarylene is optionally substituted by 1 or more independently selected $R_x$ substituents;

$R_1$ is $C_{1-6}$ alkylene-$OC_{1-6}$ alkyl, wherein the $C_{1-6}$ alkylene-$OC_{1-6}$ alkyl is optionally substituted by 1, 2, 3, or 4 substituents independently selected from the group consisting of halogen, CN, $C_{1-6}$ alkyl, OH, and =O;

Y is $NY_1Y_2$ or OH;

$Y_1$ is H or $C_{1-6}$ alkyl, wherein the $C_{1-6}$ alkyl is optionally substituted by 1, 2, 3, 4, or 5 independently selected $OC_{1-6}$ alkyl substituents; and $Y_2$ is H, $C_{1-6}$ alkyl, cycloalkyl, or heterocycloalkyl;
  wherein the $C_{1-6}$ alkyl, cycloalkyl, or heterocycloalkyl is optionally substituted by 1, 2, 3, 4, or 5 substituents independently selected from the group consisting of halogen, CN, acyl, OH, $OC_{1-4}$ alkyl, $OC_{1-6}$ haloalkyl, cyclopropyl, 4-membered heterocycloalkyl, and $C_{4-6}$ heterocycloalkyl;
  wherein each 4-membered heterocycloalkyl and $C_{4-6}$ heterocycloalkyl substituent independently contains 1, 2, or 3 heteroatoms independently selected from the group consisting of N, O, and S; and
  wherein each 4-membered heterocycloalkyl and $C_{4-6}$ heterocycloalkyl substituent is optionally and independently substituted by 1 or more $CH_3$ substituents; or $Y^1$ and $Y^2$, taken together with the N atom to which they are attached, form a 4- to 7-membered heterocycloalkyl, a 4- to 7-membered heterocycloalkenyl, a spirocyclic 6- to 9-membered heterocyclyl, or a bridged 6- to 9-membered heterocyclyl;
  wherein the 4- to 7-membered heterocycloalkyl, 4- to 7-membered heterocycloalkenyl, spirocyclic 6- to 9-membered heterocyclyl, or bridged 6- to 9-membered heterocyclyl optionally contains 1 additional heteroatom selected from the group consisting of N and O; and
  wherein the 4- to 7-membered heterocycloalkyl, 4- to 7-membered heterocycloalkenyl, spirocyclic 6- to 9-membered heterocyclyl, or bridged 6- to 9-membered heterocyclyl is optionally substituted by 1, 2, 3, or 4 substituents independently selected from the group consisting of halogen, CN, $C_{1-6}$ alkyl, OH, $OC_{1-6}$ alkyl, and =O.

14. The compound as defined in claim 13, or a pharmaceutically acceptable salt, stereoisomer, or tautomer thereof, wherein:

A is a 6-membered heteroarylene, wherein the 6-membered heteroarylene contains 1 N heteroatom;

Y is $NY_1Y_2$;

$Y_1$ is H or $C_{1-6}$ alkyl, wherein the $C_{1-6}$ alkyl is optionally substituted by 1, 2, 3, 4, or 5 independently selected $OC_{1-6}$ alkyl substituents;

$Y_2$ is H, $C_{1-6}$ alkyl, cycloalkyl, or heterocycloalkyl;
  wherein the $C_{1-6}$ alkyl is optionally substituted by 1, 2, 3, 4, or 5 substituents independently selected from the group consisting of halogen, CN, OH, $OC_{1-6}$ alkyl, $OC_{1-6}$ haloalkyl, cyclopropyl, 4-membered heterocycloalkyl, and $C_{4-6}$ heterocycloalkyl;
  wherein the cycloalkyl is optionally substituted by 1, 2, 3, 4, or 5 substituents independently selected from the group consisting of halogen and CN;
  wherein the heterocycloalkyl is optionally substituted by 1, 2, 3, 4, or 5 independently selected acyl substituents;
  wherein each 4-membered heterocycloalkyl and $C_{4-6}$ heterocycloalkyl substituent independently contains 1, 2, or 3 heteroatoms independently selected from the group consisting of N, O, and S; and
wherein each 4-membered heterocycloalkyl and $C_{4-6}$ heterocycloalkyl substituent is optionally and independently substituted by 1 or more $CH_3$ substituents; or $Y^1$ and $Y^2$, taken together with the N atom to which they are attached, form a 4- to 7-membered heterocycloalkyl, a spirocyclic 6- to 9-membered heterocyclyl, or a bridged 6- to 9-membered heterocyclyl;
wherein the 4- to 7-membered heterocycloalkyl, spirocyclic 6- to 9-membered heterocyclyl, or bridged 6- to 9-membered heterocyclyl optionally contains 1 additional heteroatom selected from the group consisting of N and O; and
wherein the 4- to 7-membered heterocycloalkyl is optionally substituted by 1, 2, 3, or 4 substituents independently selected from the group consisting of halogen, CN, $C_{1-6}$ alkyl, OH, $OC_{1-6}$ alkyl, and =O.

15. The compound as defined in claim 14, or a pharmaceutically acceptable salt, stereoisomer, or tautomer thereof, wherein:
$Y_1$ is H or $C_{1-6}$ alkyl, wherein the $C_{1-6}$ alkyl is optionally substituted by 1, 2, 3, 4, or 5 independently selected $OC_{1-6}$ alkyl substituents; and
$Y_2$ is $C_{1-6}$ alkyl, cycloalkyl, or heterocycloalkyl;
wherein the $C_{1-6}$ alkyl is optionally substituted by 1 or 2 substituents independently selected from the group consisting of CN, OH, $OC_{1-6}$ alkyl, cyclopropyl, 4-membered heterocycloalkyl, and $C_{4-6}$ heterocycloalkyl;
wherein the cycloalkyl is optionally substituted by 1, 2, 3, 4, or 5 substituents independently selected from the group consisting of halogen and CN;
wherein the heterocycloalkyl is optionally substituted by 1 or 2 independently selected acyl substituents;
wherein each 4-membered heterocycloalkyl and $C_{4-6}$ heterocycloalkyl substituent independently contains 1, 2, or 3 heteroatoms independently selected from the group consisting of N, O, and S; and
wherein each 4-membered heterocycloalkyl and $C_{4-6}$ heterocycloalkyl substituent is optionally and independently substituted by 1 or more $CH_3$ substituents; or $Y^1$ and $Y^2$, taken together with the N atom to which they are attached, form a 4- to 7-membered heterocycloalkyl, a spirocyclic 6- to 9-membered heterocyclyl, or a bridged 6- to 9-membered heterocyclyl;
wherein the 4- to 7-membered heterocycloalkyl, spirocyclic 6- to 9-membered heterocyclyl, or bridged 6- to 9-membered heterocyclyl optionally contains 1 additional heteroatom selected from the group consisting of N and O; and
wherein the 4- to 7-membered heterocycloalkyl is optionally substituted by 1, 2, 3, or 4 substituents independently selected from the group consisting of halogen, $C_{1-6}$ alkyl, OH, $OC_{1-6}$ alkyl, and =O.

16. The compound as defined in claim 15, or a pharmaceutically acceptable salt, stereoisomer, or tautomer thereof, wherein $Y_2$ is $C_{1-6}$ alkyl;
wherein the $C_{1-6}$ alkyl is substituted by 1 substituent selected from the group consisting of OH, $OC_{1-6}$ alkyl, and cyclopropyl.

17. The compound as defined in claim 14, or a pharmaceutically acceptable salt, stereoisomer, or tautomer thereof, wherein:

$Y_1$ is H or $C_{1-6}$ alkyl, wherein the $C_{1-6}$ alkyl is optionally substituted by 1, 2, 3, 4, or 5 independently selected $OC_{1-6}$ alkyl substituents; and
$Y_2$ is $C_{1-6}$ alkyl or heterocycloalkyl;
wherein the $C_{1-6}$ alkyl is substituted by 1 substituent selected from the group consisting of halogen, CN, OH, $OC_{1-6}$ alkyl, $OC_{1-6}$ haloalkyl, cyclopropyl, 4-membered heterocycloalkyl, and $C_{4-6}$ heterocycloalkyl;
wherein the heterocycloalkyl is optionally substituted by 1 acyl substituent;
wherein each 4-membered heterocycloalkyl and $C_{4-6}$ heterocycloalkyl substituent independently contains 1, 2, or 3 heteroatoms independently selected from the group consisting of N, O, and S; and
wherein each 4-membered heterocycloalkyl and $C_{4-6}$ heterocycloalkyl substituent is optionally and independently substituted by 1 or more $CH_3$ substituents; or $Y^1$ and $Y^2$, taken together with the N atom to which they are attached, form a 4- to 7-membered heterocycloalkyl, a spirocyclic 6- to 9-membered heterocyclyl, or a bridged 6- to 9-membered heterocyclyl;
wherein the 4- to 7-membered heterocycloalkyl, spirocyclic 6- to 9-membered heterocyclyl, or bridged 6- to 9-membered heterocyclyl optionally contains 1 additional heteroatom selected from the group consisting of N and O; and
wherein the 4- to 7-membered heterocycloalkyl is optionally substituted by 1, 2, 3, or 4 substituents independently selected from the group consisting of $C_{1-6}$ alkyl and =O.

18. The compound as defined in claim 1, or a pharmaceutically acceptable salt, stereoisomer, or tautomer thereof, wherein:
Z is a 5-membered heteroarylene, wherein the 5-membered heteroarylene contains 2 heteroatoms independently selected from the group consisting of N, O, and S;
A is pyridinylene;
$R_1$ is $C_{1-3}$ alkylene-$OC_{1-3}$ alkyl, wherein the $C_{1-3}$ alkylene-$OC_{1-3}$ alkyl is optionally substituted by 1, 2, 3, or 4 substituents independently selected from the group consisting of halogen, CN, $C_{1-6}$ alkyl, OH, and =O;
Y is $NY_1Y_2$;
$Y_1$ is H or $C_{1-3}$ alkyl, wherein the $C_{1-3}$ alkyl is optionally substituted by 1, 2, 3, 4, or 5 substituents independently selected from the group consisting of OH, $OC_{1-3}$ alkyl, and $OC_{1-6}$ haloalkyl; and
$Y_2$ is H, $C_{1-4}$ alkyl, cyclopropyl, cyclobutyl, cyclopentyl, cyclohexyl, bicyclo[1.1.1]pentanyl, or a 4- to 6-membered heterocycloalkyl;
wherein the 4- to 6-membered heterocycloalkyl contains 1, 2, or 3 heteroatoms independently selected from the group consisting of N, O, and S;
wherein the $C_{1-4}$ alkyl, cyclopropyl, cyclobutyl, cyclopentyl, cyclohexyl, bicyclo[1.1.1]pentanyl, or 4- to 6-membered heterocycloalkyl is optionally substituted by 1, 2, 3, 4, or 5 substituents independently selected from the group consisting of F, Cl, Br, I, $C(O)C_{1-3}$ alkyl, $OC_{1-3}$ alkyl, $OC_{1-3}$ fluoroalkyl, $OC_{1-3}$ chloroalkyl, $OC_{1-3}$ bromoalkyl, $OC_{1-3}$ iodoalkyl, oxetanyl, and tetrahydrofuranyl;
wherein each oxetanyl substituent is optionally and independently substituted by 1 or more $CH_3$ substituents; and wherein each tetrahydrofuranyl substituent is optionally and independently substituted by 1 or more $CH_3$ substituents; or $Y^1$ and $Y^2$, taken together with the N atom to which they are attached, form a 4- to 7-membered heterocycloalkyl, a spirocyclic 7- to 9-membered heterocyclyl, a bicyclic, bridged 7-membered heterocyclyl, or a tricyclic, bridged 7-membered heterocyclyl;

wherein the 4- to 7-membered heterocycloalkyl, spirocyclic 7- to 9-membered heterocyclyl, bicyclic, bridged 7-membered heterocyclyl, or tricyclic, bridged 7-membered heterocyclyl optionally contains 1 or 2 additional heteroatoms independently selected from the group consisting of N and O; and wherein the 4- to 7-membered heterocycloalkyl, spirocyclic 7- to 9-membered heterocyclyl, bicyclic, bridged 7-membered heterocyclyl, or tricyclic, bridged 7-membered heterocyclyl is optionally substituted by 1, 2, 3, or 4 substituents independently selected from the group consisting of F, Cl, Br, I, $C_{1-3}$ alkyl, and $OC_{1-3}$ alkyl.

19. The compound as defined in claim 18, or a pharmaceutically acceptable salt, stereoisomer, or tautomer thereof, wherein:

Z is isoxazolylene;
A is 2,5-pyridinylene;
$R_1$ is $C_{1-3}$ alkylene-$OC_{1-3}$ alkyl;
$Y_1$ is H or $C_{1-3}$ alkyl, wherein the $C_{1-3}$ alkyl is optionally substituted by 1 or 2 independently selected $OC_{1-3}$ alkyl substituents; and
$Y_2$ is H, $C_{1-4}$ alkyl, cyclopropyl, cyclobutyl, cyclopentyl, cyclohexyl, bicyclo[1.1.1]pentan-1-yl, azetidinyl, oxetanyl, tetrahydrofuranyl, or tetrahydropyranyl;
wherein the $C_{1-4}$ alkyl, cyclopropyl, cyclobutyl, cyclopentyl, cyclohexyl, bicyclo[1.1.1]pentanyl, azetidinyl, oxetanyl, tetrahydrofuranyl, or tetrahydropyranyl is optionally substituted by 1 or 2 substituents independently selected from the group consisting of F, $C(O)CH_3$, $OC_{1-3}$ alkyl, $OC_{1-3}$ fluoroalkyl, oxetan-3-yl, and tetrahydrofuran-3-yl;
wherein each oxetan-3-yl substituent is optionally and independently substituted by 1 or more $CH_3$ substituents; and
wherein each tetrahydrofuran-3-yl substituent is optionally and independently substituted by 1 or more $CH_3$ substituents; or $Y^1$ and $Y^2$, taken together with the N atom to which they are attached, form azetidin-1-yl, piperidin-1-yl, piperazin-1-yl, morpholin-4-yl, 1,4-oxazepin-1-yl, 2-oxa-6-azaspiro[3.3]heptan-6-yl, 2-oxa-7-azaspiro[3.5]nonan-7-yl, or (1S,4S)-2-oxa-5-azabicyclo[2.2.1]heptan-5-yl, wherein the azetidin-1-yl, pyrrolidin-1-yl, piperidin-1-yl, piperazin-1-yl, morpholin-4-yl, 1,4-oxazepin-1-yl, 2-oxa-6-azaspiro[3.3]heptan-6-yl, 2-oxa-7-azaspiro[3.5]nonan-7-yl, or (1S,4S)-2-oxa-5-azabicyclo[2.2.1] heptan-5-yl is optionally substituted by 1 or 2 substituents independently selected from the group consisting of F, $CH_3$, $CH_2CH_3$, $CH_2CH_2CH_3$, $CH(CH_3)_2$, $OCH_3$, $OCH_2CH_3$, $OCH_2CH_2CH_3$, and $OCH(CH_3)_2$.

20. The compound as defined in claim 19, or a pharmaceutically acceptable salt, stereoisomer, or tautomer thereof, wherein:

Z is 3,5-isoxazolylene;
A is 2,5-pyridinylene, wherein the 2,5-pyridinylene is bonded to —$CH_2$— at the 2-position and bonded to —C(O)— at the 5-position;
$R_1$ is $CH_2OCH_3$;
$Y_1$ is H, $CH_3$, or $CH_2CH_3$, wherein the $CH_3$ or $CH_2CH_3$ is optionally substituted by 1 or 2 $OCH_3$ substituents; and
$Y_2$ is $CH_3$, cyclopropyl, cyclobutyl, azetidin-3-yl, oxetan-3-yl, tetrahydrofuran-3-yl, or tetrahydropyran-4-yl, wherein the $CH_3$, cyclopropyl, cyclobutyl, azetidin-3-yl, oxetan-3-yl, tetrahydrofuran-3-yl, or tetrahydropyran-4-yl is optionally substituted by 1 or 2 substituents independently selected from the group consisting of F, $OCH_3$, $OCH_2F$, $OCHF_2$, $OCF_3$, and 3-methyloxetan-3-yl; or $Y^1$ and $Y^2$, taken together with the N atom to which they are attached, form azetidin-1-yl, pyrrolidin-1-yl, piperidin-1-yl, piperazin-1-yl, morpholin-4-yl, 1,4-oxazepin-1-yl, 2-oxa-6-azaspiro[3.3]heptan-6-yl, 2-oxa-7-azaspiro[3.5]nonan-7-yl, or (1S,4S)-2-oxa-5-azabicyclo[2.2.1]heptan-5-yl, wherein the azetidin-1-yl, pyrrolidin-1-yl, piperidin-1-yl, piperazin-1-yl, morpholin-4-yl, 1,4-oxazepin-1-yl, 2-oxa-6-azaspiro[3.3]heptan-6-yl, 2-oxa-7-azaspiro[3.5]nonan-7-yl, or (1S,4S)-2-oxa-5-azabicyclo[2.2.1]heptan-5-yl is optionally substituted by 1 or 2 substituents independently selected from the group consisting of $CH_3$ and $OCH_3$.

21. The compound as defined in claim 20, or a pharmaceutically acceptable salt, stereoisomer, or tautomer thereof, wherein:

Z is 3,5-isoxazolylene, wherein the 3,5-isoxazolylene is bonded to the [1,2,4]triazolo[3,4-a]phthalazinyl ring at the 3-position and bonded to $R^1$ at the 5-position;
$Y_1$ is H, $CH_3$, $CH_2CH_3$, or $CH_2CH_2OCH_3$; and
$Y_2$ is $CH_3$, cyclopropyl, cyclobutyl, azetidin-3-yl, oxetan-3-yl, tetrahydrofuran-3-yl, or tetrahydropyran-4-yl, wherein the $CH_3$, cyclopropyl, cyclobutyl, azetidin-3-yl, oxetan-3-yl, tetrahydrofuran-3-yl, or tetrahydropyran-4-yl is optionally substituted by 1 or 2 substituents independently selected from the group consisting of F, $OCH_3$, $OCF_3$, and 3-methyloxetan-3-yl.

22. The compound as defined in claim 1, wherein the compound is represented by formula II:

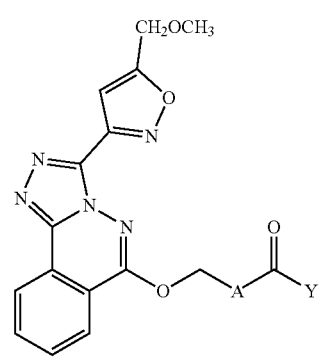

formula II or a pharmaceutically acceptable salt, stereoisomer, or tautomer thereof,
wherein:
A is pyridinylene;
Y is $NY_1Y_2$;
$Y_1$ is H, $CH_3$, or $CH_2OCH_3$; and
$Y_2$ is $C_{1-6}$ alkyl, $C_{3-6}$ cycloalkyl, or heterocycloalkyl;
wherein the heterocycloalkyl contains 1 N heteroatom;

wherein the $C_{1-6}$ alkyl is optionally substituted by 1 or 2 substituents independently selected from the group consisting of CN, OH, $OC_{1-6}$ alkyl, cyclopropyl, 4-membered heterocycloalkyl, and $C_{4-6}$ heterocycloalkyl;
wherein the heterocycloalkyl is optionally substituted by 1 acyl substituent;
wherein each 4-membered heterocycloalkyl substituent independently contains 1, 2, or 3 heteroatoms independently selected from the group consisting of N, O, and S;
wherein each $C_{4-6}$ heterocycloalkyl substituent independently contains 1 heteroatom selected from the group consisting of N and O; and
wherein each 4-membered heterocycloalkyl and $C_{4-6}$ heterocycloalkyl substituent is optionally and independently substituted by 1 or more $CH_3$ substituents; or
$Y^1$ and $Y^2$, taken together with the N atom to which they are attached, form a 4- to 7-membered heterocycloalkyl, a spirocyclic 6- to 9-membered heterocyclyl, or a bridged 6- to 9-membered heterocyclyl;
wherein the 4- to 7-membered heterocycloalkyl, spirocyclic 6- to 9-membered heterocyclyl, or bridged 6- to 9-membered heterocyclyl optionally contains 1 additional heteroatom selected from the group consisting of N and O; and
wherein the 4- to 7-membered heterocycloalkyl, spirocyclic 6- to 9-membered heterocyclyl, or bridged 6- to 9-membered heterocyclyl is optionally substituted by 1, 2, 3, or 4 substituents independently selected from the group consisting of $C_{1-6}$ alkyl, OH, $OC_{1-6}$ alkyl, and =O.

23. The compound as defined in claim 1, wherein the compound is represented by formula III:

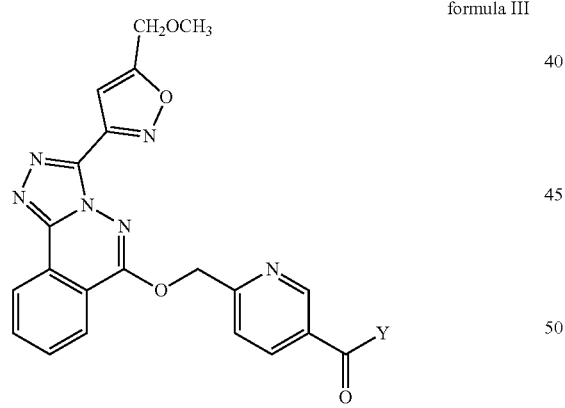

formula III or a pharmaceutically acceptable salt, stereoisomer, or tautomer thereof,
wherein:
Y is $NY_1Y_2$ or OH;
$Y_1$ is H, $CH_3$, $CH(OCH_3)CH_3$, or $CH_2CH_2OCH_3$; and
$Y_2$ is H, methyl, cyclopropylmethyl, oxetanylmethyl, (methyloxetanyl)methyl, tetrahydrofuranylmethyl, ethyl, fluoroethyl, difluoroethyl, trifluoroethyl, hydroxyethyl, methoxyethyl, trifluoromethoxyethyl, cyanopropyl, trifluoropropyl, difluorohydroxypropyl, methoxypropyl, dimethoxypropyl, isopropyl, trifluoroisopropyl, methoxyisopropyl, cyclopropyl, cyanocyclopropyl, cyclobutyl, fluorocyclobutyl, difluorocyclobutyl, difluorocyclopentyl, difluorocyclohexyl, acetylazetidinyl, oxetanyl, tetrahydrofuranyl, or tetrahydropyranyl; or
$Y^1$ and $Y^2$, taken together with the N atom to which they are attached, form difluoroazetidin-1-yl, hydroxyazetidin-1-yl, methoxyazetidin-1-yl, pyrrolidin-1-yl, difluoropyrrolidin-1-yl, piperidin-1-yl, difluoropiperidin-1-yl, hydroxypiperidin-1-yl, methoxypiperidin-1-yl, methylpiperazinon-1-yl, morpholin-4-yl, methylmorpholin-4-yl, dimethylmorpholin-4-yl, 1,2-oxazepan-2-yl, 1,3-oxazepan-3-yl, or 1,4-oxazepan-4-yl, 2-oxa-6-azaspiro[3.3]heptan-6-yl, 3-oxo-2-oxa-5-azabicyclo[2.2.1]heptan-5-yl, or 2-oxazolyl-7-azaspiro[3.5]nonan-7-yl.

24. The compound as defined in claim 1, wherein the compound is represented by formula III:

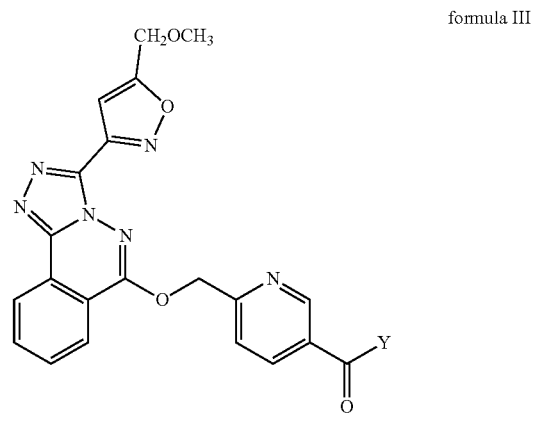

formula III or a pharmaceutically acceptable salt, stereoisomer, or tautomer thereof,
wherein:
Y is $NY_1Y_2$ or OH;
$Y_1$ is H, $CH_3$, or $CH_2CH_2OCH_3$; and
$Y_2$ is H, methyl, cyclopropylmethyl, (tetrahydrofuran-2-yl)methyl, (3-methyloxetanyl)methyl, ethyl, 2-fluoroethyl, 2,2-difluoroethyl, 2,2,2-trifluoroethyl, 2-hydroxyethyl, 2-methoxyethyl, 2-trifluoromethoxyethyl, 1,1,1-trifluoropropyl, 2,2-difluoro-3-hydroxypropyl, 3-cyanopropyl, 3-methoxypropyl, 1-methoxy-2-methylprop-2-yl, isopropyl, 1,1,1-trifluoroisopropyl, 1-methoxyisopropyl, 1,3-dimethoxyisopropyl, cyclopropyl, 1-cyanocyclopropyl, cyclobutyl, 3-fluorocyclobutyl, 3,3-difluorocyclobutyl, 3,3-difluorocyclopentyl, bicyclo[1.1.1]pentan-1-yl, 4,4-difluorocyclohexyl, 1-acetylazetidin-3-yl, oxetan-3-yl, 3-methyloxetanyl, tetrahydrofuran-3-yl, or tetrahydro-2H-pyran-4-yl; or
$Y^1$ and $Y^2$, taken together with the N atom to which they are attached, form 3,3-difluoroazetidin-1-yl, 3-hydroxyazetidin-1-yl, 3-methoxyazetidin-1-yl, pyrrolidin-1-yl, 3,3-difluoropyrrolidin-1-yl, piperidin-1-yl, 4.4-difluoropiperidin-1-yl, 4-hydroxypiperidin-1-yl, 4-methoxypiperidin-1-yl, 4-methyl-3-oxopiperazin-1-yl, morpholin-4-yl, 2-methylmorpholin-4-yl, 3-methylmorpholin-4-yl, 2,6-dimethylmorpholin-4-yl, 1,4-oxazepan-4-yl, (1S,4S)-3-oxo-2-oxa-5-azabicyclo[2.2.1]heptan-5-yl, 2-oxa-6-azaspiro[3.3]heptan-6-yl, or 2-oxazolyl-7-azaspiro[3.5]nonan-1-yl.

25. The compound as defined in claim 1, or a stereoisomer thereof, wherein the compound, or stereoisomer thereof, is selected from the group consisting of:
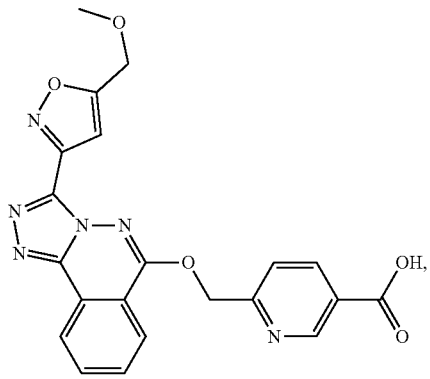
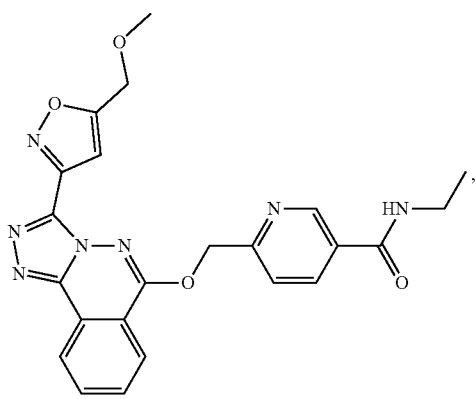
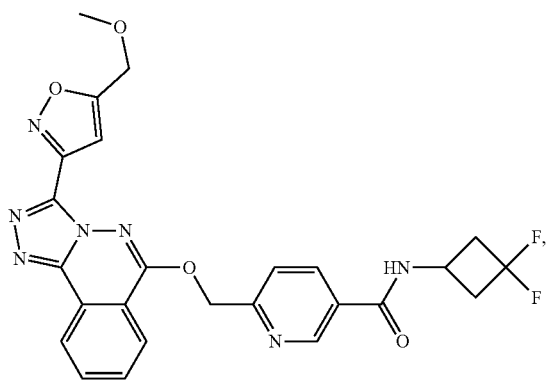
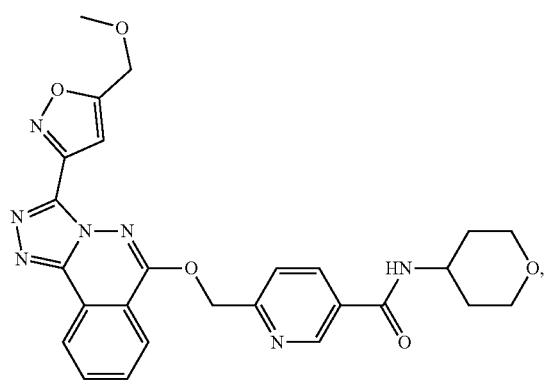
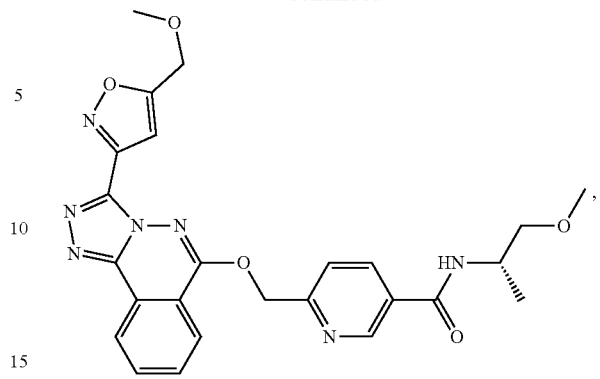
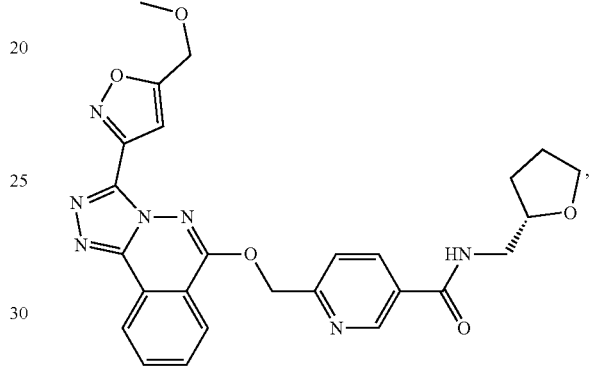
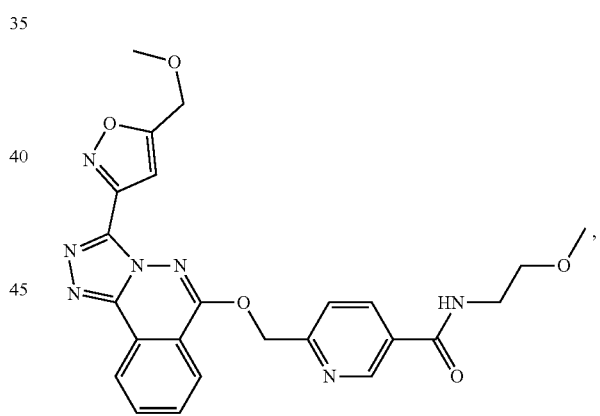
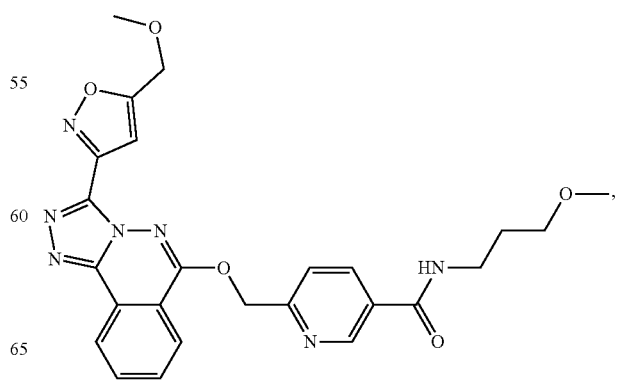

145
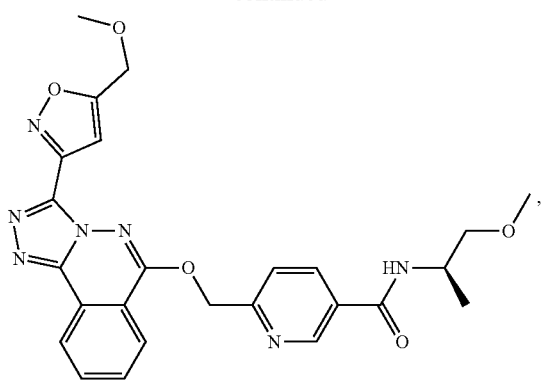
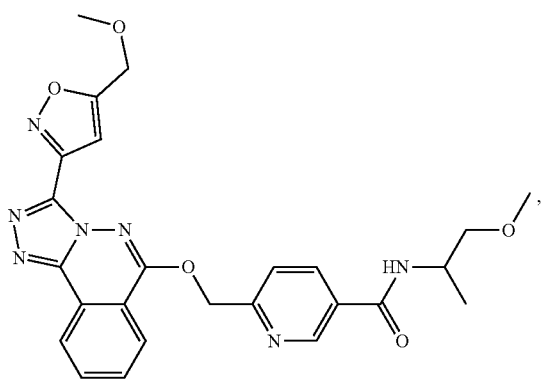
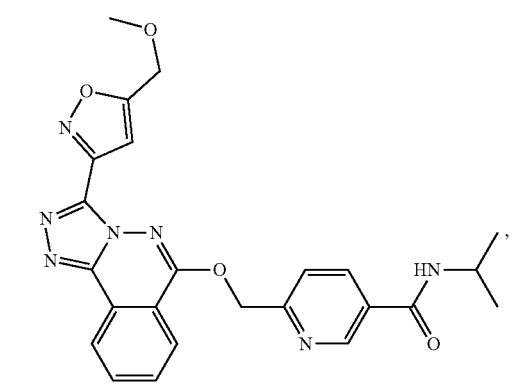
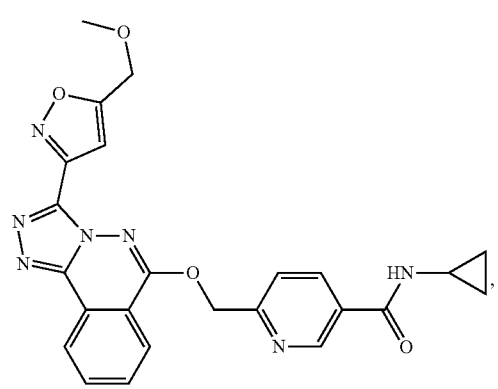
146
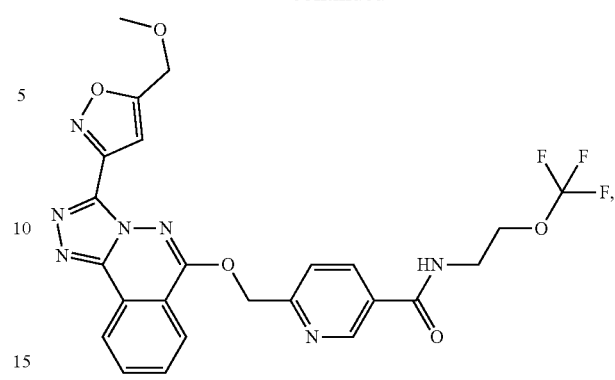
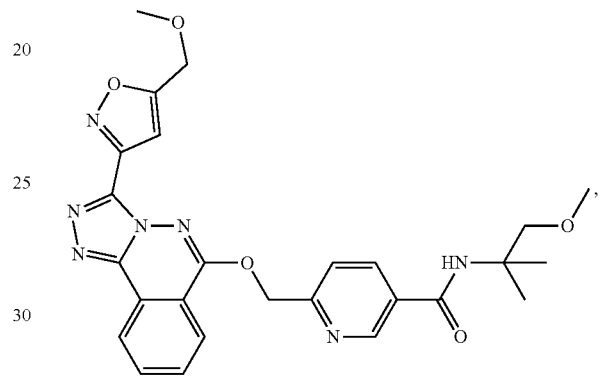
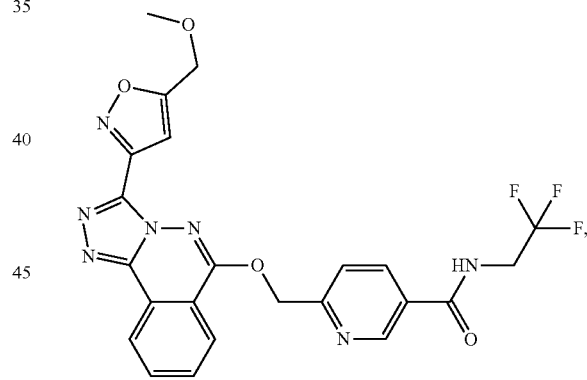
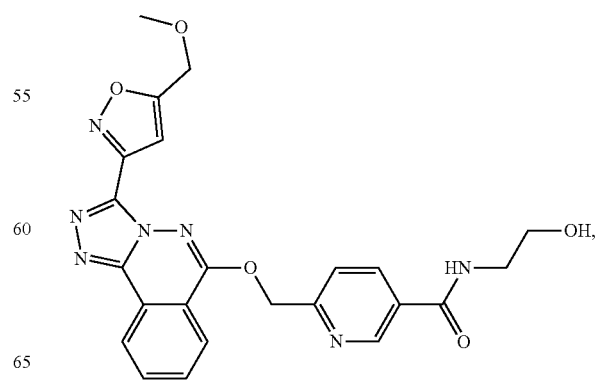

147
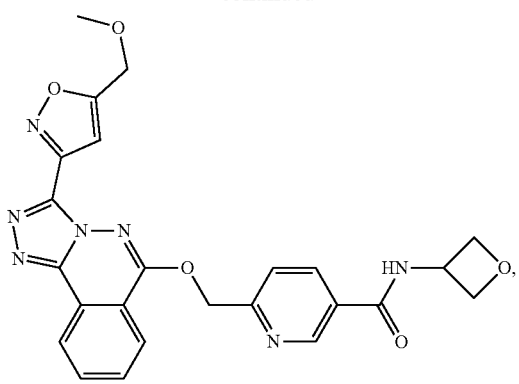
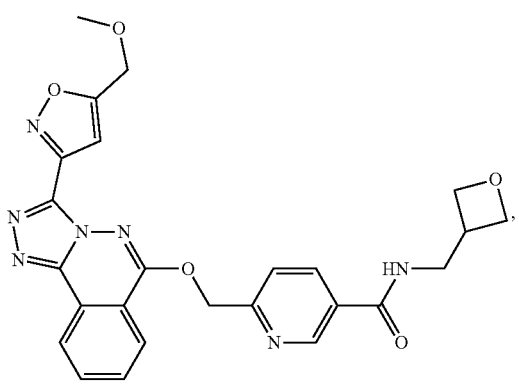
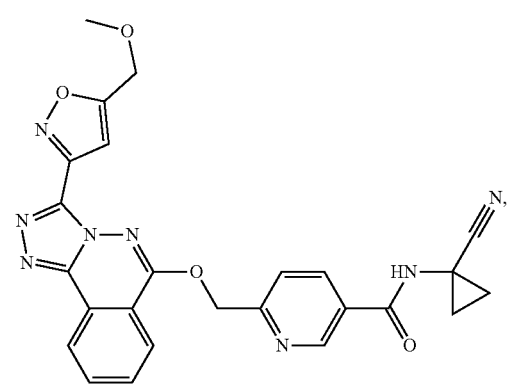
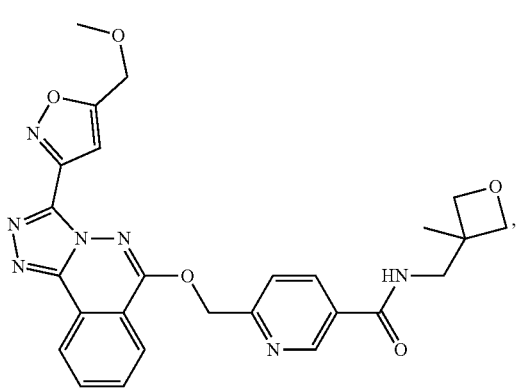
148
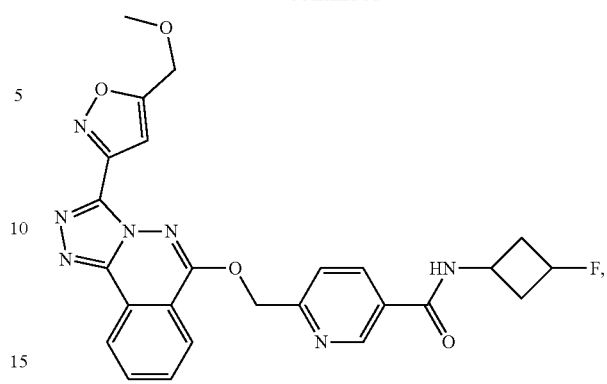
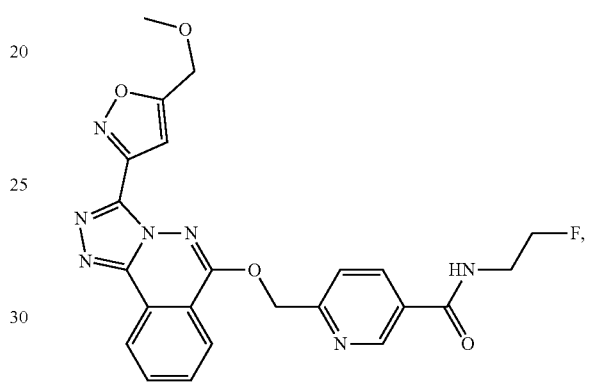
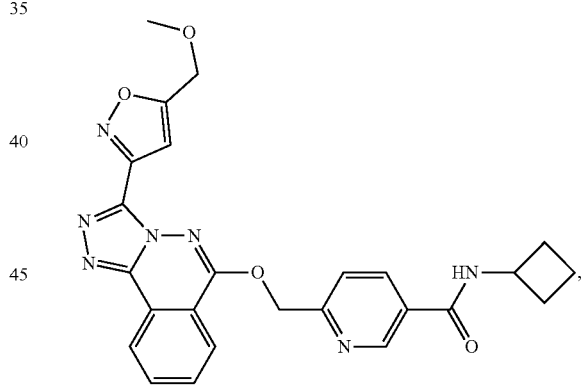
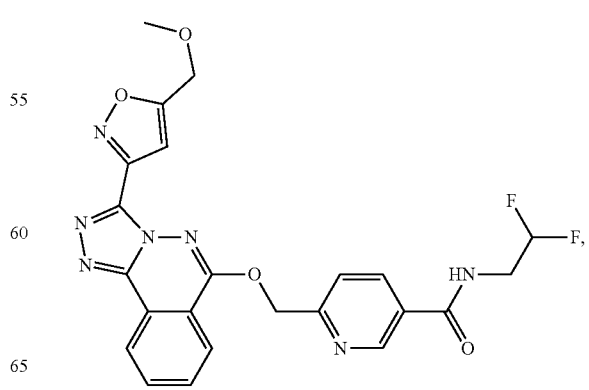

149
-continued
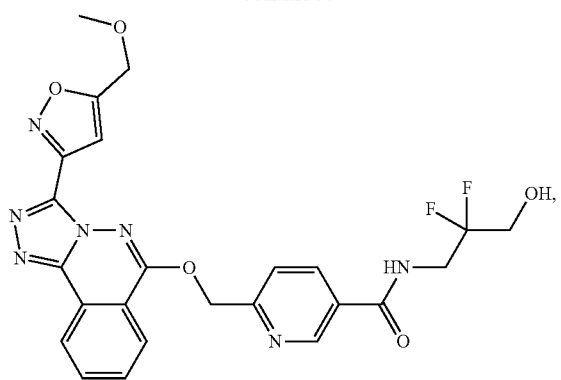
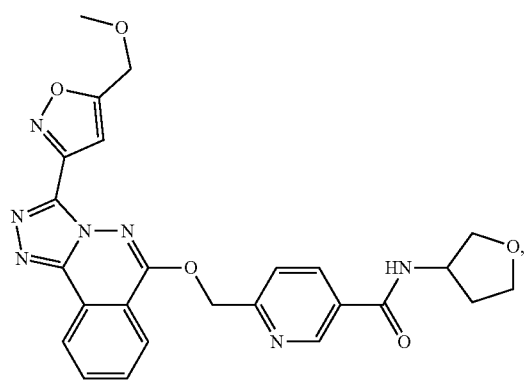
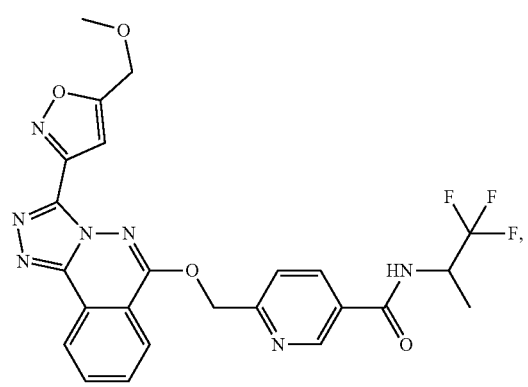
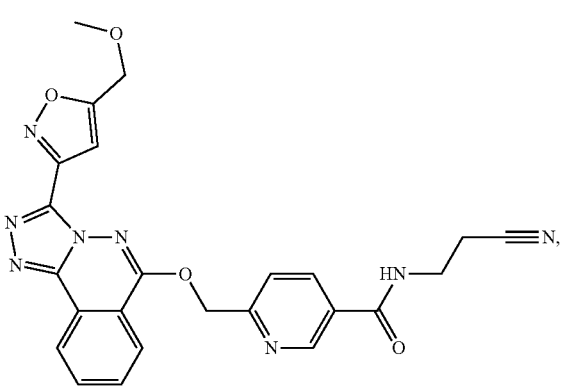
150
-continued
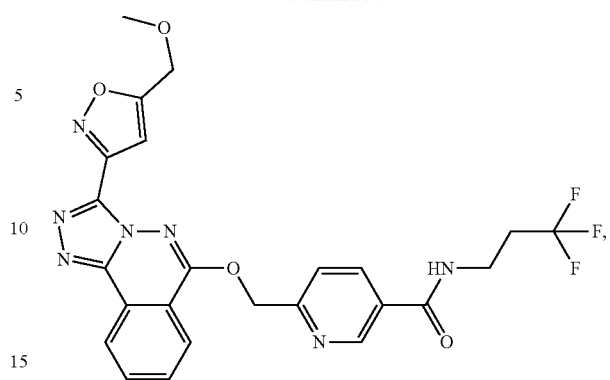
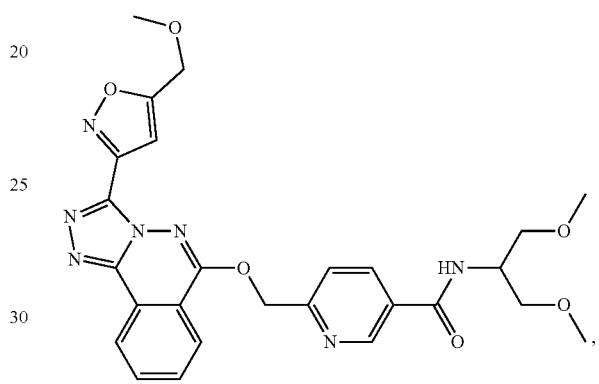
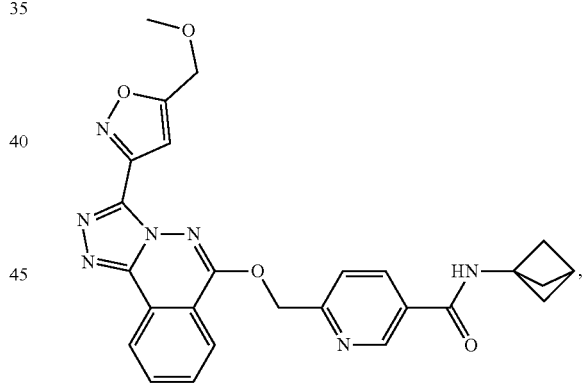
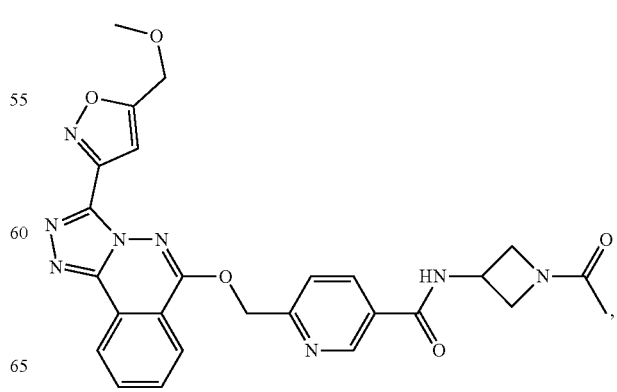

151
-continued
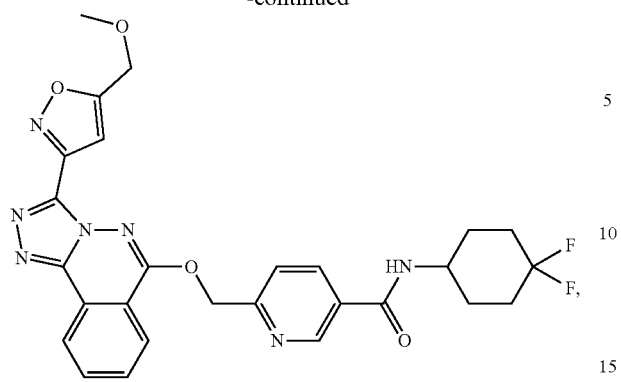
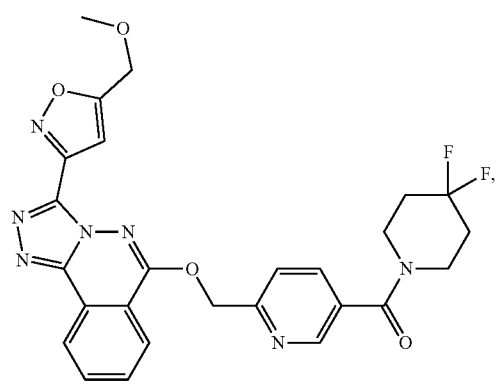
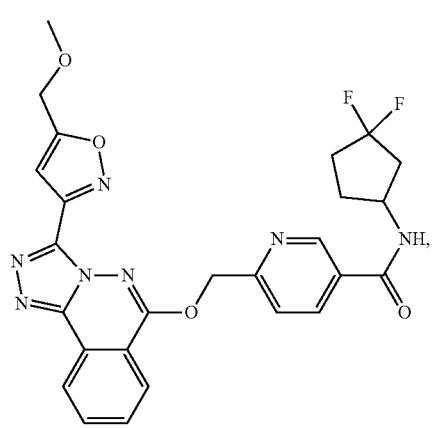
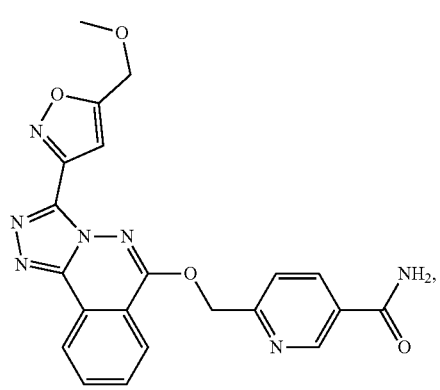
152
-continued
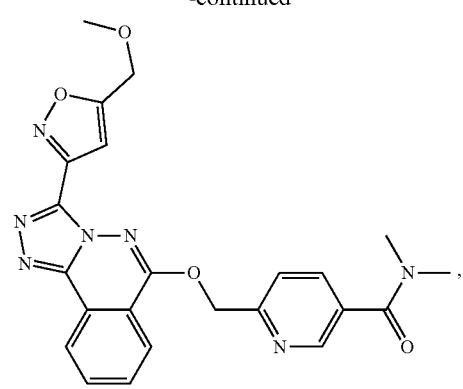
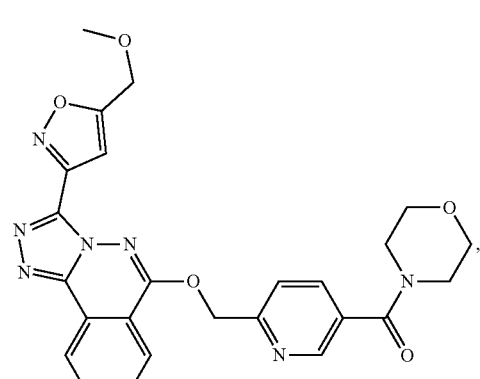
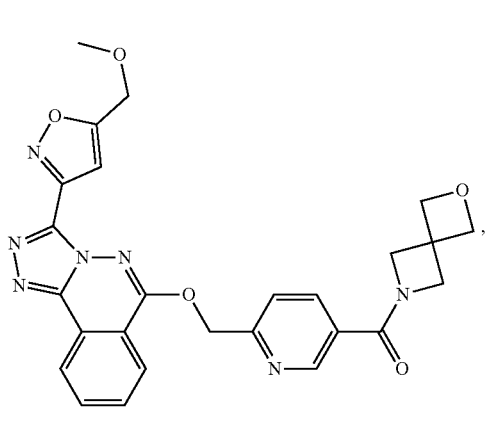
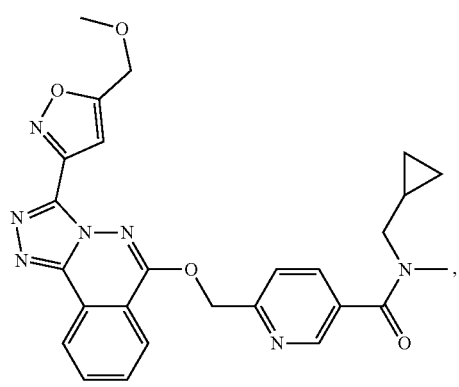

153
-continued
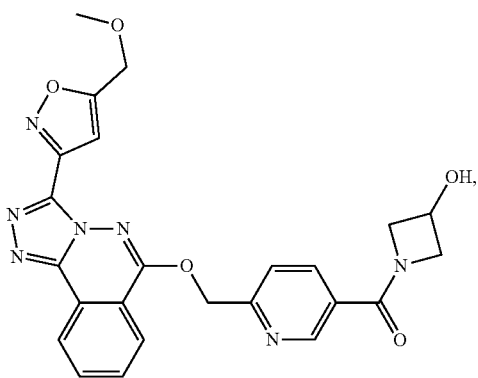
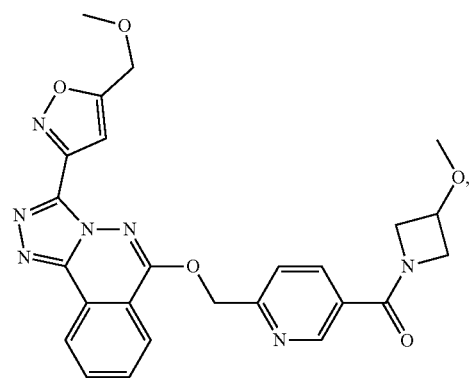
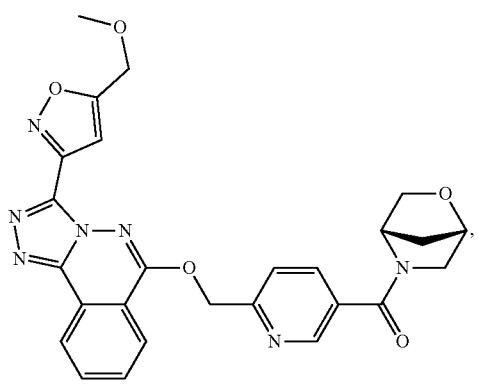
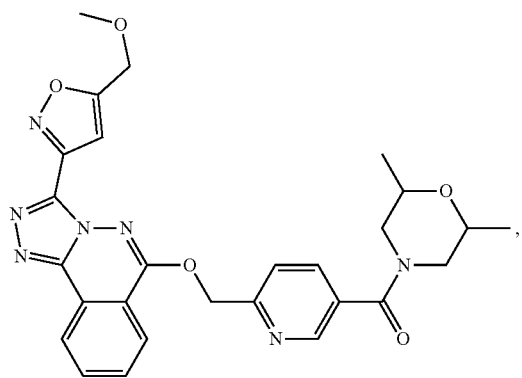
154
-continued
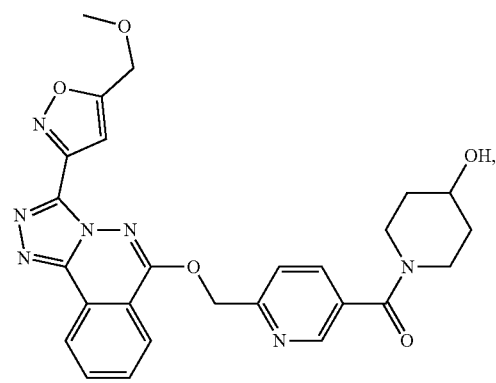
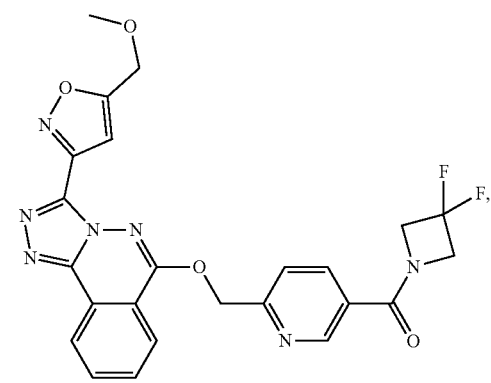
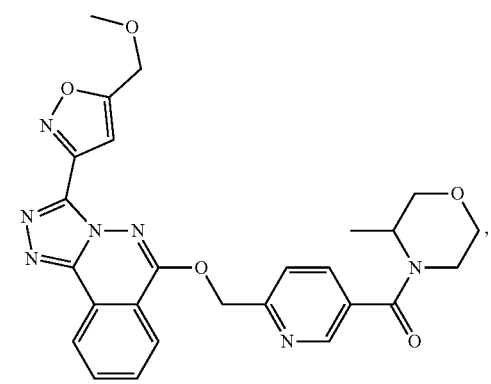
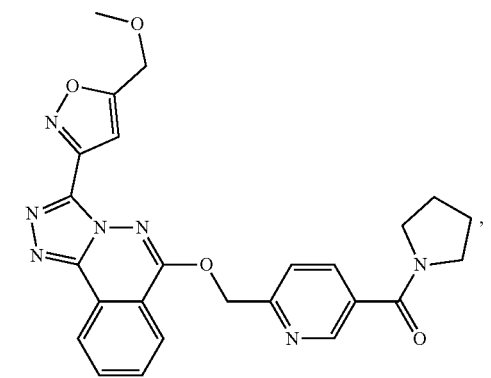

155
-continued
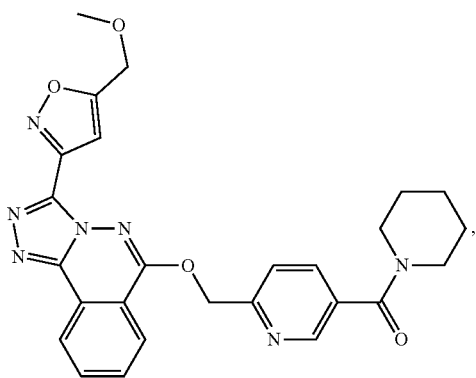
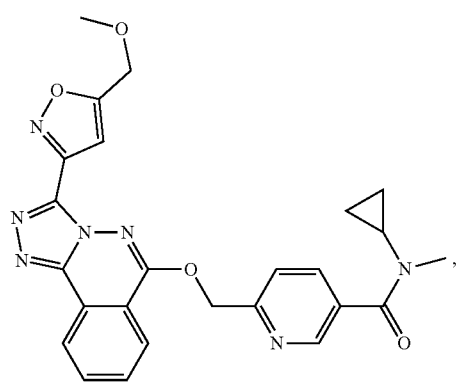
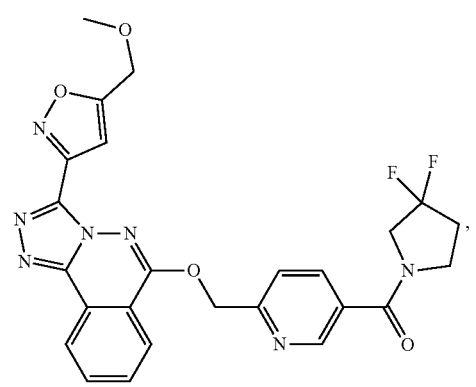
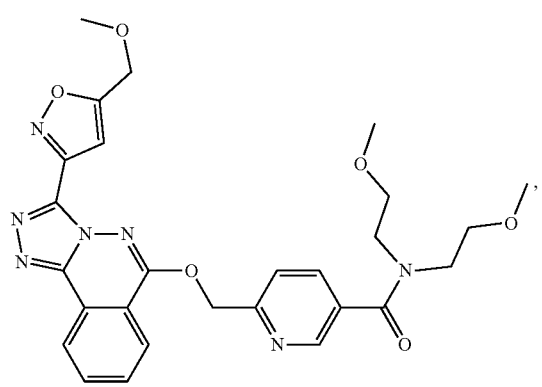
156
-continued
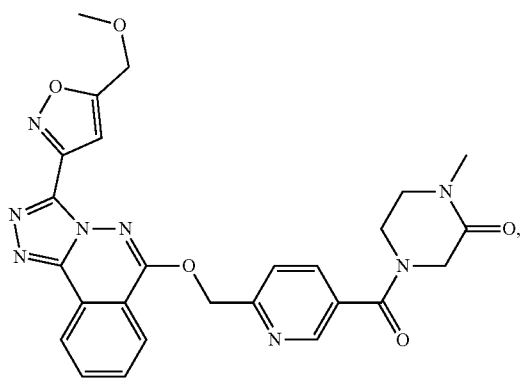
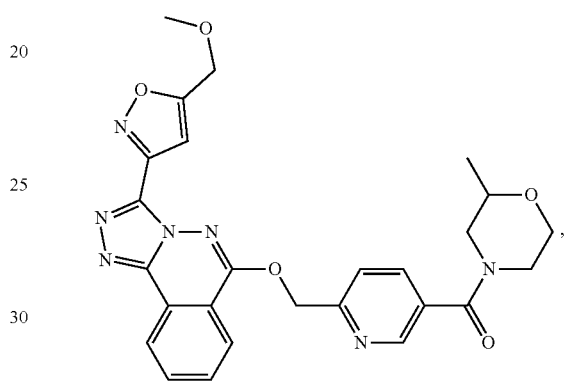
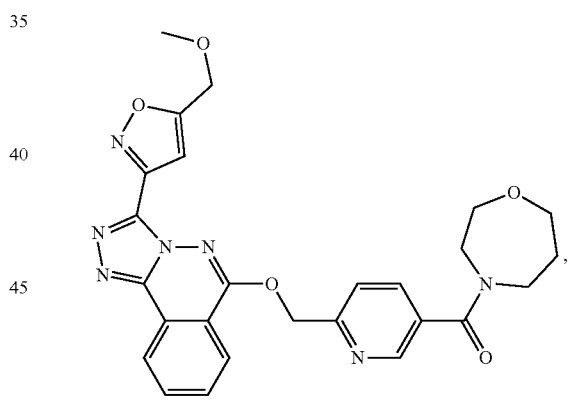
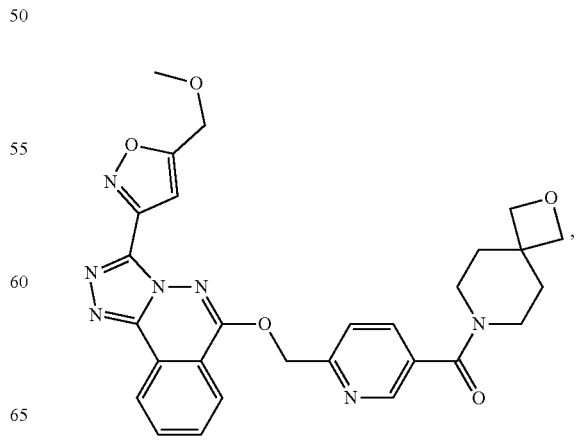

-continued

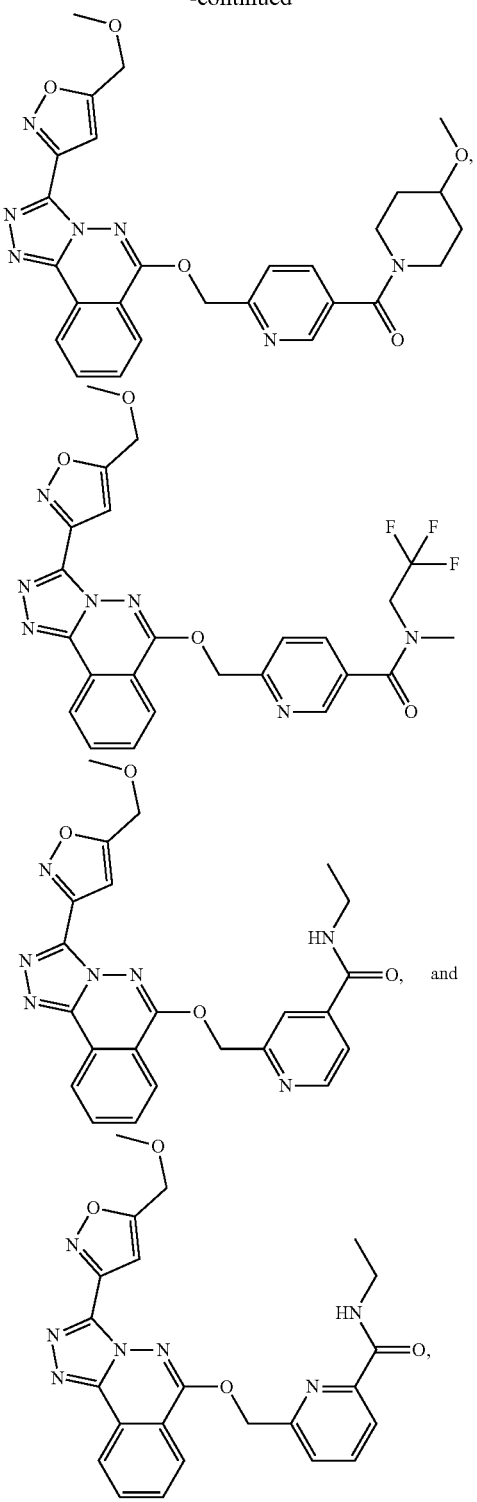

or a pharmaceutically acceptable salt or tautomer thereof.

26. A pharmaceutical composition comprising a pharmaceutically acceptable carrier and/or adjuvant and a compound as defined in claim 1, or a pharmaceutically acceptable salt, stereoisomer, or tautomer thereof.

27. A method for modulating α5-GABA$_A$ receptor in vivo, in vitro, or ex vivo, wherein the method comprises contacting the α5-GABA$_A$ receptor with a compound as defined in claim 1, or a pharmaceutically acceptable salt, stereoisomer, or tautomer thereof.

28. A method for modulating α5-GABA$_A$ receptor activity in a patient, wherein the method comprises administering to the patient in need thereof an effective dose of a compound as defined in claim 1, or a pharmaceutically acceptable salt, stereoisomer, or tautomer thereof.

29. The method as defined in claim 28, wherein the patient has a disease or disorder selected from the group consisting of amyotrophic lateral sclerosis, attention deficit disorder, a cognitive disease, a cognitive deficiency, Down's syndrome, drug addiction, multi-infarct dementia, pain, restless leg syndrome, and stroke.

30. The method as defined in claim 29, wherein the cognitive disease or cognitive deficiency is Alzheimer's disease or dysmnesia.

31. The method as defined in claim 29, wherein the pain is selected from the group consisting of abdominal pain, arthritis pain, autonomic nerve reflex pain, back pain, bone pain, boniness pain, cancer pain, cervix radiculopathy, chronic pain caused by injury, chronic pain caused by surgery, degenerative osteoarthropathy pain, dorsopathy, facial pain, glossopharyngeal neuralgia, gout, headache, inflammatory pain, lower limb pain, muscle pain, neck pain, nerve root avulsion pain, neuropathic pain, nociceptive pain, nutrition deficiency pain, painful diabetes, reflex sympathetic dystrophy pain, shoulder pain, thoracic pain, toxin pain, trigeminal neuralgia, vascular pain, visceral pain, waist pain, waist radiculopathy, pain associated with an autoimmune disease, pain associated with inflammation, pain associated with multiple sclerosis, pain associated with sickle cell anemia, and pain caused by an infectious disease.

32. The method as defined in claim 31, wherein the chronic pain caused by injury is chemical injury pain.

33. The method as defined in claim 31, wherein the pain caused by an infectious disease is pain caused by a bacterial infectious disease or pain caused by a viral infectious disease.

34. A process for preparing a compound represented by formula II:

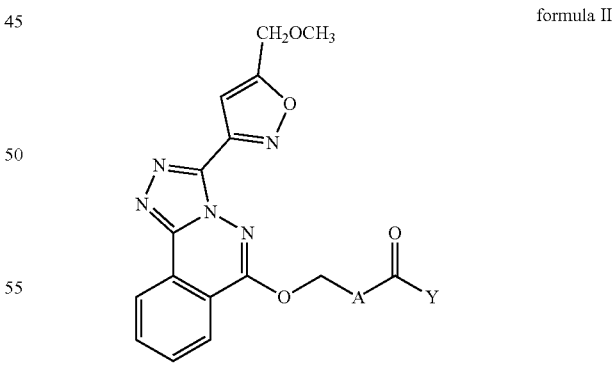

formula II wherein:
A is phenylene, a 5-membered heteroarylene, or a 6-membered heteroarylene;
  wherein the 5-membered heteroarylene contains 1, 2, 3, or 4 heteroatoms independently selected from the group consisting of N, O, and S;
  wherein at most 1 of the heteroatoms of the 5-membered heteroarylene is O or S;

wherein the 6-membered heteroarylene contains 1, 2, or 3 N heteroatoms;
wherein the phenylene is optionally substituted by 1, 2, or 3 substituents independently selected from the group consisting of halogen, CN, $C_{1-6}$ alkyl, linear $C_{2-6}$ alkenyl, $C_{2-6}$ alkynyl, and $C_{3-6}$ cycloalkyl; and
wherein the 5-membered heteroarylene or 6-membered heteroarylene is optionally substituted by 1 or more independently selected $R_x$ substituents;
each $R_x$ is independently halogen, CN, C(O)OR$_1$, OH, OC(O)R$_1$, OR$_1$, or R$_1$;
R$_1$ is $C_{1-6}$ alkylene-NHC$_{1-6}$ alkyl, $C_{1-6}$ alkylene-OC$_{1-6}$ alkyl, $C_{1-6}$ alkylene-OC$_{1-6}$ alkylene-C$_{3-6}$ cycloalkyl, $C_{1-6}$ alkylene-OC$_{1-6}$ alkylene-C$_{3-6}$ heterocycloalkyl, $C_{1-6}$ alkylene-C$_{3-6}$ heterocycloalkyl, OC$_{1-6}$ haloalkyl, OC$_{1-6}$ alkylene-C$_{3-6}$ cycloalkyl, or C$_{3-6}$ heterocycloalkyl, wherein the $C_{1-6}$ alkylene-NHC$_{1-6}$ alkyl, $C_{1-6}$ alkylene-OC$_{1-6}$ alkyl, $C_{1-6}$ alkylene-OC$_{1-6}$ alkylene-C$_{3-6}$ cycloalkyl, $C_{1-6}$ alkylene-OC$_{1-6}$ alkylene-C$_{3-6}$ heterocycloalkyl, $C_{1-6}$ alkylene-C$_{3-6}$ heterocycloalkyl, OC$_{1-6}$ haloalkyl, OC$_{1-6}$ alkylene-C$_{3-6}$ cycloalkyl, or C$_{3-6}$ heterocycloalkyl is optionally substituted by 1, 2, 3, or 4 substituents independently selected from the group consisting of halogen, CN, $C_{1-6}$ alkyl, OH, and $=O$;
Y is NY$_1$Y$_2$, NHNY$_3$Y$_4$, or OH;
Y$_1$ is H or $C_{1-6}$ alkyl, wherein the $C_{1-6}$ alkyl is optionally substituted by 1, 2, 3, 4, or 5 substituents independently selected from the group consisting of halogen, NH$_2$, NHC$_{1-6}$ alkyl, N(C$_{1-6}$ alkyl)$_2$, OH, OC$_{1-6}$ alkyl, OC$_{1-6}$ haloalkyl, and S(O)$_2$C$_{1-6}$ alkyl;
Y$_2$ is H, $C_{1-6}$ alkyl, NH$_2$, OC$_{1-6}$ alkyl, S(O)$_2$C$_{1-6}$ alkyl, S(O)$_2$NH$_2$, cycloalkyl, heterocycloalkyl, or heteroaryl;
heteroaryl;
wherein the $C_{1-6}$ alkyl, OC$_{1-6}$ alkyl, S(O)$_2$C$_{1-6}$ alkyl, cycloalkyl, heterocycloalkyl, or heteroaryl is optionally substituted by 1, 2, 3, 4, or 5 substituents independently selected from the group consisting of halogen, CN, $C_{1-6}$ alkyl, $C_{1-6}$ haloalkyl, $C_{1-6}$ alkylene-C(O)OH, $C_{1-6}$ alkylene-C(O)OC$_{1-4}$ alkyl, $C_{1-6}$ alkylene-OH, $C_{1-6}$ alkylene-OC$_{1-6}$ alkyl, acyl, NHC$_{1-6}$ alkyl, NHacyl, N(C$_{1-6}$ alkyl)$_2$, NO$_2$, OH, OC$_{1-6}$ alkyl, OC$_{1-6}$ haloalkyl, S(O)$_2$C$_{1-6}$ alkyl, C$_{3-6}$ cycloalkyl, 4-membered heterocycloalkyl, and C$_{4-6}$ heterocycloalkyl;
wherein each 4-membered heterocycloalkyl and C$_{4-6}$ heterocycloalkyl substituent independently contains 1, 2, or 3 heteroatoms independently selected from the group consisting of N, O, and S;
wherein each C$_{3-6}$ cycloalkyl substituent is optionally and independently substituted by 1 or more OH substituents;
wherein each 4-membered heterocycloalkyl substituent is optionally and independently substituted by 1 or more CH$_3$ substituents; and
wherein each C$_{4-6}$ heterocycloalkyl substituent is optionally and independently substituted by 1 or more substituents independently selected from the group consisting of halogen, CH$_3$, and OCH$_3$; or
Y$^1$ and Y$^2$, taken together with the N atom to which they are attached, form a 4- to 7-membered heterocycloalkyl, a 4- to 7-membered heterocycloalkenyl, a spirocyclic 6- to 9-membered heterocyclyl, or a bridged 6- to 9-membered heterocyclyl;

wherein the 4- to 7-membered heterocycloalkyl, 4- to 7-membered heterocycloalkenyl, spirocyclic 6- to 9-membered heterocyclyl, or bridged 6- to 9-membered heterocyclyl optionally contains 1 or more additional heteroatoms independently selected from the group consisting of N and O; and
wherein the 4- to 7-membered heterocycloalkyl, 4- to 7-membered heterocycloalkenyl, spirocyclic 6- to 9-membered heterocyclyl, or bridged 6- to 9-membered heterocyclyl is optionally substituted by 1, 2, 3, or 4 substituents independently selected from the group consisting of halogen, CN, $C_{1-6}$ alkyl, OH, OC$_{1-6}$ alkyl, and $=O$;
Y$_3$ is H, $C_{1-6}$ alkyl, S(O)$_2$C$_{1-6}$ alkyl, cycloalkyl, or heterocyclyl, wherein the $C_{1-6}$ alkyl, S(O)$_2$C$_{1-6}$ alkyl, cycloalkyl, or heterocyclyl is optionally substituted by 1, 2, 3, or 4 substituents independently selected from the group consisting of halogen, CN, $C_{1-6}$ alkyl, OH, and OC$_{1-6}$ alkyl; and
Y$_4$ is H, $C_{1-4}$ alkyl, S(O)$_2$C$_{1-6}$ alkyl, cycloalkyl, or heterocyclyl, wherein the $C_{1-6}$ alkyl, S(O)$_2$C$_{1-6}$ alkyl, cycloalkyl, or heterocyclyl is optionally substituted by 1, 2, 3, or 4 substituents independently selected from the group consisting of halogen, CN, $C_{1-6}$ alkyl, OH, and OC$_{1-6}$ alkyl; or
Y$^3$ and Y$^4$, taken together with the N atom to which they are attached, form a heterocyclyl, wherein the heterocyclyl is optionally substituted by 1, 2, 3, or 4 substituents independently selected from the group consisting of halogen, CN, $C_{1-6}$ alkyl, OH, OC$_{1-6}$ alkyl, and $=O$;
with the proviso that if A is pyridinylene, then the pyridinylene is optionally an N-oxide thereof;
wherein the process comprises the following steps:
1) reacting a compound represented by formula B:

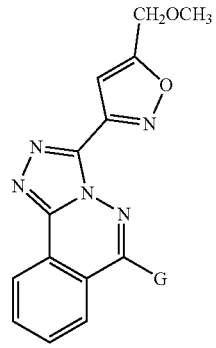

formula B wherein:
G is Cl, Br, I, OH, OMs, OTf, or OTs;
with a compound represented by formula IV:

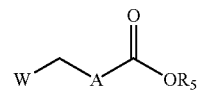

formula IV wherein:
A is phenylene, a 5-membered heteroarylene, or a 6-membered heteroarylene;

wherein the 5-membered heteroarylene contains 1, 2, 3, or 4 heteroatoms independently selected from the group consisting of N, O, and S;
wherein at most 1 of the heteroatoms of the 5-membered heteroarylene is O or S;
wherein the 6-membered heteroarylene contains 1, 2, or 3 N heteroatoms;
wherein the phenylene is optionally substituted by 1, 2, or 3 substituents independently selected from the group consisting of halogen, CN, $C_{1-6}$ alkyl, linear $C_{2-6}$ alkenyl, $C_{2-6}$ alkynyl, and $C_{3-6}$ cycloalkyl; and
wherein the 5-membered heteroarylene or 6-membered heteroarylene is optionally substituted by 1 or more independently selected $R_x$ substituents;
each $R_x$ is independently halogen, CN, C(O)OR$_1$, OH, OC(O)R$_1$, OR$_1$, or R$_1$;
R$_1$ is $C_{1-6}$ alkylene-NHC$_{1-6}$ alkyl, $C_{1-6}$ alkylene-OC$_{1-6}$ alkyl, $C_{1-6}$ alkylene-OC$_{1-6}$ alkylene-C$_{3-6}$ cycloalkyl, $C_{1-6}$ alkylene-OC$_{1-6}$ alkylene-C$_{3-6}$ heterocycloalkyl, $C_{1-6}$ alkylene-C$_{3-6}$ heterocycloalkyl, OC$_{1-6}$ haloalkyl, OC$_{1-6}$ alkylene-C$_{3-6}$ cycloalkyl, or C$_{3-6}$ heterocycloalkyl,
wherein the $C_{1-6}$ alkylene-NHC$_{1-6}$ alkyl, $C_{1-6}$ alkylene-OC$_{1-6}$ alkyl, $C_{1-6}$ alkylene-OC$_{1-6}$ alkylene-C$_{3-6}$ cycloalkyl, $C_{1-6}$ alkylene-OC$_{1-6}$ alkylene-C$_{3-6}$ heterocycloalkyl, $C_{1-6}$ alkylene-C$_{3-6}$ heterocycloalkyl, OC$_{1-6}$ haloalkyl, OC$_{1-6}$ alkylene-C$_{3-6}$ cycloalkyl, or C$_{3-6}$ heterocycloalkyl is optionally substituted by 1, 2, 3, or 4 substituents independently selected from the group consisting of halogen, CN, $C_{1-6}$ alkyl, OH, and =O;
W is Cl, Br, I, OH, OMs, OTf, or OTs; and
R$_5$ is alkyl or benzyl;
(a) in the presence of a base selected from the group consisting of lithium diisopropyl amide (LDA), sodium hydride, potassium tert-butoxide, or sodium tert-butoxide in a solvent selected from the group consisting of N,N-dimethylformamide, dioxane, and tetrahydrofuran, or (b) under Mitsunobu conditions comprising (i) triphenyl phosphine, (ii) diethyl azodicarboxylate (DEAD), and (iii) a phase transfer catalyst selected from the group consisting of a crown ether and tetrabutylammoniun bromide (TBAB), to provide a compound represented by formula 1-3:

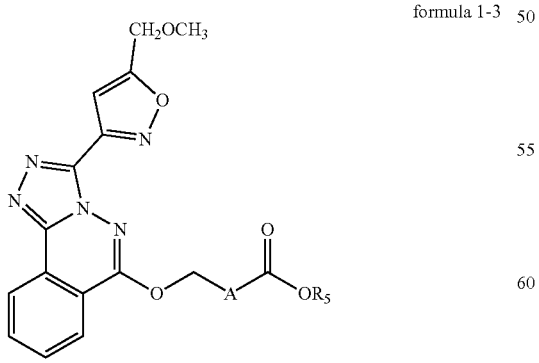

formula 1-3 wherein:
A is phenylene, a 5-membered heteroarylene, or a 6-membered heteroarylene;
wherein the 5-membered heteroarylene contains 1, 2, 3, or 4 heteroatoms independently selected from the group consisting of N, O, and S;
wherein at most 1 of the heteroatoms of the 5-membered heteroarylene is O or S;
wherein the 6-membered heteroarylene contains 1, 2, or 3 N heteroatoms;
wherein the phenylene is optionally substituted by 1, 2, or 3 substituents independently selected from the group consisting of halogen, CN, $C_{1-6}$ alkyl, linear $C_{2-6}$ alkenyl, $C_{2-6}$ alkynyl, and $C_{3-6}$ cycloalkyl; and
wherein the 5-membered heteroarylene or 6-membered heteroarylene is optionally substituted by 1 or more independently selected $R_x$ substituents;
each $R_x$ is independently halogen, CN, C(O)OR$_1$, OH, OC(O)R$_1$, OR$_1$, or R$_1$;
R$_1$ is $C_{1-6}$ alkylene-NHC$_{1-6}$ alkyl, $C_{1-6}$ alkylene-OC$_{1-6}$ alkyl, $C_{1-6}$ alkylene-OC$_{1-6}$ alkylene-C$_{3-6}$ cycloalkyl, $C_{1-6}$ alkylene-OC$_{1-6}$ alkylene-C$_{3-6}$ heterocycloalkyl, $C_{1-6}$ alkylene-C$_{3-6}$ heterocycloalkyl, OC$_{1-6}$ haloalkyl, OC$_{1-6}$ alkylene-C$_{3-6}$ cycloalkyl, or C$_{3-6}$ heterocycloalkyl, wherein the $C_{1-6}$ alkylene-NHC$_{1-6}$ alkyl, $C_{1-6}$ alkylene-OC$_{1-6}$ alkyl, $C_{1-6}$ alkylene-OC$_{1-6}$ alkylene-C$_{3-6}$ cycloalkyl, alkylene-OC$_{1-6}$ alkylene-C$_{3-6}$ heterocycloalkyl, $C_{1-6}$ alkylene-C$_{3-6}$ heterocycloalkyl, OC$_{1-6}$ haloalkyl, OC$_{1-6}$ alkylene-C$_{3-6}$ cycloalkyl, or C$_{3-6}$ heterocycloalkyl is optionally substituted by 1, 2, 3, or 4 substituents independently selected from the group consisting of halogen, CN, $C_{1-6}$ alkyl, OH, and =O; and
R$_5$ is alkyl or benzyl;
2) reacting the compound represented by formula 1-3 above (a) with aqueous sodium hydroxide, (b) with sodium hydroxide or lithium hydroxide in a solvent selected from the group consisting of tetrahydrofuran and water, or a mixture thereof, or (c) under hydrogenation conditions, to provide a compound represented by formula 1-4:

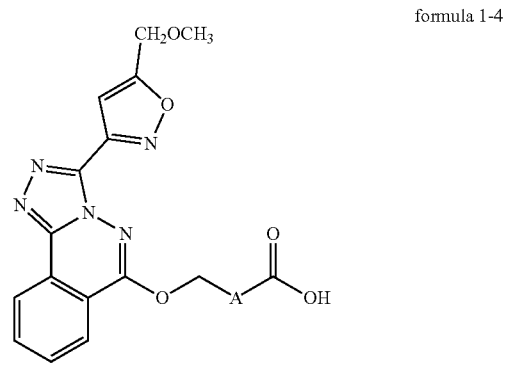

formula 1-4 wherein:
A is phenylene, a 5-membered heteroarylene, or a 6-membered heteroarylene;
wherein the 5-membered heteroarylene contains 1, 2, 3, or 4 heteroatoms independently selected from the group consisting of N, O, and S;
wherein at most 1 of the heteroatoms of the 5-membered heteroarylene is O or S;

wherein the 6-membered heteroarylene contains 1, 2, or 3 N heteroatoms;

wherein the phenylene is optionally substituted by 1, 2, or 3 substituents independently selected from the group consisting of halogen, CN, $C_{1-6}$ alkyl, linear $C_{2-6}$ alkenyl, $C_{2-6}$ alkynyl, and $C_{3-6}$ cycloalkyl; and wherein the 5-membered heteroarylene or 6-membered heteroarylene is optionally substituted by 1 or more independently selected $R_x$ substituents;

each $R_x$ is independently halogen, CN, C(O)OR$_1$, OH, OC(O)R$_1$, OR$_1$, or R$_1$;

$R_1$ is $C_{1-6}$ alkylene-NHC$_{3-6}$ alkyl, $C_{3-6}$ alkylene-OC$_{1-6}$ alkyl, $C_{3-6}$ alkylene-OC$_{1-6}$ alkylene-C$_{3-6}$ cycloalkyl, $C_{1-6}$ alkylene-OC$_{1-6}$ alkylene-C$_{3-6}$ heterocycloalkyl, $C_{1-6}$ alkylene-C$_{3-6}$ heterocycloalkyl, OC$_{1-6}$ haloalkyl, OC$_{1-6}$ alkylene-C$_{3-6}$ cycloalkyl, or $C_{3-6}$ heterocycloalkyl, wherein the $C_{1-6}$ alkylene-NHC$_{1-6}$ alkyl, $C_{1-6}$ alkylene-OC$_{1-6}$ alkyl, $C_{1-6}$ alkylene-OC$_{1-6}$ alkylene-C$_{3-6}$ cycloalkyl, $C_{1-6}$ alkylene-OC$_{1-6}$ alkylene-C$_{3-6}$ heterocycloalkyl, $C_{1-6}$ alkylene-C$_{3-6}$ heterocycloalkyl, OC$_{1-6}$ haloalkyl, OC$_{1-6}$ alkylene-C$_{3-6}$ cycloalkyl, or C$_{3-6}$ heterocycloalkyl is optionally substituted by 1, 2, 3, or 4 substituents independently selected from the group consisting of halogen, CN, $C_{1-6}$ alkyl, OH, and =O; and 3) reacting the compound represented by formula 1-4 above with a compound represented by the following formula:

Y—H wherein:
Y is NY$_1$Y$_2$, NHNY$_3$Y$_4$, or OH;
Y$_1$ is H or $C_{1-6}$ alkyl, wherein the $C_{1-6}$ alkyl is optionally substituted by 1, 2, 3, 4, or 5 substituents independently selected from the group consisting of halogen, NH$_2$, NHC$_{1-6}$ alkyl, N(C$_{1-6}$ alkyl)$_2$, OH, OC$_{1-6}$ alkyl, OC$_{1-6}$ haloalkyl, and S(O)$_2$C$_{1-6}$ alkyl;
Y$_2$ is H, $C_{1-6}$ alkyl, NH$_2$, OC$_{1-6}$ alkyl, S(O)$_2$C$_{1-6}$ alkyl, S(O)$_2$NH$_2$, cycloalkyl, heterocycloalkyl, or heteroaryl;

heteroaryl;
wherein the $C_{1-6}$ alkyl, OC$_{1-6}$ alkyl, S(O)$_2$C$_{1-6}$ alkyl, cycloalkyl, heterocycloalkyl, or heteroaryl is optionally substituted by 1, 2, 3, 4, or 5 substituents independently selected from the group consisting of halogen, CN, $C_{1-6}$ alkyl, $C_{1-6}$ haloalkyl, $C_{1-6}$ alkylene-C(O)OH, $C_{1-6}$ alkylene-C(O)OC$_{1-4}$ alkyl, $C_{1-6}$ alkylene-OH, $C_{1-6}$ alkylene-OC$_{1-6}$ alkyl, acyl, NHC$_{1-6}$ alkyl, NHacyl, N(C$_{1-6}$ alkyl)$_2$, NO$_2$, OH, OC$_{1-6}$ alkyl, OC$_{1-6}$ haloalkyl, S(O)$_2$C$_{1-6}$ alkyl, $C_{3-6}$ cycloalkyl, 4-membered heterocycloalkyl, and $C_{4-6}$ heterocycloalkyl;
wherein each 4-membered heterocycloalkyl and $C_{4-6}$ heterocycloalkyl substituent independently contains 1, 2, or 3 heteroatoms independently selected from the group consisting of N, O, and S;
wherein each $C_{3-6}$ cycloalkyl substituent is optionally and independently substituted by 1 or more OH substituents;
wherein each 4-membered heterocycloalkyl substituent is optionally and independently substituted by 1 or more CH$_3$ substituents; and wherein each $C_{4-6}$ heterocycloalkyl substituent is optionally and independently substituted by 1 or more substituents independently selected from the group consisting of halogen, CH$_3$, and OCH$_3$; or Y$^1$ and Y$^2$, taken together with the N atom to which they are attached, form a 4- to 7-membered heterocycloalkyl, a 4- to 7-membered heterocycloalkenyl, a spirocyclic 6- to 9-membered heterocyclyl, or a bridged 6- to 9-membered heterocyclyl;

wherein the 4- to 7-membered heterocycloalkyl, 4- to 7-membered heterocycloalkenyl, spirocyclic 6- to 9-membered heterocyclyl, or bridged 6- to 9-membered heterocyclyl optionally contains 1 or more additional heteroatoms independently selected from the group consisting of N and O; and wherein the 4- to 7-membered heterocycloalkyl, 4- to 7-membered heterocycloalkenyl, spirocyclic 6- to 9-membered heterocyclyl, or bridged 6- to 9-membered heterocyclyl is optionally substituted by 1, 2, 3, or 4 substituents independently selected from the group consisting of halogen, CN, $C_{1-6}$ alkyl, OH, OC$_{1-6}$ alkyl, and =O;

Y$_3$ is H, $C_{1-6}$ alkyl, S(O)$_2$C$_{1-6}$ alkyl, cycloalkyl, or heterocyclyl, wherein the $C_{1-6}$ alkyl, S(O)$_2$C$_{1-6}$ alkyl, cycloalkyl, or heterocyclyl is optionally substituted by 1, 2, 3, or 4 substituents independently selected from the group consisting of halogen, CN, $C_{1-6}$ alkyl, OH, and OC$_{1-6}$ alkyl; and Y$_4$ is H, $C_{1-6}$ alkyl, S(O)$_2$C$_{1-6}$ alkyl, cycloalkyl, or heterocyclyl, wherein the $C_{1-6}$ alkyl, S(O)$_2$C$_{1-6}$ alkyl, cycloalkyl, or heterocyclyl is optionally substituted by 1, 2, 3, or 4 substituents independently selected from the group consisting of halogen, CN, $C_{1-6}$ alkyl, OH, and OC$_{1-6}$ alkyl; or Y$^3$ and Y$^4$ taken together with the N atom to which they are attached, form a heterocyclyl, wherein the heterocyclyl is optionally substituted by 1, 2, 3, or 4 substituents independently selected from the group consisting of halogen, CN, $C_{1-6}$ alkyl, OH, OC$_{1-6}$ alkyl, and =O;

in the presence of (a) N,N-diisopropylethylamine (Hunig's base) and O-(benzotriazol-1-yl)-N,N,N',N'-tetramethyluronium tetrafluoroborate in a solvent, (b) 1-ethyl-3-(3-dimethylaminopropyl)carbodiimide hydrochloride, N'-hydroxybenzotriazole, and N,N-diisopropylethylamine (Hunig's base) in a solvent, or (c) 1,1'-carbonyldiimidazole in a solvent, to provide the compound represented by formula II above.

35. A process for preparing a compound represented by formula

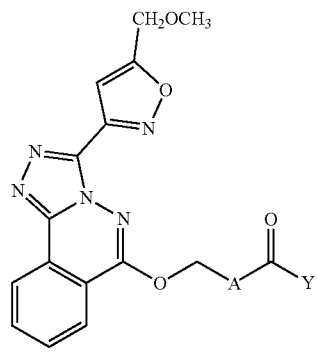

formula II wherein:
  A is phenylene, a 5-membered heteroarylene, or a 6-membered heteroarylene;
    wherein the 5-membered heteroarylene contains 1, 2, 3, or 4 heteroatoms independently selected from the group consisting of N, O, and S;
    wherein at most 1 of the heteroatoms of the 5-membered heteroarylene is O or S;
    wherein the 6-membered heteroarylene contains 1, 2, or 3 N heteroatoms;
    wherein the phenylene is optionally substituted by 1, 2, or 3 substituents independently selected from the group consisting of halogen, CN, $C_{1-6}$ alkyl, linear $C_{2-6}$ alkenyl, $C_{2-6}$ alkynyl, and $C_{3-6}$ cycloalkyl; and
    wherein the 5-membered heteroarylene or 6-membered heteroarylene is optionally substituted by 1 or more independently selected $R_x$ substituents;
  each $R_x$ is independently halogen, CN, C(O)OR$_1$, OH, OC(O)R$_1$, OR$_1$, or R$_1$;
  R$_1$ is $C_{1-6}$ alkylene-NHC$_{1-6}$ alkyl, $C_{1-6}$ alkylene-OC$_{1-6}$ alkyl, $C_{1-6}$ alkylene-OC$_{1-6}$ alkylene-C$_{3-6}$ cycloalkyl, $C_{1-6}$ alkylene-OC$_{1-6}$ alkylene-C$_{3-6}$ heterocycloalkyl, $C_{1-6}$ alkylene-C$_{3-6}$ heterocycloalkyl, OC$_{1-6}$ haloalkyl, OC$_{1-6}$ alkylene-C$_{3-6}$ cycloalkyl, or $C_{3-6}$ heterocycloalkyl, wherein the $C_{1-6}$ alkylene-NHC$_{1-6}$ alkyl, $C_{1-6}$ alkylene-OC$_{1-6}$ alkyl, $C_{1-6}$ alkylene-OC$_{1-6}$ alkylene-C$_{3-6}$ cycloalkyl, $C_{1-6}$ alkylene-OC$_{1-6}$ alkylene-C$_{3-6}$ heterocycloalkyl, $C_{1-6}$ alkylene-C$_{3-6}$ heterocycloalkyl, OC$_{1-6}$ haloalkyl, OC$_{1-6}$ alkylene-C$_{3-6}$ cycloalkyl, or $C_{3-6}$ heterocycloalkyl is optionally substituted by 0.1, 2, 3, or 4 substituents independently selected from the group consisting of halogen, CN, $C_{1-6}$ alkyl, OH, and =O;
  Y is NY$_1$Y$_2$, NHNY$_3$Y$_4$, or OH;
  Y$_1$ is H or $C_{1-6}$ alkyl, wherein the $C_{1-6}$ alkyl is optionally substituted by 1, 2, 3, 4, or 5 substituents independently selected from the group consisting of halogen, NH$_2$, NHC$_{1-6}$ alkyl, N(C$_{1-6}$ alkyl)$_2$, OH, OC$_{1-6}$ alkyl, OC$_{1-6}$ haloalkyl, and S(O)$_2$C$_{1-6}$ alkyl;
  Y$_2$ is H, $C_{1-6}$ alkyl, NH$_2$, OC$_{1-6}$ alkyl, S(O)$_2$C$_{1-6}$ alkyl, S(O)$_2$NH$_2$, cycloalkyl, heterocycloalkyl, or heteroaryl;
heteroaryl;
  wherein the $C_{1-6}$ alkyl, OC$_{1-6}$ alkyl, S(O)$_2$C$_{1-6}$ alkyl, cycloalkyl, heterocycloalkyl, or heteroaryl is optionally substituted by 1, 2, 3, 4, or 5 substituents independently selected from the group consisting of halogen, CN, $C_{1-6}$ alkyl, $C_{1-6}$ haloalkyl, $C_{1-6}$ alkylene-C(O)OH, $C_{1-6}$ alkylene-C(O)OC$_{1-4}$ alkyl, $C_{1-6}$ alkylene-OH, $C_{1-6}$ alkylene-OC$_{1-6}$ alkyl, acyl, NHC$_{1-6}$ alkyl, NHacyl, N(C$_{1-6}$ alkyl)$_2$, NO$_2$, OH, OC$_{1-6}$ alkyl, OC$_{1-6}$ haloalkyl, S(O)$_2$C$_{1-6}$ alkyl, $C_{3-6}$ cycloalkyl, 4-membered heterocycloalkyl, and $C_{4-6}$ heterocycloalkyl;
  wherein each 4-membered heterocycloalkyl and $C_{4-6}$ heterocycloalkyl substituent independently contains 1, 2, or 3 heteroatoms independently selected from the group consisting of N, O, and S;
  wherein each $C_{3-6}$ cycloalkyl substituent is optionally and independently substituted by 1 or more OH substituents;
  wherein each 4-membered heterocycloalkyl substituent is optionally and independently substituted by 1 or more CH$_3$ substituents; and
  wherein each $C_{4-6}$ heterocycloalkyl substituent is optionally and independently substituted by 1 or more substituents independently selected from the group consisting of halogen, CH$_3$, and OCH$_3$; or
  Y$^1$ and Y$^2$, taken together with the N atom to which they are attached, form a 4- to 7-membered heterocycloalkyl, a 4- to 7-membered heterocycloalkenyl, a spirocyclic 6- to 9-membered heterocyclyl, or a bridged 6- to 9-membered heterocyclyl;
    wherein the 4- to 7-membered heterocycloalkyl, 4- to 7-membered heterocycloalkenyl, spirocyclic 6- to 9-membered heterocyclyl, or bridged 6- to 9-membered heterocyclyl optionally contains 1 or more additional heteroatoms independently selected from the group consisting of N and O; and
    wherein the 4- to 7-membered heterocycloalkyl, 4- to 7-membered heterocycloalkenyl, spirocyclic 6- to 9-membered heterocyclyl, or bridged 6- to 9-membered heterocyclyl is optionally substituted by 1, 2, 3, or 4 substituents independently selected from the group consisting of halogen, CN, $C_{1-6}$ alkyl, OH, OC$_{1-6}$ alkyl, and =O;
  Y$_3$ is H, $C_{1-6}$ alkyl, S(O)$_2$C$_{1-6}$ alkyl, cycloalkyl, or heterocyclyl, wherein the $C_{1-6}$ alkyl, S(O)$_2$C$_{1-6}$ alkyl, cycloalkyl, or heterocyclyl is optionally substituted by 1, 2, 3, or 4 substituents independently selected from the group consisting of halogen, CN, $C_{1-6}$ alkyl, OH, and OC$_{1-6}$ alkyl; and
  Y$_4$ is H, $C_{1-6}$ alkyl, S(O)$_2$C$_{1-6}$ alkyl, cycloalkyl, or heterocyclyl, wherein the $C_{1-6}$ alkyl, S(O)$_2$C$_{1-6}$ alkyl, cycloalkyl, or heterocyclyl is optionally substituted by 1, 2, 3, or 4 substituents independently selected from the group consisting of halogen, CN, $C_{1-6}$ alkyl, OH, and OC$_{1-6}$ alkyl; or
  Y$^3$ and Y$^4$, taken together with the N atom to which they are attached, form a heterocyclyl, wherein the heterocyclyl is optionally substituted by 1, 2, 3; or 4 substituents independently selected from the group consisting of halogen, CN, $C_{1-6}$ alkyl, OH, OC$_{1-6}$ alkyl, and =O;
with the proviso that if A is pyridinylene, then the pyridinylene is optionally an N-oxide thereof;
wherein the process comprises the following steps:
1) reacting a compound represented by formula B:

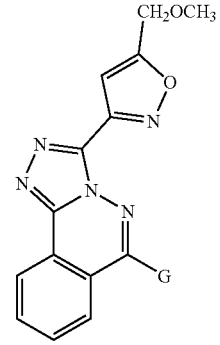

formula B wherein:
  G is Cl, Br, I, OH, OMs, OTf, or OTs;
with a compound represented by formula IV:

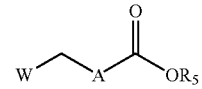

formula IV wherein:
  A is phenylene, a 5-membered heteroarylene, or a 6-membered heteroarylene;

wherein the 5-membered heteroarylene contains 1, 2, 3, or 4 heteroatoms independently selected from the group consisting of N, O, and S;

wherein at most 1 of the heteroatoms of the 5-membered heteroarylene is O or S;

wherein the 6-membered heteroarylene contains 1, 2, or 3 N heteroatoms;

wherein the phenylene is optionally substituted by 1, 2, or 3 substituents independently selected from the group consisting of halogen, CN, $C_{1-6}$ alkyl, linear $C_{2-6}$ alkenyl, $C_{2-6}$ alkynyl, and $C_{3-6}$ cycloalkyl; and wherein the 5-membered heteroarylene or 6-membered heteroarylene is optionally substituted by 1 or more independently selected $R_x$ substituents;

each $R_x$ is independently halogen, CN, C(O)OR$_1$, OH, OC(O)R$_1$, OR$_1$, or R$_1$;

$R_1$ is $C_{1-6}$ alkylene-NHC$_{1-6}$ alkyl, $C_{1-6}$ alkylene-OC$_{1-6}$ alkyl, $C_{1-6}$ alkylene-OC$_{1-6}$ alkylene-C$_{3-6}$ cycloalkyl, $C_{1-6}$ alkylene-OC$_{1-6}$ alkylene-C$_{3-6}$ heterocycloalkyl, $C_{1-6}$ alkylene-C$_{3-6}$ heterocycloalkyl, OC$_{1-6}$ haloalkyl, OC$_{1-6}$ alkylene-C$_{3-6}$ cycloalkyl, or $C_{3-6}$ heterocycloalkyl, wherein the $C_{1-6}$ alkylene-NHC$_{1-6}$ alkyl, $C_{1-6}$ alkylene-OC$_{1-6}$ alkyl, $C_{1-6}$ alkylene-OC$_{1-6}$ alkylene-C$_{3-6}$ cycloalkyl, $C_{1-6}$ alkylene-OC$_{1-6}$ alkylene-C$_{3-6}$ heterocycloalkyl, $C_{1-6}$ alkylene-C$_{3-6}$ heterocycloalkyl, OC$_{1-6}$ haloalkyl, OC$_{1-6}$ alkylene-C$_{3-6}$ cycloalkyl, or $C_{3-6}$ heterocycloalkyl is optionally substituted by 1, 2, 3, or 4 substituents independently selected from the group consisting of halogen, CN, $C_{1-6}$ alkyl, OH, and =O;

W is Cl, Br, I, OH, OMs, OTf, or OTs; and $R_5$ is alkyl or benzyl;

(a) in the presence of a base selected from the group consisting of lithium diisopropyl amide (LDA), sodium hydride, potassium tert-butoxide, or sodium tert-butoxide in a solvent selected from the group consisting of N,N-dimethylformamide, dioxane, and tetrahydrofuran, or (b) under Mitsunobu conditions comprising (i) biphenyl phosphine, (ii) diethyl azodicarboxylate (DEAD), and (iii) a phase transfer catalyst selected from the group consisting of a crown ether and tetrabutylammoniun bromide (TBAB), to provide a compound represented by formula 1-3:

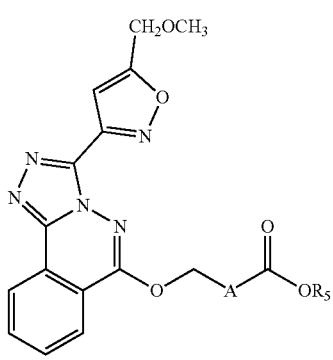

formula 1-3 wherein:
A is phenylene, a 5-membered heteroarylene, or a 6-membered heteroarylene;

wherein the 5-membered heteroarylene contains 1, 2, 3, or 4 heteroatoms independently selected from the group consisting of N, O, and S;

wherein at most 1 of the heteroatoms of the 5-membered heteroarylene is O or S;

wherein the 6-membered heteroarylene contains 1, 2, or 3 N heteroatoms;

wherein the phenylene is optionally substituted by 1, 2, or 3 substituents independently selected from the group consisting of halogen, CN, $C_{1-6}$ alkyl, linear $C_{2-6}$ alkenyl, $C_{2-6}$ alkynyl, and $C_{3-6}$ cycloalkyl; and wherein the 5-membered heteroarylene or 6-membered heteroarylene is optionally substituted by 1 or more independently selected $R_x$ substituents;

each $R_x$ is independently halogen, CN, C(O)OR$_1$, OH, OC(O)R$_1$, OR$_1$, or R$_1$;

$R_1$ is $C_{1-6}$ alkylene-NHC$_{1-6}$ alkyl, $C_{1-6}$ alkylene-OC$_{1-6}$ alkyl, $C_{1-6}$ alkylene-OC$_{1-6}$ alkylene-C$_{3-6}$ cycloalkyl, $C_{1-6}$ alkylene-OC$_{1-6}$ alkylene-C$_{3-6}$ heterocycloalkyl, $C_{1-6}$ alkylene-C$_{3-6}$ heterocycloalkyl, OC$_{1-6}$ haloalkyl, OC$_{1-6}$ alkylene-C$_{3-6}$ cycloalkyl, or $C_{3-6}$ heterocycloalkyl, wherein the $C_{1-6}$ alkylene-NHC$_{1-6}$ alkyl, $C_{1-6}$ alkylene-OC$_{1-6}$ alkyl, $C_{1-6}$ alkylene-OC$_{1-6}$ alkylene-C$_{3-6}$ cycloalkyl, $C_{1-6}$ alkylene-OC$_{1-6}$ alkylene-C$_{3-6}$ heterocycloalkyl, $C_{1-6}$ alkylene-C$_{3-6}$ heterocycloalkyl, OC$_{1-6}$ haloalkyl, OC$_{1-6}$ alkylene-C$_{3-6}$ cycloalkyl, or $C_{3-6}$ heterocycloalkyl is optionally substituted by 1, 2, 3, or 4 substituents independently selected from the group consisting of halogen, CN, $C_{1-6}$ alkyl, OH, and =O; and $R_5$ is alkyl or benzyl; and 2) reacting the compound represented by formula 1-3 above (a) with aqueous sodium hydroxide, (b) with sodium hydroxide or lithium hydroxide in a solvent selected from the group consisting of tetrahydrofuran and water, or a mixture thereof, or (c) under hydrogenation conditions, to provide the compound represented by formula II above.

36. A process for preparing a compound represented by formula II:

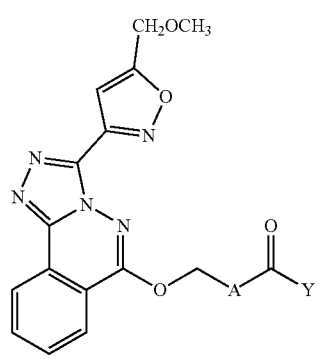

formula II wherein:
A is phenylene, a 5-membered heteroarylene, or a 6-membered heteroarylene;

wherein the 5-membered heteroarylene contains 1, 2, 3, or 4 heteroatoms independently selected from the group consisting of N, O, and S;
wherein at most 1 of the heteroatoms of the 5-membered heteroarylene is O or S;
wherein the 6-membered heteroarylene contains 1, 2, or 3 N heteroatoms;
wherein the phenylene is optionally substituted by 1, 2, or 3 substituents independently selected from the group consisting of halogen, CN, $C_{1-6}$ alkyl, linear $C_{2-6}$ alkenyl, $C_{2-6}$ alkynyl, and $C_{3-6}$ cycloalkyl; and
wherein the 5-membered heteroarylene or 6-membered heteroarylene is optionally substituted by 1 or more independently selected $R_x$ substituents;
each $R_x$ is independently halogen, CN, C(O)OR$_1$, OH, OC(O)R$_1$, OR$_1$, or R$_1$;
R$_1$ is $C_{1-6}$ alkylene-NHC$_{1-6}$ alkyl, $C_{1-6}$ alkylene-OC$_{1-6}$ alkyl, $C_{1-6}$ alkylene-OC$_{1-6}$ alkylene-C$_{3-6}$ cycloalkyl, $C_{1-6}$ alkylene-OC$_{1-6}$ alkylene-C$_{3-6}$ heterocycloalkyl, $C_{1-6}$ alkylene-C$_{3-6}$ heterocycloalkyl, OC$_{1-6}$ haloalkyl, OC$_{1-6}$ alkylene-C$_{3-6}$ cycloalkyl, or C$_{3-6}$ heterocycloalkyl, wherein the $C_{1-6}$ alkylene-NHC$_{1-6}$ alkyl, $C_{1-6}$ alkylene-OC$_{1-6}$alkyl, $C_{1-6}$ alkylene-OC$_{1-6}$ alkylene-C$_{3-6}$ cycloalkyl, $C_{1-6}$ alkylene-OC$_{1-6}$ alkylene-C$_{3-6}$ heterocycloalkyl, $C_{1-6}$ alkylene-C$_{3-6}$ heterocycloalkyl, OC$_{1-6}$ haloalkyl, OC$_{1-6}$ alkylene-C$_{3-6}$ cycloalkyl, or C$_{3-6}$ heterocycloalkyl is optionally substituted by 1, 2, 3, or 4 substituents independently selected from the group consisting of halogen, CN, $C_{1-6}$ alkyl, OH, and =O;
Y is NY$_1$Y$_2$, NHNY$_3$Y$_4$, or OH;
Y$_1$ is H or $C_{1-6}$ alkyl, wherein the $C_{1-6}$ alkyl is optionally substituted by 1, 2, 3, 4, or 5 substituents independently selected from the group consisting of halogen, NH$_2$, NHC$_{1-6}$ alkyl, N(C$_{1-6}$ alkyl)$_2$, OH, OC$_{1-6}$ alkyl, OC$_{1-6}$ haloalkyl, and S(O)$_2$C$_{1-6}$ alkyl;
Y$_2$ is H, $C_{1-6}$ alkyl, NH$_2$, OC$_{1-6}$alkyl, S(O)$_2$C$_{1-6}$ alkyl, S(O)$_2$NH$_2$, cycloalkyl, heterocycloalkyl, or heteroaryl;
heteroaryl;
wherein the $C_{1-6}$ alkyl, OC$_{1-6}$ alkyl, S(O)$_2$C$_{1-6}$ alkyl, cycloalkyl, heterocycloalkyl, or heteroaryl is optionally substituted by 1, 2, 3, 4, or 5 substituents independently selected from the group consisting of halogen, CN, $C_{1-6}$ alkyl, $C_{1-6}$ haloalkyl, $C_{1-6}$ alkylene-C(O)OH, $C_{1-6}$ alkylene-C(O)OC$_{1-4}$ alkyl, $C_{1-6}$ alkylene-OH, $C_{1-6}$ alkylene-OC$_{1-6}$ alkyl, acyl, NHC$_{1-6}$ alkyl, NHacyl, N(C$_{1-6}$ alkyl)$_2$, NO$_2$, OH, OC$_{1-6}$ alkyl, OC$_{1-6}$ haloalkyl, S(O)$_2$C$_{1-6}$ alkyl, C$_{3-6}$ cycloalkyl, 4-membered heterocycloalkyl, and C$_{4-6}$ heterocycloalkyl;
wherein each 4-membered heterocycloalkyl and C$_{4-6}$ heterocycloalkyl substituent independently contains 1, 2, or 3 heteroatoms independently selected from the group consisting of N, O, and S;
wherein each $C_{3-6}$ cycloalkyl substituent is optionally and independently substituted by 1 or more OH substituents;
wherein each 4-membered heterocycloalkyl substituent is optionally and independently substituted by 1 or more CH$_3$ substituents; and
wherein each 04.6 heterocycloalkyl substituent is optionally and independently substituted by 1 or more substituents independently selected from the group consisting of halogen, CH$_3$, and OCH$_3$; or
Y$^1$ and Y$^2$, taken together with the N atom to which they are attached, form a 4- to 7-membered heterocycloalkyl, a 4- to 7-membered heterocycloalkenyl, a spirocyclic 6- to 9-membered heterocyclyl, or a bridged 6- to 9-membered heterocyclyl;

wherein the 4- to 7-membered heterocycloalkyl, 4- to 7-membered heterocycloalkenyl, spirocyclic 6- to 9-membered heterocyclyl, or bridged 6- to 9-membered heterocyclyl optionally contains 1 or more additional heteroatoms independently selected from the group consisting of N and O; and
wherein the 4- to 7-membered heterocycloalkyl, 4- to 7-membered heterocycloalkenyl, spirocyclic 6- to 9-membered heterocyclyl, or bridged 6- to 9-membered heterocyclyl is optionally substituted by 1, 2, 3, or 4 substituents independently selected from the group consisting of halogen, CN, $C_{1-6}$ alkyl, OH, OC$_{1-6}$ alkyl, and =O;
Y$_3$ is H, $C_{1-6}$ alkyl, S(O)$_2$C$_{1-6}$ alkyl, cycloalkyl, or heterocyclyl, wherein the $C_{1-6}$ alkyl, S(O)$_2$C$_{1-6}$ alkyl, cycloalkyl, or heterocyclyl is optionally substituted by 1, 2, 3, or 4 substituents independently selected from the group consisting of halogen, CN, $C_{1-6}$ alkyl, OH, and OC$_{1-6}$ alkyl; and
Y$_4$ is H, $C_{1-6}$ alkyl, S(O)$_2$C$_{1-6}$ alkyl, cycloalkyl, or heterocyclyl, wherein the $C_{1-6}$ alkyl, S(O)$_2$C$_{1-6}$ alkyl, cycloalkyl, or heterocyclyl is optionally substituted by 1, 2, 3, or 4 substituents independently selected from the group consisting of halogen, CN, $C_{1-6}$ alkyl, OH, and OC$_{1-6}$ alkyl; or
Y$^3$ and Y$^4$, taken together with the N atom to which they are attached, form a heterocyclyl, wherein the heterocyclyl is optionally substituted by 1, 2, 3, or 4 substituents independently selected from the group consisting of halogen, CN, $C_{1-6}$ alkyl, OH, OC$_{1-6}$ alkyl, and =O;
with the proviso that if A is pyridinylene, then the pyridinylene is optionally an N-oxide thereof;
wherein the process comprises the following step:
1) reacting a compound represented by formula B:

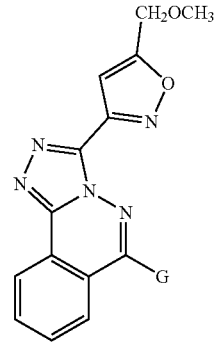

formula B wherein:
G is Cl, Br, I, OH, OMs, OTf, or OTs;
with a compound represented by formula V:

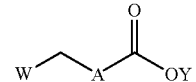

formula V wherein:
A is phenylene, a 5-membered heteroarylene, or a 6-membered heteroarylene;

wherein the 5-membered heteroarylene contains 1, 2, 3, or 4 heteroatoms independently selected from the group consisting of N, O, and S;

wherein at most 1 of the heteroatoms of the 5-membered heteroarylene is O or S;

wherein the 6-membered heteroarylene contains 1, 2, or 3 N heteroatoms;

wherein the phenylene is optionally substituted by 1, 2, or 3 substituents independently selected from the group consisting of halogen, CN, $C_{1-6}$ alkyl, linear $C_{2-6}$ alkenyl, $C_{2-6}$ alkynyl, and $C_{3-6}$ cycloalkyl; and wherein the 5-membered heteroarylene or 6-membered heteroarylene is optionally substituted by 1 or more independently selected $R_x$ substituents;

each $R_x$ is independently halogen, CN, $C(O)OR_1$, OH, $OC(O)R_1$, $OR_1$, or $R_1$;

$R_1$ is $C_{1-6}$ alkylene-$NHC_{1-6}$ alkyl, $C_{1-6}$ alkylene-$OC_{1-6}$ alkyl, $C_{1-6}$ alkylene-$OC_{1-6}$ alkylene-$C_{3-6}$ cycloalkyl, $C_{1-6}$ alkylene-$OC_{1-6}$ alkylene-$C_{3-6}$ heterocycloalkyl, $C_{1-6}$ alkylene-$C_{3-6}$ heterocycloalkyl, $OC_{1-6}$ haloalkyl, $OC_{1-6}$ alkylene-$C_{3-6}$ cycloalkyl, or $C_{3-6}$ heterocycloalkyl, wherein the $C_{1-6}$ alkylene-$NHC_{1-6}$ alkyl, $C_{1-6}$ alkylene-$OC_{1-6}$ alkyl, $C_{1-6}$ alkylene-$OC_{1-6}$ alkylene-$C_{3-6}$ cycloalkyl, $C_{1-6}$ alkylene-$OC_{1-6}$ alkylene-$C_{3-6}$ heterocycloalkyl, $C_{1-6}$ alkylene-$C_{3-6}$ heterocycloalkyl, $OC_{1-6}$ haloalkyl, $OC_{1-6}$ alkylene-$C_{3-6}$ cycloalkyl, or $C_{3-6}$ heterocycloalkyl is optionally substituted by 1, 2, 3, or 4 substituents independently selected from the group consisting of halogen, CN, $C_{1-6}$ alkyl, OH, and =O;

W is Cl, Br, I, OH, OMs, OTf, or OTs; and

Y is $NY_1Y_2$, $NHNY_3Y_4$, or OH;

$Y_1$ is H or $C_{1-6}$ alkyl, wherein the $C_{1-6}$ alkyl is optionally substituted by 1, 2, 3, 4, or 5 substituents independently selected from the group consisting of halogen, $NH_2$, $NHC_{1-6}$ alkyl, $N(C_{1-6}$ alkyl$)_2$, OH, $OC_{1-6}$ alkyl, $OC_{1-6}$ haloalkyl, and $S(O)_2C_{1-6}$ alkyl;

$Y_2$ is H, $C_{1-6}$ alkyl, $NH_2$, $OC_{1-6}$ alkyl, $S(O)_2C_{1-6}$ alkyl, $S(O)_2NH_2$, cycloalkyl, heterocycloalkyl, or heteroaryl;

wherein the $C_{1-6}$ alkyl, $OC_{1-6}$ alkyl, $S(O)_2C_{1-6}$ alkyl, cycloalkyl, heterocycloalkyl, or heteroaryl is optionally substituted by 1, 2, 3, 4, or 5 substituents independently selected from the group consisting of halogen, CN, $C_{1-6}$ alkyl, $C_{1-6}$ haloalkyl, $C_{1-6}$ alkylene-$C(O)OH$, $C_{1-6}$ alkylene-$C(O)OC_{1-4}$ alkyl, $C_{1-6}$ alkylene-OH, $C_{1-6}$ alkylene-$OC_{1-6}$ alkyl, acyl, $NHC_{1-6}$ alkyl, NHacyl, $N(C_{1-6}$ alkyl$)_2$, $NO_2$, OH, $OC_{1-6}$ alkyl, $OC_{1-6}$ haloalkyl, $S(O)_2C_{1-6}$ alkyl, $C_{3-6}$ cycloalkyl, 4-membered heterocycloalkyl, and $C_{4-6}$ heterocycloalkyl;

wherein each 4-membered heterocycloalkyl and $C_{4-6}$ heterocycloalkyl substituent independently contains 1, 2, or 3 heteroatoms independently selected from the group consisting of N, O, and S;

wherein each $C_{3-6}$ cycloalkyl substituent is optionally and independently substituted by 1 or more OH substituents;

wherein each 4-membered heterocycloalkyl substituent is optionally and independently substituted by 1 or more $CH_3$ substituents; and wherein each $C_{4-6}$ heterocycloalkyl substituent is optionally and independently substituted by 1 or more substituents independently selected from the group consisting of halogen, $CH_3$, and $OCH_3$; or $Y^1$ and $Y^2$, taken together with the N atom to which they are attached, form a 4- to 7-membered heterocycloalkyl, a 4- to 7-membered heterocycloalkenyl, a spirocyclic 6- to 9-membered heterocyclyl, or a bridged 6- to 9-membered heterocyclyl;

wherein the 4- to 7-membered heterocycloalkyl, 4- to 7-membered heterocycloalkenyl, spirocyclic 6- to 9-membered heterocyclyl, or bridged 6- to 9-membered heterocyclyl optionally contains 1 or more additional heteroatoms independently selected from the group consisting of N and O; and wherein the 4- to 7-membered heterocycloalkyl, 4- to 7-membered heterocycloalkenyl, spirocyclic 6- to 9-membered heterocyclyl, or bridged 6- to 9-membered heterocyclyl is optionally substituted by 1, 2, 3, or 4 substituents independently selected from the group consisting of halogen, CN, $C_{1-6}$ alkyl, OH, $OC_{1-6}$ alkyl, and =O;

$Y_3$ is H, $C_{1-6}$ alkyl, $S(O)_2C_{1-6}$ alkyl, cycloalkyl, or heterocyclyl, wherein the $C_{1-6}$ alkyl, $S(O)_2C_{1-6}$ alkyl, cycloalkyl, or heterocyclyl is optionally substituted by 1, 2, 3, or 4 substituents independently selected from the group consisting of halogen, CN, $C_{1-6}$ alkyl, OH, and $OC_{1-6}$ alkyl; and $Y_4$ is H, $C_{1-6}$ alkyl, $S(O)_2C_{1-6}$ alkyl, cycloalkyl, or heterocyclyl, wherein the $C_{1-6}$ alkyl, $S(O)_2C_{1-6}$ alkyl, cycloalkyl, or heterocyclyl is optionally substituted by 1, 2, 3, or 4 substituents independently selected from the group consisting of halogen, CN, $C_{1-6}$ alkyl, OH, and $OC_{1-6}$ alkyl; or $Y^3$ and $Y^4$, taken together with the N atom to which they are attached, form a heterocyclyl, wherein the heterocyclyl is optionally substituted by 1, 2, 3, or 4 substituents independently selected from the group consisting of halogen, CN, $C_{1-6}$ alkyl, OH, $OC_{1-6}$ alkyl, and =O;

(a) in the presence of a base selected from the group consisting of lithium diisopropyl amide (LDA), sodium hydride, potassium tert-butoxide, or sodium tert-butoxide in a solvent selected from the group consisting of N,N-dimethylformamide, dioxane, and tetrahydrofuran, or (b) under Mitsunobu conditions comprising (i) triphenyl phosphine, (ii) diethyl azodicarboxylate (DEAD), and (iii) a phase transfer catalyst selected from the group consisting of a crown ether and tetrabutylammonium bromide (TBAB), optionally in the presence of a base or, catalyst, to provide the compound represented by formula II above.

\* \* \* \* \*